US011324815B2

(12) United States Patent
Malouin et al.

(10) Patent No.: US 11,324,815 B2
(45) Date of Patent: May 10, 2022

(54) **VACCINE CONSTRUCTS AND USES THEREOF AGAINST *STAPHYLOCOCCUS* INFECTIONS**

(71) Applicant: SOCPRA SCIENCES ET GÉNIE S.E.C., Sherbrooke (CA)

(72) Inventors: François Malouin, Eastman (CA); Céline Ster, Compton (CA); Julie Côté-Gravel, Sherbrooke (CA); Éric Brouillette, Sherbrooke (CA)

(73) Assignee: SOCPRA—SCIENCES ET GENIE, s.e.c., Sherbrooke (CA)

( * ) Notice: Subject to any disclaimer, the term of this patent is extended or adjusted under 35 U.S.C. 154(b) by 0 days.

(21) Appl. No.: 16/337,457

(22) PCT Filed: Oct. 20, 2017

(86) PCT No.: PCT/CA2017/051253
§ 371 (c)(1),
(2) Date: Mar. 28, 2019

(87) PCT Pub. No.: WO2018/072031
PCT Pub. Date: Apr. 26, 2018

(65) Prior Publication Data
US 2019/0216913 A1 Jul. 18, 2019

Related U.S. Application Data

(60) Provisional application No. 62/411,120, filed on Oct. 21, 2016.

(51) Int. Cl.
| | | |
|---|---|---|
| *A61K 39/00* | (2006.01) | |
| *A61K 39/085* | (2006.01) | |
| *C07K 14/31* | (2006.01) | |
| *A61P 31/04* | (2006.01) | |
| *A61P 37/04* | (2006.01) | |
| *C12N 15/62* | (2006.01) | |
| *C12N 15/85* | (2006.01) | |

(52) U.S. Cl.
CPC ............ *A61K 39/085* (2013.01); *A61P 31/04* (2018.01); *A61P 37/04* (2018.01); *C07K 14/31* (2013.01);
(Continued)

(58) Field of Classification Search
CPC .................................................. A61K 39/085
See application file for complete search history.

(56) References Cited

U.S. PATENT DOCUMENTS

| | | | |
|---|---|---|---|
| 6,228,844 B1 | 5/2001 | Wolff et al. | |
| 6,380,370 B1 * | 4/2002 | Doucette-Stamm ... | C12Q 1/689 536/23.1 |

(Continued)

FOREIGN PATENT DOCUMENTS

| | | |
|---|---|---|
| CA | 2758490 A1 | 8/2009 |
| CA | 2758490 | 10/2010 |

(Continued)

OTHER PUBLICATIONS

Allard, M., Moisan, H., Brouillette, E., Gervais, A., Jacques, M., Lacasse, P., Diarra, M.S., and Malouin, F, Transcriptional modulation of some *Staphylococcus aureus* iron-regulated genes during growth in vitro and in a tissue cage model in vivo. Microb. Infect. 8:1679-1690. 2006.

(Continued)

*Primary Examiner* — Albert M Navarro
(74) *Attorney, Agent, or Firm* — McBee Moore & Vanik IP, LLC

(57) ABSTRACT

There is provided a fusion construct of formula (I): X-A-linker-B-Z (I) wherein: (1) A and B are identical or different and are independently: (a) a polypeptide comprising a SACOL0029 polypeptide as set forth in any one of the sequences depicted in FIG. 24 (SEQ ID NOs: 5 and 121 to 131), a SACOL0264 polypeptide (SEQ ID NO: 185), a SACOL0442 polypeptide as set forth in any one of the sequences depicted in FIG. 22D (SEQ ID NOs: 29 and 82 to 92), a SACOL0718 polypeptide (SEQ ID NO: 186), a SACOL0720 polypeptide as set forth in any one of the sequences depicted in FIGS. 23I-J (SEQ ID NOs: 11 and 109 to 120), a SACOL1353 polypeptide (SEQ ID NO: 187), a SACOL1416 polypeptide (SEQ ID NO: 188), a SACOL1611 polypeptide (SEQ ID NO: 189), a SACOL1867 polypeptide as set forth in any one of the sequences depicted in FIG. 25D (SEQ ID NOs: 152 to 164), a SACOL1912 polypeptide (SEQ ID NO: 43), a SACOL1944 polypeptide (SEQ ID NO: 190), a SACOL2144 polypeptide (SEQ ID NO: 191), a SACOL2365 polypeptide (SEQ ID NO: 192), a SACOL2385 polypeptide (SEQ ID NO: 50) or a SACOL2599 polypeptide (SEQ ID NO: 193), based on the gene nomenclature from the *Staphylococcus aureus* COL (SACOL) genome set forth in NCBI Reference Sequence NC_002951.2; (b) a polypeptide encoded by a gene from a same operon as a gene encoding the polypeptide of (a); (c) a polypeptide comprising an immunogenic fragment of at least 13 consecutive amino acids of (a) or (b); (d) a polypeptide comprising an amino acid sequence at least 60% identical overall to the sequence of the polypeptide of any one of (a) to (c); or (e) a polypeptide comprising an immunogenic variant comprising at least 13 consecutive amino acids of any one of (a) to (c); (2) the linker is an amino acid sequence of at least one amino acid or is absent; (3) X is absent or is an amino acid sequence of at least one amino acid; and (4) Z is absent or is an amino acid sequence of at least one amino acid. Also provided are compositions and kits comprising the fusion and uses of these fusions, compositions and kits.

33 Claims, 49 Drawing Sheets
Specification includes a Sequence Listing.

(52) U.S. Cl.
CPC .............. *C12N 15/62* (2013.01); *C12N 15/85* (2013.01); *A61K 2039/522* (2013.01); *A61K 2039/552* (2013.01); *C07K 2319/00* (2013.01)

(56) References Cited

U.S. PATENT DOCUMENTS

| | | | |
|---|---|---|---|
| 7,060,458 | B1 | 6/2006 | Doucette-Stamm |
| 7,608,276 | B2 | 10/2009 | Masignani et al. |
| 8,110,198 | B2 | 2/2012 | Doucette-Stamm |
| 8,889,150 | B2 | 11/2014 | Malouin et al. |
| 9,566,322 | B2 | 2/2017 | Malouin et al. |
| 10,029,004 | B2 | 7/2018 | Malouin et al. |
| 2004/0147734 | A1 | 7/2004 | Doucette-Stamm |
| 2012/0034258 | A1 | 2/2012 | Herron-Olson et al. |
| 2015/0132335 | A1 | 5/2015 | Malouin et al. |
| 2018/0289791 | A1 | 10/2018 | Malouin et al. |

FOREIGN PATENT DOCUMENTS

| | | |
|---|---|---|
| CA | 2792956 | 9/2011 |
| CA | 2792956 A1 | 9/2011 |
| EP | 0187702 | 2/1991 |
| EP | 1719520 | 1/2005 |
| JP | 2012/521441 A | 9/2012 |
| JP | 2012/523246 A | 10/2012 |
| RU | 2521501 C2 | 6/2014 |
| RU | 2013154779 A | 6/2015 |
| WO | 02/094868 A2 | 11/2002 |
| WO | 2003091279 | 11/2003 |
| WO | 2004043405 | 5/2004 |
| WO | 2005007683 | 1/2005 |
| WO | 2006059846 | 6/2006 |
| WO | 2008152447 | 12/2008 |
| WO | 2010/111273 A1 | 9/2010 |
| WO | 2010/119343 A2 | 10/2010 |
| WO | 2012177658 A2 | 12/2012 |

OTHER PUBLICATIONS

Allard, M., Ster, C., St-James, L., Lacasse, P., Diarra, M.S., Jacob, C.L., and Malouin, F Transcriptional Analysis of In Vivo-Expressed Genes in *Staphylococcus aureus* During Bovine Mastitis, 108th Annual Meeting of the American Society for Microbiology, Boston. Jun. 1-6, 2008.

Allard, M., Ster, C., St-James, L., Lacasse, P., Diarra, M.S., Jacob, C.L., and Malouin, F., Transcriptomic Analysis of In Vivo-Expressed Genes in *Staphylococcus aureus* During Bovine Mastitis, WCDS Advances in Dairy Technology (2008) vol. 20, Abstract, p. 362.

Allard, M., Ster, C., St-James, L., Lacasse, P., Diarra, M.S., Jacob, C.L., and Malouin, F., Identification of Specific *Staphylococcus aureus* Genes Expressed In Vivo During Bovine Mastitis, Mastitis Research Workers Conference (MRWC), Toronto, Nov. 4-5, 2008.

Allard, M., Ster, C., Jacob, C.L., Diarra, M.S., Scholl, D, Lacasse, P., and Malouin, F., Identification of genes expressed by *S. aureus* during bovine mastitis for vaccine and drug development. In Mastitis research into practice: Proceedings of the 5th IDF Mastitis Conference, Christchurch, New Zealand, Mar. 21-24, 2010, p. 342-347.

Allard, M., Ster, C., Jacob, C.L., Scholl, D, Diarra, M.S., Lacasse, P., and Malouin, F., The expression of a putative exotoxin and an ABC transporter during bovine intramammary infection contributes to the virulence of *Staphylococcus aureus*, Veterinary Microbiology 162 (2013) 761-770.

Bran-Barrera, DV, Brouillette, E., Ster, C., and Malouin, F., Development of a multivalent peptide vaccine for prevention of important infections in dairy cows. International conference on production diseases in farm animals (ICPD). Bern, Switzerland, Jun. 27-29, 2019.

Cote-Gravel, J., Brouillette, E., Obradovic, N., Talbot, B., Ster, C., and Malouin, F., Use of a *Staphylococcus aureus* small colony variant as an attenuated live vaccine for the prevention of intramammary infections. ECCMID, May 10-13, 2014. Barcelona, Spain.

Cote-Gravel, J., Brouillette, E., Obradovic, N., Talbot, B., Ster, C., and Malouin, F., Characterization of a vraG mutant in a genetically stable *S. aureus* small-colony variant and preliminary assessment for use as a live-attenuated vaccine against intrammamary infections. PLoSONE 11(11): e0166621., 2016.

Cote-Gravel, J., and Malouin, F., *Staphylococcus aureus* Mastitis Pathogenesis Features that guide Vaccine Development Strategies. J. Dairy Sci. 102:4727-4740, 2019, https://doi.org/10.3168/jds.2018-15272.

Fortin, C., A vaccine to help dairy cows—Research, partnerships and entrepreneurship—Université de Sherbrooke, May 30, 2016, https://www.usherbrooke.ca/recherche/fr/accueil/nouvelles/nouvelles-details/article/31830/.

Jacob, C.L., Lefebvre, B., Poirier, E., Roy, J.P., Scholl, D., and Malouin, F., Comparative Genomics and Virulence Potential of *Staphylococcus aureus* Isolates from Chronic Mastitis, 108th Annual Meeting of the American Society for Microbiology, Boston. Jun. 1-6, 2008.

Lafrance, M., Rivest, M., Lacasse, P., Perez-Casal, J., Malouin, F, and Talbot, B., Third Global Vaccine Conference, Singapore, Oct. 4-6, 2009.

Lafrance, M., Rivest, M., Lacasse, P., Perez-Casal, J., Malouin, F, and Talbot, B., Vaccine against *Staphylococcus aureus*: a work-in-progress, Annual Meeting of the American Society for Microbiology, San Diego. May 23-27, 2010.

Malouin, F., Ster, C., Brouillette, E., Cote-Gravel, J., Bran-Barrera, D. V., Cyrenne, M., Demontier, E., Beaulieu, J., Dube-Duquette, A., Belley, V., Veh, A.K., Pichette-Jolette, S., Asli, A., and Allard, M., Novel control and treatment approaches for *Staphylococcus aureus* intramammary infections M2-magazine, No. 21 (Jun. 2018), p. 26-30.

Poirier, H., The story of the Canadian discovery of the *S. aureus* vaccine, Feb. 10, 2017, https://bloguerecherchelaitiere.ca/2017/02/10/lhistoire-de-la-decouverte-canadienne-du-vaccin-contre-s-aureus/.

Ster C., Beaudoin, F., Jacques, M., Malouin, F., Diarra, M.S., and Lacasse, P., Preliminary evaluation of lsdH as an antigen for vaccination against bovine *Staphylococcus aureus* mastitis, Conference of Research Workers in Animal Diseases (CRWAD), Conference of Research Workers in Animal Diseases, Chicago, Dec. 2-4, 2007.

Ster C., Beaudoin, F., Diarra, M.S., Jacques, M., Malouin, F., and Lacasse, P., Evaluation of some *Staphylococcus aureus* iron-regulated proteins as vaccine targets, Vet. Immunol. Immunopathol. 136:311-318, Mar. 15, 2010.

Ster, C., Allard, M., Boulanger, S., Talbot, B.G., Lacasse, P., and Malouin, F., Identification of *Staphylococcus aureus* genes highly expressed during bovine mastitis: A unique opportunity for vaccine development, Conference of Research Workers in Animal diseases, Chicago, Dec. 5-7, 2010.

Ster C., Cote-Gravel, J., Allard, M., Gagnon, S., Potter, A., Talbot, B., Lacasse, P., and Malouin, F., A focus on genes expressed by *Staphylococcus aureus* during bovine intramammary infection for vaccine development. World Dairy Summit, Cape Town, S. Africa, Nov. 4-8, 2012.

Ster, C., Allard, M., Cote-Gravel, J., Boulanger, S., Lacasse, P., and Malouin, F., Vaccination and challenge against *Staphylococcus aureus* in dairy cows using antigens expressed during bovine intramammary infections, International conference on production diseases in farm animals (ICPD) Bern, Switzerland, Jun. 27-29, 2019.

Supplementary European Search Report in EP 11755607.6, dated Feb. 17, 2014 to SOCPRA—Sciences et Genie, S.E.C. et al.

Sandholm et al., "Bovine mastitis—why does antibiotic therapy not always work? An overview", J Vet Phamacol Therap., 1990, 13:248-260.

Schaffer et al., "Staphylococcal vaccines and immunotherapies", Infect Dis Clin North Am., 2009, 23:153-171.

Sears et al., "Management and treatment of staphylococcal mastitis", Vet Clin North Am Food Anim Pract, 2003, 19:171-185.

(56) References Cited

OTHER PUBLICATIONS

Sibbald et al., "Mapping the pathways to staphylococcal pathogenesis by comparative secretomics", Microbial Mal Biol Rev., 2006, 70:755-788.
Silanikove et al., "Posttranslational ruling of xanthine oxidase activity in bovine milk by its substrates", Biochem Biophys Res Commun., 2007, 363:561-565.
Somerville et al., "At the crossroads of bacterial metabolism and virulence factor synthesis in *Staphylococci*", Microbial Mal Biol Rev., 2009, 73:233-248.
Spickler et al., "Adjuvants in veterinary vaccines: mode of action and adverse effects", J Vet Intern Med, 2003, 17:273-281.
Srinivasan et al., "Prevalence of enterotoxin and toxic shock syndrome toxin genes in *Staphylococcus aureus* isolated from milk of cows with mastitis", Foodborne Pathog Dis., 2006, 3:274-83.
Srivastava et al., "Identification of regulatory elements in 16S rRNA gene of *Acinetobacter* species isolated from water sample", Bioinformation, 2008, 3(4):173-6. (Epub Dec. 6, 2008).
Taverna et al., "Characterization of cell wall associated proteins of a *Staphylococcus aureus* isolated from bovine mastitis case by a proteomic approach", Vet Microbial., 2007, 119:240-247.
Tollersrud et al., "*Staphylococcus aureus* enterotoxin Dis secreted in milk and stimulates specific antibody responses in cows in the course of experimental intramammary infection", Infect Immun., 2006, 74:3507-3512.
Tuchscherr et al., "Antibodies to capsular polysaccharide and clumping factor A prevent mastitis and the emergence of unencapsulated and small-colony variants of *Staphylococcus aureus* in mice", Infect Immun., 2008, 76:5738-5744.
Tusnady et al., The HMMTOP transmembrane topology prediction server, Bioinformatics, 2001, 17, 849-850.
Voyich et al., "Insights into mechanisms used by *Staphylococcus aureus* to avoid destruction by human neutrophils", J Immunol., 2005, 175:3907-3919.
Ziebandt et al., "Proteomics uncovers extreme heterogeneity in the *Staphylococcus aureus* exoproteome due to genomic plasticity and variant gene regulation", Proteomics, 2010, 285(47): 36794-36803.
Saha et al., "Prediction of Continuous B-Cell Epitopes in Antigenic Sequences Using Physico-chemical Properties", In G.Nicosia, V.Cutello, P.J. Bentley and J.Timis (Eds.) !CARIS 2004, LNCS 3239, Springer, 2004, 197-204.
Saha et al., "Prediction of Continuous B-cell Epitopes in an Antigen Using Recurrent Neural Network", Proteins, 2006, 65(1 ):40-48.
Houghten et al., "Relative Importance of Position and Individual Amino Acids . . . " Vaccines, 1986, Edited by Fred Brown: Cold Spring Harbor Laboratory).
Holmes, "PSMA Specific Antibodies and their Diagnostic and Therapeutic Use", Exp. Opin. Invest. Drugs, 2001, 10(3): 511-519).
Greenspan et al., "Defining Epitopes: It's Not as Easy as it Seems", Nature Biotechnology, 1999, 7:936-937.
Accession: B1GVC1 (Apr. 29, 2008).
USPTO, Final Rejection dated Apr. 3, 2014 in U.S. Appl. No. 13/583,054 to Malouin et al.
USPTO, Notice of allowance dated Jul. 18, 2014 in U.S. Appl. No. 13/583,054 to Malouin et al.
USPTO, Restriction Requirement dated Aug. 20, 2013 in U.S. Appl. No. 13/583,054 to Malouin et al.
USPTO, Non Final Rejection dated Oct. 17, 2013 in U.S. Appl. No. 13/583,054 to Malouin et al.
USPTO, Restriction Requirement dated Jul. 22, 2015 in U.S. Appl. No. 14/513,987 to Malouin et al.
USPTO, Non Final Rejection dated Nov. 30, 2015 in U.S. Appl. No. 14/513,987 to Malouin et al.
USPTO, Notice of allowance and Examiner's amendment dated Aug. 5, 2016 in U.S. Appl. No. 14/513,987 to Malouin et al.
Allard et al., "The expression of a putative exotoxin and an ABC transporter during bovine intramammary infection contributes to the virulence of *Staphylococcus aureus*", Veterinary Microbiology, 2013,162:761-770.
Allard et al., "The expression of a putative exotoxin and an ABC transporter during bovine intramammary infection contributes to the virulence of *Staphylococcus aureus*", Veterinary Microbiology, 2013, 162. Supplemental tables and figures.
Allard et al., "Identification of genes expressed by *S. aureus* during bovine mastitis for vaccine and drug development", In Mastitis research into practice: Proceedings of the 5th IDF Mastitis Conference, Christchurch, New Zealand, Mar. 21-24, 2010, p. 342-347.
Bradley et al., "An investigation of the efficacy of a polyvalent mastitis vaccine using different vaccination regimens under field conditions in the United Kingdom", 2014, J. Dairy Sci. 98 :1-15.
Landin et al. "Vaccination against *Staphylococcus aureus* mastitis in two Swedish dairy herds" Acta Vet Scand (2015) 57(81): 1-6.
Schukken, "Estimation of efficacy of Startvac® vaccination in dairy herds", Results of Mastitis Vaccination, HIPRA Symposium, Tuesday Jun. 5, 2012, WBC'12, Lisbon.
Schukken et al., "Efficacy of vaccination on *Staphylococcus aureus* and coagulase-negative *staphylococci* intramammary infection dynamics in 2 dairy herds", 2014, J. Dairy Sci 97 :5250-5264.
Ster et al. "Evaluation of some *Staphylococcus aureus* iron-regulated proteins as vaccine targets", Vet. Immunol. Immunopathol. 2010,136:311-318.
Tedeschi et al., "Serological proteome analysis of *Staphylococcus aureus* isolated from sub-clinical mastitis", Veterinary Microbiology 134 (2009) 388-391.
Canadian Intellectual Property Office, Office Action in CA2,792,956 to Malouin dated Jan. 6, 2017.
USPTO, Restriction Requirement dated May 13, 2019 in U.S. Appl. No. 16/013,494 to Malouin et al.
USPTO, Restriction Requirement dated Jun. 1, 2017 in U.S. Appl. No. 15/344,688 to Malouin et al.
USPTO, Non Final Office Action dated Aug. 30, 2017 in U.S. Appl. No. 15/344,688 to Malouin et al.
USPTO, Notice of Allowance dated Mar. 27, 2018 in U.S. Appl. No. 15/344,688 to Malouin et al.
Canadian Intellectual Property Office, Office Action in CA2,792,956 to Malouin dated Mar. 29, 2018.
Burton et al., "Immunity and mastitis Some new ideas for an old disease" Vet Clin Food Anim (2003) 19 : 1-45.
Chen et al., "Fusion Protein Linkers: Property, Design and Functionality" Adv Drug Deliv Rev. Oct. 15, 2013; 65 (10): 1357-1369.
Christensen et al., "Vaccine-induced Th17 cells are established as resident memory cells in the lung and promote local IgA responses" Mucosal Immunol. Jan. 2017;10(1):260-270. doi: 10.1038/mi.2016.28. Epub Apr. 6, 2016.
Falla et al., "Mode of Action of the Antimicrobial Peptide Indolicidin" J Biol Chem. Aug. 9, 1996;271(32):19298-303.
Hancock et al., "The role of cationic antimicrobial peptides in innate host defences" Trends Microbiol. Sep. 2000;8 (9):402-10.
Bowdish et al."Immunomodulatory Activities of Small Host Defense Peptides" Antimicrobial Agents and Chemotherapy, May 2005, p. 1727-1732.
Kahl, "Small colony variants (SCVs) of *Staphylococcus aureus*—A bacterial survival strategy" Infection, Genetics and Evolution 21 (2014) 515-522.
IPRP CA2011050145, WO, dated Sep. 27, 2012, SOCPRA—Sciences et Genie, S.E.C. et al.
ISR CA2011050145, WO, dated Jun. 23, 2011, SOCPRA—Sciences et Genie, S.E.C. et al.
Allard et al., "Transcriptional modulation of some *Staphylococcus aureus* iron-regulated genes during growth in vitro and in a tissue cage model in vivo", Microbes Infect., 2006, 7:1679-1690.
Allard et al., "Transcriptional Analysis of In Vivo-Expressed Genes in *Staphylococcus aureus* During Bovine Mastitis", American Society for Microbiology General Meeting. Boston, USA. Jun. 1-5, 2008 (Poster).
Atalla et al., "Characterization of a *Staphylococcus aureus* small colony variant (SCV) associated with persistent bovine mastitis", Foodborne Pathog, 2008, 5:785-799.
Barkema et al., "Invited Review: The role of cow, pathogen, and treatment regimen in the therapeutic success of bovine *Staphylococcus aureus* mastitis", J Dairy Sci. 2006, 89:1877-1895.

(56) References Cited

OTHER PUBLICATIONS

Bradley A., "Bovine mastitis: an evolving disease", Vet J. 2002, 164:116-128.
Barrio et al., "Assessment of the opsonic activity of purified bovine sIgA following intramammary immunization of cows with *Staphylococcus aureus*", J. Dairy Sci, 2003, 86 :2884-2894.
Brouillette et al., "3',5'-cyclic diguanylic acid reduces the virulence of biofilm-forming *Staphylococcus aureus* strains in a mouse model of mastitis infection", Antimicrob. Agents Chemother, 2005, 49:3109-3113.
Burlak et al., "Global analysis of community-associated methicillin-resistant *Staphylococcus aureus* exoproteins reveals molecules produced in vitro and during infection", Cell Microbiol., 2007, 9:1172-1190.
Chang et al., "Protective effects of recombinant staphylococcal enterotoxin type C mutant vaccine against experimental bovine infection by a strain of *Staphylococcus aureus* isolated from subclinical mastitis in dairy cattle", Vaccine, 2008, 26:2081-2091.
Chen et al., "Prediction of linear B-cell epitopes using amino acid pair antigenicity scale", Amino Acids, 2007, 33:423-428.
Chen et al., "Disruption of a toxin by introduction of a foreign gene into the chromosome of Clostridium perfringens using targetron induced mutagenesis", Plasmid., 2007, 58:182-189.
De Groot et al., "Prediction of immunogenicity: in silico paradigms, ex vivo and in vivo correlates", Curr Opinion in Pharmacol, 2008, 8:620-626.
Dehal et al., MicrobesOnline: an integrated portal for comparative and functional genomics. Nucleic Acids Res. Jan. 2010; 38(Database issue): D396-400. Epub Nov. 11, 2009.
Diarra et al., "Response of *Staphylococcus aureus* isolates from bovine mastitis to exogenous iron sources", J. Dairy Sci. ,2002, 85:2141-2148.
El-Manzalawy et al., "Predicting linear B-cell epitopes using string kernels" J Mol Recognit, 2008a, 21: 243-255.
El-Manzalawy et al., "Predicting flexible length linear B-cell epitopes. 7th International Conference on Computational Systems Bioinformatics", Stanford, CA. 2008b., pp. 121-131.
Eng et al., "The Potential of Polyphosphazenes for Delivery of Vaccine Antigens and Immunotherapeutic Agents", Curr Drug Deliv. 2010, 7(1):13-30.
Gardy et al., "PSORTb v.2.0: Expanded prediction of bacterial protein subcellular localization and insights gained from comparative proteome analysis", Bioinformatics, 2005, 21(5):617-623; doi:10.1093/bioinformatics/bti057.
Garzoni et al., "A global view of *Staphylococcus aureus* whole genome expression upon internalization in human epithelial cells", BMC Genomics. 2007, 8:171.
Goerke et al., "Direct quantitative transcript analysis of the agr regulon of *Staphylococcus aureus* during human infection in comparison to the expression profile in vitro", Infect Immun. 2000, 68:1304-1311.
Guidry et al., "Opsonization of *Staphylococcus aureus* by bovine immunoglobulin isotypes", J. of Dairy Sci., 1993. 76:1285-1289.
Haveri et al., "Virulence genes of bovine *Staphylococcus aureus* from persistent and nonpersistent intramammary infections with different clinical characteristics", J Appl Microbiol., 2007, 103:993-1000.
Hogarth et al., "Differential protein composition of bovine whey: a comparison of whey from healthy animals and from those with clinical mastitis", Proteomics, 2004, 4:2094-2100.
Jayarao et al., "Prevalence of foodbome pathogens in bulk tank milk", J Dairy Sci., 2001, 84:2157-2162.
Karaolis et al., Bacterial c-di-GMP is an immunostimulatory molecule. J Immunol., 2007, 178:2171-2181.
Kasturi et al. "Programming the magnitude and persistence of antibody responses with innate immunity", Nature, 2011, 470:543-547.
Lammers et al., "Identification of *Staphylococcus aureus* genes expressed during growth in milk: a useful model for selection of genes important in bovine mastitis?", Microbiology, 2000, 146:981-987.
Larkin et al., "ClustalW and ClustalX version 2. Bioinformatics", 2007, 23(21): 2947-2948.
Linghua et al., "The efficacy of CpG oligodinucleotides, in combination with conventional adjuvants, as immunological adjuvants to swine streptococcic septicemia vaccine in piglets in vivo", Int Immunopharmacol., 2006, 6:1267-76.
Loiselle et al., "Impact of postpartum milking frequency on the immune system and the blood metabolite concentration of dairy cows", J Dairy Sci. ,2009, 92:1900-1912.
Lowe et al., "Identification of novel staphylococcal virulence genes by in vivo expression technology", Mol Microbiol, 1998, 27:967-976.
Mamo et al., "Vaccination with *Staphylococcus aureus* fibrinogen binding protein (FgBPs) reduces colonisation of *S. aureus* in a mouse mastitis model", FEMS Immunology and Medical Microbiology, 1994, 10:47-54.
Maresso et al., "Iron acquisition and transport in *Staphylococcus aureus*", Biometals, 2006, 19:193-203.
Mayer et al., "Oxygen concentration in milk of healthy and mastitic cows and implications of low oxygen tension for the killing of *Staphylococcus aureus* by bovine neutrophils", J Dairy Res, 1988, 55:513-519.
Melchior et al., "Biofilm formation and genotyping of *Staphylococcus aureus* bovine mastitis isolates: evidence for lack of penicillin-resistance in Agr-type II strains", Vet. Microbiol., 2009, 137:83-89.
Middleton J.R., "*Staphylococcus aureus* antigens and challenges in vaccine development", Expert Rev Vaccines, 2008, 7:805-815.
Moisan et al., "Transcription of virulence factors in *Staphylococcus aureus* small-colony variants isolated from cystic fibrosis patients is influenced by SigB", J Bacteriol., 2006, 188:64-76.
Mitchell et al., "*Staphylococcus aureus* SigB activity promotes a strong fibronectin-bacterium interaction which may sustain host tissue colonization by small-colony variants isolated from cystic fibrosis patients", Mol Microbiol, 2008, 70:1540-1555.
Myllys et al., "Persistence in bovine mastitis of *Staphylococcus aureus* clones as assessed by random amplified polymorphic DNA analysis, ribotyping and biotyping", Vet Microbiol., 1997, 57:245-251.
National Mastitis Council 1996. Current Concept of Bovine Mastitis. 4 ed. National Mastitis Council, Madison, WI.
Nickerson et al., "Comparison of tilmicosin and cephapirin as therapeutics for *Staphylococcus aureus* mastitis at dry-off", J Dairy Sci, 1999, 82:696-703.
Owens et al., "Comparison of success of antibiotic therapy during lactation and results of antimicrobial susceptibility tests for bovine mastitis", J Dairy Sci, 1997, 80:313-317.
Park et al., "The analysis of milk components and pathogenic bacteria isolated from bovine raw milk in Korea", J Dairy Sci., 1997, 90:5405-5414.
Peles et al., "Characterization of *Staphylococcus aureus* strains isolated from bovine milk in Hungary", Int J Food Microbiol., 2007, 118:186-93.
Peterson et al., "The Comprehensive Microbial Resource", Nucleic Acids Res., 2001, 29(1): 123-5.
Petitclerc et al., "Efficacy of a lactoferrin-penicillin combination to treat {beta}lactam-resistant *Staphylococcus aureus* mastitis", J Dairy Sci, 2007, 90:2778-2787.
Pragman et al., "Virulence regulation in *Staphylococcus aureus*: the need for in vivo analysis of virulence factor regulation", FEMS Immunol Med Microbiol., 2004, 42:147-154.
Reinoso et al., "Bovine and rabbit models for the study of a *Staphylococcus aureus* a virulent mutant strain, RC122", Canadian Journal of Veterinary Research, 2002, 66:285-288.
Office Action in EP 11755607.6, dated Oct. 22, 2014 to SOCPRA—Sciences et Genie, S.E.C et al.
Thorberg: "Coagulase-Negative *Staphylococci* in Bovine Sub-Clinical Mastitis", Swedish University of Agricultural Sciences, 2008, Uppsala.

(56) References Cited

OTHER PUBLICATIONS

Chang, et al. Protective effects of recombinant staphylococcal enterotoxin type C mutant vaccine against experimental bovine infection by a strain of *Staphylococcus aureus* isolated from subclinical mastitis in dairy cattle, Vaccine. 2008, 26(17): 2081-2091. (Abstract).
Kuroda et al. Whole genome sequencing of meticillin-resistant *Staphylococcus aureus*, The Lancet, Apr. 2001, 357(9264): 1225-1240.
Gill et al. Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis*Strain, Journal of Bacteriology. 2005 187(7): 2426-2438.
Torres et al. Abstract of Patent Application: CL201303650, application date:Dec. 19, 2013, pp. 2.
UniProt Accession No. A0A0H3JK22 (Sep. 16, 2015).
Spencer et al. PloS One (2012) 7(3): e33555.
Maeda et al. Analytical Biochemistry (1997) 249(2): 147-152 [Abstract].
J. Arnau et al., "Current strategies for the use of affinity tags and tag removal for the purification of recombinant proteins", Elsevier, Protein Expression and Purification, 2006, pp. 1-13, vol. 48, No. 1.
X. Chen et al., "Fusion protein linkers: property, design and functionality", Advanced drug delivery reviews, Oct. 15, 2013, pp. 1357-1369, vol. 65, No. 10.
A.E. Frankel et al, "Characterization of diphtheria fusion proteins targeted to the human interleukin-3 receptor", Protein Engineering, 2000, pp. 575-581, vol. 13, No. 8.
Pakula A.A. et al., "Genetic analysis of protein stability and function", Annual review of genetics, 1989, pp. 289-310 and 305-306, vol. 23, No. 1.—Abstract attached.
Riollet et al. "Cell Subpopulations and Cytokine Expression in Cow Milk in Response to Chronic *Staphylococcus aureus* Infection.", 2001, J. Dairy Sci., pp. 1077-1084, vol. No. 84.

\* cited by examiner

FIG. 4C
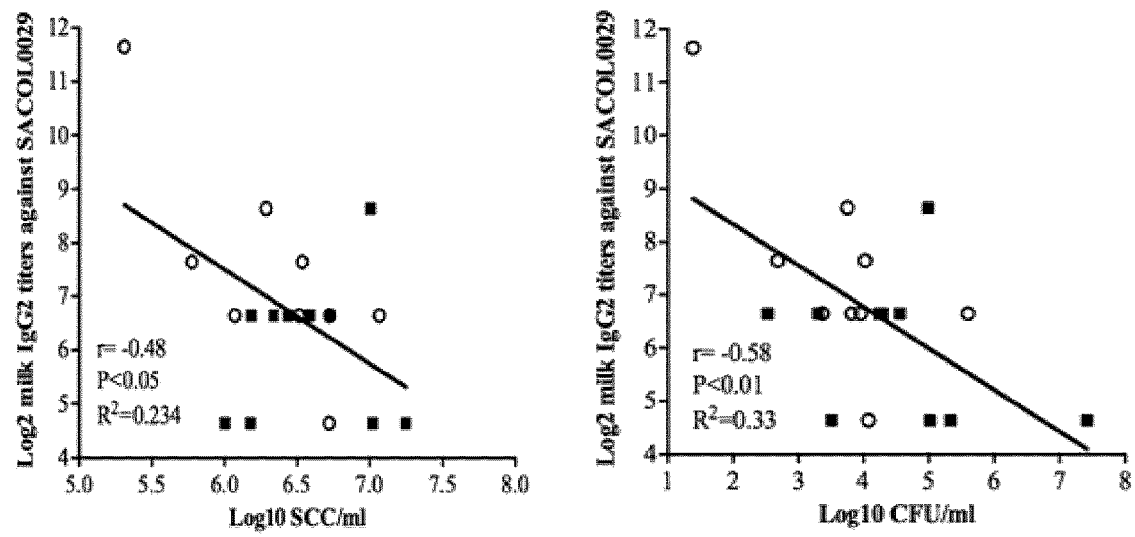
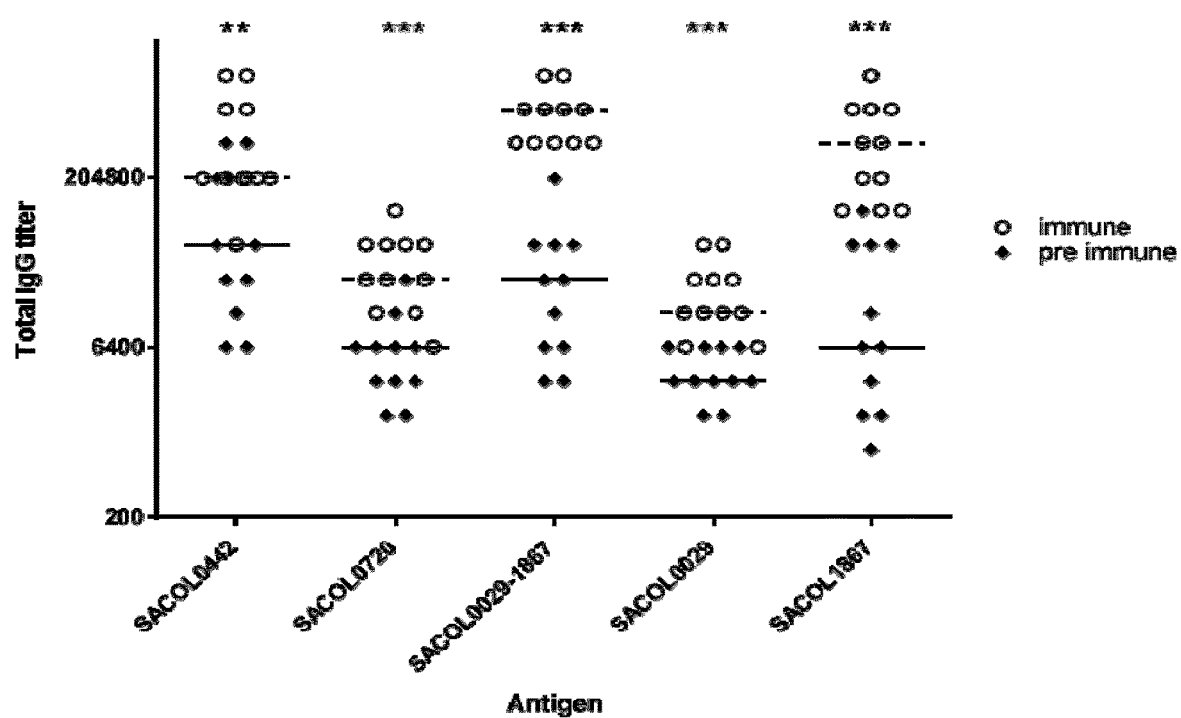
FIG. 5

I.  SACOL0029

FULL LENGTH

POLYNUCLEOTIDE

>SEQ ID NO:4 (GENBANK GENE ID 3236748)

ATGCTAGAATCTAGAGAGCAATTATCAGTCGAAGAATACGAAACATTCTTTAACAGATTTGATAATCAAGAATTTGATTT
CGAACGTGAATTGACACAAGATCCATATTCAAAAGTATACTTATACAGTATAGAAGACCATATCAGAACATATAAGATAG
AGAAATAA

POLYPEPTIDE

>SEQ ID NO: 5 (GENBANK PROTEIN ID YP_184940.1); Size: 55AA.

MLESREQLSVEEYETFFNRFDNQEFDFERELTQDPYSKVYLYSIEDHIRTYKIEK

FRAGMENTS

>SEQ ID NO:6

CTAGAATCTAGAGAGCAATTATCAGTCGAAGAATACGAAACATTCTTTAACAGATTTGATAATCAAGAATTTGATTTCGA
ACGTGAATTGACACAAGATCCATATTCAAAAGTATACTTATACAGTATAGAAGACCATATCAGAACATATAAGATAGAGA
AATAA

>SEQ ID NO:7; localization in full length SACOL0029: 2-55; size: 54 AA.

LESREQLSVEEYETFFNRFDNQEFDFERELTQDPYSKVYLYSIEDHIRTYKIEK

VARIANT

>SEQ ID NO:8; Comprising a SACOL0029 fragment localized in the full length SACOL0029: 2-55. The polyhistidine is double underlined.

MHHHHHHLESREQLSVEEYETFFNRFDNQEFDFERELTQDPYSKVYLYSIEDHIRTYKIEK

>SEQ ID NO:9; Comprising a SACOL0029 fragment localized in the full length SACOL0029: 2-55. The RGS-polyhistidine-GS tag is double underlined.

MRGSHHHHHHGSLESREQLSVEEYETFFNRFDNQEFDFERELTQDPYSKVYLYSIEDHIRTYKIEK

FIG. 21A

II. SACOL0720

FULL LENGTH

POLYNUCLEOTIDE

>SEQ ID NO: 10 (GENBANK GENE ID 3236600).

ATGACCTTTAACGAGATAATATTTAAAAATTTCCGTCAAAATTTATCACATTATGCCATCTATCTTTTTTCGTTAATTAC
GAGTGTAGTATTGTATTTTAGCTTTGTAGCATTAAAATACGCTCATAAACTAAACATGACAGAGTCATATCCAATTATAA
AGGAAGGCTCACAAGTCGGAAGCTACTTTCTATTTTTCATCATAATTGCATTTTTGTTATATGCCAATGTGTTATTTATT
AAACGACGAAGTTATGAGCTTGCATTATATCAAACATTAGGTTTATCTAAATTCAACATTATTTATATACTAATGCTCGA
ACAATTACTAATATTTATAATTACGGCAATATTAGGTATTATTATTGGTATTTTTGGTTCGAAACTGTTATTAATGATTG
TCTTTACATTATTAGGAATTAAAGAAAAGGTTCCAATTATTTTTAGTTTGAGGGCGGTATTTGAAACATTAATGTTAATC
GGTGTCGCTTATTTTTTAACATCTGCTCAAAATTTTATATTAGTGTTCAAACAATCTATTTCACAGATGTCAAAGAATAA
CCAGGTTAAAGAAACAAATCATAATAAAATTACATTTGAAGAGGTTGTTTTAGGCATCTTAGGTATAGTATTGATTACCA
CAGGATACTATCTATCTTTGAACATTGTTCAATATATGATTCTATCGGTACACTTATGTTTATTTTATTGTCAACTGTG
ATTGGGGCATACTTATTTTTTAAAAGCTCTGTTTCTCTAGTTTTTAAAATGGTGAAGAAGTTTAGAAAAGGTGTTATAAG
TGTAAATGATGTCATGTTCTCATCATCTATTATGTATCGTATTAAGAAAAATGCTTTTTCACTTACGGTCATGGCAATCA
TTTCAGCGATTACTGTTTCAGTTCTTTGCTTTGCTGCTATAAGTAGAGCGTCCTTATCAAGTGAAATAAAATATACTGCA
CCACACGACGTTACAATTAAAGACCAACAAAAAGCTAATCAATTAGCAAGTGAATTAAACAATCAAAAAATTCCTCATTT
TTATAATTATAAAGAAGTAATTCATACGAAATTGTATAAAGATAATTTATTTGATGTAAAAGCGAAAGAACCATACAATG
TAACAATTACTAGTGATAAATACATCCCTAATACTGATTTGAAACGTGGGCAAGCTGATTTATTTGTAGCGGAAGGTTCT
ATCAAAGATTTAGTGAAACATAAGAAGCATGGTAAGGCAATTATAGGAACGAAAAAACATCATGTTAATATTAAGTTACG
TAAAGATATTAATAAAATCTATTTTATGACAGATGTTGATTTAGGTGGACCAACGTTTGTCTTAAATGACAAAGACTATC
AAGAAATAAGAAAGTATACAAAGGCAAAGCATATCGTCTCTCAATTTGGATTCGATTTGAAACATAAAAAAGATGCTTTA
GCATTAGAAAAAGCGAAAAATAAAGTTGATAAATCTATTGAAACAAGAAGTGAAGCGATAAGCTCAATATCAAGTTTAAC
CGGAATATTATTATTTGTAACATCATTTTTAGGTATTACATTCTTGATTGCTGTATGTTGCATTATATACATAAAGCAAA
TAGATGAAACCGAAGATGAGTTAGAGAATTATAGTATTTTGAGAAAGCTTGGATTTACACAAAAAGATATGGCAAGGGGA
CTAAAGTTTAAAATTATGTTTAATTTTGGGTTACCTTTAGTTATTGCACTATCACATGCATATTTTACATCATTAGCATA
TATGAAATTAATGGGTACAACGAATCAAATACCGGTTTTCATAGTAATGGGATTATACATTTGTATGTATGCTGTTTTTG
CAGTGACGGCTTATAATCATTCCAAGCGAACATTAGACATTCCATATAA

POLYPEPTIDE

> SEQ ID NO: 11 (GENBANK PROTEIN ID YP_185601.1); Size: 629AA.

MTFNEIIFKNFRQNLSHYAIYLFSLITSVVLYFSFVALKYAHKLNMTESYPIIKEGSQVGSYFLFFIIIAFLLYANVLFI
KRRSYELALYQTLGLSKFNIIYILMLEQLLIFIITAILGIIIGIFGSKLLLMIVFTLLGIKEKVPIIFSLRAVFETLMLI
GVAYFLTSAQNFILVFKQSISQMSKNNQVKETNHNKITFEEVVLGILGIVLITTGYYLSLNIVQYYDSIGTLMFILLSTV
IGAYLFFKSSVSLVFKMVKKFRKGVISVNDVMFSSSIMYRIKKNAFSLTVMAIISAITVSVLCFAAISRASLSSEIKYTA
PHDVTIKDQQKANQLASELNNQKIPHFYNYKEVIHTKLYKDNLFDVKAKEPYNVTITSDKYIPNTDLKRGQADLFVAEGS
IKDLVKHKKHGKAIIGTKKHHVNIKLRKDINKIYFMTDVDLGGPTFVLNDKDYQEIRKYTKAKHIVSQFGFDLKHKKDAL
ALEKAKNKVDKSIETRSEAISSISSLTGILLFVTSFLGITFLIAVCCIIYIKQIDETEDELENYSILRKLGFTQKDMARG
LKFKIMFNFGLPLVIALSHAYFTSLAYMKLMGTTNQIPVFIVMGLYICMYAVFAVTAYNHSKRTIRHSI

FIG. 21B

FRAGMENTS

>SEQ ID NO : 12 ; localization in full length SACOL0720: 309-508; size: 200 AA.

RASLSSEIKYTAPHDVTIKDQQKANQLASELNNQKIPHFYNYKEVIHTKLYKDNLFDVKAKEPYNVTITSDKYIPNTDLKRG
QADLFVAEGSIKDLVKHKKHGKAIIGTKKHHVNIKLRKDINKIYFMTDVDLGGPTFVLNDKDYQEIRKYTKAKHIVSQFGFDL
KHKKDALALEKAKNKVDKSIETRSEAISSISSLTG

>SEQ ID NO : 13; localization in full length SACOL0720: 310-508; size: 199 AA.

ASLSSEIKYTAPHDVTIKDQQKANQLASELNNQKIPHFYNYKEVIHTKLYKDNLFDVKAKEPYNVTITSDKYIPNTDLKRGQ
ADLFVAEGSIKDLVKHKKHGKAIIGTKKHHVNIKLRKDINKIYFMTDVDLGGPTFVLNDKDYQEIRKYTKAKHIVSQFGFDLK
HKKDALALEKAKNKVDKSIETRSEAISSISSLTG

>SEQ ID NO : 14 ; localization in full length SACOL0720: 310-455; size: 146 AA.

ASLSSEIKYTAPHDVTIKDQQKANQLASELNNQKIPHFYNYKEVIHTKLYKDNLFDVKAKEPYNVTITSDKYIPNTDLKRGQ
ADLFVAEGSIKDLVKHKKHGKAIIGTKKHHVNIKLRKDINKIYFMTDVDLGGPTFVLNDKDYQE

>SEQ ID NO : 15 ; localization in full length SACOL0720: 428-481; size: 54 AA.

KDINKIYFMTDVDLGGPTFVLNDKDYQEIRKYTKAKHIVSQFGFDLKHKKDALA

>SEQ ID NO : 16 ; localization in full length SACOL0720: 428-452; size: 25 AA.

KDINKIYFMTDVDLGGPTFVLNDKD

>SEQ ID NO : 17 ; localization in full length SACOL0720: 428-453; size: 26 AA.

KDINKIYFMTDVDLGGPTFVLNDKDY

>SEQ ID NO : 18 ; localization in full length SACOL0720: 467-481; size: 15 AA.

SQFGFDLKHKKDALA

>SEQ ID NO : 19 ; localization in full length SACOL0720: 428-450; size: 23 AA.

KDINKIYFMTDVDLGGPTFVLND

>SEQ ID NO : 20 ; localization in full length SACOL0720: 463-481; size: 19 AA.

KHIVSQFGFDLKHKKDALA

>SEQ ID NO : 21 ; localization in full length SACOL0720: 468-481; size: 14 AA.

QFGFDLKHKKDALA

>SEQ ID NO : 22 ; localization in full length SACOL0720: 325-337; size: 13 AA.

FIG. 21C

TIKDQQKANQLAS

>SEQ ID NO : 23 ; localization in full length SACOL0720: 428-441; size: 14 AA.

KDINKIYFMTDVDL

>SEQ ID NO : 24 ; localization in full length SACOL0720: 438-450; size: 13 AA.

DVDLGGPTEVLND

VARIANT

>SEQ ID NO: 25 with polyhistidine in N-terminus; Comprises fragment localized in full length SACOL0720 at positions 310-455. The polyhistidine is double underlined.

M<u>HHHHHH</u>ASLSSEIKYTAPHDVTIKDQQKANQLASELNNQKIPHFYNYKEVIHTKLYKDNLFDVKAKEPYNVTITSDKYIPNTDLKRGQ
ADLFVAEGSIKDLVKHKKHGKAIIGTKKHHVNIKLRKDINKIYFMTDVDLGGPTEVLNDKDYQE

>SEQ ID NO: 26 with polyhistidine in N-terminus; Comprises fragment localized in full length SACOL0720 at positions 310-455. The RGS-polyhistidine-GS tag is double underlined.

<u>MRGSHHHHHHGS</u>ASLSSEIKYTAPHDVTIKDQQKANQLASELNNQKIPHFYNYKEVIHTKLYKDNLFDVKAKEPYNVTITSDKYIPN
TDLKRGQADLFVAEGSIKDLVKHKKHGKAIIGTKKHHVNIKLRKDINKIYFMTDVDLGGPTEVLNDKDYQE

>SEQ ID NO: 27 Comprises fragments localized in full length SACOL0720 at positions 428-450 and 463-481. Size: 50 AA. The underlined sequence is variant vs. native sequence. The remaining portions are native.

KDINKIYFMTDVDLGGPTEVLNDKDY<u>ERKYKKHIVS</u>QFGFDLKHKKDALA

III. SACOL0442

FULL LENGTH

POLYNUCLEOTIDE

>SEQ ID NO:28(GENBANK GENE ID 3236485).

ATGTTCAAAAAATATGACTCAAAAAATTCAATCGTATTAAAATCTATTCTATCGCTAGGTATCATCTATGGGGGAACATTTGGAATATA
TCCAAAAGCAGACGCGTCAACACAAAATTCCTCAAGTGTACAAGATAAACAATTACAAAAAGTTGAAGAAGTACCAAATAATTCAGAAA
AAGCTTTGGTTAAAAAACTTTACGATAGATACAGCAAGGATACAATAAATGGAAAATCTAATAAATCTAGGAATTGGGTTTATTCAGAG
AGACCTTTAAATGAAAACCAAGTTCGTATACATTTAGAAGGAACATACACAGTTGCTGGCAGAGTGTATACACCTAAGAGGAATATTAC
TCTTAATAAAGAAGTTGTCACTTTAAAAGAATTGGATCATATCATAAGATTTGCTCATATTTCCTATGGCTTGTATATGGGAGAACATT
TGCCTAAAGGTAACATCGTCATAAATACAAAAGATGGTGGTAAATATACATTAGAGTCGCATAAAGAGCTACAAAAAGATAGGGAAAAT
GTAAAAATTAATACAGCCGATATAAAAAATGTAACTTTCAAACTTGTGAAAAGTGTTAATGACATTGAACAAGTTTGA

POLYPEPTIDE

>SEQ ID NO: 29 (GENBANK PROTEIN ID YP_185332.1); Size:203AA.

MFKKYDSKNSIVLKSILSLGIIYGGTFGIYPKADASTQNSSSVQDKQLQKVEEVPNNSEKALVKKLYDRYSKDTINGKSNKSRNIVYSE
RPLNENQVRIHLEGTYTVAGRVYTPKRNITLNKEVVTLKELDHIIRFAHISYGLYMGEHLPKGNIVINTKDGGKITLESHKELQKDREN
VKINTADIKNVTFKLVKSVNDIEQV

FIG. 21D

FRAGMENTS

>SEQ ID NO: 30; localization in full length SACOL0442: 36-203; Size: 168 AA.

STQNSSSVQDKQLQKVEEVPNNSEKALVKKLYDRYSKDTINGKSNKSRNWVYSERPLNENQVRIHLEGTYTVAGRVYTPK
RNITLNKEVVTLKELDHIIRFAHISYGLYMGEHLPKGNIVINTKDGGKYTLESHKELQKDRENVKINTADIKNVTFKLVK
SVNDIEQV

>SEQ ID NO: 31; localization in full length SACOL0442: 44-159; Size: 116 AA.

QDKQLQKVEEVPNNSEKALVKKLYDRYSKDTINGKSNKSRNWVYSERPLNENQVRIHLEGTYTVAGRVYTPKRNITLNKE
VVTLKELDHIIRFAHISYGLYMGEHLPKGNIVINTK

>SEQ ID NO: 33; localization in full length SACOL0442: 45-203; Size: 159 AA.

DKQLQKVEEVPNNSEKALVKKLYDRYSKDTINGKSNKSRNWVYSERPLNENQVRIHLEGTYTVAGRVYTPKRNITLNKEV
VTLKELDHIIRFAHISYGLYMGEHLPKGNIVINTKDGGKYTLESHKELQKDRENVKINTADIKNVTFKLVKSVNDIEQV

> SEQ ID NO: 34 ; localization in full length SACOL0442: 72-85; Size: 14 AA.

KDTINGKSNKSRNW

> SEQ ID NO: 1 ; localization in full length SACOL0442: 159-173; Size: 15 AA.

KDGGKYTLESHKELQ

VARIANTS

>SEQ ID NO: 35 ; Comprises fragment localized in full length SACOL0442 at positions 45-203. The polyhistidine is double underlined.

MHHHHHHDKQLQKVEEVPNNSEKALVKKLYDRYSKDTINGKSNKSRNWVYSERPLNENQVRIHLEGTYTVAGRVYTPKRN
ITLNKEVVTLKELDHIIRFAHISYGLYMGEHLPKGNIVINTKDGGKYTLESHKELQKDRENVKINTADIKNVTFKLVKSV
NDIEQV

>SEQ ID NO: 36 ; Comprises fragment localized in full length SACOL0442 at positions 45-203. The RGS-polyhistidine-GS tag is double underlined.

MRGSHHHHHHGSDKQLQKVEEVPNNSEKALVKKLYDRYSKDTINGKSNKSRNWVYSERPLNENQVRIHLEGTYTVAGRVY
TPKRNITLNKEVVTLKELDHIIRFAHISYGLYMGEHLPKGNIVINTKDGGKYTLESHKELQKDRENVKINTADIKNVTFK
LVKSVNDIEQV

FIG. 21E

IV. SACOL1867

FULL LENGTH

POLYNUCLEOTIDE

>SEQ ID NO: 37 (GENBANK GENE ID 3236101).

ATGAATAAAAATATAGTCATTAAAAGCATGGCAGCATTAGCCATTCTAACCTCAGTAACTGGAATAAATGCTGCAGTCGT
TGAAGAGACACAACAAATAGCAAATGCAGAGAAGAATGTTACGCAAGTTAAAGATACAAATATTTTTCCATATAATGGCG
TCGTTTCATTTAAAGATGCGACAGGTTTTGTAATTGGAAAAAATACAATTATCACCAATAAACATGTATCAAAAGATTAT
AAAGTTGGCGATAGAATTACTGCCCATCCAAACGGTGACAAAGGAAATGGTGGTATATATAAAATTAAAAGCATTTCTGA
TTATCCGGGTGATGAAGACATCTCTGTCATGAATATTGAAGAACAAGCAGTCGAACGTGGACCAAAAGGCTTTAATTTTA
ATGAAAATGTCCAAGCATTCAATTTTGCGAAAGATGCTAAAGTTGATGACAAAATTAAAGTTATTGGTTACCCATTACCT
GCTCAAAATAGTTTTAAACAGTTTGAATCTACAGGAACTATAAAAAGAATCAAAGACAATATTTTAAATTTTGATGCATA
CATTGAACCCGGGAATTCAGGATCACCAGTTCTAAATTCTAACAATGAGGTCATAGGTGTGGTGTATGGCGGTATTGGAA
AAATTGGTTCTGAATATAATGGTGCCGTATACTTTACGCCTCAAATCAAAGATTTTATTCAAAAGCACATTGAACAATAA

POLYPEPTIDE

>SEQ ID NO: 38 (GENBANK PROTEIN ID YP_186695.1); Size: 239 AA.

MNKNIVIKSMAALAILTSVTGINAAVVEETQQIANAEKNVTQVKDTNIFPYNGVVSFKDATGFVIGKNTIITNKHVSKDY
KVGDRITAHPNGDKGNGGIYKIKSISDYPGDEDISVMNIEEQAVERGPKGFNFNENVQAFNFAKDAKVDDKIKVIGYPLP
AQNSFKQFESTGTIKRIKDNILNFDAYIEPGNSGSPVLNSNNEVIGVVYGGIGKIGSEYNGAVYFTPQIKDFIQKHIEQ

FRAGMENTS

>SEQ ID NO: 39; localization in full length SACOL1867: 41-239; Size: 199 AA.

TQVKDTNIFPYNGVVSFKDATGFVIGKNTIITNKHVSKDYKVGDRITAHPNGDKGNGGIYKIKSISDYPGDEDISVMNIE
EQAVERGPKGFNFNENVQAFNFAKDAKVDDKIKVIGYPLPAQNSFKQFESTGTIKRIKDNILNFDAYIEPGNSGSPVLNS
NNEVIGVVYGGIGKIGSEYNGAVYFTPQIKDFIQKHIEQ

VARIANT

>SEQ ID NO: 40; Comprises fragment localized in full length SACOL1867 at positions 41-239.
Polyhistidine double underlined.

MHHHHHHTQVKDTNIFPYNGVVSFKDATGFVIGKNTIITNKHVSKDYKVGDRITAHPNGDKGNGGIYKIKSISDYPGDED
ISVMNIEEQAVERGPKGFNFNENVQAFNFAKDAKVDDKIKVIGYPLPAQNSFKQFESTGTIKRIKDNILNFDAYIEPGNS
GSPVLNSNNEVIGVVYGGIGKIGSEYNGAVYFTPQIKDFIQKHIEQ

>SEQ ID NO: 41; Comprises fragment localized in full length SACOL1867 at positions 41-239. The
RGS-polyhistidine-GS tag is double underlined.

MRGSHHHHHHGSTQVKDTNIFPYNGVVSFKDATGFVIGKNTIITNKHVSKDYKVGDRITAHPNGDKGNGGIYKIKSISDY
PGDEDISVMNIEEQAVERGPKGFNFNENVQAFNFAKDAKVDDKIKVIGYPLPAQNSFKQFESTGTIKRIKDNILNFDAYI
EPGNSGSPVLNSNNEVIGVVYGGIGKIGSEYNGAVYFTPQIKDFIQKHIEQ

FIG. 21F

V. SACOL1912

FULL LENGTH

POLYNUCLEOTIDE

>SEQ ID NO: 42(GENBANK GENE ID 3236086).

ATGGCAATGAACTTTAAAGTCTTTGACAATAGTCAACTTGTAGCAGAATATGCTGCTGATATTATTAGAAAGCAATTTAA
CAATAATCCTACTACAATTGCAGGTTTTCATTTAGATACAGATCAAGCGCCAGTTCTAGATGAATTAAAGAAAAATGTTG
AAAAACATGCTGTTGATTTTAGCCAAATAAATATTTTAGATTATGACGATAAAAAATCATATTTCGAAGCGTTAGGTGTA
CCAGCAGGTCAAGTTTATCCAATTGCTTATGAAAAAGATGCAATCGAATTAATCGCTGATAAGATTAAAACTAAAGAAAA
TAAAGGGAAATTAACATTACAAGTTGTTTCTATCGATGAGCAAGGTAAGTTAAATGTTAGTATTCGTCAAGGACTAATGG
AAGCAAGAGAAATTTTCTTAGTAGTGACAGGTGCTAATAAACGAGATGTAGTTGAAAAATTATATCAAGAAATGGTAAA
ACAAGCTTCGAACCAGCCGATTTAAAAGCACATAGAATGGTAAATGTTATTCTTGATAAAGAAGCGGCTGCAGGTTTACC
TGAAGATGTTAAAGCTTACTTTACGTCACGCTTTGCTTAA

POLYPEPTIDE

>SEQ ID NO: 43 (GENBANK PROTEIN ID YP_186737.1); Size: 199AA.

MAMNFKVFDNSQLVAEYAADIIRKQFNNNPTTIAGFHLDTDQAPVLDELKKNVEKHAVDFSQINILDYDDKKSYFEALGV
PAGQVYPIAYEKDAIELIADKIKTKENKGKLTLQVVSIDEQGKLNVSIRQGLMEAREIFLVVTGANKRDVVEKLYQENGK
TSFEPADLKAHRMVNVILDKEAAAGLPEDVKAYFTSRFA

VARIANT

>SEQ ID NO: 44 ; Comprises full length SACOL1912. The polyhistidine is double underlined.

MHHHHHHMAMNFKVFDNSQLVAEYAADIIRKQFNNNPTTIAGFHLDTDQAPVLDELKKNVEKHAVDFSQINILDYDDKKS
YFEALGVPAGQVYPIAYEKDAIELIADKIKTKENKGKLTLQVVSIDEQGKLNVSIRQGLMEAREIFLVVTGANKRDVVEK
LYQENGKTSFEPADLKAHRMVNVILDKEAAAGLPEDVKAYFTSRFA

VI. SACOL2385

FULL LENGTH

POLYNUCLEOTIDE

> SEQ ID NO: 49 (GENBANK GENE ID 3238646).

ATGATATTGAACTTCAATCAATTCGAGAATCAAAACTTTTTTAACGGTAATCCAAGTGATACATTTAAAGATTTAGGTAA
ACAAGTATTTAATTACTTTTCAACACCTTCATTTGTAACGAATATATATGAAACAGACGAATTATATTACTTAGAAGCTG
AACTAGCAGGTGTAAATAAAGAAGATATTAGTATCGATTTCAATAATAATACGCTCACTATTCAAGCTACTAGAAGCGCA
AAATACAAATCTGAACAACTCATTTTAGATGAGCGTAACTTCGAATCATTAATGCGTCAATTTGATTTTGAAGCTGTTGA
TAAGCAACATATTACTGCTAGTTTTGAAAATGGGTTATTAACCATTACCTTGCCTAAAATCAAACCAAGCAATGAAACTA
CTTCATCAACATCTATTCCAATTTCATAG

FIG. 21G

POLYPEPTIDE

> SEQ ID NO: 50 (GENBANK PROTEIN ID YP_187189.1); Size: 93AA.

MILNFNQFENQNFFNGNPSDTFKDLGKQVFNYFSTPSFVTNIYETDELYYLEAELAGVNKEDISIDFNNNTLTIQATRSA
KYKSEQLILDERN

VARIANT

>SEQ ID NO: 51; Comprises full length SACOL2385.

MHHHHHHMILNFNQFENQNFFNGNPSDTFKDLGKQVFNYFSTPSFVTNIYETDELYYLEAELAGVNKEDISIDFNNNTLT
IQATRSAKYKSEQLILDERN

VII. FUSIONS

>SACOL0029-1867 (1)

POLYNUCLEOTIDE

>SEQ ID NO: 54

*CTAGAATCTAGAGAGCAATTATCAGTCGAAGAATACGAAACATTCTTTAACAGATTTGATAATCAAGAATTTGATTTCGA
ACGTGAATTGACACAAGATCCATATTCAAAAGTATACTTATACAGTATAGAAGACCATATCAGAACATATAAGATAGAGA
AAGGAGGTGGCGGTTCAGGAGGTGGAGGATCTGGAGGCGGTGGATCA*ACGCAAGTTAAAGATACAAATATTTTTCCATAT
AATGGCGTCGTTTCATTTAAAGATGCGACAGGTTTTGTAATTGGAAAAAATACAATTATCACCAATAAACATGTATCAAA
AGATTATAAAGTTGGCGATAGAATTACTGCCCATCCAAACGGTGACAAAGGAAATGGTGGTATATATAAAATTAAAAGCA
TTTCTGATTATCCGGGTGATGAAGACATCTCTGTCATGAATATTGAAGAACAAGCAGTCGAACGTGGACCAAAAGGCTTT
AATTTTAATGAAAATGTCCAAGCATTCAATTTTGCGAAAGATGCTAAAGTTGATGACAAAATTAAAGTTATTGGTTACCC
ATTACCTGCTCAAAATAGTTTTAAACAGTTTGAATCTACAGGAACTATAAAAAGAATCAAAGACAATATTTTAAATTTTG
ATGCATACATTGAACCCGGGAATTCAGGATCACCAGTTCTAAATTCTAACAATGAGGTCATAGGTGTGGTGTATGGCGGT
ATTGGAAAAATTGGTTCTGAATATAATGGTGCCGTATACTTTACGCCTCAAATCAAAGATTTTATTCAAAAGCACATTGA
ACAATAA*

POLYPEPTIDE

>SEQ ID NO: 55; Size: 268AA.

*LESREQLSVEEYETF*FNRFDNQEFDFERELTQDP*YS*KVYLYSIEDHIRTYKIEKGGGGSGGGGSGGGGSTQVKDTNIFPY
NGVVSFKDATGFVIGKNTIITNKHVSKDYKVGDRITAHPNGDKGNGGIYKIKSISDYPGDEDISVMNIEEQAVERGPKGF
NFNENVQAFNFAKDAKVDDKIKVIGYPLPAQNSFKQFESTGTIKRIKDNILNFDAYIEPGNSGSPVLNSNNEVIGVVYGG
IGKIGSEYNGAVYFTPQIKDFIQKHIEQ

FIG. 21H

>SACOL0029-1867 (2)

POLYNUCLEOTIDE

>SEQ ID NO: 56

ATG<u>CACCACCACCACCACCACC</u>TGGAATCCCGTGAACAACTGTCCGTCGAAGAATACGAAACCTTCTTTAACCGCTTTGATAACCAAGA
ATTTGATTTCGAACGTGAACTGACCCAGGATCCGTATTCTAAAGTGTATCTGTACAGTATCGAAGATCATATTCGCACGTACAAAATCG
AAAAAG<u>GCGGTGGCGGTTCTGGCGGTGGCGGTAGTGGCGGTGGCGGTAGC</u>ACCCAGGTGAAAGATACGAATATCTTTCCGTATAACGGC
GTGGTTTCTTTTAAAGATGCGACCGGCTTCGTTATCGGTAAAAACACCATCATCACGAACAAACATGTGAGCAAAGATTACAAAGTTGG
CGATCGTATTACCGCCCACCCGAATGGCGATAAGGGTAACGGCGGTATCTACAAAATCAAAAGCATCTCTGATTACCCGGGTGATGAAG
ATATCAGCGTGATGAATATTGAAGAACAGGCAGTTGAACGCGGCCCGAAAGGTTTTAACTTCAATGAAAACGTTCAGGCGTTTAATTTC
GCGAAAGATGCCAAAGTGGATGATAAAATCAAAGTTATTGGCTATCCGCTGCCGGCCCAGAACAGCTTTAAACAGTTCGAATCTACCGG
TACGATCAAACGTATCAAAGATAACATCCTGAACTTCGATGCATATATTGAACCGGGCAATAGTGGTAGCCCGGTGCTGAACAGTAACA
ATGAAGTTATTGGTGTGGTTTATGGCGGTATCGGCAAAATTGGTAGCGAATACAACGGTGCTGTGTATTTTACGCCGCAGATCAAAGAC
TTCATCCAGAAACATATCGAACAA

POLYPEPTIDE

>SEQ ID NO: 57; Size: 275AA. The polyhistidine is double underlined

M<u>HHHHHH</u>LESREQLSVEEYEIRFNRFDNQEFDFERELTQDPYSKVYLYSIEDHIRTYKIEKGGGGSGGGGSGGGGSTQVKDTNIFPYNG
VVSFKDATGFVIGKNTIITNKHVSKDYKVGDRITAHPNGDKGNGGIYKIKSISDYPGDEDISVMNIEEQAVERGPKGFNFNENVQAFNF
AKDAKVDDKIKVIGYPLPAQNSFKQFESTGTIKRIKDNILNFDAYIEPGNSGSPVLNSNNEVIGVVYGGIGKIGSEYNGAVYFTPQIKD
FIQKHIEQ

>SEQ ID NO: 58; Size: 280AA. The RGS-polyhistidine-GS tag is double underlined.

<u>MRGSHHHHHHGS</u>LESREQLSVEEYEIRFNRFDNQEFDFERELTQDPYSKVYLYSIEDHIRTYKIEKGGGGSGGGGSGGGGSTQVKDT
NIFPYNGVVSFKDATGFVIGKNTIITNKHVSKDYKVGDRITAHPNGDKGNGGIYKIKSISDYPGDEDISVMNIEEQAVERGPKGFNFNE
NVQAFNFAKDAKVDDKIKVIGYPLPAQNSFKQFESTGTIKRIKDNILNFDAYIEPGNSGSPVLNSNNEVIGVVYGGIGKIGSEYNGAVY
FTPQIKDFIQKHIEQ

>SACOL0720-720

POLYPEPTIDE

>SEQ ID NO: 27.

KDINKIYFMTDVDLGGPTFVLNDKDYERKYKKHIVSQPGEDLKHKKTALA

>SACOL00442-720

POLYPEPTIDE

>SEQ ID NO: 3.

KDGGKYTIESHFELQEAAAKEAAAKKDINKIYFMTDVDLGGPTFVLND

FIG. 21I

VIII. LINKERS

Used in exemplified fusion SACOL0029-1867.

POLYNUCLEOTIDE

>SEQ ID NO: 59

GGAGGTGGCGGTTCAGGAGGTGGAGGATCTGGAGGCGGTGGATCA

POLYPEPTIDE

>SEQ ID NO: 60.

GGGGSGGGGSGGGGS

POLYPEPTIDE Used in exemplified fusion SACOL00720-720

>SEQ ID NO: 61.

ERKYK

POLYPEPTIDE Used in exemplified fusion SACOL00442-720

>SEQ ID NO: 62.

EAAAKEAAAK

Other exemplary linker polypeptides

>SEQ ID NO: 63.
EAAAK
>SEQ ID NO: 64.
EAAAKEAAAKEAAAK
>SEQ ID NO: 65.
ERKYKERKYK
>SEQ ID NO: 66.
ERKYKERKYKERKYK
>SEQ ID NO: 67.
GGGGS
>SEQ ID NO: 68.
GGGGSGGGGS
>SEQ ID NO: 69.
XPXPXP wherein x may be any amino acid.
>SEQ ID NO: 70.
XPXPXPXPXPXP, wherein x may be any amino acid.

FIG. 21J

I- SACOL0442 : Multiple polynucleotide sequences alignment

```
MW0345 (MW2)                    ATGTTCAAAAAAAATGACTCGAAAAATTCAATTCTATTAAAATCTATTCT 50
SAS0347 (MSSA476)               ATGTTCAAAAAAAATGACTCGAAAAATTCAATTCTATTAAAATCTATTCT 50
SACOL0442 (COL)                 ATGTTCAAAAAATATGACTCAAAAAATTCAATCGTATTAAAATCTATTCT 50
SAOUHSC_00354 (NCTC8325)        ATGTTCAAAAAATATGACTCAAAAAATTCAATCGTATTAAAATCTATTCT 50
NWMN_0362 (Newman)              ATGTTCAAAAAATATGACTCAAAAAATTCAATCGTATTAAAATCTATTCT 50
SAUSA300_0370 (USA300-FPR3757)  ATGTTCAAAAAATATGACTCAAAAAATTCAATCGTATTAAAATCTATTCT 50
SaurJH1_0429 (JH1)              ATGTTCAAAAAATATGACTCAAAAAATTCAATCGTATTAAAATCTATTCT 50
SAHV_0367 (Mu3)                 ATGTTCAAAAAATATGACTCAAAAAATTCAATCGTATTAAAATCTATTCT 50
SaurJH9_0419 (JH9)              ATGTTCAAAAAATATGACTCAAAAAATTCAATCGTATTAAAATCTATTCT 50
SAV0370 (Mu50)                  ATGTTCAAAAAATATGACTCAAAAAATTCAATCGTATTAAAATCTATTCT 50
SA0357 (N315)                   ATGTTCAAAAAATATGACTCAAAAAATTCAATCGTATTAAAATCTATTCT 50
SAB0321 (RF122)                 ATGTTCAAAAAATATGACTCAAAAAATTCAATCGTATTAAAATCTATTCT 50
                                ***************  ******  **********   ***************

MW0345 (MW2)                    ATCGCTAGGTATCATCTATGGGGGAACATTTGGAATATATCCAAAAGCAG 100
SAS0347 (MSSA476)               ATCGCTAGGTATCATCTATGGGGGAACATTTGGAATATATCCAAAAGCAG 100
SACOL0442 (COL)                 ATCGCTAGGTATCATCTATGGGGGAACATTTGGAATATATCCAAAAGCAG 100
SAOUHSC_00354 (NCTC8325)        ATCGCTAGGTATCATCTATGGGGGAACATTTGGAATATATCCAAAAGCAG 100
NWMN_0362 (Newman)              ATCGCTAGGTATCATCTATGGGGGAACATTTGGAATATATCCAAAAGCAG 100
SAUSA300_0370 (USA300-FPR3757)  ATCGCTAGGTATCATCTATGGGGGAACATTTGGAATATATCCAAAAGCAG 100
SaurJH1_0429 (JH1)              ATCGCTAGGTATCATCTATGGGGGAACATTTGGAATATATCCAAAAGCAG 100
SAHV_0367 (Mu3)                 ATCGCTAGGTATCATCTATGGGGGAACATTTGGAATATATCCAAAAGCAG 100
SaurJH9_0419 (JH9)              ATCGCTAGGTATCATCTATGGGGGAACATTTGGAATATATCCAAAAGCAG 100
SAV0370 (Mu50)                  ATCGCTAGGTATCATCTATGGGGGAACATTTGGAATATATCCAAAAGCAG 100
SA0357 (N315)                   ATCGCTAGGTATCATCTATGGGGGAACATTTGGAATATATCCAAAAGCAG 100
SAB0321 (RF122)                 ATCGCTAGGTATCATCTATGGGGGAACATTTGGAATATATCCAAAAGCAG 100
                                **************************************************

MW0345 (MW2)                    ACGCGTCAACACAAAATTCCCCAAGTGTACAAGATAAACAATTCCAAAAA 150
SAS0347 (MSSA476)               ACGCGTCAACACAAAATTCCCCAAGTGTACAAGATAAACAATTCCAAAAA 150
SACOL0442 (COL)                 ACGCGTCAACACAAAATTCCTCAAGTGTACAAGATAAACAATTCAAAAAA 150
SAOUHSC_00354 (NCTC8325)        ACGCGTCAACACAAAATTCCTCAAGTGTACAAGATAAACAATTACAAAAA 150
NWMN_0362 (Newman)              ACGCGTCAACACAAAATTCCTCAAGTGTACAAGATAAACAATTACAAAAA 150
SAUSA300_0370 (USA300-FPR3757)  ACGCGTCAACACAAAATTCCTCAAGTGTACAAGATAAACAATTACAAAAA 150
SaurJH1_0429 (JH1)              ACGCGTCAACACAAAATTCCTCAAGTGTACAAGATAAACAATTACAAAAA 150
SAHV_0367 (Mu3)                 ACGCGTCAACACAAAATTCCTCAAGTGTACAAGATAAACAATTACAAAAA 150
SaurJH9_0419 (JH9)              ACGCGTCAACACAAAATTCCTCAAGTGTACAAGATAAACAATTACAAAAA 150
SAV0370 (Mu50)                  ACGCGTCAACACAAAATTCCTCAAGTGTACAAGATAAACAATTACAAAAA 150
SA0357 (N315)                   ACGCGTCAACACAAAATTCCTCAAGTGTACAAGATAAACAATTACAAAAA 150
SAB0321 (RF122)                 ACGCGTCAACACAAAATTCCTCAAGTGTACAAGATAAACAATTCCAAAAA 150
                                ******************** ********************  ******

MW0345 (MW2)                    GTTGAAGAAGTACCAAATAATTCAGAAAAAGCTTTGGTTAAAAAACTTTA 200
SAS0347 (MSSA476)               GTTGAAGAAGTACCAAATAATTCAGAAAAAGCTTTGGTTAAAAAACTTTA 200
SACOL0442 (COL)                 GTTGAAGAAGTACCAAATAATTCAGAAAAAGCTTTGGTTAAAAAACTTTA 200
SAOUHSC_00354 (NCTC8325)        GTTGAAGAAGTACCAAATAATTCAGAAAAAGCTTTGGTTAAAAAACTTTA 200
NWMN_0362 (Newman)              GTTGAAGAAGTACCAAATAATTCAGAAAAAGCTTTGGTTAAAAAACTTTA 200
SAUSA300_0370 (USA300-FPR3757)  GTTGAAGAAGTACCAAATAATTCAGAAAAAGCTTTGGTTAAAAAACTTTA 200
SaurJH1_0429 (JH1)              GTTGAAGAAGTACCAAATAATTCAGAAAAAGCTTTGGTTAAAAAACTTTA 200
SAHV_0367 (Mu3)                 GTTGAAGAAGTACCAAATAATTCAGAAAAAGCTTTGGTTAAAAAACTTTA 200
SaurJH9_0419 (JH9)              GTTGAAGAAGTACCAAATAATTCAGAAAAAGCTTTGGTTAAAAAACTTTA 200
SAV0370 (Mu50)                  GTTGAAGAAGTACCAAATAATTCAGAAAAAGCTTTGGTTAAAAAACTTTA 200
SA0357 (N315)                   GTTGAAGAAGTACCAAATAATTCAGAAAAAGCTTTGGTTAAAAAACTTTA 200
SAB0321 (RF122)                 GTTGAAGAAGTACCAAATAATTCAGAAAAAGCTTTGGTTAAAAAACTGTA 200
                                ***********************************************  **
```

FIG. 22A

```
MW0345 (MW2)                    CGATAGATACAGCCAAAATACAATAAACGGAAAATCTAATAAATCTAGGA 250
SAS0347 (MSSA476)               CGATAGATACAGCCAAAATACAATAAACGGAAAATCTAATAAATCTAGGA 250
SACOL0442 (COL)                 CGATAGATACAGCAAGGATACAATAAATGGAAAATCTAATAAATCTAGGA 250
SAOUHSC_00354 (NCTC8325)        CGATAGATACAGCAAGGATACAATAAATGGAAAATCTAATAAATCTAGGA 250
NWMN_0362 (Newman)              CGATAGATACAGCAAGGATACAATAAATGGAAAATCTAATAAATCTAGGA 250
SAUSA300_0370 (USA300-FPR3757)  CGATAGATACAGCAAGGATACAATAAATGGAAAATCTAATAAATCTAGGA 250
SaurJH1_0429 (JH1)              CGATAGATACAGCAAGGATACAATAAATGGAAAATCTAATAAATCTAGGA 250
SAHV_0367 (Mu3)                 CGATAGATACAGCAAGGATACAATAAATGGAAAATCTAATAAATCTAGGA 250
SaurJH9_0419 (JH9)              CGATAGATACAGCAAGGATACAATAAATGGAAAATCTAATAAATCTAGGA 250
SAV0370 (Mu50)                  CGATAGATACAGCAAGGATACAATAAATGGAAAATCTAATAAATCTAGGA 250
SA0357 (N315)                   CGATAGATACAGCAAGGATACAATAAATGGAAAATCTAATAAATCTAGGA 250
SAB0321 (RF122)                 CGATAGATACAGCCAAAATACAATAAACGGAAAATCTAATAAAGCTAGGA 250
                                ************* *  ********* **************** ******

MW0345 (MW2)                    ATTGGGTTTATTCAGAGAGACCTTTAAATGAAAACCAAGTTCGTATAAAT 300
SAS0347 (MSSA476)               ATTGGGTTTATTCAGAGAGACCTTTAAATGAAAACCAAGTTCGTATAAAT 300
SACOL0442 (COL)                 ATTGGGTTTATTCAGAGAGACCTTTAAATGAAAACCAAGTTCGTATACAT 300
SAOUHSC_00354 (NCTC8325)        ATTGGGTTTATTCAGAGAGACCTTTAAATGAAAACCAAGTTCGTATACAT 300
NWMN_0362 (Newman)              ATTGGGTTTATTCAGAGAGACCTTTAAATGAAAACCAAGTTCGTATACAT 300
SAUSA300_0370 (USA300-FPR3757)  ATTGGGTTTATTCAGAGAGACCTTTAAATGAAAACCAAGTTCGTATACAT 300
SaurJH1_0429 (JH1)              ATTGGGTTTATTCAGAGAGACCTTTAAATGAAAACCAAGTTCGTATACAT 300
SAHV_0367 (Mu3)                 ATTGGGTTTATTCAGAGAGACCTTTAAATGAAAACCAAGTTCGTATACAT 300
SaurJH9_0419 (JH9)              ATTGGGTTTATTCAGAGAGACCTTTAAATGAAAACCAAGTTCGTATACAT 300
SAV0370 (Mu50)                  ATTGGGTTTATTCAGAGAGACCTTTAAATGAAAACCAAGTTCGTATACAT 300
SA0357 (N315)                   ATTGGGTTTATTCAGAGAGACCTTTAAATGAAAACCAAGTTCGTATACAT 300
SAB0321 (RF122)                 ATTGGGTTTATTCAGAGAGACCTTTAAATGAAAATCAAGTTCGCATACAT 300
                                ********************************** ******* *** **

MW0345 (MW2)                    TTAGAAGGAACATACAGAGTTGCTGATAGAGTATATACACCTAAGAGAAA 350
SAS0347 (MSSA476)               TTAGAAGGAACATACAGAGTTGCTGATAGAGTATATACACCTAAGAGAAA 350
SACOL0442 (COL)                 TTAGAAGGAACATACACAGTTGCTGGCAGAGTGTATACACCTAAGAGGAA 350
SAOUHSC_00354 (NCTC8325)        TTAGAAGGAACATACACAGTTGCTGGCAGAGTGTATACACCTAAGAGGAA 350
NWMN_0362 (Newman)              TTAGAAGGAACATACACAGTTGCTGGCAGAGTGTATACACCTAAGAGGAA 350
SAUSA300_0370 (USA300-FPR3757)  TTAGAAGGAACATACACAGTTGCTGGCAGAGTGTATACACCTAAGAGGAA 350
SaurJH1_0429 (JH1)              TTAGAAGGAACATACACAGTTGCTGATAGAGTATATACACCTAAGAGAAA 350
SAHV_0367 (Mu3)                 TTAGAAGGAACATACACAGTTGCTGATAGAGTATATACACCTAAGAGAAA 350
SaurJH9_0419 (JH9)              TTAGAAGGAACATACACAGTTGCTGATAGAGTATATACACCTAAGAGAAA 350
SAV0370 (Mu50)                  TTAGAAGGAACATACACAGTTGCTGATAGAGTATATACACCTAAGAGAAA 350
SA0357 (N315)                   TTAGAAGGAACATACACAGTTGCTGATAGAGTATATACACCTAAGAGAAA 350
SAB0321 (RF122)                 TTAGAAGGTACATACAGAGTTGCTGATAGAGTGTATACACCTAAGAGGAA 350
                                ******** ******* *******  *****  ************** **

MW0345 (MW2)                    TATTACTCTTAATAAAGAAGTTGTCACTTTAAAGGAATTGGATCATATCA 400
SAS0347 (MSSA476)               TATTACTCTTAATAAAGAAGTTGTCACTTTAAAGGAATTGGATCATATCA 400
SACOL0442 (COL)                 TATTACTCTTAATAAAGAAGTTGTCACTTTAAAAGAATTGGATCATATCA 400
SAOUHSC_00354 (NCTC8325)        TATTACTCTTAATAAAGAAGTTGTCACTTTAAAAGAATTGGATCATATCA 400
NWMN_0362 (Newman)              TATTACTCTTAATAAAGAAGTTGTCACTTTAAAAGAATTGGATCATATCA 400
SAUSA300_0370 (USA300-FPR3757)  TATTACTCTTAATAAAGAAGTTGTCACTTTAAAAGAATTGGATCATATCA 400
SaurJH1_0429 (JH1)              TATTACTCTTAATAAAGAAGTTGTCACTTTAAAGGAATTGGATCATATCA 400
SAHV_0367 (Mu3)                 TATTACTCTTAATAAAGAAGTTGTCACTTTAAAGGAATTGGATCATATCA 400
SaurJH9_0419 (JH9)              TATTACTCTTAATAAAGAAGTTGTCACTTTAAAAGAATTGGATCATATCA 400
SAV0370 (Mu50)                  TATTACTCTTAATAAAGAAGTTGTCACTTTAAAGGAATTGGATCATATCA 400
SA0357 (N315)                   TATTACTCTTAATAAAGAAGTTGTCACTTTAAAGGAATTGGATCATATCA 400
SAB0321 (RF122)                 CATTACTCTTAATAAAGAAGTTGTCACTTTAAAAGAATTGGATCATATCA 400
                                 ********************************  ***************

MW0345 (MW2)                    TAAGATTTGCTCATATTTCTTATGGCTTATATATGGGAGAACATTTGCCT 450
SAS0347 (MSSA476)               TAAGATTTGCTCATATTTCTTATGGCTTATATATGGGAGAACATTTGCCT 450
SACOL0442 (COL)                 TAAGATTTGCTCATATTTCCTATGGCTTGTATATGGGAGAACATTTGCCT 450
SAOUHSC_00354 (NCTC8325)        TAAGATTTGCTCATATTTCCTATGGCTTGTATATGGGAGAACATTTGCCT 450
NWMN_0362 (Newman)              TAAGATTTGCTCATATTTCCTATGGCTTGTATATGGGAGAACATTTGCCT 450
SAUSA300_0370 (USA300-FPR3757)  TAAGATTTGCTCATATTTCCTATGGCTTGTATATGGGAGAACATTTGCCT 450
SaurJH1_0429 (JH1)              TAAGATTTGCTCATATTTCTTATGGCTTATATATGGGAGAACATTTGCCT 450
SAHV_0367 (Mu3)                 TAAGATTTGCTCATATTTCTTATGGCTTATATATGGGAGAACATTTGCCT 450
SaurJH9_0419 (JH9)              TAAGATTTGCTCATATTTCTTATGGCTTATATATGGGAGAACATTTGCCT 450
SAV0370 (Mu50)                  TAAGATTTGCTCATATTTCTTATGGCTTATATATGGGAGAACATTTGCCT 450
SA0357 (N315)                   TAAGATTTGCTCATATTTCTTATGGCTTATATATGGGAGAACATTTGCCT 450
SAB0321 (RF122)                 TAAGATTTGCTCATATTTCTTATGGCTTATATATGGGAGAACATTTGCCT 450
                                ******************* ******** ********************
```

FIG. 22B

```
MW0345 (MW2)                    AAAGGTAACATCGTCATAAATACAAAAGATGGCGGTAAATATACATTAGA 500
SAS0347 (MSSA476)               AAAGGTAACATCGTCATAAATACAAAAGATGGCGGTAAATATACATTAGA 500
SACOL0442 (COL)                 AAAGGTAACATCGTCATAAATACAAAAGATGGTGGTAAATATACATTAGA 500
SAOUHSC_00354 (NCTC8325)        AAAGGTAACATCGTCATAAATACAAAAGATGGTGGTAAATATACATTAGA 500
NWMN_0362 (Newman)              AAAGGTAACATCGTCATAAATACAAAAGATGGTGGTAAATATACATTAGA 500
SAUSA300_0370 (USA300-FPR3757)  AAAGGTAACATCGTCATAAATACAAAAGATGGTGGTAAATATACATTAGA 500
SaurJH1_0429 (JH1)              AAAGGTAACATCGTCATAAATACAAAAGATGGCGGTAAATATACATTAGA 500
SAHV_0367 (Mu3)                 AAAGGTAACATCGTCATAAATACAAAAGATGGCGGTAAATATACATTAGA 500
SaurJH9_0419 (JH9)              AAAGGTAACATCGTCATAAATACAAAAGATGGCGGTAAATATACATTAGA 500
SAV0370 (Mu50)                  AAAGGTAACATCGTCATAAATACAAAAGATGGCGGTAAATATACATTAGA 500
SA0357 (N315)                   AAAGGTAACATCGTCATAAATACAAAAGATGGCGGTAAATATACATTAGA 500
SAB0321 (RF122)                 AAAGGTAACATCGTCATAAATACAAAGAATGGCGGTAAATATACATTAGA 500
                                **************************     *** ***************

MW0345 (MW2)                    GTCGCATAAAGAGCTACAAAAAGATAGGGAAAATGTAAAAATTAATACAG 550
SAS0347 (MSSA476)               GTCGCATAAAGAGCTACAAAAAGATAGGGAAAATGTAAAAATTAATACAG 550
SACOL0442 (COL)                 GTCGCATAAAGAGCTACAAAAAGATAGGGAAAATGTAAAAATTAATACAG 550
SAOUHSC_00354 (NCTC8325)        GTCGCATAAAGAGCTACAAAAAGATAGGGAAAATGTAAAAATTAATACAG 550
NWMN_0362 (Newman)              GTCGCATAAAGAGCTACAAAAAGATAGGGAAAATGTAAAAATTAATACAG 550
SAUSA300_0370 (USA300-FPR3757)  GTCGCATAAAGAGCTACAAAAAGATAGGGAAAATGTAAAAATTAATACAG 550
SaurJH1_0429 (JH1)              GTCGCATAAAGAGCTACAAAAAGATAGGGAAAATGTAAAAATTAATACAG 550
SAHV_0367 (Mu3)                 GTCGCATAAAGAGCTACAAAAAGATAGGGAAAATGTAAAAATTAATACAG 550
SaurJH9_0419 (JH9)              GTCGCATAAAGAGCTACAAAAAGATAGGGAAAATGTAAAAATTAATACAG 550
SAV0370 (Mu50)                  GTCGCATAAAGAGCTACAAAAAGATAGGGAAAATGTAAAAATTAATACAG 550
SA0357 (N315)                   GTCGCATAAAGAGCTACAAAAAGATAGGGAAAATGTAAAAATTAATACAG 550
SAB0321 (RF122)                 GTCGCACAAAGAGTTACAAAAGAATAGGGAAAATGTAGAAATTAATACTG 550
                                ****** ****** ******  ****************** ******** *

MW0345 (MW2)                    CCGATATAAAAAATGTAACTTTCAAACTTGTGAAAAGTGTTAATGACATT 600
SAS0347 (MSSA476)               CCGATATAAAAAATGTAACTTTCAAACTTGTGAAAAGTGTTAATGACATT 600
SACOL0442 (COL)                 CCGATATAAAAAATGTAACTTTCAAACTTGTGAAAAGTGTTAATGACATT 600
SAOUHSC_00354 (NCTC8325)        CCGATATAAAAAATGTAACTTTCAAACTTGTGAAAAGTGTTAATGACATT 600
NWMN_0362 (Newman)              CCGATATAAAAAATGTAACTTTCAAACTTGTGAAAAGTGTTAATGACATT 600
SAUSA300_0370 (USA300-FPR3757)  CCGATATAAAAAATGTAACTTTCAAACTTGTGAAAAGTGTTAATGACATT 600
SaurJH1_0429 (JH1)              CCGATATAAAAAATGTAACTTTCAAACTTGTGAAAAGTGTTAATGACATT 600
SAHV_0367 (Mu3)                 CCGATATAAAAAATGTAACTTTCAAACTTGTGAAAAGTGTTAATGACATT 600
SaurJH9_0419 (JH9)              CCGATATAAAAAATGTAACTTTCAAACTTGTGAAAAGTGTTAATGACATT 600
SAV0370 (Mu50)                  CCGATATAAAAAATGTAACTTTCAAACTTGTGAAAAGTGTTAATGACATT 600
SA0357 (N315)                   CCGATATAAAAAATGTAACTTTCAAACTTGTGAAAAGTGTTAATGACATT 600
SAB0321 (RF122)                 ATGATATAAAAAATGTAACTTTCGAACTTGTGAAAAGTGTTAATGACATT 600
                                  *********************** ************************

MW0345 (MW2)                    GAACAAGTTTGA 612
SAS0347 (MSSA476)               GAACAAGTTTGA 612
SACOL0442 (COL)                 GAACAAGTTTGA 612
SAOUHSC_00354 (NCTC8325)        GAACAAGTTTGA 612
NWMN_0362 (Newman)              GAACAAGTTTGA 612
SAUSA300_0370 (USA300-FPR3757)  GAACAAGTTTGA 612
SaurJH1_0429 (JH1)              GAACAAGTTTGA 612
SAHV_0367 (Mu3)                 GAACAAGTTTGA 612
SaurJH9_0419 (JH9)              GAACAAGTTTGA 612
SAV0370 (Mu50)                  GAACAAGTTTGA 612
SA0357 (N315)                   GAACAAGTTTGA 612
SAB0321 (RF122)                 GAACAAGTTTGA 612
                                ************
```

FIG. 22C

II-SACOL0442 : Multiple polypeptide sequences alignment : selected epitopes shaded

```
SACOL0442 (COL)                  MFKKYDSKNSIVLKSILSLGIIYGGTFGIYPKADASTQNSSSVQDKQLQK 50
SAOUHSC_00354 (NCTC8325)         MFKKYDSKNSIVLKSILSLGIIYGGTFGIYPKADASTQNSSSVQDKQLQK 50
NWMN_0362 (Newman)               MFKKYDSKNSIVLKSILSLGIIYGGTFGIYPKADASTQNSSSVQDKQLQK 50
SAUSA300_0370 (USA300-FPR3757)   MFKKYDSKNSIVLKSILSLGIIYGGTFGIYPKADASTQNSSSVQDKQLQK 50
SaurJH1_0429 (JH1)               MFKKYDSKNSIVLKSILSLGIIYGGTFGIYPKADASTQNSSSVQDKQLQK 50
SAHV_0367 (Mu3)                  MFKKYDSKNSIVLKSILSLGIIYGGTFGIYPKADASTQNSSSVQDKQLQK 50
SaurJH9_0419 (JH9)               MFKKYDSKNSIVLKSILSLGIIYGGTFGIYPKADASTQNSSSVQDKQLQK 50
SAV0370 (Mu50)                   MFKKYDSKNSIVLKSILSLGIIYGGTFGIYPKADASTQNSSSVQDKQLQK 50
SA0357 (N315)                    MFKKYDSKNSIVLKSILSLGIIYGGTFGIYPKADASTQNSSSVQDKQLQK 50
SAS0347 (MSSA476)                MFKKNDSKNSILLKSILSLGIIYGGTFGIYPKADASTQNSPSVQDKQFQK 50
SAB0321 (RF122)                  MFKKYDSKNSIVLKSILSLGIIYGGTFGIYPKADASTQNSSSVQDKQFQK 50
                                 ****.*****.*********************.******.**
Consensus                        MFKKXDSKNSIXLKSILSLGIIYGGTFGIYPKADASTQNSXSVQDKQXQK SACOL0442 (COL)                  VEEVPNNSEKALVKKLYDRYSKDTINGKSNKSRNWVYSERPLNENQVRIH 100
SAOUHSC_00354 (NCTC8325)         VEEVPNNSEKALVKKLYDRYSKDTINGKSNKSRNWVYSERPLNENQVRIH 100
NWMN_0362 (Newman)               VEEVPNNSEKALVKKLYDRYSKDTINGKSNKSRNWVYSERPLNENQVRIH 100
SAUSA300_0370 (USA300-FPR3757)   VEEVPNNSEKALVKKLYDRYSKDTINGKSNKSRNWVYSERPLNENQVRIH 100
SaurJH1_0429 (JH1)               VEEVPNNSEKALVKKLYDRYSKDTINGKSNKSRNWVYSERPLNENQVRIH 100
SAHV_0367 (Mu3)                  VEEVPNNSEKALVKKLYDRYSKDTINGKSNKSRNWVYSERPLNENQVRIH 100
SaurJH9_0419 (JH9)               VEEVPNNSEKALVKKLYDRYSKDTINGKSNKSRNWVYSERPLNENQVRIH 100
SAV0370 (Mu50)                   VEEVPNNSEKALVKKLYDRYSKDTINGKSNKSRNWVYSERPLNENQVRIH 100
SA0357 (N315)                    VEEVPNNSEKALVKKLYDRYSKDTINGKSNKSRNWVYSERPLNENQVRIH 100
SAS0347 (MSSA476)                VEEVPNNSEKALVKKLYDRYSQNTINGKSNKSNRNWVYSERPLNENQVRIN 100
SAB0321 (RF122)                  VEEVPNNSEKALVKKLYDRYSQNTINGKSNKARNWVYSERPLNENQVRIH 100
                                 *********************::.*********.***************:
Consensus                        VEEVPNNSEKALVKKLYDRYSXXTINGKSNKXRNWVYSERPLNENQVRIX SACOL0442 (COL)                  LEGTYTVAGRVYTPKRNITLNKEVVTLKELDHIIRFAHISYGLYMGEHLP 150
SAOUHSC_00354 (NCTC8325)         LEGTYTVAGRVYTPKRNITLNKEVVTLKELDHIIRFAHISYGLYMGEHLP 150
NWMN_0362 (Newman)               LEGTYTVAGRVYTPKRNITLNKEVVTLKELDHIIRFAHISYGLYMGEHLP 150
SAUSA300_0370 (USA300-FPR3757)   LEGTYTVAGRVYTPKRNITLNKEVVTLKELDHIIRFAHISYGLYMGEHLP 150
SaurJH1_0429 (JH1)               LEGTYTVADRVYTPKRNITLNKEVVTLKELDHIIRFAHISYGLYMGEHLP 150
SAHV_0367 (Mu3)                  LEGTYTVADRVYTPKRNITLNKEVVTLKELDHIIRFAHISYGLYMGEHLP 150
SaurJH9_0419 (JH9)               LEGTYTVADRVYTPKRNITLNKEVVTLKELDHIIRFAHISYGLYMGEHLP 150
SAV0370 (Mu50)                   LEGTYTVADRVYTPKRNITLNKEVVTLKELDHIIRFAHISYGLYMGEHLP 150
SA0357 (N315)                    LEGTYTVADRVYTPKRNITLNKEVVTLKELDHIIRFAHISYGLYMGEHLP 150
SAS0347 (MSSA476)                LEGTYRVADRVYTPKRNITLNKEVVTLKELDHIIRFAHISYGLYMGEHLP 150
SAB0321 (RF122)                  LEGTYRVADRVYTPKRNITLNKEVVTLKELDHIIRFAHISYGLYMGEHLP 150
                                 ***** **.*.**************************************
Consensus                        LEGTYXVAXRVYTPKRNITLNKEVVTLKELDHIIRFAHISYGLYMGEHLP SACOL0442 (COL)                  KGNIVINTKDGGKYTLESHKELQKDRENVKINTADIKNVTFKLVKSVNDI 200
SAOUHSC_00354 (NCTC8325)         KGNIVINTKDGGKYTLESHKELQKDRENVKINTADIKNVTFKLVKSVNDI 200
NWMN_0362 (Newman)               KGNIVINTKDGGKYTLESHKELQKDRENVKINTADIKNVTFKLVKSVNDI 200
SAUSA300_0370 (USA300-FPR3757)   KGNIVINTKDGGKYTLESHKELQKDRENVKINTADIKNVTFKLVKSVNDI 200
SaurJH1_0429 (JH1)               KGNIVINTKDGGKYTLESHKELQKDRENVKINTADIKNVTFKLVKSVNDI 200
SAHV_0367 (Mu3)                  KGNIVINTKDGGKYTLESHKELQKDRENVKINTADIKNVTFKLVKSVNDI 200
SaurJH9_0419 (JH9)               KGNIVINTKDGGKYTLESHKELQKDRENVKINTADIKNVTFKLVKSVNDI 200
SAV0370 (Mu50)                   KGNIVINTKDGGKYTLESHKELQKDRENVKINTADIKNVTFKLVKSVNDI 200
SA0357 (N315)                    KGNIVINTKDGGKYTLESHKELQKDRENVKINTADIKNVTFKLVKSVNDI 200
SAS0347 (MSSA476)                KGNIVINTKDGGKYTLESHKELQKDRENVKINTADIKNVTFKLVKSVNDI 200
SAB0321 (RF122)                  KGNIVINTKNGGKYTLESHKELQKNRENVEINTDDIKNVTFELVKSVNDI 200
                                 ********.*:*************..****.***.******.*******
Consensus                        KGNIVINTKXGGKYTLESHKELQKXRENVXINTXDIKNVTFXLVKSVNDI SACOL0442 (COL)                  EQV 203
SAOUHSC_00354 (NCTC8325)         EQV 203
NWMN_0362 (Newman)               EQV 203
SAUSA300_0370 (USA300-FPR3757)   EQV 203
SaurJH1_0429 (JH1)               EQV 203
SAHV_0367 (Mu3)                  EQV 203
SaurJH9_0419 (JH9)               EQV 203
SAV0370 (Mu50)                   EQV 203
SA0357 (N315)                    EQV 203
SAS0347 (MSSA476)                EQV 203
SAB0321 (RF122)                  EQV 203
                                 ***
Consensus                        XXX
```

FIG. 22D

I- SACOL0720 : Multiple polynucleotide sequences alignment

```
SaurJH1_0700 (JH1)              --------------------------------------------------
SaurJH9_0685 (JH9)              --------------------------------------------------
SAHV_0659 (Mu3)                 --------------------------------------------------
SAV0662 (Mu50)                  ATGACCTTTAACGAGATAATATTTAAAAATTTCCGTCAAAATTTATCACA 50
SA0617 (N315)                   ATGACCTTTAACGAGATAATATTTAAAAATTTCCGTCAAAATTTATCACA 50
MW0624 (MW2)                    ATGACCTTTAACGAGATAATATTTAAAAATTTCCGTCAAAATTTATCACA 50
SAS0627 (MSSA476)               ATGACCTTTAACGAGATAATATTTAAAAATTTCCGTCAAAATTTATCACA 50
SACOL0720_                      ATGACCTTTAACGAGATAATATTTAAAAATTTCCGTCAAAATTTATCACA 50
SAUSA300_0648 (USA300-FPR3757)  ATGACCTTTAACGAGATAATATTTAAAAATTTCCGTCAAAATTTATCACA 50
SAOUHSC_00668 (NCTC8325)        --------------------------------------------------
NWMN_0631 (Newman)              --------------------------------------------------
SAB0611 (RF122)                 ATGACCTTTAACGAGATAATATTTAAAAATTTCCGTCAAAATTTATCACA 50

SaurJH1_0700 (JH1)              --------------------------------------------------
SaurJH9_0685 (JH9)              --------------------------------------------------
SAHV_0659 (Mu3)                 --------------------------------------------------
SAV0662 (Mu50)                  TTATGCCATCTATCTTTTTTCATTAATTACGAGTGTAGTATTGTATTTTA 100
SA0617 (N315)                   TTATGCCATCTATCTTTTTTCATTAATTACGAGTGTAGTATTGTATTTTA 100
MW0624 (MW2)                    TTATGCCATCTATCTTTTTTCATTAATTACGAGTGTAGTATTGTATTTTA 100
SAS0627 (MSSA476)               TTATGCCATCTATCTTTTTTCATTAATTACGAGTGTAGTATTGTATTTTA 100
SACOL0720_                      TTATGCCATCTATCTTTTTTCGTTAATTACGAGTGTAGTATTGTATTTTA 100
SAUSA300_0648 (USA300-FPR3757)  TTATGCCATCTATCTTTTTTCGTTAATTACGAGTGTAGTATTGTATTTTA 100
SAOUHSC_00668 (NCTC8325)        ----------------------------------------TTGTATTTTA 10
NWMN_0631 (Newman)              --------------------------------------------------
SAB0611 (RF122)                 TTATGCCATCTATCTTTTTTCATTAATTACGAGTGTAGTATTGTATTTTA 100

SaurJH1_0700 (JH1)              -----------------------------------ATGACAGAGTCATAT 15
SaurJH9_0685 (JH9)              -----------------------------------ATGACAGAGTCATAT 15
SAHV_0659 (Mu3)                 -----------------------------------ATGACAGAGTCATAT 15
SAV0662 (Mu50)                  GCTTTGTAGCATTAAAATACGCGCATAAACTAAACATGACAGAGTCATAT 150
SA0617 (N315)                   GCTTTGTAGCATTAAAATACGCGCATAAACTAAACATGACAGAGTCATAT 150
MW0624 (MW2)                    GCTTTGTAGCATTAAAATACGCGCATAAACTAAACATGACAGAGTCATAT 150
SAS0627 (MSSA476)               GCTTTGTAGCATTAAAATACGCGCATAAACTAAACATGACAGAGTCATAT 150
SACOL0720_                      GCTTTGTAGCATTAAAATACGCTCATAAACTAAACATGACAGAGTCATAT 150
SAUSA300_0648 (USA300-FPR3757)  GCTTTGTAGCATTAAAATACGCTCATAAACTAAACATGACAGAGTCATAT 150
SAOUHSC_00668 (NCTC8325)        GCTTTGTAGCATTAAAATACGCTCATAAACTAAACATGACAGAGTCATAT 60
NWMN_0631 (Newman)              -----------------------------------ATGACAGAGTCATAT 15
SAB0611 (RF122)                 GCTTTGTAGCATTAAAATACGCTCATAAACTAAACATGACAGAGTCATAT 150
                                                                   ***************

SaurJH1_0700 (JH1)              CCAATTATTAAGGAAGGCTCACAAGTCGGAAGCTACTTTCTATTTTTCAT 65
SaurJH9_0685 (JH9)              CCAATTATTAAGGAAGGCTCACAAGTCGGAAGCTACTTTCTATTTTTCAT 65
SAHV_0659 (Mu3)                 CCAATTATTAAGGAAGGCTCACAAGTCGGAAGCTACTTTCTATTTTTCAT 65
SAV0662 (Mu50)                  CCAATTATTAAGGAAGGCTCACAAGTCGGAAGCTACTTTCTATTTTTCAT 200
SA0617 (N315)                   CCAATTATTAAGGAAGGCTCACAAGTCGGAAGCTACTTTCTATTTTTCAT 200
MW0624 (MW2)                    CCAATTATTAAGGAAGGCTCACAAGTCGGAAGCTACTTTCTATTTTTCAT 200
SAS0627 (MSSA476)               CCAATTATTAAGGAAGGCTCACAAGTCGGAAGCTACTTTCTATTTTTCAT 200
SACOL0720_                      CCAATTATTAAGGAAGGCTCACAAGTCGGAAGCTACTTTCTATTTTTCAT 200
SAUSA300_0648 (USA300-FPR3757)  CCAATTATAAAGGAAGGCTCACAAGTCGGAAGCTACTTTCTATTTTTCAT 200
SAOUHSC_00668 (NCTC8325)        CCAATTATAAAGGAAGGCTCACAAGTCGGAAGCTACTTTCTATTTTTCAT 110
NWMN_0631 (Newman)              CCAATTATAAAGGAAGGCTCACAAGTCGGAAGCTACTTTCTATTTTTCAT 65
SAB0611 (RF122)                 CCAATTATAAAGGAAGGCTCACAAGTCGGAAGCTACTTTCTATTTTTCAT 200
                                ******** *****************************************
```

FIG. 23A

```
SaurJH1_0700 (JH1)              CATAATTGCATTTTTGTTATATGCCAATGTGTTATTTATTAAACGACGAA 115
SaurJH9_0685 (JH9)              CATAATTGCATTTTTGTTATATGCCAATGTGTTATTTATTAAACGACGAA 115
SAHV_0659 (Mu3)                 CATAATTGCATTTTTGTTATATGCCAATGTGTTATTTATTAAACGACGAA 115
SAV0662 (Mu50)                  CATAATTGCATTTTTGTTATATGCCAATGTGTTATTTATTAAACGACGAA 250
SA0617 (N315)                   CATAATTGCATTTTTGTTATATGCCAATGTGTTATTTATTAAACGACGAA 250
MW0624 (MW2)                    CATAATTGCATTTTTGTTATATGCCAATGTGTTATTTATTAAACGACGAA 250
SAS0627 (MSSA476)               CATAATTGCATTTTTGTTATATGCCAATGTGTTATTTATTAAACGACGAA 250
SACOL0720_                      CATAATTGCATTTTTGTTATATGCCAATGTGTTATTTATTAAACGACGAA 250
SAUSA300_0648 (USA300-FPR3757)  CATAATTGCATTTTTGTTATATGCCAATGTGTTATTTATTAAACGACGAA 250
SAOUHSC_00668 (NCTC8325)        CATAATTGCATTTTTGTTATATGCCAATGTGTTATTTATTAAACGACGAA 160
NWMN_0631 (Newman)              CATAATTGCATTTTTGTTATATGCCAATGTGTTATTTATTAAACGACGAA 115
SAB0611 (RF122)                 CATAATTGCATTTTTGTTATATGCCAATGTGTTATTTATTAAACGACGAA 250
                                **************************************************

SaurJH1_0700 (JH1)              GTTATGAGCTTGCATTATATCAAACATTAGGTTTATCTAAATTCAACATT 165
SaurJH9_0685 (JH9)              GTTATGAGCTTGCATTATATCAAACATTAGGTTTATCTAAATTCAACATT 165
SAHV_0659 (Mu3)                 GTTATGAGCTTGCATTATATCAAACATTAGGTTTATCTAAATTCAACATT 165
SAV0662 (Mu50)                  GTTATGAGCTTGCATTATATCAAACATTAGGTTTATCTAAATTCAACATT 300
SA0617 (N315)                   GTTATGAGCTTGCATTATATCAAACATTAGGTTTATCTAAATTCAACATT 300
MW0624 (MW2)                    GTTATGAGCTTGCATTATATCAAACATTAGGTTTATCTAAATTCAACATT 300
SAS0627 (MSSA476)               GTTATGAGCTTGCATTATATCAAACATTAGGTTTATCTAAATTCAACATT 300
SACOL0720_                      GTTATGAGCTTGCATTATATCAAACATTAGGTTTATCTAAATTCAACATT 300
SAUSA300_0648 (USA300-FPR3757)  GTTATGAGCTTGCATTATATCAAACATTAGGTTTATCTAAATTCAACATT 300
SAOUHSC_00668 (NCTC8325)        GTTATGAGCTTGCATTATATCAAACATTAGGTTTATCTAAATTCAACATT 210
NWMN_0631 (Newman)              GTTATGAGCTTGCATTATATCAAACATTAGGTTTATCTAAATTCAACATT 165
SAB0611 (RF122)                 GTTATGAGCTTGCATTATATCAAACATTAGGTTTATCTAAATTCAACATT 300
                                **************************************************

SaurJH1_0700 (JH1)              ATTTATATACTAATGCTCGAACAATTACTAATATTTATAATTACGGCAAT 215
SaurJH9_0685 (JH9)              ATTTATATACTAATGCTCGAACAATTACTAATATTTATAATTACGGCAAT 215
SAHV_0659 (Mu3)                 ATTTATATACTAATGCTCGAACAATTACTAATATTTATAATTACGGCAAT 215
SAV0662 (Mu50)                  ATTTATATACTAATGCTCGAACAATTACTAATATTTATAATTACGGCAAT 350
SA0617 (N315)                   ATTTATATACTAATGCTCGAACAATTACTAATATTTATAATTACGGCAAT 350
MW0624 (MW2)                    ATTTATATACTAATGCTCGAACAATTACTAATATTTATAATTACGGCAAT 350
SAS0627 (MSSA476)               ATTTATATACTAATGCTCGAACAATTACTAATATTTATAATTACGGCAAT 350
SACOL0720_                      ATTTATATACTAATGCTCGAACAATTACTAATATTTATAATTACGGCAAT 350
SAUSA300_0648 (USA300-FPR3757)  ATTTATATACTAATGCTCGAACAATTACTAATATTTATAATTACGGCAAT 350
SAOUHSC_00668 (NCTC8325)        ATTTATATACTAATGCTCGAACAATTACTAATATTTATAATTACGGCAAT 260
NWMN_0631 (Newman)              ATTTATATACTAATGCTCGAACAATTACTAATATTTATAATTACGGCAAT 215
SAB0611 (RF122)                 ATTTATATACTAATGCTCGAACAATTACTAATATTTATAATTACGGCAAT 350
                                **************************************************

SaurJH1_0700 (JH1)              ATTAGGTATTATTATTGGTATTTTTGGTTCAAAACTGTTATTAATGATTG 265
SaurJH9_0685 (JH9)              ATTAGGTATTATTATTGGTATTTTTGGTTCAAAACTGTTATTAATGATTG 265
SAHV_0659 (Mu3)                 ATTAGGTATTATTATTGGTATTTTTGGTTCAAAACTGTTATTAATGATTG 265
SAV0662 (Mu50)                  ATTAGGTATTATTATTGGTATTTTTGGTTCAAAACTGTTATTAATGATTG 400
SA0617 (N315)                   ATTAGGTATTATTATTGGTATTTTTGGTTCAAAACTGTTATTAATGATTG 400
MW0624 (MW2)                    ATTAGGTATTATTATTGGTATTTTTGGTTCAAAACTGTTATTAATGATTG 400
SAS0627 (MSSA476)               ATTAGGTATTATTATTGGTATTTTTGGTTCAAAACTGTTATTAATGATTG 400
SACOL0720_                      ATTAGGTATTATTATTGGTATTTTTGGTCGAAACTGTTATTAATGATTG 400
SAUSA300_0648 (USA300-FPR3757)  ATTAGGTATTATTATTGGTATTTTTGGTCGAAACTGTTATTAATGATTG 400
SAOUHSC_00668 (NCTC8325)        ATTAGGTATTATTATTGGTATTTTTGGTCGAAACTGTTATTAATGATTG 310
NWMN_0631 (Newman)              ATTAGGTATTATTATTGGTATTTTTGGTCGAAACTGTTATTAATGATTG 265
SAB0611 (RF122)                 ATTAGGTATTATTATTGGTATTTTTGGTCGAAACTGTTATTAATGATTG 400
                                ****************************  ********************

SaurJH1_0700 (JH1)              TCTTTACATTATTAGGAATTAAAGAAAAGGTTCCAATTATTTTTAGTTTG 315
SaurJH9_0685 (JH9)              TCTTTACATTATTAGGAATTAAAGAAAAGGTTCCAATTATTTTTAGTTTG 315
SAHV_0659 (Mu3)                 TCTTTACATTATTAGGAATTAAAGAAAAGGTTCCAATTATTTTTAGTTTG 315
SAV0662 (Mu50)                  TCTTTACATTATTAGGAATTAAAGAAAAGGTTCCAATTATTTTTAGTTTG 450
SA0617 (N315)                   TCTTTACATTATTAGGAATTAAAGAAAAGGTTCCAATTATTTTTAGTTTG 450
MW0624 (MW2)                    TCTTTACATTATTAGGAATTAAAGAAAAGGTTCCAATTATTTTTAGTTTG 450
SAS0627 (MSSA476)               TCTTTACATTATTAGGAATTAAAGAAAAGGTTCCAATTATTTTTAGTTTG 450
SACOL0720_                      TCTTTACATTATTAGGAATTAAAGAAAAGGTTCCAATTATTTTTAGTTTG 450
SAUSA300_0648 (USA300-FPR3757)  TCTTTACATTATTAGGAATTAAAGAAAAGGTTCCAATTATTTTTAGTTTG 450
SAOUHSC_00668 (NCTC8325)        TCTTTACATTATTAGGAATTAAAGAAAAGGTTCCAATTATTTTTAGTTTG 360
NWMN_0631 (Newman)              TCTTTACATTATTAGGAATTAAAGAAAAGGTTCCAATTATTTTTAGTTTG 315
SAB0611 (RF122)                 TCTTTACATTATTAGGAATTAAAGAAAAGGTTCCAATTATTTTTAGTTTG 450
                                **************************************************
```

FIG. 23B

```
SaurJH1_0700 (JH1)                  AGGGCGGTATTTGAAACATTAATGTTAATCGGTGTCGCTTATTTTTTAAC 365
SaurJH9_0685 (JH9)                  AGGGCGGTATTTGAAACATTAATGTTAATCGGTGTCGCTTATTTTTTAAC 365
SAHV_0659 (Mu3)                     AGGGCGGTATTTGAAACATTAATGTTAATCGGTGTCGCTTATTTTTTAAC 365
SAV0662 (Mu50)                      AGGGCGGTATTTGAAACATTAATGTTAATCGGTGTCGCTTATTTTTTAAC 500
SA0617 (N315)                       AGGGCGGTATTTGAAACATTAATGTTAATCGGTGTCGCTTATTTTTTAAC 500
MW0624 (MW2)                        AGGGCGGTATTTGAAACATTAATGTTAATCGGTGTCGCTTATTTTTTAAC 500
SAS0627 (MSSA476)                   AGGGCGGTATTTGAAACATTAATGTTAATCGGTGTCGCTTATTTTTTAAC 500
SACOL0720_                          AGGGCGGTATTTGAAACATTAATGTTAATCGGTGTCGCTTATTTTTTAAC 500
SAUSA300_0648 (USA300-FPR3757)      AGGGCGGTATTTGAAACATTAATGTTAATCGGTGTCGCTTATTTTTTAAC 500
SAOUHSC_00668 (NCTC8325)            AGGGCGGTATTTGAAACATTAATGTTAATCGGTGTCGCTTATTTTTTAAC 410
NWMN_0631 (Newman)                  AGGGCGGTATTTGAAACATTAATGTTAATCGGTGTCGCTTATTTTTTAAC 365
SAB0611 (RF122)                     AGGGCGGTATTTGAAACATTAATGTTAATCGGTGTCGCTTATTTTTTAAC 500
                                    **************************************************

SaurJH1_0700 (JH1)                  CTCTGCTCAAAATTTTATATTAGTGTTCAAACAATCTATTTCACAGATGT 415
SaurJH9_0685 (JH9)                  CTCTGCTCAAAATTTTATATTAGTGTTCAAACAATCTATTTCACAGATGT 415
SAHV_0659 (Mu3)                     CTCTGCTCAAAATTTTATATTAGTGTTCAAACAATCTATTTCACAGATGT 415
SAV0662 (Mu50)                      CTCTGCTCAAAATTTTATATTAGTGTTCAAACAATCTATTTCACAGATGT 550
SA0617 (N315)                       CTCTGCTCAAAATTTTATATTAGTGTTCAAACAATCTATTTCACAGATGT 550
MW0624 (MW2)                        CTCTGCTCAAAATTTTATATTAGTGTTCAAACAATCTATTTCACAGATGT 550
SAS0627 (MSSA476)                   CTCTGCTCAAAATTTTATATTAGTGTTCAAACAATCTATTTCACAGATGT 550
SACOL0720_                          ATCTGCTCAAAATTTTATATTAGTGTTCAAACAATCTATTTCACAGATGT 550
SAUSA300_0648 (USA300-FPR3757)      ATCTGCTCAAAATTTTATATTAGTGTTCAAACAATCTATTTCACAGATGT 550
SAOUHSC_00668 (NCTC8325)            ATCTGCTCAAAATTTTATATTAGTGTTCAAACAATCTATTTCACAGATGT 460
NWMN_0631 (Newman)                  ATCTGCTCAAAATTTTATATTAGTGTTCAAACAATCTATTTCACAGATGT 415
SAB0611 (RF122)                     ATCTGCTCAAAATTTTATATTAGTGTTCAAACAATCTATTTCACAGATGT 550
                                     *************************************************

SaurJH1_0700 (JH1)                  CAAAGAATAACCAGGTTAAAGAAACAAATCATAATAAAATTACATTTGAA 465
SaurJH9_0685 (JH9)                  CAAAGAATAACCAGGTTAAAGAAACAAATCATAATAAAATTACATTTGAA 465
SAHV_0659 (Mu3)                     CAAAGAATAACCAGGTTAAAGAAACAAATCATAATAAAATTACATTTGAA 465
SAV0662 (Mu50)                      CAAAGAATAACCAGGTTAAAGAAACAAATCATAATAAAATTACATTTGAA 600
SA0617 (N315)                       CAAAGAATAACCAGGTTAAAGAAACAAATCATAATAAAATTACATTTGAA 600
MW0624 (MW2)                        CAAAGAATAACCAGGTTAAAGAAACAAATCATAATAAAATTACATTTGAA 600
SAS0627 (MSSA476)                   CAAAGAATAACCAGGTTAAAGAAACAAATCATAATAAAATTACATTTGAA 600
SACOL0720_                          CAAAGAATAACCAGGTTAAAGAAACAAATCATAATAAAATTACATTTGAA 600
SAUSA300_0648 (USA300-FPR3757)      CAAAGAATAACCAGGTTAAAGAAACAAATCATAATAAAATTACATTTGAA 600
SAOUHSC_00668 (NCTC8325)            CAAAGAATAACCAGGTTAAAGAAACAAATCATAATAAAATTACATTTGAA 510
NWMN_0631 (Newman)                  CAAAGAATAACCAGGTTAAAGAAACAAATCATAATAAAATTACATTTGAA 465
SAB0611 (RF122)                     CAAAGAATAACCAGGTTAAAGAAACAAATCATAATAAAATTACATTTGAA 600
                                    **************************************************

SaurJH1_0700 (JH1)                  GAGGTTGTTTTAGGCATCTTAGGTATAGTATTGATTATCACAGGATACTA 515
SaurJH9_0685 (JH9)                  GAGGTTGTTTTAGGCATCTTAGGTATAGTATTGATTATCACAGGATACTA 515
SAHV_0659 (Mu3)                     GAGGTTGTTTTAGGCATCTTAGGTATAGTATTGATTACCACAGGATACTA 515
SAV0662 (Mu50)                      GAGGTTGTTTTAGGCATCTTAGGTATAGTATTGATTACCACAGGATACTA 650
SA0617 (N315)                       GAGGTTGTTTTAGGCATCTTAGGTATAGTATTGATTACCACAGGATACTA 650
MW0624 (MW2)                        GAGGTTGTTTTAGGCATCTTAGGTATAGTATTGATTACCACAGGATACTA 650
SAS0627 (MSSA476)                   GAGGTTGTTTTAGGCATCTTAGGTATAGTATTGATTACCACAGGATACTA 650
SACOL0720_                          GAGGTTGTTTTAGGCATCTTAGGTATAGTATTGATTACCACAGGATACTA 650
SAUSA300_0648 (USA300-FPR3757)      GAGGTTGTTTTAGGCATCTTAGGTATAGTATTGATTACCACAGGATACTA 650
SAOUHSC_00668 (NCTC8325)            GAGGTTGTTTTAGGCATCTTAGGTATAGTATTGATTACCACAGGATACTA 560
NWMN_0631 (Newman)                  GAGGTTGTTTTAGGCATCTTAGGTATAGTATTGATTACCACAGGATACTA 515
SAB0611 (RF122)                     GAGGTTGTTTTAGGCATCTTAGGTATAGTATTGATTACCACAGGATACTA 650
                                    ************************************ ***********

SaurJH1_0700 (JH1)                  TCTATCTTTGAACATTGTTCAATATTATGATTCTATCGGTATACTTATGT 565
SaurJH9_0685 (JH9)                  TCTATCTTTGAACATTGTTCAATATTATGATTCTATCGGTATACTTATGT 565
SAHV_0659 (Mu3)                     TCTATCTTTGAACATTGTTCAATATTATGATTCTATCGGTATACTTATGT 565
SAV0662 (Mu50)                      TCTATCTTTGAACATTGTTCAATATTATGATTCTATCGGTATACTTATGT 700
SA0617 (N315)                       TCTATCTTTGAACATTGTTCAATATTATGATTCTATCGGTATACTTATGT 700
MW0624 (MW2)                        TCTATCTTTGAACATTGTTCAATATTATGATTCTATCGGTATACTTATGT 700
SAS0627 (MSSA476)                   TCTATCTTTGAACATTGTTCAATATTATGATTCTATCGGTATACTTATGT 700
SACOL0720_                          TCTATCTTTGAACATTGTTCAATATTATGATTCTATCGGTACACTTATGT 700
SAUSA300_0648 (USA300-FPR3757)      TCTATCTTTGAACATTGTTCAATATTATGATTCTATCGGTACACTTATGT 700
SAOUHSC_00668 (NCTC8325)            TCTATCTTTGAACATTGTTCAATATTATGATTCTATCGGTACACTTATGT 610
NWMN_0631 (Newman)                  TCTATCTTTGAACATTGTTCAATATTATGATTCTATCGGTATACTTATGT 565
SAB0611 (RF122)                     TCTATCTTTGAACATTGTTCAATATTATGATTCTATCGGTACACTTATGT 700
                                    ***************************************** *******
```

FIG. 23C

```
SaurJH1_0700 (JH1)              TTATTTTATTGTCAACTGTGATTGGGGCATACTTATTTTTTAAAAGCTCT 615
SaurJH9_0685 (JH9)              TTATTTTATTGTCAACTGTGATTGGGGCATACTTATTTTTTAAAAGCTCT 615
SAHV_0659 (Mu3)                 TTATTTTATTGTCAACTGTGATTGGGGCATACTTATTTTTTAAAAGCTCT 615
SAV0662 (Mu50)                  TTATTTTATTGTCAACTGTGATTGGGGCATACTTATTTTTTAAAAGCTCT 750
SA0617 (N315)                   TTATTTTATTGTCAACTGTGATTGGGGCATACTTATTTTTTAAAAGCTCT 750
MW0624 (MW2)                    TTATTTTATTGTCAACTGTGATTGGGGCATACTTATTTTTTAAAAGCTCT 750
SAS0627 (MSSA476)               TTATTTTATTGTCAACTGTGATTGGGGCATACTTATTTTTTAAAAGCTCT 750
SACOL0720_                      TTATTTTATTGTCAACTGTGATTGGGGCATACTTATTTTTTAAAAGCTCT 750
SAUSA300_0648 (USA300-FPR3757)  TTATTTTATTGTCAACTGTGATTGGGGCATACTTATTTTTTAAAAGCTCT 750
SAOUHSC_00668 (NCTC8325)        TTATTTTATTGTCAACTGTGATTGGGGCATACTTATTTTTTAAAAGCTCT 660
NWMN_0631 (Newman)              TTATTTTATTGTCAACTGTGATTGGGGCATACTTATTTTTTAAAAGCTCT 615
SAB0611 (RF122)                 TTATTTTATTGTCAACTGTGATTGGGGCATACTTATTTTTTAAAAGCTCT 750
                                **************************************************

SaurJH1_0700 (JH1)              GTTTCTCTAGTTTTTAAAATGGTGAAGAAGTTTAGAAAAGGTGTTATAAG 665
SaurJH9_0685 (JH9)              GTTTCTCTAGTTTTTAAAATGGTGAAGAAGTTTAGAAAAGGTGTTATAAG 665
SAHV_0659 (Mu3)                 GTTTCTCTAGTTTTTAAAATGGTGAAGAAGTTTAGAAAAGGTGTTATAAG 665
SAV0662 (Mu50)                  GTTTCTCTAGTTTTTAAAATGGTGAAGAAGTTTAGAAAAGGTGTTATAAG 800
SA0617 (N315)                   GTTTCTCTAGTTTTTAAAATGGTGAAGAAGTTTAGAAAAGGTGTTATAAG 800
MW0624 (MW2)                    GTTTCTCTAGTTTTTAAAATGGTGAAGAAGTTTAGAAAAGGTGTTATAAG 800
SAS0627 (MSSA476)               GTTTCTCTAGTTTTTAAAATGGTGAAGAAGTTTAGAAAAGGTGTTATAAG 800
SACOL0720_                      GTTTCTCTAGTTTTTAAAATGGTGAAGAAGTTTAGAAAAGGTGTTATAAG 800
SAUSA300_0648 (USA300-FPR3757)  GTTTCTCTAGTTTTTAAAATGGTGAAGAAGTTTAGAAAAGGTGTTATAAG 800
SAOUHSC_00668 (NCTC8325)        GTTTCTCTAGTTTTTAAAATGGTGAAGAAGTTTAGAAAAGGTGTTATAAG 710
NWMN_0631 (Newman)              GTTTCTCTAGTTTTTAAAATGGTGAAGAAGTTTAGAAAAGGTGTTATAAG 665
SAB0611 (RF122)                 GTTTCTCTAGTTTTTAAAATGGTGAAGAAGTTTAGAAAAGGTGTTATAAG 800
                                **************************************************

SaurJH1_0700 (JH1)              TGTAAATGATGTCATGTTCTCATCATCTATTATGTATCGTATTAAGAAAA 715
SaurJH9_0685 (JH9)              TGTAAATGATGTCATGTTCTCATCATCTATTATGTATCGTATTAAGAAAA 715
SAHV_0659 (Mu3)                 TGTAAATGATGTCATGTTCTCATCATCTATTATGTATCGTATTAAGAAAA 715
SAV0662 (Mu50)                  TGTAAATGATGTCATGTTCTCATCATCTATTATGTATCGTATTAAGAAAA 850
SA0617 (N315)                   TGTAAATGATGTCATGTTCTCATCATCTATTATGTATCGTATTAAGAAAA 850
MW0624 (MW2)                    TGTAAATGATGTCATGTTCTCATCATCTATTATGTATCGTATTAAGAAAA 850
SAS0627 (MSSA476)               TGTAAATGATGTCATGTTCTCATCATCTATTATGTATCGTATTAAGAAAA 850
SACOL0720_                      TGTAAATGATGTCATGTTCTCATCATCTATTATGTATCGTATTAAGAAAA 850
SAUSA300_0648 (USA300-FPR3757)  TGTAAATGATGTCATGTTCTCATCATCTATTATGTATCGTATTAAGAAAA 850
SAOUHSC_00668 (NCTC8325)        TGTAAATGATGTCATGTTCTCATCATCTATTATGTATCGTATTAAGAAAA 760
NWMN_0631 (Newman)              TGTAAATGATGTCATGTTCTCATCATCTATTATGTATCGTATTAAGAAAA 715
SAB0611 (RF122)                 TGTAAATGATGTCATGTTCTCATCATCTATTATGTATCGTATTAAGAAAA 850
                                **************************************************

SaurJH1_0700 (JH1)              ATGCTTTTTCACTTACGGTCATGGCAATCATTTCAGCGATTACTGTTTCA 765
SaurJH9_0685 (JH9)              ATGCTTTTTCACTTACGGTCATGGCAATCATTTCAGCGATTACTGTTTCA 765
SAHV_0659 (Mu3)                 ATGCTTTTTCACTTACGGTCATGGCAATCATTTCAGCGATTACTGTTTCA 765
SAV0662 (Mu50)                  ATGCTTTTTCACTTACGGTCATGGCAATCATTTCAGCGATTACTGTTTCA 900
SA0617 (N315)                   ATGCTTTTTCACTTACGGTCATGGCAATCATTTCAGCGATTACTGTTTCA 900
MW0624 (MW2)                    ATGCTTTTTCACTTACGGTCATGGCAATCATTTCAGCGATTACTGTTTCA 900
SAS0627 (MSSA476)               ATGCTTTTTCACTTACGGTCATGGCAATCATTTCAGCGATTACTGTTTCA 900
SACOL0720_                      ATGCTTTTTCACTTACGGTCATGGCAATCATTTCAGCGATTACTGTTTCA 900
SAUSA300_0648 (USA300-FPR3757)  ATGCTTTTTCACTTACGGTCATGGCAATCATTTCAGCGATTACTGTTTCA 900
SAOUHSC_00668 (NCTC8325)        ATGCTTTTTCACTTACGGTCATGGCAATCATTTCAGCGATTACTGTTTCA 810
NWMN_0631 (Newman)              ATGCTTTTTCACTTACGGTCATGGCAATCATTTCAGCGATTACTGTTTCA 765
SAB0611 (RF122)                 ATGCTTTTTCACTTACGGTCATGGCAATCATTTCAGCGATTACTGTTTCA 900
                                **************************************************

SaurJH1_0700 (JH1)              GTTCTTTGCTTTGCTGCTATAAGTAGAGCGTCCTTATCAAGTGAAATAAA 815
SaurJH9_0685 (JH9)              GTTCTTTGCTTTGCTGCTATAAGTAGAGCGTCCTTATCAAGTGAAATAAA 815
SAHV_0659 (Mu3)                 GTTCTTTGCTTTGCTGCTATAAGTAGAGCGTCCTTATCAAGTGAAATAAA 815
SAV0662 (Mu50)                  GTTCTTTGCTTTGCTGCTATAAGTAGAGCGTCCTTATCAAGTGAAATAAA 950
SA0617 (N315)                   GTTCTTTGCTTTGCTGCTATAAGTAGAGCGTCCTTATCAAGTGAAATAAA 950
MW0624 (MW2)                    GTTCTTTGCTTTGCTGCTATAAGTAGAGCGTCCTTATCAAGTGAAATAAA 950
SAS0627 (MSSA476)               GTTCTTTGCTTTGCTGCTATAAGTAGAGCGTCCTTATCAAGTGAAATAAA 950
SACOL0720_                      GTTCTTTGCTTTGCTGCTATAAGTAGAGCGTCCTTATCAAGTGAAATAAA 950
SAUSA300_0648 (USA300-FPR3757)  GTTCTTTGCTTTGCTGCTATAAGTAGAGCGTCCTTATCAAGTGAAATAAA 950
SAOUHSC_00668 (NCTC8325)        GTTCTTTGCTTTGCTGCTATAAGTAGAGCGTCCTTATCAAGTGAAATAAA 860
NWMN_0631 (Newman)              GTTCTTTGCTTTGCTGCTATAAGTAGAGCGTCCTTATCAAGTGAAATAAA 815
SAB0611 (RF122)                 GTTCTTTGCTTTGCTGCTATAAGTAGAGCGTCCTTATCAAGTGAAATAAA 950
                                **************************************************
```

FIG. 23D

```
SaurJH1_0700 (JH1)                   ATATACTGCACCACACGACGTTACAATTAAAGACCAACAAAAAGCTAATC 865
SaurJH9_0685 (JH9)                   ATATACTGCACCACACGACGTTACAATTAAAGACCAACAAAAAGCTAATC 865
SAHV_0659 (Mu3)                      ATATACTGCACCACACGACGTTACAATTAAAGACCAACAAAAAGCTAATC 865
SAV0662 (Mu50)                       ATATACTGCACCACACGACGTTACAATTAAAGACCAACAAAAAGCTAATC 1000
SA0617 (N315)                        ATATACTGCACCACACGACGTTACAATTAAAGACCAACAAAAAGCTAATC 1000
MW0624 (MW2)                         ATATACTGCACCACACGACGTTACAATTAAAGACCAACAAAAAGCTAATC 1000
SAS0627 (MSSA476)                    ATATACTGCACCACACGACGTTACAATTAAAGACCAACAAAAAGCTAATC 1000
SACOL0720_                           ATATACTGCACCACACGACGTTACAATTAAAGACCAACAAAAAGCTAATC 1000
SAUSA300_0648 (USA300-FPR3757)       ATATACTGCACCACACGACGTTACAATTAAAGACCAACAAAAAGCTAATC 1000
SAOUHSC_00668 (NCTC8325)             ATATACTGCACCACACGACGTTACAATTAAAGACCAACAAAAAGCTAATC 910
NWMN_0631 (Newman)                   ATATACTGCACCACACGACGTTACAATTAAAGACCAACAAAAAGCTAATC 865
SAB0611 (RF122)                      ATATACTGCACCACACGACGTTACAATTAAAGACCAACAAAAAGCTAATC 1000
                                     **************************************************

SaurJH1_0700 (JH1)                   AATTAGCAAGTGAATTAAACAATCAAAAAATTCCTCATTTTTATAATTAT 915
SaurJH9_0685 (JH9)                   AATTAGCAAGTGAATTAAACAATCAAAAAATTCCTCATTTTTATAATTAT 915
SAHV_0659 (Mu3)                      AATTAGCAAGTGAATTAAACAATCAAAAAATTCCTCATTTTTATAATTAT 915
SAV0662 (Mu50)                       AATTAGCAAGTGAATTAAACAATCAAAAAATTCCTCATTTTTATAATTAT 1050
SA0617 (N315)                        AATTAGCAAGTGAATTAAACAATCAAAAAATTCCTCATTTTTATAATTAT 1050
MW0624 (MW2)                         AATTAGCAAGTGAATTAAACAATCAAAAAATTCCTCATTTTTATAATTAT 1050
SAS0627 (MSSA476)                    AATTAGCAAGTGAATTAAACAATCAAAAAATTCCTCATTTTTATAATTAT 1050
SACOL0720_                           AATTAGCAAGTGAATTAAACAATCAAAAAATTCCTCATTTTTATAATTAT 1050
SAUSA300_0648 (USA300-FPR3757)       AATTAGCAAGTGAATTAAACAATCAAAAAATTCCTCATTTTTATAATTAT 1050
SAOUHSC_00668 (NCTC8325)             AATTAGCAAGTGAATTAAACAATCAAAAAATTCCTCATTTTTATAATTAT 960
NWMN_0631 (Newman)                   AATTAGCAAGTGAATTAAACAATCAAAAAATTCCTCATTTTTATAATTAT 915
SAB0611 (RF122)                      AATTAGCAAGTGAATTAAACAATCAAAAAATTCCTCATTTTTATAATTAT 1050
                                     **************************************************

SaurJH1_0700 (JH1)                   AAAGAAGTAATTCATACGAAATTGTATAAAGATAATTTATTTGATGTAAA 965
SaurJH9_0685 (JH9)                   AAAGAAGTAATTCATACGAAATTGTATAAAGATAATTTATTTGATGTAAA 965
SAHV_0659 (Mu3)                      AAAGAAGTAATTCATACGAAATTGTATAAAGATAATTTATTTGATGTAAA 965
SAV0662 (Mu50)                       AAAGAAGTAATTCATACGAAATTGTATAAAGATAATTTATTTGATGTAAA 1100
SA0617 (N315)                        AAAGAAGTAATTCATACGAAATTGTATAAAGATAATTTATTTGATGTAAA 1100
MW0624 (MW2)                         AAAGAAGTAATTCATACGAAATTGTATAAAGATAATTTATTTGATGTAAA 1100
SAS0627 (MSSA476)                    AAAGAAGTAATTCATACGAAATTGTATAAAGATAATTTATTTGATGTAAA 1100
SACOL0720_                           AAAGAAGTAATTCATACGAAATTGTATAAAGATAATTTATTTGATGTAAA 1100
SAUSA300_0648 (USA300-FPR3757)       AAAGAAGTAATTCATACGAAATTGTATAAAGATAATTTATTTGATGTAAA 1100
SAOUHSC_00668 (NCTC8325)             AAAGAAGTAATTCATACGAAATTGTATAAAGATAATTTATTTGATGTAAA 1010
NWMN_0631 (Newman)                   AAAGAAGTAATTCATACGAAATTGTATAAAGATAATTTATTTGATGTAAA 965
SAB0611 (RF122)                      AAAGAAGTAATTCATACGAAATTGTATAAAGATAATTTATTTGATGTAAA 1100
                                     **************************************************

SaurJH1_0700 (JH1)                   AGCGAAAGAACCATACAATGTAACAATTACTAGTGATAAATATATCCCTA 1015
SaurJH9_0685 (JH9)                   AGCGAAAGAACCATACAATGTAACAATTACTAGTGATAAATATATCCCTA 1015
SAHV_0659 (Mu3)                      AGCGAAAGAACCATACAATGTAACAATTACTAGTGATAAATATATCCCTA 1015
SAV0662 (Mu50)                       AGCGAAAGAACCATACAATGTAACAATTACTAGTGATAAATATATCCCTA 1150
SA0617 (N315)                        AGCGAAAGAACCATACAATGTAACAATTACTAGTGATAAATATATCCCTA 1150
MW0624 (MW2)                         AGCGAAAGAACCATACAATGTAACAATTACTAGTGATAAATATATCCCTA 1150
SAS0627 (MSSA476)                    AGCGAAAGAACCATACAATGTAACAATTACTAGTGATAAATATATCCCTA 1150
SACOL0720_                           AGCGAAAGAACCATACAATGTAACAATTACTAGTGATAAATACATCCCTA 1150
SAUSA300_0648 (USA300-FPR3757)       AGCGAAAGAACCATACAATGTAACAATTACTAGTGATAAATACATCCCTA 1150
SAOUHSC_00668 (NCTC8325)             AGCGAAAGAACCATACAATGTAACAATTACTAGTGATAAATACATCCCTA 1060
NWMN_0631 (Newman)                   AGCGAAAGAACCATACAATGTAACAATTACTAGTGATAAATACATCCCTA 1015
SAB0611 (RF122)                      ATCGAAACAACCATACAATGTAACAATTACTAGTGATAAATACATCCCTA 1150
                                     * ***** ********************************** *******

SaurJH1_0700 (JH1)                   ATACTGATTTGAAACGTGGACAAGCTGATTTGTTTGTAGCGGAAGGTTCT 1065
SaurJH9_0685 (JH9)                   ATACTGATTTGAAACGTGGACAAGCTGATTTGTTTGTAGCGGAAGGTTCT 1065
SAHV_0659 (Mu3)                      ATACTGATTTGAAACGTGGACAAGCTGATTTGTTTGTAGCGGAAGGTTCT 1065
SAV0662 (Mu50)                       ATACTGATTTGAAACGTGGACAAGCTGATTTGTTTGTAGCGGAAGGTTCT 1200
SA0617 (N315)                        ATACTGATTTGAAACGTGGACAAGCTGATTTGTTTGTAGCGGAAGGTTCT 1200
MW0624 (MW2)                         ATACTGATTTGAAACGTGGACAAGCTGATTTGTTTGTAGCGGAAGGTTCT 1200
SAS0627 (MSSA476)                    ATACTGATTTGAAACGTGGACAAGCTGATTTGTTTGTAGCGGAAGGTTCT 1200
SACOL0720_                           ATACTGATTTGAAACGTGGGCAAGCTGATTTATTTGTAGCGGAAGGTTCT 1200
SAUSA300_0648 (USA300-FPR3757)       ATACTGATTTGAAACGTGGGCAAGCTGATTTATTTGTAGCGGAAGGTTCT 1200
SAOUHSC_00668 (NCTC8325)             ATACTGATTTGAAACGTGGGCAAGCTGATTTATTTGTAGCGGAAGGTTCT 1110
NWMN_0631 (Newman)                   ATACTGATTTGAAACGTGGGCAAGCTGATTTATTTGTAGCGGAAGGTTCT 1065
SAB0611 (RF122)                      GTACTGATTTGAAACGTGGGCAAGCTGATTTGTTTGTAGCGGAAGGTTCT 1200
                                     **************** ********** ** *******************
```

FIG. 23E

```
SaurJH1_0700 (JH1)              ATCAAAGATTTAGTGAAACATAAGAAGCATGGTAAGGCAATTATAGGAAC 1115
SaurJH9_0685 (JH9)              ATCAAAGATTTAGTGAAACATAAGAAGCATGGTAAGGCAATTATAGGAAC 1115
SAHV_0659 (Mu3)                 ATCAAAGATTTAGTGAAACATAAGAAGCATGGTAAGGCAATTATAGGAAC 1115
SAV0662 (Mu50)                  ATCAAAGATTTAGTGAAACATAAGAAGCATGGTAAGGCAATTATAGGAAC 1250
SA0617 (N315)                   ATCAAAGATTTAGTGAAACATAAGAAGCATGGTAAGGCAATTATAGGAAC 1250
MW0624 (MW2)                    ATCAAAGATTTAGTGAAACATAAGAAGCATGGTAAAGCAGTTATAGGAAC 1250
SAS0627 (MSSA476)               ATCAAAGATTTAGTGAAACATAAGAAGCATGGTAAAGCAGTTATAGGAAC 1250
SACOL0720_                      ATCAAAGATTTAGTGAAACATAAGAAGCATGGTAAGGCAATTATAGGAAC 1250
SAUSA300_0648 (USA300-FPR3757)  ATCAAAGATTTAGTGAAACATAAGAAGCATGGTAAGGCAATTATAGGAAC 1250
SAOUHSC_00668 (NCTC8325)        ATCAAAGATTTAGTGAAACATAAGAAGCATGGTAAGGCAATTATAGGAAC 1160
NWMN_0631 (Newman)              ATCAAAGATTTAGTGAAACATAAGAAGCATGGTAAGGCAATTATAGGAAC 1115
SAB0611 (RF122)                 ATCAAAGATTTAGTGAAACATAAGAAGCATGGTAAAGCAGTTATAGGAAC 1250
                                ************************************ *** *********

SaurJH1_0700 (JH1)              GAAAAAACATCATGTTAATATTAAGTTACGGAAAGATATTAATAAAATCT 1165
SaurJH9_0685 (JH9)              GAAAAAACATCATGTTAATATTAAGTTACGGAAAGATATTAATAAAATCT 1165
SAHV_0659 (Mu3)                 GAAAAAACATCATGTTAATATTAAGTTACGGAAAGATATTAATAAAATCT 1165
SAV0662 (Mu50)                  GAAAAAACATCATGTTAATATTAAGTTACGGAAAGATATTAATAAAATCT 1300
SA0617 (N315)                   GAAAAAACATCATGTTAATATTAAGTTACGGAAAGATATTAATAAAATCT 1300
MW0624 (MW2)                    GAAAAAACATCATGTTAATATTAAGTTGCGGAAAGATATTAATAAAATCT 1300
SAS0627 (MSSA476)               GAAAAAACATCATGTTAATATTAAGTTGCGGAAAGATATTAATAAAATCT 1300
SACOL0720_                      GAAAAAACATCATGTTAATATTAAGTTACGTAAAGATATTAATAAAATCT 1300
SAUSA300_0648 (USA300-FPR3757)  GAAAAAACATCATGTTAATATTAAGTTACGTAAAGATATTAATAAAATCT 1300
SAOUHSC_00668 (NCTC8325)        GAAAAAACATCATGTTAATATTAAGTTACGTAAAGATATTAATAAAATCT 1210
NWMN_0631 (Newman)              GAAAAAACATCATGTTAATATTAAGTTACGGAAAGATATTAATAAAATCT 1165
SAB0611 (RF122)                 GAAAAAACATCATGTTAATATTAAGTTACGTAAAGATATTAATAAAATCT 1300
                                ************************** ** ********************

SaurJH1_0700 (JH1)              ATTTTATGACAGATGTTGATTTAGGTGGACCAACGTTTGTCTTAAATGAC 1215
SaurJH9_0685 (JH9)              ATTTTATGACAGATGTTGATTTAGGTGGACCAACGTTTGTCTTAAATGAC 1215
SAHV_0659 (Mu3)                 ATTTTATGACAGATGTTGATTTAGGTGGACCAACGTTTGTCTTAAATGAC 1215
SAV0662 (Mu50)                  ATTTTATGACAGATGTTGATTTAGGTGGACCAACGTTTGTCTTAAATGAC 1350
SA0617 (N315)                   ATTTTATGACAGATGTTGATTTAGGTGGACCAACGTTTGTCTTAAATGAC 1350
MW0624 (MW2)                    ATTTTATGACAGATGTTGATTTAGGTGGACCAACGTTTGTCTTAAATGAC 1350
SAS0627 (MSSA476)               ATTTTATGACAGATGTTGATTTAGGTGGACCAACGTTTGTCTTAAATGAC 1350
SACOL0720_                      ATTTTATGACAGATGTTGATTTAGGTGGACCAACGTTTGTCTTAAATGAC 1350
SAUSA300_0648 (USA300-FPR3757)  ATTTTATGACAGATGTTGATTTAGGTGGACCAACGTTTGTCTTAAATGAC 1350
SAOUHSC_00668 (NCTC8325)        ATTTTATGACAGATGTTGATTTAGGTGGACCAACGTTTGTCTTAAATGAC 1260
NWMN_0631 (Newman)              ATTTTATGACAGATGTTGATTTAGGTGGACCAACGTTTGTCTTAAATGAC 1215
SAB0611 (RF122)                 ATTTTATGACAGATGTTGATTTAGGTGGACCAACGTTTGTCTTAAATGAC 1350
                                **************************************************

SaurJH1_0700 (JH1)              AAAGACTATCAAGAAATAAGAAAGTATACAAAAGCAAAGCATATCGTCTC 1265
SaurJH9_0685 (JH9)              AAAGACTATCAAGAAATAAGAAAGTATACAAAAGCAAAGCATATCGTCTC 1265
SAHV_0659 (Mu3)                 AAAGACTATCAAGAAATAAGAAAGTATACAAAAGCAAAGCATATCGTCTC 1265
SAV0662 (Mu50)                  AAAGACTATCAAGAAATAAGAAAGTATACAAAAGCAAAGCATATCGTCTC 1400
SA0617 (N315)                   AAAGACTATCAAGAAATAAGAAAGTATACAAAAGCAAAGCATATCGTCTC 1400
MW0624 (MW2)                    AAAGACTATCAAGAAATAAGAAAGTATACAAAAGCAAAGCATATCGTCTC 1400
SAS0627 (MSSA476)               AAAGACTATCAAGAAATAAGAAAGTATACAAAAGCAAAGCATATCGTCTC 1400
SACOL0720_                      AAAGACTATCAAGAAATAAGAAAGTATACAAAGGCAAAGCATATCGTCTC 1400
SAUSA300_0648 (USA300-FPR3757)  AAAGACTATCAAGAAATAAGAAAGTATACAAAGGCAAAGCATATCGTCTC 1400
SAOUHSC_00668 (NCTC8325)        AAAGACTATCAAGAAATAAGAAAGTATACAAAGGCAAAGCATATCGTCTC 1310
NWMN_0631 (Newman)              AAAGACTATCAAGAAATAAGAAAGTATACAAAGGCAAAGCATATCGTCTC 1265
SAB0611 (RF122)                 AAAGACTATCAAGAAATAAGAAAGTATACAAAGGCAAAGCATATCGTCTC 1400
                                ******************************** *****************

SaurJH1_0700 (JH1)              TCAATTTGGATTCGATTTGAAACATAAAAAAGATGCTTTAGCATTAGAAA 1315
SaurJH9_0685 (JH9)              TCAATTTGGATTCGATTTGAAACATAAAAAAGATGCTTTAGCATTAGAAA 1315
SAHV_0659 (Mu3)                 TCAATTTGGATTCGATTTGAAACATAAAAAAGATGCTTTAGCATTAGAAA 1315
SAV0662 (Mu50)                  TCAATTTGGATTCGATTTGAAACATAAAAAAGATGCTTTAGCATTAGAAA 1450
SA0617 (N315)                   TCAATTTGGATTCGATTTGAAACATAAAAAAGATGCTTTAGCATTAGAAA 1450
MW0624 (MW2)                    TCAATTTGGATTCGATTTGAAACATAAAAAAGATGCTTTAGCATTAGAAA 1450
SAS0627 (MSSA476)               TCAATTTGGATTCGATTTGAAACATAAAAAAGATGCTTTAGCATTAGAAA 1450
SACOL0720_                      TCAATTTGGATTCGATTTGAAACATAAAAAAGATGCTTTAGCATTAGAAA 1450
SAUSA300_0648 (USA300-FPR3757)  TCAATTTGGATTCGATTTGAAACATAAAAAAGATGCTTTAGCATTAGAAA 1450
SAOUHSC_00668 (NCTC8325)        TCAATTTGGATTCGATTTGAAACATAAAAAAGATGCTTTAGCATTAGAAA 1360
NWMN_0631 (Newman)              TCAATTTGGATTCGATTTGAAACATAAAAAAGATGCTTTAGCATTAGAAA 1315
SAB0611 (RF122)                 TCAATTTGGATTCGATTTGAAACATAAAAAAGATGCTTTAGCATTAGAAA 1450
                                **************************************************
```

FIG. 23F

```
SaurJH1_0700 (JH1)                  AAGTGAAAAATAAAGTTGATAAATCTATTAAAACAAGAAGTGAAGCGATA 1365
SaurJH9_0685 (JH9)                  AAGTGAAAAATAAAGTTGATAAATCTATTAAAACAAGAAGTGAAGCGATA 1365
SAHV_0659 (Mu3)                     AAGTGAAAAATAAAGTTGATAAATCTATTAAAACAAGAAGTGAAGCGATA 1365
SAV0662 (Mu50)                      AAGTGAAAAATAAAGTTGATAAATCTATTAAAACAAGAAGTGAAGCGATA 1500
SA0617 (N315)                       AAGTGAAAAATAAAGTTGATAAATCTATTAAAACAAGAAGTGAAGCGATA 1500
MW0624 (MW2)                        AAGTGAAAAATAAAGTTGATAAATCTATTAAAACAAGAAGTGAAGCGATA 1500
SAS0627 (MSSA476)                   AAGTGAAAAATAAAGTTGATAAATCTATTAAAACAAGAAGTGAAGCGATA 1500
SACOL0720_                          AAGCGAAAAATAAAGTTGATAAATCTATTGAAACAAGAAGTGAAGCGATA 1500
SAUSA300_0648 (USA300-FPR3757)      AAGCGAAAAATAAAGTTGATAAATCTATTGAAACAAGAAGTGAAGCGATA 1500
SAOUHSC_00668 (NCTC8325)            AAGCGAAAAATAAAGTTGATAAATCTATTGAAACAAGAAGTGAAGCGATA 1410
NWMN_0631 (Newman)                  AAGCGAAAAATAAAGTTGATAAATCTATTGAAACAAGAAGTGAAGCGATA 1365
SAB0611 (RF122)                     AAGCGAAAAATAAAGTTGATAAATCTATTGAGACAAGAAGTGAAGCGATA 1500
                                    ***  ********************** * *******************

SaurJH1_0700 (JH1)                  AGCTCAATATCAAGTTTAACCGGAATATTATTATTTGTAACATCATTTTT 1415
SaurJH9_0685 (JH9)                  AGCTCAATATCAAGTTTAACCGGAATATTATTATTTGTAACATCATTTTT 1415
SAHV_0659 (Mu3)                     AGCTCAATATCAAGTTTAACCGGAATATTATTATTTGTAACATCATTTTT 1415
SAV0662 (Mu50)                      AGCTCAATATCAAGTTTAACCGGAATATTATTATTTGTAACATCATTTTT 1550
SA0617 (N315)                       AGCTCAATATCAAGTTTAACCGGAATATTATTATTTGTAACATCATTTTT 1550
MW0624 (MW2)                        AGCTCAATATCAAGTTTAACCGGAATATTATTATTTGTAACATCATTTTT 1550
SAS0627 (MSSA476)                   AGCTCAATATCAAGTTTAACCGGAATATTATTATTTGTAACATCATTTTT 1550
SACOL0720_                          AGCTCAATATCAAGTTTAACCGGAATATTATTATTTGTAACATCATTTTT 1550
SAUSA300_0648 (USA300-FPR3757)      AGCTCAATATCAAGTTTAACCGGAATATTATTATTTGTAACATCATTTTT 1550
SAOUHSC_00668 (NCTC8325)            AGCTCAATATCAAGTTTAACCGGAATATTATTATTTGTAACATCATTTTT 1460
NWMN_0631 (Newman)                  AGCTCAATATCAAGTTTAACCGGAATATTATTATTTGTAACATCATTTTT 1415
SAB0611 (RF122)                     AGCTCAATATCAAGTTTAACCGGAATATTATTATTTGTAACATCATTTTT 1550
                                    **************************************************

SaurJH1_0700 (JH1)                  AGGTATTACATTCTTGATTGCTGTATGTTGCATTATATACATTAAGCAAA 1465
SaurJH9_0685 (JH9)                  AGGTATTACATTCTTGATTGCTGTATGTTGCATTATATACATTAAGCAAA 1465
SAHV_0659 (Mu3)                     AGGTATTACATTCTTGATTGCTGTATGTTGCATTATATACATTAAGCAAA 1465
SAV0662 (Mu50)                      AGGTATTACATTCTTGATTGCTGTATGTTGCATTATATACATTAAGCAAA 1600
SA0617 (N315)                       AGGTATTACATTCTTGATTGCTGTATGTTGCATTATATACATTAAGCAAA 1600
MW0624 (MW2)                        AGGTATTACATTCTTGATTGCTGTATGTTGCATTATATACATAAAGCAAA 1600
SAS0627 (MSSA476)                   AGGTATTACATTCTTGATTGCTGTATGTTGCATTATATACATAAAGCAAA 1600
SACOL0720_                          AGGTATTACATTCTTGATTGCTGTATGTTGCATTATATACATAAAGCAAA 1600
SAUSA300_0648 (USA300-FPR3757)      AGGTATTACATTCTTGATTGCTGTATGTTGCATTATATACATAAAGCAAA 1600
SAOUHSC_00668 (NCTC8325)            AGGTATTACATTCTTGATTGCTGTATGTTGCATTATATACATAAAGCAAA 1510
NWMN_0631 (Newman)                  AGGTATTACATTCTTGATTGCTGTATGTTGCATTATATACATAAAGCAAA 1465
SAB0611 (RF122)                     AGGTATTACATTCTTGATTGCTGTATGTTGCATTATATACATTAAGCAAA 1600
                                    ******************************************* ******

SaurJH1_0700 (JH1)                  TAGATGAAACCGAAGATGAGTTAGAGAATTATAGTATATTGAGAAAGCTT 1515
SaurJH9_0685 (JH9)                  TAGATGAAACCGAAGATGAGTTAGAGAATTATAGTATATTGAGAAAGCTT 1515
SAHV_0659 (Mu3)                     TAGATGAAACCGAAGATGAGTTAGAGAATTATAGTATATTGAGAAAGCTT 1515
SAV0662 (Mu50)                      TAGATGAAACCGAAGATGAGTTAGAGAATTATAGTATATTGAGAAAGCTT 1650
SA0617 (N315)                       TAGATGAAACCGAAGATGAGTTAGAGAATTATAGTATATTGAGAAAGCTT 1650
MW0624 (MW2)                        TAGATGAAACCGAAGATGAGTTAGAGAATTATAGTATTTTGAGAAAGCTT 1650
SAS0627 (MSSA476)                   TAGATGAAACCGAAGATGAGTTAGAGAATTATAGTATTTTGAGAAAGCTT 1650
SACOL0720_                          TAGATGAAACCGAAGATGAGTTAGAGAATTATAGTATTTTGAGAAAGCTT 1650
SAUSA300_0648 (USA300-FPR3757)      TAGATGAAACCGAAGATGAGTTAGAGAATTATAGTATTTTGAGAAAGCTT 1650
SAOUHSC_00668 (NCTC8325)            TAGATGAAACCGAAGATGAGTTAGAGAATTATAGTATTTTGAGAAAGCTT 1560
NWMN_0631 (Newman)                  TAGATGAAACCGAAGATGAGTTAGAGAATTATAGTATTTTGAGAAAGCTT 1515
SAB0611 (RF122)                     TAGATGAAACCGAAGATGAGTTAGAGAATTATAGTATATTGAGAAAGCTT 1650
                                    ************************************* ************

SaurJH1_0700 (JH1)                  GGATTTACACAAAAGATATGGCAAGGGGACTAAAGTTTAAAATTATGTT 1565
SaurJH9_0685 (JH9)                  GGATTTACACAAAAGATATGGCAAGGGGACTAAAGTTTAAAATTATGTT 1565
SAHV_0659 (Mu3)                     GGATTTACACAAAAGATATGGCAAGGGGACTAAAGTTTAAAATTATGTT 1565
SAV0662 (Mu50)                      GGATTTACACAAAAGATATGGCAAGGGGACTAAAGTTTAAAATTATGTT 1700
SA0617 (N315)                       GGATTTACACAAAAGATATGGCAAGGGGACTAAAGTTTAAAATTATGTT 1700
MW0624 (MW2)                        GGATTTACACAAAAGATATGGCAAGGGGACTAAAGTTTAAAATTATGTT 1700
SAS0627 (MSSA476)                   GGATTTACACAAAAGATATGGCAAGGGGACTAAAGTTTAAAATTATGTT 1700
SACOL0720_                          GGATTTACACAAAAGATATGGCAAGGGGACTAAAGTTTAAAATTATGTT 1700
SAUSA300_0648 (USA300-FPR3757)      GGATTTACACAAAAGATATGGCAAGGGGACTAAAGTTTAAAATTATGTT 1700
SAOUHSC_00668 (NCTC8325)            GGATTTACACAAAAGATATGGCAAGGGGACTAAAGTTTAAAATTATGTT 1610
NWMN_0631 (Newman)                  GGATTTACACAAAAGATATGGCAAGGGGACTAAAGTTTAAAATTATGTT 1565
SAB0611 (RF122)                     GGATTTACACAAAAGATATGGCAAGGGGACTAAAGTTTAAAATTATGTT 1700
                                    **************************************************
```

FIG. 23G

```
SaurJH1_0700 (JH1)              TAATTTTGGGTTACCTTTAGTTATTGCACTATCACATGCATATTTTACAT 1615
SaurJH9_0685 (JH9)              TAATTTTGGGTTACCTTTAGTTATTGTACTATCACATGCATATTTTACAT 1615
SAHV_0659 (Mu3)                 TAATTTTGGGTTACCTTTAGTTATTGCACTATCACATGCATATTTTACAT 1615
SAV0662 (Mu50)                  TAATTTTGGGTTACCTTTAGTTATTGCACTATCACATGCATATTTTACAT 1750
SA0617 (N315)                   TAATTTTGGGTTACCTTTAGTTATTGCACTATCACATGCATATTTTACAT 1750
MW0624 (MW2)                    TAATTTTGGGTTACCTTTAGTTATTGCACTATCACATGCATATTTTACAT 1750
SAS0627 (MSSA476)               TAATTTTGGGTTACCTTTAGTTATTGCACTATCACATGCATATTTTACAT 1750
SACOL0720_                      TAATTTTGGGTTACCTTTAGTTATTGCACTATCACATGCATATTTTACAT 1750
SAUSA300_0648 (USA300-FPR3757)  TAATTTTGGGTTACCTTTAGTTATTGCACTATCACATGCATATTTTACAT 1750
SAOUHSC_00668 (NCTC8325)        TAATTTTGGGTTACCTTTAGTTATTGCACTATCACATGCATATTTTACAT 1660
NWMN_0631 (Newman)              TAATTTTGGGTTACCTTTAGTTATTGCACTATCACATGCATATTTTACAT 1615
SAB0611 (RF122)                 TAATTTTGGGTTACCTTTAGTTATTGCACTATCACATGCATATTTTACAT 1750
                                ************************** ***********************

SaurJH1_0700 (JH1)              CATTAGCATATATGAAATTAATGGGTACAACGAATCAAATACCGGTTTTC 1665
SaurJH9_0685 (JH9)              CATTAGCATATATGAAATTAATGGGTACAACGAATCAAATACCGGTTTTC 1665
SAHV_0659 (Mu3)                 CATTAGCATATATGAAATTAATGGGTACAACGAATCAAATACCGGTTTTC 1665
SAV0662 (Mu50)                  CATTAGCATATATGAAATTAATGGGTACAACGAATCAAATACCGGTTTTC 1800
SA0617 (N315)                   CATTAGCATATATGAAATTAATGGGTACAACGAATCAAATACCGGTTTTC 1800
MW0624 (MW2)                    CATTAGCATATATGAAATTAATGGGTACAACGAATCAAATACCGGTTTTC 1800
SAS0627 (MSSA476)               CATTAGCATATATGAAATTAATGGGTACAACGAATCAAATACCGGTTTTC 1800
SACOL0720_                      CATTAGCATATATGAAATTAATGGGTACAACGAATCAAATACCGGTTTTC 1800
SAUSA300_0648 (USA300-FPR3757)  CATTAGCATATATGAAATTAATGGGTACAACGAATCAAATACCGGTTTTC 1800
SAOUHSC_00668 (NCTC8325)        CATTAGCATATATGAAATTAATGGGTACAACGAATCAAATACCGGTTTTC 1710
NWMN_0631 (Newman)              CATTAGCATATATGAAATTAATGGGTACAACGAATCAAATACCGGTTTTC 1665
SAB0611 (RF122)                 CATTAGCATATATGAAATTAATGGGTACAACGAATCAAATACCGGTTTTC 1800
                                **************************************************

SaurJH1_0700 (JH1)              ATAGTAATGGGATTATACATTTGTATGTATGCTGTTTTTGCAGTGACGGC 1715
SaurJH9_0685 (JH9)              ATAGTAATGGGATTATACATTTGTATGTATGCTGTTTTTGCAGTGACGGC 1715
SAHV_0659 (Mu3)                 ATAGTAATGGGATTATACATTTGTATGTATGCTGTTTTTGCAGTGACGGC 1715
SAV0662 (Mu50)                  ATAGTAATGGGATTATACATTTGTATGTATGCTGTTTTTGCAGTGACGGC 1850
SA0617 (N315)                   ATAGTAATGGGATTATACATTTGTATGTATGCTGTTTTTGCAGTGACGGC 1850
MW0624 (MW2)                    ATAGTAATGGGATTATACATTTGTATGTATGCTGTTTTTGCAGTGACGGC 1850
SAS0627 (MSSA476)               ATAGTAATGGGATTATACATTTGTATGTATGCTGTTTTTGCAGTGACGGC 1850
SACOL0720_                      ATAGTAATGGGATTATACATTTGTATGTATGCTGTTTTTGCAGTGACGGC 1850
SAUSA300_0648 (USA300-FPR3757)  ATAGTAATGGGATTATACATTTGTATGTATGCTGTTTTTGCAGTGACGGC 1850
SAOUHSC_00668 (NCTC8325)        ATAGTAATGGGATTATACATTTGTATGTATGCTGTTTTTGCAGTGACGGC 1760
NWMN_0631 (Newman)              ATAGTAATGGGATTATACATTTGTATGTATGCTGTTTTTGCAGTGACGGC 1715
SAB0611 (RF122)                 ATAGTAATGGGATTATACATTTGTATGTATGCTGTTTTTGCAGTGACGGC 1850
                                **************************************************

SaurJH1_0700 (JH1)              TTATAATCATTCCAAGCGAACAATTAGACATTCCATATAA 1755
SaurJH9_0685 (JH9)              TTATAATCATTCCAAGCGAACAATTAGACATTCCATATAA 1755
SAHV_0659 (Mu3)                 TTATAATCATTCCAAGCGAACAATTAGACATTCCATATAA 1755
SAV0662 (Mu50)                  TTATAATCATTCCAAGCGAACAATTAGACATTCCATATAA 1890
SA0617 (N315)                   TTATAATCATTCCAAGCGAACAATTAGACATTCCATATAA 1890
MW0624 (MW2)                    TTATAATCATTCCAAGCGAACAATTAGACATTCCATATAA 1890
SAS0627 (MSSA476)               TTATAATCATTCCAAGCGAACAATTAGACATTCCATATAA 1890
SACOL0720_                      TTATAATCATTCCAAGCGAACAATTAGACATTCCATATAA 1890
SAUSA300_0648 (USA300-FPR3757)  TTATAATCATTCCAAGCGAACAATTAGACATTCCATATAA 1890
SAOUHSC_00668 (NCTC8325)        TTATAATCATTCCAAGCGAACAATTAGACATTCCATATAA 1800
NWMN_0631 (Newman)              TTATAATCATTCCAAGCGAACAATTAGACATTCCATATAA 1755
SAB0611 (RF122)                 TTATAATCATTCCAAGCGAACAATTAGACATTCCATATAA 1890
                                ****************************************
```

FIG. 23H

II- SACOL0720 : Multiple polypeptide sequences alignment: selected epitopes shaded

```
SACOL0720_                      MTFNEIIFKNFRQNLSHYAIYLFSLITSVVLYFSFVALKYAHKLNMTESY  50
SAUSA300_0648 (USA300-FPR3757)  MTFNEIIFKNFRQNLSHYAIYLFSLITSVVLYFSFVALKYAHKLNMTESY  50
SAOUHSC_00668 (NCTC8325)        ------------------------------MYFSFVALKYAHKLNMTESY  20
NWMN_0631 (Newman)              ---------------------------------------------MTESY   5
SaurJH1_0700 (JH1)              ---------------------------------------------MTESY   5
SaurJH9_0685 (JH9)              ---------------------------------------------MTESY   5
SAHV_0659 (Mu3)                 ---------------------------------------------MTESY   5
SAV0662 (Mu50)                  MTFNEIIFKNFRQNLSHYAIYLFSLITSVVLYFSFVALKYAHKLNMTESY  50
SA0617 (N315)                   MTFNEIIFKNFRQNLSHYAIYLFSLITSVVLYFSFVALKYAHKLNMTESY  50
MW0624 (MW2)                    MTFNEIIFKNFRQNLSHYAIYLFSLITSVVLYFSFVALKYAHKLNMTESY  50
SAS0627 (MSSA476)               MTFNEIIFKNFRQNLSHYAIYLFSLITSVVLYFSFVALKYAHKLNMTESY  50
SAB0611 (RF122)                 MTFNEIIFKNFRQNLSHYAIYLFSLITSVVLYFSFVALKYAHKLNMTESY  50
                                                                             *****
Consensus                       XXXXXXXXXXXXXXXXXXXXXXXXXXXXXXXXXXXXXXXXXXXXXMTESY SACOL0720_                      PIIKEGSQVGSYFLFFIIIAFLLYANVLFIKRRSYELALYQTLGLSKFNI 100
SAUSA300_0648 (USA300-FPR3757)  PIIKEGSQVGSYFLFFIIIAFLLYANVLFIKRRSYELALYQTLGLSKFNI 100
SAOUHSC_00668 (NCTC8325)        PIIKEGSQVGSYFLFFIIIAFLLYANVLFIKRRSYELALYQTLGLSKFNI  70
NWMN_0631 (Newman)              PIIKEGSQVGSYFLFFIIIAFLLYANVLFIKRRSYELALYQTLGLSKFNI  55
SaurJH1_0700 (JH1)              PIIKEGSQVGSYFLFFIIIAFLLYANVLFIKRRSYELALYQTLGLSKFNI  55
SaurJH9_0685 (JH9)              PIIKEGSQVGSYFLFFIIIAFLLYANVLFIKRRSYELALYQTLGLSKFNI  55
SAHV_0659 (Mu3)                 PIIKEGSQVGSYFLFFIIIAFLLYANVLFIKRRSYELALYQTLGLSKFNI  55
SAV0662 (Mu50)                  PIIKEGSQVGSYFLFFIIIAFLLYANVLFIKRRSYELALYQTLGLSKFNI 100
SA0617 (N315)                   PIIKEGSQVGSYFLFFIIIAFLLYANVLFIKRRSYELALYQTLGLSKFNI 100
MW0624 (MW2)                    PIIKEGSQVGSYFLFFIIIAFLLYANVLFIKRRSYELALYQTLGLSKFNI 100
SAS0627 (MSSA476)               PIIKEGSQVGSYFLFFIIIAFLLYANVLFIKRRSYELALYQTLGLSKFNI 100
SAB0611 (RF122)                 PIIKEGSQVGSYFLFFIIIAFLLYANVLFIKRRSYELALYQTLGLSKFNI 100
                                **************************************************
Consensus                       PIIKEGSQVGSYFLFFIIIAFLLYANVLFIKRRSYELALYQTLGLSKFNI SACOL0720_                      IYILMLEQLLIFIITAILGIIIGIFGSKLLLMIVFTLLGIKEKVPIIFSL 150
SAUSA300_0648 (USA300-FPR3757)  IYILMLEQLLIFIITAILGIIIGIFGSKLLLMIVFTLLGIKEKVPIIFSL 150
SAOUHSC_00668 (NCTC8325)        IYILMLEQLLIFIITAILGIIIGIFGSKLLLMIVFTLLGIKEKVPIIFSL 120
NWMN_0631 (Newman)              IYILMLEQLLIFIITAILGIIIGIFGSKLLLMIVFTLLGIKEKVPIIFSL 105
SaurJH1_0700 (JH1)              IYILMLEQLLIFIITAILGIIIGIFGSKLLLMIVFTLLGIKEKVPIIFSL 105
SaurJH9_0685 (JH9)              IYILMLEQLLIFIITAILGIIIGIFGSKLLLMIVFTLLGIKEKVPIIFSL 105
SAHV_0659 (Mu3)                 IYILMLEQLLIFIITAILGIIIGIFGSKLLLMIVFTLLGIKEKVPIIFSL 105
SAV0662 (Mu50)                  IYILMLEQLLIFIITAILGIIIGIFGSKLLLMIVFTLLGIKEKVPIIFSL 150
SA0617 (N315)                   IYILMLEQLLIFIITAILGIIIGIFGSKLLLMIVFTLLGIKEKVPIIFSL 150
MW0624 (MW2)                    IYILMLEQLLIFIITAILGIIIGIFGSKLLLMIVFTLLGIKEKVPIIFSL 150
SAS0627 (MSSA476)               IYILMLEQLLIFIITAILGIIIGIFGSKLLLMIVFTLLGIKEKVPIIFSL 150
SAB0611 (RF122)                 IYILMLEQLLIFIITAILGIIIGIFGSKLLLMIVFTLLGIKEKVPIIFSL 150
                                **************************************************
Consensus                       IYILMLEQLLIFIITAILGIIIGIFGSKLLLMIVFTLLGIKEKVPIIFSL SACOL0720_                      RAVFETLMLIGVAYFLTSAQNFILVFKQSISQMSKNNQVKETNHNKITFE 200
SAUSA300_0648 (USA300-FPR3757)  RAVFETLMLIGVAYFLTSAQNFILVFKQSISQMSKNNQVKETNHNKITFE 200
SAOUHSC_00668 (NCTC8325)        RAVFETLMLIGVAYFLTSAQNFILVFKQSISQMSKNNQVKETNHNKITFE 170
NWMN_0631 (Newman)              RAVFETLMLIGVAYFLTSAQNFILVFKQSISQMSKNNQVKETNHNKITFE 155
SaurJH1_0700 (JH1)              RAVFETLMLIGVAYFLTSAQNFILVFKQSISQMSKNNQVKETNHNKITFE 155
SaurJH9_0685 (JH9)              RAVFETLMLIGVAYFLTSAQNFILVFKQSISQMSKNNQVKETNHNKITFE 155
SAHV_0659 (Mu3)                 RAVFETLMLIGVAYFLTSAQNFILVFKQSISQMSKNNQVKETNHNKITFE 155
SAV0662 (Mu50)                  RAVFETLMLIGVAYFLTSAQNFILVFKQSISQMSKNNQVKETNHNKITFE 200
SA0617 (N315)                   RAVFETLMLIGVAYFLTSAQNFILVFKQSISQMSKNNQVKETNHNKITFE 200
MW0624 (MW2)                    RAVFETLMLIGVAYFLTSAQNFILVFKQSISQMSKNNQVKETNHNKITFE 200
SAS0627 (MSSA476)               RAVFETLMLIGVAYFLTSAQNFILVFKQSISQMSKNNQVKETNHNKITFE 200
SAB0611 (RF122)                 RAVFETLMLIGVAYFLTSAQNFILVFKQSISQMSKNNQVKETNHNKITFE 200
                                **************************************************
Consensus                       RAVFETLMLIGVAYFLTSAQNFILVFKQSISQMSKNNQVKETNHNKITFE
```

FIG. 23I

```
SACOL0720_                       EVVLGILGIVLITTGYYLSLNIVQYYDSIGTLMFILLSTVIGAYLFFKSS 250
SAUSA300_0648 (USA300-FPR3757)   EVVLGILGIVLITTGYYLSLNIVQYYDSIGTLMFILLSTVIGAYLFFKSS 250
SAOUHSC_00668 (NCTC8325)         EVVLGILGIVLITTGYYLSLNIVQYYDSIGTLMFILLSTVIGAYLFFKSS 220
NWMN_0631 (Newman)               EVVLGILGIVLITTGYYLSLNIVQYYDSIGTLMFILLSTVIGAYLFFKSS 205
SaurJH1_0700 (JH1)               EVVLGILGIVLIITGYYLSLNIVQYYDSIGILMFILLSTVIGAYLFFKSS 205
SaurJH9_0685 (JH9)               EVVLGILGIVLIITGYYLSLNIVQYYDSIGILMFILLSTVIGAYLFFKSS 205
SAHV_0659 (Mu3)                  EVVLGILGIVLITTGYYLSLNIVQYYDSIGILMFILLSTVIGAYLFFKSS 205
SAV0662 (Mu50)                   EVVLGILGIVLITTGYYLSLNIVQYYDSIGILMFILLSTVIGAYLFFKSS 250
SA0617 (N315)                    EVVLGILGIVLITTGYYLSLNIVQYYDSIGILMFILLSTVIGAYLFFKSS 250
MW0624 (MW2)                     EVVLGILGIVLITTGYYLSLNIVQYYDSIGILMFILLSTVIGAYLFFKSS 250
SAS0627 (MSSA476)                EVVLGILGIVLITTGYYLSLNIVQYYDSIGILMFILLSTVIGAYLFFKSS 250
SAB0611 (RF122)                  EVVLGILGIVLITTGYYLSLNIVQYYDSIGTLMFILLSTVIGAYLFFKSS 250
                                 ************ ***************** ******************

Consensus                        EVVLGILGIVLIXTGYYLSLNIVQYYDSIGXLMFILLSTVIGAYLFFKSS SACOL0720_                       VSLVFKMVKKFRKGVISVNDVMFSSSIMYRIKKNAFSLTVMAIISAITVS 300
SAUSA300_0648 (USA300-FPR3757)   VSLVFKMVKKFRKGVISVNDVMFSSSIMYRIKKNAFSLTVMAIISAITVS 300
SAOUHSC_00668 (NCTC8325)         VSLVFKMVKKFRKGVISVNDVMFSSSIMYRIKKNAFSLTVMAIISAITVS 270
NWMN_0631 (Newman)               VSLVFKMVKKFRKGVISVNDVMFSSSIMYRIKKNAFSLTVMAIISAITVS 255
SaurJH1_0700 (JH1)               VSLVFKMVKKFRKGVISVNDVMFSSSIMYRIKKNAFSLTVMAIISAITVS 255
SaurJH9_0685 (JH9)               VSLVFKMVKKFRKGVISVNDVMFSSSIMYRIKKNAFSLTVMAIISAITVS 255
SAHV_0659 (Mu3)                  VSLVFKMVKKFRKGVISVNDVMFSSSIMYRIKKNAFSLTVMAIISAITVS 255
SAV0662 (Mu50)                   VSLVFKMVKKFRKGVISVNDVMFSSSIMYRIKKNAFSLTVMAIISAITVS 300
SA0617 (N315)                    VSLVFKMVKKFRKGVISVNDVMFSSSIMYRIKKNAFSLTVMAIISAITVS 300
MW0624 (MW2)                     VSLVFKMVKKFRKGVISVNDVMFSSSIMYRIKKNAFSLTVMAIISAITVS 300
SAS0627 (MSSA476)                VSLVFKMVKKFRKGVISVNDVMFSSSIMYRIKKNAFSLTVMAIISAITVS 300
SAB0611 (RF122)                  VSLVFKMVKKFRKGVISVNDVMFSSSIMYRIKKNAFSLTVMAIISAITVS 300
                                 **************************************************

Consensus                        VSLVFKMVKKFRKGVISVNDVMFSSSIMYRIKKNAFSLTVMAIISAITVS SACOL0720                        VLCFAAISRASLSSEIKYTAPHDVTIKDQQKANQLASELNNQKIPHFYNY 350
SAUSA300_0648 (USA300-FPR3757)   VLCFAAISRASLSSEIKYTAPHDVTIKDQQKANQLASELNNQKIPHFYNY 350
SAOUHSC_00668 (NCTC8325)         VLCFAAISRASLSSEIKYTAPHDVTIKDQQKANQLASELNNQKIPHFYNY 320
NWMN_0631 (Newman)               VLCFAAISRASLSSEIKYTAPHDVTIKDQQKANQLASELNNQKIPHFYNY 305
SaurJH1_0700 (JH1)               VLCFAAISRASLSSEIKYTAPHDVTIKDQQKANQLASELNNQKIPHFYNY 305
SaurJH9_0685 (JH9)               VLCFAAISRASLSSEIKYTAPHDVTIKDQQKANQLASELNNQKIPHFYNY 305
SAHV_0659 (Mu3)                  VLCFAAISRASLSSEIKYTAPHDVTIKDQQKANQLASELNNQKIPHFYNY 305
SAV0662 (Mu50)                   VLCFAAISRASLSSEIKYTAPHDVTIKDQQKANQLASELNNQKIPHFYNY 350
SA0617 (N315)                    VLCFAAISRASLSSEIKYTAPHDVTIKDQQKANQLASELNNQKIPHFYNY 350
MW0624 (MW2)                     VLCFAAISRASLSSEIKYTAPHDVTIKDQQKANQLASELNNQKIPHFYNY 350
SAS0627 (MSSA476)                VLCFAAISRASLSSEIKYTAPHDVTIKDQQKANQLASELNNQKIPHFYNY 350
SAB0611 (RF122)                  VLCFAAISRASLSSEIKYTAPHDVTIKDQQKANQLASELNNQKIPHFYNY 350
                                 **************************************************

Consensus                        VLCFAAISRASLSSEIKYTAPHDVTIKDQQKANQLASELNNQKIPHFYNY SACOL0720_                       KEVIHTKLYKDNLFDVKAKEPYNVTITSDKYIPNTDLKRGQADLFVAEGS 400
SAUSA300_0648 (USA300-FPR3757)   KEVIHTKLYKDNLFDVKAKEPYNVTITSDKYIPNTDLKRGQADLFVAEGS 400
SAOUHSC_00668 (NCTC8325)         KEVIHTKLYKDNLFDVKAKEPYNVTITSDKYIPNTDLKRGQADLFVAEGS 370
NWMN_0631 (Newman)               KEVIHTKLYKDNLFDVKAKEPYNVTITSDKYIPNTDLKRGQADLFVAEGS 355
SaurJH1_0700 (JH1)               KEVIHTKLYKDNLFDVKAKEPYNVTITSDKYIPNTDLKRGQADLFVAEGS 355
SaurJH9_0685 (JH9)               KEVIHTKLYKDNLFDVKAKEPYNVTITSDKYIPNTDLKRGQADLFVAEGS 355
SAHV_0659 (Mu3)                  KEVIHTKLYKDNLFDVKAKEPYNVTITSDKYIPNTDLKRGQADLFVAEGS 355
SAV0662 (Mu50)                   KEVIHTKLYKDNLFDVKAKEPYNVTITSDKYIPNTDLKRGQADLFVAEGS 400
SA0617 (N315)                    KEVIHTKLYKDNLFDVKAKEPYNVTITSDKYIPNTDLKRGQADLFVAEGS 400
MW0624 (MW2)                     KEVIHTKLYKDNLFDVKAKEPYNVTITSDKYIPNTDLKRGQADLFVAEGS 400
SAS0627 (MSSA476)                KEVIHTKLYKDNLFDVKAKEPYNVTITSDKYIPNTDLKRGQADLFVAEGS 400
SAB0611 (RF122)                  KEVIHTKLYKDNLFDVKSKQPYNVTITSDKYIPSTDLKRGQADLFVAEGS 400
                                 *****************::*************:***************

Consensus                        KEVIHTKLYKDNLFDVKXKXPYNVTITSDKYIPXTDLKRGQADLFVAEGS SACOL0720_                       IKDLVKHKKHGKAIIGTKKHHVNIKLRKDINKIYFMTDVDLGGPTFVLND 450
SAUSA300_0648 (USA300-FPR3757)   IKDLVKHKKHGKAIIGTKKHHVNIKLRKDINKIYFMTDVDLGGPTFVLND 450
SAOUHSC_00668 (NCTC8325)         IKDLVKHKKHGKAIIGTKKHHVNIKLRKDINKIYFMTDVDLGGPTFVLND 420
NWMN_0631 (Newman)               IKDLVKHKKHGKAIIGTKKHHVNIKLRKDINKIYFMTDVDLGGPTFVLND 405
SaurJH1_0700 (JH1)               IKDLVKHKKHGKAIIGTKKHHVNIKLRKDINKIYFMTDVDLGGPTFVLND 405
SaurJH9_0685 (JH9)               IKDLVKHKKHGKAIIGTKKHHVNIKLRKDINKIYFMTDVDLGGPTFVLND 405
SAHV_0659 (Mu3)                  IKDLVKHKKHGKAIIGTKKHHVNIKLRKDINKIYFMTDVDLGGPTFVLND 405
SAV0662 (Mu50)                   IKDLVKHKKHGKAIIGTKKHHVNIKLRKDINKIYFMTDVDLGGPTFVLND 450
SA0617 (N315)                    IKDLVKHKKHGKAIIGTKKHHVNIKLRKDINKIYFMTDVDLGGPTFVLND 450
MW0624 (MW2)                     IKDLVKHKKHGKAVIGTKKHHVNIKLRKDINKIYFMTDVDLGGPTFVLND 450
SAS0627 (MSSA476)                IKDLVKHKKHGKAVIGTKKHHVNIKLRKDINKIYFMTDVDLGGPTFVLND 450
SAB0611 (RF122)                  IKDLVKHKKHGKAVIGTKKHHVNIKLRKDINKIYFMTDVDLGGPTFVLND 450
                                 *************:***********************************

Consensus                        IKDLVKHKKHGKAXIGTKKHHVNIKLRKDINKIYFMTDVDLGGPTFVLND
```

FIG. 23J

```
SACOL0720_                     KDYQEIRKYTKAKHIVSQFGFDLKHKKDALALEKAKNKVDKSIETRSEAI 500
SAUSA300_0648 (USA300-FPR3757) KDYQEIRKYTKAKHIVSQFGFDLKHKKDALALEKAKNKVDKSIETRSEAI 500
SAOUHSC_00668 (NCTC8325)       KDYQEIRKYTKAKHIVSQFGFDLKHKKDALALEKAKNKVDKSIETRSEAI 470
NWMN_0631 (Newman)             KDYQEIRKYTKAKHIVSQFGFDLKHKKDALALEKAKNKVDKSIETRSEAI 455
SaurJH1_0700 (JH1)             KDYQEIRKYTKAKHIVSQFGFDLKHKKDALALEKVKNKVDKSIKTRSEAI 455
SaurJH9_0685 (JH9)             KDYQEIRKYTKAKHIVSQFGFDLKHKKDALALEKVKNKVDKSIKTRSEAI 455
SAHV_0659 (Mu3)                KDYQEIRKYTKAKHIVSQFGFDLKHKKDALALEKVKNKVDKSIKTRSEAI 455
SAV0662 (Mu50)                 KDYQEIRKYTKAKHIVSQFGFDLKHKKDALALEKVKNKVDKSIKTRSEAI 500
SA0617 (N315)                  KDYQEIRKYTKAKHIVSQFGFDLKHKKDALALEKVKNKVDKSIKTRSEAI 500
MW0624 (MW2)                   KDYQEIRKYTKAKHIVSQFGFDLKHKKDALALEKVKNKVDKSIKTRSEAI 500
SAS0627 (MSSA476)              KDYQEIRKYTKAKHIVSQFGFDLKHKKDALALEKVKNKVDKSIKTRSEAI 500
SAB0611 (RF122)                KDYQEIRKYTKAKHIVSQFGFDLKHKKDALALEKAKNKVDKSIETRSEAI 500
                               **************** ***************  *******:******

Consensus                      KDYQEIRKYTKAKHIVSQFGFDLKHKKDALALEKAXNKVDKSIXTRSEAI SACOL0720_                     SSISSLTGILLFVTSFLGITFLIAVCCIIYIKQIDETEDELENYSILRKL 550
SAUSA300_0648 (USA300-FPR3757) SSISSLTGILLFVTSFLGITFLIAVCCIIYIKQIDETEDELENYSILRKL 550
SAOUHSC_00668 (NCTC8325)       SSISSLTGILLFVTSFLGITFLIAVCCIIYIKQIDETEDELENYSILRKL 520
NWMN_0631 (Newman)             SSISSLTGILLFVTSFLGITFLIAVCCIIYIKQIDETEDELENYSILRKL 505
SaurJH1_0700 (JH1)             SSISSLTGILLFVTSFLGITFLIAVCCIIYIKQIDETEDELENYSILRKL 505
SaurJH9_0685 (JH9)             SSISSLTGILLFVTSFLGITFLIAVCCIIYIKQIDETEDELENYSILRKL 505
SAHV_0659 (Mu3)                SSISSLTGILLFVTSFLGITFLIAVCCIIYIKQIDETEDELENYSILRKL 505
SAV0662 (Mu50)                 SSISSLTGILLFVTSFLGITFLIAVCCIIYIKQIDETEDELENYSILRKL 550
SA0617 (N315)                  SSISSLTGILLFVTSFLGITFLIAVCCIIYIKQIDETEDELENYSILRKL 550
MW0624 (MW2)                   SSISSLTGILLFVTSFLGITFLIAVCCIIYIKQIDETEDELENYSILRKL 550
SAS0627 (MSSA476)              SSISSLTGILLFVTSFLGITFLIAVCCIIYIKQIDETEDELENYSILRKL 550
SAB0611 (RF122)                SSISSLTGILLFVTSFLGITFLIAVCCIIYIKQIDETEDELENYSILRKL 550
                               **************************************************

Consensus                      SSISSLTGILLFVTSFLGITFLIAVCCIIYIKQIDETEDELENYSILRKL SACOL0720_                     GFTQKDMARGLKFKIMFNFGLPLVIALSHAYFTSLAYMKLMGTTNQIPVF 600
SAUSA300_0648 (USA300-FPR3757) GFTQKDMARGLKFKIMFNFGLPLVIALSHAYFTSLAYMKLMGTTNQIPVF 600
SAOUHSC_00668 (NCTC8325)       GFTQKDMARGLKFKIMFNFGLPLVIALSHAYFTSLAYMKLMGTTNQIPVF 570
NWMN_0631 (Newman)             GFTQKDMARGLKFKIMFNFGLPLVIALSHAYFTSLAYMKLMGTTNQIPVF 555
SaurJH1_0700 (JH1)             GFTQKDMARGLKFKIMFNFGLPLVIALSHAYFTSLAYMKLMGTTNQIPVF 555
SaurJH9_0685 (JH9)             GFTQKDMARGLKFKIMFNFGLPLVIVLSHAYFTSLAYMKLMGTTNQIPVF 555
SAHV_0659 (Mu3)                GFTQKDMARGLKFKIMFNFGLPLVIALSHAYFTSLAYMKLMGTTNQIPVF 555
SAV0662 (Mu50)                 GFTQKDMARGLKFKIMFNFGLPLVIALSHAYFTSLAYMKLMGTTNQIPVF 600
SA0617 (N315)                  GFTQKDMARGLKFKIMFNFGLPLVIALSHAYFTSLAYMKLMGTTNQIPVF 600
MW0624 (MW2)                   GFTQKDMARGLKFKIMFNFGLPLVIALSHAYFTSLAYMKLMGTTNQIPVF 600
SAS0627 (MSSA476)              GFTQKDMARGLKFKIMFNFGLPLVIALSHAYFTSLAYMKLMGTTNQIPVF 600
SAB0611 (RF122)                GFTQKDMARGLKFKIMFNFGLPLVIALSHAYFTSLAYMKLMGTTNQIPVF 600
                               *************************.************************

Consensus                      GFTQKDMARGLKFKIMFNFGLPLVIXLSHAYFTSLAYMKLMGTTNQIPVF SACOL0720_                     IVMGLYICMYAVFAVTAYNHSKRTIRHSI 629
SAUSA300_0648 (USA300-FPR3757) IVMGLYICMYAVFAVTAYNHSKRTIRHSI 629
SAOUHSC_00668 (NCTC8325)       IVMGLYICMYAVFAVTAYNHSKRTIRHSI 599
NWMN_0631 (Newman)             IVMGLYICMYAVFAVTAYNHSKRTIRHSI 584
SaurJH1_0700 (JH1)             IVMGLYICMYAVFAVTAYNHSKRTIRHSI 584
SaurJH9_0685 (JH9)             IVMGLYICMYAVFAVTAYNHSKRTIRHSI 584
SAHV_0659 (Mu3)                IVMGLYICMYAVFAVTAYNHSKRTIRHSI 584
SAV0662 (Mu50)                 IVMGLYICMYAVFAVTAYNHSKRTIRHSI 629
SA0617 (N315)                  IVMGLYICMYAVFAVTAYNHSKRTIRHSI 629
MW0624 (MW2)                   IVMGLYICMYAVFAVTAYNHSKRTIRHSI 629
SAS0627 (MSSA476)              IVMGLYICMYAVFAVTAYNHSKRTIRHSI 629
SAB0611 (RF122)                IVMGLYICMYAVFAVTAYNHSKRTIRHSI 629
                               *****************************

Consensus                      IVMGLYICMYAVFAVTAYNHSKRTIRHSI
```

FIG. 23K

SACOL0029: Multiple polypeptide sequences alignment: hypothetical epitope shaded

```
SACOL0029(COL)                  --------------------------------MLESREQLSVEEYETFFNRFDNQEFDF
MW0028(MW2)                     --------------------------------MLESREQLSVEEYETFFNRFDNQEFDF
SAUSA300_0029(USA300-FPR3757)   --------------------------------MLESREQLSVEEYETFFNRFDNQEFDF
SAHV_0037(Mu3)                  CLFSYGSGAVGEIFSGSIVKGYDKALDKEKHLNMLESREQLSVEEYETFFNRFDNQEFDF
SAV0038(Mu)                     CLFSYGSGAVGEIFSGSIVKGYDKALDKEKHLNMLESREQLSVEEYETFFNRFDNQEFDF
SA0035                          CLFSYGSGAVGEIFSGSIVKGYDKALDKEKHLNMLESREQLSVEEYETFFNRFDNQEFDF
SAB2420                         ----------GEFYSATLVEGYKDHLDQAAHKALLNNRTEVSVDAYETFFKRFDDVDFDE
SHY97-3906                      GLFSYGSGSVGEFYSATLVEGYKDHLDQAAHKALLNNRTEVSVDAYETFFKRFDDVDFDE
SACOL2561                       ----------GEFYSATLVEGYKDHLDQAAHKALLNNRTEVSVDAYETFFKRFDDVDFDE
CLJ08-1290                      GLFSYGSGSVGEFYSATLVEGYKDHLDQAAHKALLNNRTEVSVDAYETFFKRFDDVEFDE
CLJ08-3                         GLFSYGSGSVGEFYSATLVEGYKDHLDQAAHKALLNNRTEVSVDAYETFFKRFDDVEFDE
                                                                  :*:.*  ::**:  *****:***: :**

Consensus                       XXXXXXXXXXXXXXXXXXXXXXXXXXXXXXXXXLXXRXXXSVXXYETFFXRFDXXXFDX SACOL0029(COL)                  ERELTQDPYSKVYLYSIEDHIRTYKIEK
MW0028(MW2)                     ERELTQDPYSKVYLYSIEDHIRTYKIEK
SAUSA300_0029(USA300-FPR3757)   ERELTQDPYSKVYLYSIEDHIRTYKIEK
SAHV_0037(Mu3)                  ERELTQDPYSKVYLYSIEDHIRTYKIEK
SAV0038(Mu)                     ERELTQDPYSKVYLYSIEDHIRTYKIEK
SA0035                          ERELTQDPYSKVYLYSIEDHIRTYKIEK
SAB2420                         QQDAVHEDRRIFYLSNIENNVREYHRPE
SHY97-3906                      QQDAVHEDRRIFYLSNIENNVREYHRPE
SACOL2561                       EQDAVHEDRHIFYLSNIENNVREYHRPE
CLJ08-1290                      EQDAVHEDRHIFYLSNIENNVREYHRPE
CLJ08-3                         EQDAVHEDRHIFYLSNIENNVREYHRPE
                                :::  .::     .** .**:.:* *:  :

Consensus                       XXXXXXXXXXXYLXXIEXXXRXYXXXX
```

FIG. 24

I    SACOL1867 : Multiple polynucleotide sequences alignment

```
MW1753 (MW2)                        TTATTGTTCAATGTGCTTTTGAATAAAATCTTTGATTTGAGGCGTAAAGTATACGGCACC 60
SAS1734 (MSSA476)                   TTATTGTTCAATGTGCTTTTGAATAAAATCTTTGATTTGAGGCGTAAAGTATACGGCACC 60
SACOL1867 (COL)                     TTATTGTTCAATGTGCTTTTGAATAAAATCTTTGATTTGAGGCGTAAAGTATACGGCACC 60
SAOUHSC_01939 (NCTC8325)            TTATTGTTCAATGTGCTTTTGAATAAAATCTTTGATTTGAGGCGTAAAGTATACGGCACC 60
NWMN_1704 (Newman)                  TTATTGTTCAATGTGCTTTTGAATAAAATCTTTGATTTGAGGCGTAAAGTATACGGCACC 60
SAUSA300_1756 (USA300-FPR3757)      TTATTGTTCAATGTGCTTTTGAATAAAATCTTTGATTTGAGGCGTAAAGTATACGGCACC 60
SaurJH1_1897 (JH1)                  TTATTGTTCAATGTGCTTTTGAATAAAATCTTTGATTTGAGGCGTAAAGTATACGGCACC 60
SAHV_1796 (Mu3)                     TTATTGTTCAATGTGCTTTTGAATAAAATCTTTGATTTGAGGCGTAAAGTATACGGCACC 60
SaurJH9_1862 (JH9)                  TTATTGTTCAATGTGCTTTTGAATAAAATCTTTGATTTGAGGCGTAAAGTATACGGCACC 60
SAV1811 (Mu50)                      TTATTGTTCAATGTGCTTTTGAATAAAATCTTTGATTTGAGGCGTAAAGTATACGGCACC 60
SA1629 (N315)                       TTATTGTTCAATGTGCTTTTGAATAAAATCTTTGATTTGAGGCGTAAAGTATACGGCACC 60
SAB1671c (RF122)                    TTATTGTTCAATGTGCTTTTGAATAAATTCTTTGATTTGAGGCGTAAATAAACTGCACC  60
                                    ****************************  ******************* ** ** *****

MW1753 (MW2)                        ATTATATTCAGAACCAATTTTTCCAATACCGCCATACACCACACCTATGACCTCATTGTT 120
SAS1734 (MSSA476)                   ATTATATTCAGAACCAATTTTTCCAATACCGCCATACACCACACCTATGACCTCATTGTT 120
SACOL1867 (COL)                     ATTATATTCAGAACCAATTTTTCCAATACCGCCATACACCACACCTATGACCTCATTGTT 120
SAOUHSC_01939 (NCTC8325)            ATTATATTCAGAACCAATTTTTCCAATACCGCCATACACCACACCTATGACCTCATTGTT 120
NWMN_1704 (Newman)                  ATTATATTCAGAACCAATTTTTCCAATACCGCCATACACCACACCTATGACCTCATTGTT 120
SAUSA300_1756 (USA300-FPR3757)      ATTATATTCAGAACCAATTTTTCCAATACCGCCATACACCACACCTATGACCTCATTGTT 120
SaurJH1_1897 (JH1)                  ATTATATTCAGAACCAATTTTTCCAATACCGCCATACACCACACCTATGACCTCATTGTT 120
SAHV_1796 (Mu3)                     ATTATATTCAGAACCAATTTTTCCAATACCGCCATACACCACACCTATGACCTCATTGTT 120
SaurJH9_1862 (JH9)                  ATTATATTCAGAACCAATTTTTCCAATACCGCCATACACCACACCTATGACCTCATTGTT 120
SAV1811 (Mu50)                      ATTATATTCAGAACCAATTTTTCCAATACCGCCATACACCACACCTATGACCTCATTGTT 120
SA1629 (N315)                       ATTATATTCAGAACCAATTTTTCCAATACCGCCATACACCACACCTATGACCTCATTGTT 120
SAB1671c (RF122)                    ATTGTATTCTGATCCGATTTTTCCAATACCTCCATACACAACTCCTACGACTTCATTATT 120
                                    *** ***** ** ** ************** ******* ** ** *** *** ***** **

MW1753 (MW2)                        AGAATTTAGAACTGGTGATCCTGAATTCCCGGGTTCAATGTATGCATCAAAATTTAAAAT 180
SAS1734 (MSSA476)                   AGAATTTAGAACTGGTGATCCTGAATTCCCGGGTTCAATGTATGCATCAAAATTTAAAAT 180
SACOL1867 (COL)                     AGAATTTAGAACTGGTGATCCTGAATTCCCGGGTTCAATGTATGCATCAAAATTTAAAAT 180
SAOUHSC_01939 (NCTC8325)            AGAATTTAGAACTGGTGATCCTGAATTCCCGGGTTCAATGTATGCATCAAAATTTAAAAT 180
NWMN_1704 (Newman)                  AGAATTTAGAACTGGTGATCCTGAATTCCCGGGTTCAATGTATGCATCAAAATTTAAAAT 180
SAUSA300_1756 (USA300-FPR3757)      AGAATTTAGAACTGGTGATCCTGAATTCCCGGGTTCAATGTATGCATCAAAATTTAAAAT 180
SaurJH1_1897 (JH1)                  AGAATTTAGAACTGGTGATCCTGAATTCCCGGGTTCAATGTATGCATCAAAATTTAAAAT 180
SAHV_1796 (Mu3)                     AGAATTTAGAACTGGTGATCCTGAATTCCCGGGTTCAATGTATGCATCAAAATTTAAAAT 180
SaurJH9_1862 (JH9)                  AGAATTTAGAACTGGTGATCCTGAATTCCCGGGTTCAATGTATGCATCAAAATTTAAAAT 180
SAV1811 (Mu50)                      AGAATTTAGAACTGGTGATCCTGAATTCCCGGGTTCAATGTATGCATCAAAATTTAAAAT 180
SA1629 (N315)                       AGAATTTAGAACTGGTGATCCTGAATTCCCGGGTTCAATGTATGCATCAAAATTTAAAAT 180
SAB1671c (RF122)                    TAAATTTAAAACTGGGGATCCTGAATTTCCAGGCTCGATATATGCATCAAAATTTAAATT 180
                                     ***** ******* ** ** ** ** ** ******************* *

MW1753 (MW2)                        ATTGTCTTTGATTCTTTTTATAGTTCCTGTAGATTCAAACTGTTTAAAACTATTTTGAGC 240
SAS1734 (MSSA476)                   ATTGTCTTTGATTCTTTTTATAGTTCCTGTAGATTCAAACTGTTTAAAACTATTTTGAGC 240
SACOL1867 (COL)                     ATTGTCTTTGATTCTTTTTATAGTTCCTGTAGATTCAAACTGTTTAAAACTATTTTGAGC 240
SAOUHSC_01939 (NCTC8325)            ATTGTCTTTGATTCTTTTTATAGTTCCTGTAGATTCAAACTGTTTAAAACTATTTTGAGC 240
NWMN_1704 (Newman)                  ATTGTCTTTGATTCTTTTTATAGTTCCTGTAGATTCAAACTGTTTAAAACTATTTTGAGC 240
SAUSA300_1756 (USA300-FPR3757)      ATTGTCTTTGATTCTTTTTATAGTTCCTGTAGATTCAAACTGTTTAAAACTATTTTGAGC 240
SaurJH1_1897 (JH1)                  ATTGTCTTTGATTCTTTTTATAGTTCCTGTAGATTCAAACTGTTTAAAACTATTTTGAGC 240
SAHV_1796 (Mu3)                     ATTGTCTTTGATTCTTTTTATAGTTCCTGTAGATTCAAACTGTTTAAAACTATTTTGAGC 240
SaurJH9_1862 (JH9)                  ATTGTCTTTGATTCTTTTTATAGTTCCTGTAGATTCAAACTGTTTAAAACTATTTTGAGC 240
SAV1811 (Mu50)                      ATTGTCTTTGATTCTTTTTATAGTTCCTGTAGATTCAAACTGTTTAAAACTATTTTGAGC 240
SA1629 (N315)                       ATTGTCTTTGATTCTTTTTATAGTTCCTGTAGATTCAAACTGTTTAAAACTATTTTGAGC 240
SAB1671c (RF122)                    ATTATCTTTAATACTTTTTACAGTTCCAGTTGATTCAAATTGTTTGAATGTATTTTGAGC 240
                                    *** ***** ** ******* ****** ** ******** ***** **   **********

MW1753 (MW2)                        AGGTAATGGGTAACCAATAACTTTAATTTTGTCATCAACTTTAGCATCTTTCGCAAAATT 300
SAS1734 (MSSA476)                   AGGTAATGGGTAACCAATAACTTTAATTTTGTCATCAACTTTAGCATCTTTCGCAAAATT 300
SACOL1867 (COL)                     AGGTAATGGGTAACCAATAACTTTAATTTTGTCATCAACTTTAGCATCTTTCGCAAAATT 300
SAOUHSC_01939 (NCTC8325)            AGGTAATGGGTAACCAATAACTTTAATTTTGTCATCAACTTTAGCATCTTTCGCAAAATT 300
NWMN_1704 (Newman)                  AGGTAATGGGTAACCAATAACTTTAATTTTGTCATCAACTTTAGCATCTTTCGCAAAATT 300
SAUSA300_1756 (USA300-FPR3757)      AGGTAATGGGTAACCAATAACTTTAATTTTGTCATCAACTTTAGCATCTTTCGCAAAATT 300
SaurJH1_1897 (JH1)                  AGGTAATGGGTAACCAATAACTTTAATTTTGTCATCAACTTTAGCATCTTTCGCAAAATT 300
SAHV_1796 (Mu3)                     AGGTAATGGGTAACCAATAACTTTAATTTTGTCATCAACTTTAGCATCTTTCGCAAAATT 300
SaurJH9_1862 (JH9)                  AGGTAATGGGTAACCAATAACTTTAATTTTGTCATCAACTTTAGCATCTTTCGCAAAATT 300
SAV1811 (Mu50)                      AGGTAATGGGTAACCAATAACTTTAATTTTGTCATCAACTTTAGCATCTTTCGCAAAATT 300
SA1629 (N315)                       AGGTAATGGGTAACCAATAACTTTAATTTTGTCATCAACTTTAGCATCTTTCGCAAAATT 300
SAB1671c (RF122)                    TGGTAAAGGGTATCCAATAACTTTAATTTTGTCGTCAACTTTAGCATCTTTCGCAAAATT 300
                                     ***** ***** ******************** **************************
```

FIG. 25A

```
MW1753 (MW2)                          TAATGCTTGGACATTTTCATTAAAATTAAAGCCTTTTGGTCCACGTTCAACTGCTTGTTC 360
SAS1734 (MSSA476)                     TAATGCTTGGACATTTTCATTAAAATTAAAGCCTTTTGGTCCACGTTCAACTGCTTGTTC 360
SACOL1867 (COL)                       GAATGCTTGGACATTTTCATTAAAATTAAAGCCTTTTGGTCCACGTTCGACTGCTTGTTC 360
SAOUHSC_01939 (NCTC8325)              GAATGCTTGGACATTTTCATTAAAATTAAAGCCTTTTGGTCCACGTTCGACTGCTTGTTC 360
NWMN_1704 (Newman)                    TAATGCTTGGACATTTTCATTAAAATTAAAGCCTTTTGGTCCACGTTCGACTGCTTGTTC 360
SAUSA300_1756 (USA300-FPR3757)        GAATGCTTGGACATTTTCATTAAAATTAAAGCCTTTTGGTCCACGTTCGACTGCTTGTTC 360
SaurJH1_1897 (JH1)                    GAATGCTTGGACATTTTCATTAAAATTAAAGCCTTTTGGTCCACGTTCAACTGCTTGTTC 360
SAHV_1796 (Mu3)                       GAATGCTTGGACATTTTCATTAAAATTAAAGCCTTTTGGTCCACGTTCAACTGCTTGTTC 360
SaurJH9_1862 (JH9)                    GAATGCTTGGACATTTTCATTAAAATTAAAGCCTTTTGGTCCACGTTCAACTGCTTGTTC 360
SAV1811 (Mu50)                        GAATGCTTGGACATTTTCATTAAAATTAAAGCCTTTTGGTCCACGTTCAACTGCTTGTTC 360
SA1629 (N315)                         GAATGCTTGGACATTTTCATTAAAATTAAAGCCTTTTGGTCCACGTTCAACTGCTTGTTC 360
SAB1671c (RF122)                      GAATGCTTGGACATTTTCATTAAAATTATAACCATTTGCTCCACGTTCAACAGCATTTTC 360
                                       *************** * ** **** ********* ** ** * ***

MW1753 (MW2)                          TTCAATATTCATGACAGAGATGTCTTCATCACCCGGATAATCAGAAATGCTTTTAATTTT 420
SAS1734 (MSSA476)                     TTCAATATTCATGACAGAGATGTCTTCATCACCCGGATAATCAGAAATGCTTTTAATTTT 420
SACOL1867 (COL)                       TTCAATATTCATGACAGAGATGTCTTCATCACCCGGATAATCAGAAATGCTTTTAATTTT 420
SAOUHSC_01939 (NCTC8325)              TTCAATATTCATGACAGAGATGTCTTCATCACCCGGATAATCAGAAATGCTTTTAATTTT 420
NWMN_1704 (Newman)                    TTCAATATTCATGACAGAGATGTCTTCATCACCCGGATAATCAGAAATGCTTTTAATTTT 420
SAUSA300_1756 (USA300-FPR3757)        TTCAATATTCATGACAGAGATGTCTTCATCACCCGGATAATCAGAAATGCTTTTAATTTT 420
SaurJH1_1897 (JH1)                    TTCAATATTCATGACAGAGATGTCTTCATCACCCGGATAATCAGAAATGCTTTTAATTTT 420
SAHV_1796 (Mu3)                       TTCAATATTCATGACAGAGATGTCTTCATCACCCGGATAATCAGAAATGCTTTTAATTTT 420
SaurJH9_1862 (JH9)                    TTCAATATTCATGACAGAGATGTCTTCATCACCCGGATAATCAGAAATGCTTTTAATTTT 420
SAV1811 (Mu50)                        TTCAATATTCATGACAGAGATGTCTTCATCACCCGGATAATCAGAAATGCTTTTAATTTT 420
SA1629 (N315)                         TTCAATATTCATGACAGAGATGTCTTCATCACCCGGATAATCAGAAATGCTTTTAATTTT 420
SAB1671c (RF122)                      TTCAACGTTCATTACTGATATATCCTCATTACCTGGATAATCAGAAATATTTTTAATTTT 420
                                      *****  ***** ** ** ** **** *** ************* **********

MW1753 (MW2)                          ATATATACCACCATTTCCTTTGTCACCGTCTGGATGGGCAGTAATTCTATCGCCAACTTT 480
SAS1734 (MSSA476)                     ATATATACCACCATTTCCTTTGTCACCGTCTGGATGGGCAGTAATTCTATCGCCAACTTT 480
SACOL1867 (COL)                       ATATATACCACCATTTCCTTTGTCACCGTTTGGATGGGCAGTAATTCTATCGCCAACTTT 480
SAOUHSC_01939 (NCTC8325)              ATATATACCACCATTTCCTTTGTCACCGTTTGGATGGGCAGTAATTCTATCGCCAACTTT 480
NWMN_1704 (Newman)                    ATATATACCACCATTTCCTTTGTCACCGTTTGGATGGGCAGTAATTCTATCGCCAACTTT 480
SAUSA300_1756 (USA300-FPR3757)        ATATATACCACCATTTCCTTTGTCACCGTTTGGATGGGCAGTAATTCTATCGCCAACTTT 480
SaurJH1_1897 (JH1)                    ATATATACCACCATTTCCTTTGTCACCGTCTGGATGGGCAGTAATTCTATCGCCAACTTT 480
SAHV_1796 (Mu3)                       ATATATACCACCATTTCCTTTGTCACCGTTTGGATGGGCAGTAATTCTATCGCCAACTTT 480
SaurJH9_1862 (JH9)                    ATATATACCACCATTTCCTTTGTCACCGTTTGGATGGGCAGTAATTCTATCGCCAACTTT 480
SAV1811 (Mu50)                        ATATATACCACCATTTCCTTTGTCACCGTCTGGATGGGCAGTAATTCTATCGCCAACTTT 480
SA1629 (N315)                         ATATATACCACCATTTCCTTTGTCACCGTTTGGATGGGCAGTAATTCTATCGCCAACTTT 480
SAB1671c (RF122)                      ATAAATTCCACCGTTGCCTTTGTCACCATTTGGGTGGGCAGTAATTCTATCGCCAACTTT 480
                                      *** ** ***** ** *********** * *** **************************

MW1753 (MW2)                          ATAATCTTTTGATACATGTTTATTGGTGATAATTGTATTTTTTCCAATTACAAAACCTGT 540
SAS1734 (MSSA476)                     ATAATCTTTTGATACATGTTTATTGGTGATAATTGTATTTTTTCCAATTACAAAACCTGT 540
SACOL1867 (COL)                       ATAATCTTTTGATACATGTTTATTGGTGATAATTGTATTTTTTCCAATTACAAAACCTGT 540
SAOUHSC_01939 (NCTC8325)              ATAATCTTTTGATACATGTTTATTGGTGATAATTGTATTTTTTCCAATTACAAAACCTGT 540
NWMN_1704 (Newman)                    ATAATCTTTTGATACATGTTTATTGGTGATAATTGTATTTTTTCCAATTACAAAACCTGT 540
SAUSA300_1756 (USA300-FPR3757)        ATAATTTTTTGATACATGTTTATTGGTGATAATTGTATTTTTTCCAATTACAAAACCTGT 540
SaurJH1_1897 (JH1)                    ATAATCTTTTGATACATGTTTATTGGTGATAATTGTATTTTTTCCAATTACAAAACCTGT 540
SAHV_1796 (Mu3)                       ATAATCTTTTGATACATGTTTATTGGTGATAATTGTATTTTTTCCAATTACAAAACCTGT 540
SaurJH9_1862 (JH9)                    ATAATCTTTTGATACATGTTTATTGGTGATAATTGTATTTTTTCCAATTACAAAACCTGT 540
SAV1811 (Mu50)                        ATAATCTTTTGATACATGTTTATTGGTGATAATTGTATTTTTTCCAATTACAAAACCTGT 540
SA1629 (N315)                         ATAATCTTTTGATACATGTTTATTGGTGATAATTGTATTTTTTCCAATTACAAAACCTGT 540
SAB1671c (RF122)                      ATAGTCCTTTGATACATGTTTATTGGTGATAATTGTATTTTTTTCAATTGCAAAACCTGT 540
                                      *** ** ************************************* ***** ********

MW1753 (MW2)                          CGCATCTTTAAATGAAACGACGCCATTATATGGAAAAATATTTGTATCTTTAACTTGCGT 600
SAS1734 (MSSA476)                     CGCATCTTTAAATGAAACGACGCCATTATATGGAAAAATATTTGTATCTTTAACTTGCGT 600
SACOL1867 (COL)                       CGCATCTTTAAATGAAACGACGCCATTATATGGAAAAATATTTGTATCTTTAACTTGCGT 600
SAOUHSC_01939 (NCTC8325)              CGCATCTTTAAATGAAACGACGCCATTATATGGAAAAATATTTGTATCTTTAACTTGCGT 600
NWMN_1704 (Newman)                    CGCATCTTTAAATGAAACGACGCCATTATATGGAAAAATATTTGTATCTTTAACTTGCGT 600
SAUSA300_1756 (USA300-FPR3757)        CGCATCTTTAAATGAAACGACGCCATTATATGGAAAAATATTTGTATCTTTAACTTGCGT 600
SaurJH1_1897 (JH1)                    CGCATCCTTAAATGAAACGACGCCATTATATGGAAAATATTTGTATCTTTAACTTGCGT 600
SAHV_1796 (Mu3)                       CGCATCCTTAAATGAAACGACGCCATTATATGGAAAATATTTGTATCTTTAACTTGCGT 600
SaurJH9_1862 (JH9)                    CGCATCCTTAAATGAAACGACGCCATTATATGGAAAATATTTGTATCTTTAACTTGCGT 600
SAV1811 (Mu50)                        CGCATCCTTAAATGAAACGACGCCATTATATGGAAAATATTTGTATCTTTAACTTGCGT 600
SA1629 (N315)                         CGCATCCTTAAATGAAACGACGCCATTATATGGAAAATATTTGTATCTTTAACTTGCGT 600
SAB1671c (RF122)                      CGCATCTTTAAATGAAACGACGCCATTATATGGAAAACATTTGTATCTTTAACTTGCGT 600
                                      ******  *********************************   ****************

MW1753 (MW2)                          AACATTCTTCTCTGCATTTGCTATTGTTGTGTCTCTTCAACGACTGCAGCATTTATTCC 660
SAS1734 (MSSA476)                     AACATTCTTCTCTGCATTTGCTATTGTTGTGTCTCTTCAACGACTGCAGCATTTATTCC 660
SACOL1867 (COL)                       AACATTCTTCTCTGCATTTGCTATTGTTGTGTCTCTTCAACGACTGCAGCATTTATTCC 660
SAOUHSC_01939 (NCTC8325)              AACATTCTTCTCTGCATTTGCTATTGTTGTGTCTCTTCAACGACTGCAGCATTTATTCC 660
NWMN_1704 (Newman)                    AACATTCTTCTCTGCATTTGCTATTGTTGTGTCTCTTCAACGACTGCAGCATTTATTCC 660
SAUSA300_1756 (USA300-FPR3757)        AACATTCTTCTCTGCATTTGCTATTGTTGTGTCTCTTCAACGACTGCAGCATTTATTCC 660
SaurJH1_1897 (JH1)                    AACATTCTTCTCTGCATTTGCTATTGTTGTGTCTCTTCAACGACTGCAGCATTTATTCC 660
SAHV_1796 (Mu3)                       AACATTCTTCTCTGCATTTGCTATTGTTGTGTCTCTTCAACGACTGCAGCATTTATTCC 660
SaurJH9_1862 (JH9)                    AACATTCTTCTCTGCATTTGCTATTGTTGTGTCTCTTCAACGACTGCAGCATTTATTCC 660
SAV1811 (Mu50)                        AACATTCTTCTCTGCATTTGCTATTGTTGTGTCTCTTCAACGACTGCAGCATTTATTCC 660
SA1629 (N315)                         AACATTCTTCTCTGCATTTGCTATTGTTGTGTCTCTTCAACGACTGCAGCATTTATTCC 660
SAB1671c (RF122)                      AACATTCTTCTCTGCATTTGCTATTGTTGTGTCTCATCAACGACTGCAGCATTTATTCC 660
                                      *********************************** ************************
```

FIG. 25B

```
MW1753 (MW2)                       AGTTACTGAGGTTAGAATGGCTAATGCTGCCATGCTTTTAATGACTATATTTTTATTCAT 720
SAS1734 (MSSA476)                  AGTTGCTGAGGTTAGAATGGCTAATGCTGCCATGCTTTTAATGACTATATTTTTATTCAT 720
SACOL1867 (COL)                    AGTTACTGAGGTTAGAATGGCTAATGCTGCCATGCTTTTAATGACTATATTTTTATTCAT 720
SAOUHSC_01939 (NCTC8325)           AGTTACTGAGGTTAGAATGGCTAATGCTGCCATGCTTTTAATGACTATATTTTTATTCAT 720
NWMN_1704 (Newman)                 AGTTACTGAGGTTAGAATGGCTAATGCTGCCATGCTTTTAATGACTATATTTTTATTCAT 720
SAUSA300_1756 (USA300-FPR3757)     AGTTACTGAGGTTAGAATGGCTAATGCTGCCATGCTTTTAATGACTATATTTTTATTCAT 720
SaurJH1_1897 (JH1)                 AGTTACTGAGGTTAGAATGGCTAATGCTGCCATGCTTTTAATGACTATATTTTTATTCAT 720
SAHV_1796 (Mu3)                    AGTTACTGAGGTTAGAATGGCTAATGCTGCCATGCTTTTAATGACTATATTTTTATTCAT 720
SaurJH9_1862 (JH9)                 AGTTACTGAGGTTAGAATGGCTAATGCTGCCATGCTTTTAATGACTATATTTTTATTCAT 720
SAV1811 (Mu50)                     AGTTACTGAGGTTAGAATGGCTAATGCTGCCATGCTTTTAATGACTATATTTTTATTCAT 720
SA1629 (N315)                      AGTTACTGAGGTTAGAATGGCTAATGCTGCCATGCTTTTAATGACTATATTTTTATTCAT 720
SAB1671c (RF122)                   AGTTACTGAGGTTAGAATGGCTAATGCTGCCATGCTTTTAATGACTATATTTTTATTCAT 720
                                   **** *******************************************************

MW1753 (MW2)                       --------------------
SAS1734 (MSSA476)                  --------------------
SACOL1867 (COL)                    AAAAGCACATTGAACAATAA 740
SAOUHSC_01939 (NCTC8325)           --------------------
NWMN_1704 (Newman)                 --------------------
SAUSA300_1756 (USA300-FPR3757)     --------------------
SaurJH1_1897 (JH1)                 --------------------
SAHV_1796 (Mu3)                    --------------------
SaurJH9_1862 (JH9)                 --------------------
SAV1811 (Mu50)                     --------------------
SA1629 (N315)                      --------------------
SAB1671c (RF122)                   --------------------
```

FIG. 25C

II- SACOL1867: Multiple polypeptide sequences alignment: hypothetical epitopes shaded

```
MW1753 (MW2)                    MNKNIVIKSMAALAILTSVTGINAAVVEETQQIANAEKNVTQVKDTNIFPYNGVVSFKDA 60
SAS1734 (MSSA476)               MNKNIVIKSMAALAILTSATGINAAVVEETQQIANAEKNVTQVKDTNIFPYNGVVSFKDA 60
SACOL1867 (COL)                 MNKNIVIKSMAALAILTSVTGINAAVVEETQQIANAEKNVTQVKDTNIFPYNGVVSFKDA 60
SAOUHSC_01939 (NCTC8325)        MNKNIVIKSMAALAILTSVTGINAAVVEETQQIANAEKNVTQVKDTNIFPYNGVVSFKDA 60
NWMN_1704 (Newman)              MNKNIVIKSMAALAILTSVTGINAAVVEETQQIANAEKNVTQVKDTNIFPYNGVVSFKDA 60
SAUSA300_1756 (USA300-FPR3757)  MNKNIVIKSMAALAILTSVTGINAAVVEETQQIANAEKNVTQVKDTNIFPYNGVVSFKDA 60
SaurJH1_1897 (JH1)              MNKNIVIKSMAALAILTSVTGINAAVVEETQQIANAEKNVTQVKDTNNFPYNGVVSFKDA 60
SAHV_1796 (Mu3)                 MNKNIVIKSMAALAILTSVTGINAAVVEETQQIANAEKNVTQVKDTNNFPYNGVVSFKDA 60
SaurJH9_1862 (JH9)              MNKNIVIKSMAALAILTSVTGINAAVVEETQQIANAEKNVTQVKDTNNFPYNGVVSFKDA 60
SAV1811 (Mu50)                  MNKNIVIKSMAALAILTSVTGINAAVVEETQQIANAEKNVTQVKDTNNFPYNGVVSFKDA 60
SA1629 (N315)                   MNKNIVIKSMAALAILTSVTGINAAVVEETQQIANAEKNVTQVKDTNNFPYNGVVSFKDA 60
SAB1671c (RF122)                MNKNIVIKSMAALAILTSVTGINAAVVDETQQIANAEKNVTQVKDTNVFPYNGVVSFKDA 60
                                *****************.*********:***********:****** ************
Consensus                       MNKNIVIKSMAALAILTSXTGINAAVXETQQIANAEKNVTQVKDTNXFPYNGVVSFKDA MW1753 (MW2)                    TGFVIGKNTIITNKHVSKDYKVGDRITAHPDGDKGNGGIYKIKSISDYPGDEDISVMNIE 120
SAS1734 (MSSA476)               TGFVIGKNTIITNKHVSKDYKVGDRITAHPDGDKGNGGIYKIKSISDYPGDEDISVMNIE 120
SACOL1867 (COL)                 TGFVIGKNTIITNKHVSKDYKVGDRITAHPNGDKGNGGIYKIKSISDYPGDEDISVMNIE 120
SAOUHSC_01939 (NCTC8325)        TGFVIGKNTIITNKHVSKDYKVGDRITAHPNGDKGNGGIYKIKSISDYPGDEDISVMNIE 120
NWMN_1704 (Newman)              TGFVIGKNTIITNKHVSKDYKVGDRITAHPNGDKGNGGIYKIKSISDYPGDEDISVMNIE 120
SAUSA300_1756 (USA300-FPR3757)  TGFVIGKNTIITNKHVSKDYKVGDRITAHPNGDKGNGGIYKIKSISDYPGDEDISVMNIE 120
SaurJH1_1897 (JH1)              TGFVIGKNTIITNKHVSKDYKVGDRITAHPNGDKGNGGIYKIKSISDYPGDEDISVMNIE 120
SAHV_1796 (Mu3)                 TGFVIGKNTIITNKHVSKDYKVGDRITAHPNGDKGNGGIYKIKSISDYPGDEDISVMNIE 120
SaurJH9_1862 (JH9)              TGFVIGKNTIITNKHVSKDYKVGDRITAHPNGDKGNGGIYKIKSISDYPGDEDISVMNIE 120
SAV1811 (Mu50)                  TGFVIGKNTIITNKHVSKDYKVGDRITAHPNGDKGNGGIYKIKSISDYPGDEDISVMNIE 120
SA1629 (N315)                   TGFVIGKNTIITNKHVSKDYKVGDRITAHPNGDKGNGGIYKIKSISDYPGDEDISVMNIE 120
SAB1671c (RF122)                TGFAIEKNTIITNKHVSKDYKVGDRITAHPNGDKGNGGIYKIKNISDYPGNEDISVMNVE 120
                                ***.* *********************:************:*.******* *******:*
Consensus                       TGFXIXKNTIITNKHVSKDYKVGDRITAHPXGDKGNGGIYKIKXISDYPGXEDISVMNXE MW1753 (MW2)                    EQAVERGPKGFNFNENVQALNFAKDAKVDDKIKVIGYPLPAQNSFKQFESTGTIKRIKDN 180
SAS1734 (MSSA476)               EQAVERGPKGFNFNENVQALNFAKDAKVDDKIKVIGYPLPAQNSFKQFESTGTIKRIKDN 180
SACOL1867 (COL)                 EQAVERGPKGFNFNENVQAFNFAKDAKVDDKIKVIGYPLPAQNSFKQFESTGTIKRIKDN 180
SAOUHSC_01939 (NCTC8325)        EQAVERGPKGFNFNENVQAFNFAKDAKVDDKIKVIGYPLPAQNSFKQFESTGTIKRIKDN 180
NWMN_1704 (Newman)              EQAVERGPKGFNFNENVQAFNFAKDAKVDDKIKVIGYPLPAQNSFKQFESTGTIKRIKDN 180
SAUSA300_1756 (USA300-FPR3757)  EQAVERGPKGFNFNENVQAFNFAKDAKVDDKIKVIGYPLPAQNSFKQFESTGTIKRIKDN 180
SaurJH1_1897 (JH1)              EQAVERGPKGFNFNENVQAFNFAKDAKVDDKIKVIGYPLPAQNSFKQFESTGTIKRIKDN 180
SAHV_1796 (Mu3)                 EQAVERGPKGFNFNENVQAFNFAKDAKVDDKIKVIGYPLPAQNSFKQFESTGTIKRIKDN 180
SaurJH9_1862 (JH9)              EQAVERGPKGFNFNENVQAFNFAKDAKVDDKIKVIGYPLPAQNSFKQFESTGTIKRIKDN 180
SAV1811 (Mu50)                  EQAVERGPKGFNFNENVQAFNFAKDAKVDDKIKVIGYPLPAQNSFKQFESTGTIKRIKDN 180
SA1629 (N315)                   EQAVERGPKGFNFNENVQAFNFAKDAKVDDKIKVIGYPLPAQNSFKQFESTGTIKRIKDN 180
SAB1671c (RF122)                ENAVERGANGYNFNENVQAFNFAKDAKVDDKIKVIGYPLPAQNTFKQFESTGTVKSIKDN 180
                                *:****:.:*:********:***********************:***********:*.****
Consensus                       EXAVERGXXGXNFNENVQAXNFAKDAKVDDKIKVIGYPLPAQNXFKQFESTGTXKXIKDN MW1753 (MW2)                    ILNFDAYIEPGNSGSPVLNSNNEVIGVVYGGIGKIGSEYNGAVYFTPQIKDFIQKHIEQ 239
SAS1734 (MSSA476)               ILNFDAYIEPGNSGSPVLNSNNEVIGVVYGGIGKIGSEYNGAVYFTPQIKDFIQKHIEQ 239
SACOL1867 (COL)                 ILNFDAYIEPGNSGSPVLNSNNEVIGVVYGGIGKIGSEYNGAVYFTPQIKDFIQKHIEQ 239
SAOUHSC_01939 (NCTC8325)        ILNFDAYIEPGNSGSPVLNSNNEVIGVVYGGIGKIGSEYNGAVYFTPQIKDFIQKHIEQ 239
NWMN_1704 (Newman)              ILNFDAYIEPGNSGSPVLNSNNEVIGVVYGGIGKIGSEYNGAVYFTPQIKDFIQKHIEQ 239
SAUSA300_1756 (USA300-FPR3757)  ILNFDAYIEPGNSGSPVLNSNNEVIGVVYGGIGKIGSEYNGAVYFTPQIKDFIQKHIEQ 239
SaurJH1_1897 (JH1)              ILNFDAYIEPGNSGSPVLNSNNEVIGVVYGGIGKIGSEYNGAVYFTPQIKDFIQKHIEQ 239
SAHV_1796 (Mu3)                 ILNFDAYIEPGNSGSPVLNSNNEVIGVVYGGIGKIGSEYNGAVYFTPQIKDFIQKHIEQ 239
SaurJH9_1862 (JH9)              ILNFDAYIEPGNSGSPVLNSNNEVIGVVYGGIGKIGSEYNGAVYFTPQIKDFIQKHIEQ 239
SAV1811 (Mu50)                  ILNFDAYIEPGNSGSPVLNSNNEVIGVVYGGIGKIGSEYNGAVYFTPQIKDFIQKHIEQ 239
SA1629 (N315)                   ILNFDAYIEPGNSGSPVLNSNNEVIGVVYGGIGKIGSEYNGAVYFTPQIKDFIQKHIEQ 239
SAB1671c (RF122)                NLNFDAYIEPGNSGSPVLNLNNEVGVVYGGIGKIGSEYNGAVYFTPQIKEFIQKHIEQ 239
                                ********.******:***.****:***************************:*******
Consensus                       XLNFDAYIEPGNSGSPVLNXNNEVXGVVYGGIGKIGSEYNGAVYFTPQIKXFIQKHIEQ
```

FIG. 25D

I- SACOL1715(hemB): Nucleotide sequence (SEQ ID NO: 181)

atgaaatttgatagacatagaagattgagatcatcagcgacaatgagagatatggttaga
gagaatcatgtaagaaaagaagatttaatatatccaattttttgtagttgaaaaagacgat
gtgaaaaagaaattaagtcattgccaggtgtataccaaatcagtttgaatttacttgaa
agtgaattaaaagaagcttatgacttaggcatacgtgccattatgttttttcggtgttcca
aactcaaaagatgatataggtactggtgcatacattcacgatggtgttattcaacaggca
acacgtattgctaaaaaaatgtatgatgacttattaattgttgcagacacttgtttatgt
gaatatactgatcatggtcattgtggcgtgattgatgaccatacacatgacgttgacaat
gataaatcattgccactacttgttaaaacagcaatttctcaagtggaagctggtgctgat
attattgcgccaagtaatatgatggatggttttgttgctgaaattcgtcgtggattagat
gaagccggctattacaatattcctataatgagttatggtgtcaagtatgcatcaagtttc
tttggacctttagagatgcagcagattcagcgccatcatttggggatagaaaaacgtat
cagatggaccctgctaaccgtttggaagcacttcgtgaattagaaagtgatcttaaagaa
gggtgcgacatgatgattgttaaacctgctctaagttatttagatatagttcgagatgtt
aaaaatcatacgaatgttccagttgttgcatataatgtgagtggagaatatagtatgact
aaagcagcggcacaaaatggttggatagatgaagaacgtgtcgttatggaacaaatggtt
tcaatgaaacgtgcaggtgctgatatgattattacgtattttgcaaaggacatttgtcgc
tatttagataaataa II- hemB: amino acid sequence (SEQ ID NO: 182)

MKFDRHRRLRSSATMRDMVRENHVRKEDLIYPIFVVEKDDVKKEIKSLPGVYQISLNLLE
SELKEAYDLGIRAIMFFGVPNSKDDIGTGAYIHDGVIQQATRIAKKMYDDLLIVADTCLC
EYTDHGHCGVIDDHTHDVDNDKSLPLLVKTAISQVEAGADIIAPSNMMDGFVAEIRRGLD
EAGYYNIPIMSYGVKYASSFFGPFRDAADSAPSFGDRKTYQMDPANRLEALRELESDLKE
GCDMMIVKPALSYLDIVRDVKNHTNVPVVAYNVSGEYSMTKAAAQNGWIDEERVVMEQMV
SMKRAGADMIITYFAKDICRYLDK

FIG. 26

>ClfA (NWMN_0756, newman) (SEQ ID NO: 183)
ATGAATATGAAGAAAAAGAAAAACACGCAATTCGGAAAAAATCGATTGGCGTGGCTTCAGTGCTTGTAGGTACGTTAAT
CGGTTTTGGACTACTCAGCAGTAAAGAAGCAGATGCAAGTGAAAATAGTGTTACGCAATCTGATAGCGCAAGTAACGAAA
GCAAAAGTAATGATTCAAGTAGCGTTAGTGCTGCACCTAAAACAGACGACACAAACGTGAGTGATACTAAAACATCGTCA
AACACTAATAATGGCGAAACGAGTGTGGCGCAAAATCCAGCACAACAGGAAACGACACAATCATCATCAACAAATGCAAC
TACGGAAGAAACGCCGGTAACTGGTGAAGCTACTACTACGACAACGAATCAAGCTAATACACCGGCAACAACTCAATCAA
GCAATACAAATGCGGAGGAATTAGTGAATCAAACAAGTAATGAAACGACTTTTAATGATACTAATACAGTATCATCTGTA
AATTCACCTCAAAATTCTACAAATGCGGAAAATGTTTCAACAACGCAAGATACTTCAACTGAAGCAACACCTTCAAACAA
TGAATCAGCTCCACAGAGTACAGATGCAAGTAATAAAGATGTAGTTAATCAAGCGGTTAATACAAGTGCGCCTAGAATGA
GAGCATTTAGTTTAGCGGCAGTAGCTGCAGATGCACCGGCAGCTGGCACAGATATTACGAATCAGTTGACGAATGTGACA
GTTGGTATTGACTCTGGTACGACTGTGTATCCGCACCAAGCAGGTTATGTCAAACTGAATTATGGTTTTTCAGTGCCTAA
TTCTGCTGTTAAAGGTGACACATTCAAAATAACTGTACCTAAAGAATTAAACTTAAATGGTGTAACTTCAACTGCTAAAG
TGCCACCAATTATGGCTGGAGATCAAGTATTGGCAAATGGTGTAATCGATAGTGATGGTAATGTTATTTATACATTTACA
GACTATGTAAATACTAAAGATGATGTAAAAGCAACTTTGACCATGCCCGCTTATATTGACCCTGAAAATGTTAAAAAGAC
AGGTAATGTGACATTGGCTACTGGCATAGGTAGTACAACAGCAAACAAAACAGTATTAGTAGATTATGAAAAATATGGTA
AGTTTTATAACTTATCTATTAAAGGTACAATTGACCAAATCGATAAAACAAATAATACGTATCGTCAGACAATTTATGTC
AATCCAAGTGGAGATAACGTTATTGCGCCGGTTTTAACAGGTAATTTAAAACCAAATACGGATAGTAATGCATTAATAGA
TCAGCAAAATACAAGTATTAAAGTATATAAAGTAGATAATGCAGCTGATTTATCTGAAAGTTACTTTGTGAATCCAGAAA
ACTTTGAGGATGTCACTAATAGTGTGAATATTACATTCCCAAATCCAAATCAATATAAAGTAGAGTTTAATACGCCTGAT
GATCAAATTACAACACCGTATATAGTAGTTGTTAATGGTCATATTGATCCGAATAGCAAAGGTGATTTAGCTTTACGTTC
AACTTTATATGGGTATAACTCGAATATAATTTGGCGCTCTATGTCATGGGACAACGAAGTAGCATTTAATAACGGATCAG
GTTCTGGTGACGGTATCGATAAACCAGTTGTTCCTGAACAACCTGATGAGCCTGGTGAAATTGAACCAATTCCAGAGGAT
TCAGATTCTGACCCAGGTTCAGATTCTGGCAGCGATTCTAATTCAGATAGCGGTTCAGATTCGGGTAGTGATTCTACATC
AGATAGTGGTTCAGATTCAGCGAGTGATTCAGATTCAGCAAGTGATTCAGACTCAGCGAGTGATTCAGATTCAGCAAGCG
ATTCCGACTCAGCGAGCGATTCCGACTCAGACAATGACTCGGATTCAGATAGCGATTCTGACTCAGACAGTGACTCAGAT
TCCGACAGTGACTCAGATTCAGATAGCGATTCTGACTCAGACAGTGACTCAGATTCAGATAGCGATTCAGATTCAGATAG
CGATTCAGATTCCGACAGTGATTCCGACTCAGACAGCGATTCTGACTCCGACAGTGATTCCGACTCAGACAGCGATTCAG
ATTCCGACAGTGATTCCGACTCAGATAGCGATTCCGACTCAGATAGCGACTCAGATTCAGACAGCGATTCAGATTCAGAC
AGCGATTCAGATTCAGATAGCGATTCAGATTCCGACAGTGACTCAGATTCCGACAGTGACTCGGATTCAGATAGCGATTC
AGATTCCGACAGTGACTCAGATTCCGACAGTGACTCAGACTCAGACAGTGATTCGGATTCAGCGAGTGATTCGGATTCAG
ATAGTGATTCCGACTCCGACAGTGACTCGGATTCAGATAGCGACTCAGACTCGGATAGCGACTCGGATTCAGATAGCGAT
TCGGACTCAGATAGCGATTCAGAATCAGACAGCGATTCAGAATCAGACAGCGATTCAGATTCAGACAGCGACTCAGACAG
TGACTCAGATTCAGATAGTGACTCGGATTCAGCGAGTGATTCAGACTCAGGTAGTGACTCCGATTCATCAAGTGATTCCG
ACTCAGAAAGTGATTCAAATAGCGATTCCGAGTCAGGTTCTAACAATAATGTAGTTCCGCCTAATTCACCTAAAAATGGT
ACTAATGCTTCTAATAAAAATGAGGCTAAAGATAGTAAAGAACCATTACCAGATACAGGTTCTGAAGATGAAGCAAATAC
GTCACTAATTTGGGGATTATTAGCATCAATAGGTTCATTACTACTTTTCAGAAGAAAAAAGAAAATAAAGATAAGAAAT
AA >ClfA (NWMN_0756, newman) (SEQ ID NO: 184)
MNMKKKEKHAIRKKSIGVASVLVGTLIGFGLLSSKEADASENSVTQSDSASNESKSNDSSSVSAAPKTDDTNVSDTKTSS
NTNNGETSVAQNPAQQETTQSSSTNATTEETPVTGEATTTTTNQANTPATTQSSNTNAEELVNQTSNETTFNDTNTVSSV
NSPQNSTNAENVSTTQDTSTEATPSNNESAPQSTDASNKDVVNQAVNTSAPRMRAFSLAAVAADAPAAGTDITNQLTNVT
VGIDSGTTVYPHQAGYVKLNYGFSVPNSAVKGDTFKITVPKELNLNGVTSTAKVPPIMAGDQVLANGVIDSDGNVIYTFT
DYVNTKDDVKATLTMPAYIDPENVKKTGNVTLATGIGSTTANKTVLVDYEKYGKFYNLSIKGTIDQIDKTNNTYRQTIYV
NPSGDNVIAPVLTGNLKPNTDSNALIDQQNTSIKVYKVDNAADLSESYFVNPENFEDVTNSVNITFPNPNQYKVEFNTPD
DQITTPYIVVVNGHIDPNSKGDLALRSTLYGYNSNIIWRSMSWDNEVAFNNGSGSGDGIDKPVVPEQPDEPGEIEPIPED
SDSDPGSDSGSDSNSDSGSDSGSDSTSDSGSDSASDSDSASDSDSASDSDSASDSDSASDSDSDNDSDSDSDSDSDSDSD
SDSDSDSDSDSDSDSDSDSDSDSDSDSDSDSDSDSDSDSDSDSDSDSDSDSDSDSDSDSDSDSDSDSDSDSDSDSDSDSD
SDSDSDSDSDSDSDSDSDSDSDSDSDSDSDSDSDSDSDSDSDSDSDSASDSDSDSDSDSDSDSDSDSDSDSDSDSDSDSD
SDSDSDSESDSDSESDSDSDSDSDSDSDSDSDSDSDSASDSDSGSDSDSSSDSDSESDSNSDSESGSNNNVVPPNSPKNG
TNASNKNEAKDSKEPLPDTGSEDEANTSLIWGLLASIGSLLLFRRKKENKDKK

FIG. 27

SEQUENCE LISTING

```
<160> NUMBER OF SEQ ID NOS: 196

<210> SEQ ID NO 1
<211> LENGTH: 15
<212> TYPE: PRT
<213> ORGANISM: Staphylococcus aureus

<400> SEQUENCE: 1

Lys Asp Gly Gly Lys Tyr Thr Leu Glu Ser His Lys Glu Leu Gln
1               5                   10                  15

<210> SEQ ID NO 2
<211> LENGTH: 40
<212> TYPE: PRT
<213> ORGANISM: Staphylococcus aureus

<400> SEQUENCE: 2

Gly Glu His Leu Pro Lys Gly Asn Ile Val Ile Asn Thr Lys Asp Gly
1               5                   10                  15

Gly Lys Tyr Thr Leu Glu Ser His Lys Glu Leu Gln Lys Asp Arg Glu
            20                  25                  30

Asn Val Lys Ile Asn Thr Ala Asp
        35                  40

<210> SEQ ID NO 3
<211> LENGTH: 48
<212> TYPE: PRT
<213> ORGANISM: Artificial sequence
<220> FEATURE:
<223> OTHER INFORMATION: synthetic sequence

<400> SEQUENCE: 3

Lys Asp Gly Gly Lys Tyr Thr Leu Glu Ser His Lys Glu Leu Gln Glu
1               5                   10                  15

Ala Ala Ala Lys Glu Ala Ala Ala Lys Lys Asp Ile Asn Lys Ile Tyr
            20                  25                  30

Phe Met Thr Asp Val Asp Leu Gly Gly Pro Thr Phe Val Leu Asn Asp
        35                  40                  45

<210> SEQ ID NO 4
<211> LENGTH: 168
<212> TYPE: DNA
<213> ORGANISM: Staphylococcus aureus

<400> SEQUENCE: 4
atgctagaat ctagagagca attatcagtc gaagaatacg aaacattctt taacagattt      60
gataatcaag aatttgattt cgaacgtgaa ttgacacaag atccatattc aaaagtatac     120
ttatacagta tagaagacca tatcagaaca tataagatag agaaataa                 168

<210> SEQ ID NO 5
<211> LENGTH: 55
```

```
<212> TYPE: PRT
<213> ORGANISM: Staphylococcus aureus

<400> SEQUENCE: 5

Met Leu Glu Ser Arg Glu Gln Leu Ser Val Glu Glu Tyr Glu Thr Phe
1               5                   10                  15

Phe Asn Arg Phe Asp Asn Gln Glu Phe Asp Phe Glu Arg Glu Leu Thr
                20                  25                  30

Gln Asp Pro Tyr Ser Lys Val Tyr Leu Tyr Ser Ile Glu Asp His Ile
            35                  40                  45

Arg Thr Tyr Lys Ile Glu Lys
    50                  55

<210> SEQ ID NO 6
<211> LENGTH: 165
<212> TYPE: DNA
<213> ORGANISM: Staphylococcus aureus

<400> SEQUENCE: 6
ctagaatcta gagagcaatt atcagtcgaa gaatacgaaa cattctttaa cagatttgat      60
aatcaagaat tgatttcga acgtgaattg acacaagatc catattcaaa agtatactta     120
tacagtatag aagaccatat cagaacatat aagatagaga ataa                     165

<210> SEQ ID NO 7
<211> LENGTH: 54
<212> TYPE: PRT
<213> ORGANISM: Staphylococcus aureus

<400> SEQUENCE: 7

Leu Glu Ser Arg Glu Gln Leu Ser Val Glu Glu Tyr Glu Thr Phe Phe
1               5                   10                  15

Asn Arg Phe Asp Asn Gln Glu Phe Asp Phe Glu Arg Glu Leu Thr Gln
                20                  25                  30

Asp Pro Tyr Ser Lys Val Tyr Leu Tyr Ser Ile Glu Asp His Ile Arg
            35                  40                  45

Thr Tyr Lys Ile Glu Lys
    50

<210> SEQ ID NO 8
<211> LENGTH: 61
<212> TYPE: PRT
<213> ORGANISM: Artificial sequence
<220> FEATURE:
<223> OTHER INFORMATION: synthetic sequence

<400> SEQUENCE: 8

Met His His His His His His Leu Glu Ser Arg Glu Gln Leu Ser Val
1               5                   10                  15

Glu Glu Tyr Glu Thr Phe Phe Asn Arg Phe Asp Asn Gln Glu Phe Asp
                20                  25                  30

Phe Glu Arg Glu Leu Thr Gln Asp Pro Tyr Ser Lys Val Tyr Leu Tyr
            35                  40                  45

Ser Ile Glu Asp His Ile Arg Thr Tyr Lys Ile Glu Lys
    50                  55                  60

<210> SEQ ID NO 9
<211> LENGTH: 66
<212> TYPE: PRT
<213> ORGANISM: Artificial sequence
<220> FEATURE:
```

<223> OTHER INFORMATION: synthetic sequence

<400> SEQUENCE: 9

```
Met Arg Gly Ser His His His His His Gly Ser Leu Glu Ser Arg
1               5                   10                  15

Glu Gln Leu Ser Val Glu Glu Tyr Glu Thr Phe Phe Asn Arg Phe Asp
            20                  25                  30

Asn Gln Glu Phe Asp Phe Glu Arg Glu Leu Thr Gln Asp Pro Tyr Ser
        35                  40                  45

Lys Val Tyr Leu Tyr Ser Ile Glu Asp His Ile Arg Thr Tyr Lys Ile
    50                  55                  60

Glu Lys
65
```

<210> SEQ ID NO 10
<211> LENGTH: 1889
<212> TYPE: DNA
<213> ORGANISM: Staphylococcus aureus

<400> SEQUENCE: 10

| | | | | | |
|---|---|---|---|---|---|
| atgaccttta | acgagataat | atttaaaaat | ttccgtcaaa | atttatcaca | ttatgccatc | 60 |
| tatcttttt | cgttaattac | gagtgtagta | ttgtatttta | gctttgtagc | attaaaatac | 120 |
| gctcataaac | taaacatgac | agagtcatat | ccaattataa | aggaaggctc | acaagtcgga | 180 |
| agctactttc | tatttttcat | cataattgca | tttttgttat | atgccaatgt | gttatttatt | 240 |
| aaacgacgaa | gttatgagct | tgcattatat | caaacattag | gtttatctaa | attcaacatt | 300 |
| atttatatac | taatgctcga | acaattacta | atatttataa | ttacggcaat | attaggtatt | 360 |
| attattggta | ttttttggttc | gaaactgtta | ttaatgattg | tctttacatt | attaggaatt | 420 |
| aaagaaaagg | ttccaattat | ttttagtttg | agggcggtat | ttgaaacatt | aatgttaatc | 480 |
| ggtgtcgctt | atttttaac | atctgctcaa | aatttttat | tagtgttcaa | acaatctatt | 540 |
| tcacagatgt | caaagaataa | ccaggttaaa | gaaacaaatc | ataataaaat | tacatttgaa | 600 |
| gaggttgttt | taggcatctt | aggtatagta | ttgattacca | caggatacta | tctatctttg | 660 |
| aacattgttc | aatattatga | ttctatcggt | acacttatgt | ttattttatt | gtcaactgtg | 720 |
| attggggcat | acttattttt | taaaagctct | gtttctctag | ttttaaaat | ggtgaagaag | 780 |
| tttagaaaag | gtgttataag | tgtaaatgat | gtcatgttct | catcatctat | tatgtatcgt | 840 |
| attaagaaaa | atgcttttc | acttacggtc | atggcaatca | tttcagcgat | tactgtttca | 900 |
| gttctttgct | tgctgctat | aagtagagcg | tccttatcaa | gtgaaataaa | atatactgca | 960 |
| ccacacgacg | ttacaattaa | agaccaacaa | aaagctaatc | aattagcaag | tgaattaaac | 1020 |
| aatcaaaaaa | ttcctcattt | ttataattat | aaagaagtaa | ttcatacgaa | attgtataaa | 1080 |
| gataatttat | ttgatgtaaa | agcgaaagaa | ccatacaatg | taacaattac | tagtgataaa | 1140 |
| tacatcccta | atactgattt | gaaacgtggg | caagctgatt | tatttgtagc | ggaaggttct | 1200 |
| atcaaagatt | tagtgaaaca | taagaagcat | ggtaaggcaa | ttataggaac | gaaaaaacat | 1260 |
| catgttaata | ttaagttacg | taaagatatt | aataaaatct | attttatgac | agatgttgat | 1320 |
| ttaggtggac | caacgtttgt | cttaaatgac | aaagactatc | aagaaataag | aaagtataca | 1380 |
| aaggcaaagc | atatcgtctc | tcaatttgga | ttcgatttga | acataaaaa | agatgcttta | 1440 |
| gcattagaaa | aagcgaaaaa | taagttgat | aaatctattg | aaacaagaag | tgaagcgata | 1500 |
| agctcaatat | caagtttaac | cggaatatta | ttatttgtaa | catcattttt | aggtattaca | 1560 |

```
ttcttgattg ctgtatgttg cattatatac ataaagcaaa tagatgaaac cgaagatgag   1620
ttagagaatt atagtatttt gagaaagctt ggatttacac aaaaagatat ggcaagggga   1680
ctaaagttta aaattatgtt taattttggg ttacctttag ttattgcact atcacatgca   1740
tattttacat cattagcata tatgaaatta atgggtacaa cgaatcaaat accggttttc   1800
atagtaatgg gattatacat ttgtatgtat gctgttttg cagtgacggc ttataatcat    1860
tccaagcgaa cattagacat tccatataa                                     1889
```

<210> SEQ ID NO 11
<211> LENGTH: 629
<212> TYPE: PRT
<213> ORGANISM: Staphylococcus aureus

<400> SEQUENCE: 11

```
Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Gly Ile Phe Gly Ser Lys
        115                 120                 125

Leu Leu Leu Met Ile Val Phe Thr Leu Gly Ile Lys Glu Lys Val
    130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
    210                 215                 220

Tyr Tyr Asp Ser Ile Gly Thr Leu Met Phe Ile Leu Leu Ser Thr Val
225                 230                 235                 240

Ile Gly Ala Tyr Leu Phe Phe Lys Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
    290                 295                 300

Ala Ala Ile Ser Arg Ala Ser Leu Ser Ser Glu Ile Lys Tyr Thr Ala
305                 310                 315                 320
```

```
Pro His Asp Val Thr Ile Lys Asp Gln Gln Lys Ala Asn Gln Leu Ala
            325                 330                 335

Ser Glu Leu Asn Asn Gln Lys Ile Pro His Phe Tyr Asn Tyr Lys Glu
        340                 345                 350

Val Ile His Thr Lys Leu Tyr Lys Asp Asn Leu Phe Asp Val Lys Ala
    355                 360                 365

Lys Glu Pro Tyr Asn Val Thr Ile Thr Ser Asp Lys Tyr Ile Pro Asn
370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Ile Ile Gly
                405                 410                 415

Thr Lys Lys His His Val Asn Ile Lys Leu Arg Lys Asp Ile Asn Lys
                420                 425                 430

Ile Tyr Phe Met Thr Asp Val Asp Leu Gly Gly Pro Thr Phe Val Leu
            435                 440                 445

Asn Asp Lys Asp Tyr Gln Glu Ile Arg Lys Tyr Thr Lys Ala Lys His
    450                 455                 460

Ile Val Ser Gln Phe Gly Phe Asp Leu Lys His Lys Lys Asp Ala Leu
465                 470                 475                 480

Ala Leu Glu Lys Ala Lys Asn Lys Val Asp Lys Ser Ile Glu Thr Arg
                485                 490                 495

Ser Glu Ala Ile Ser Ser Ile Ser Ser Leu Thr Gly Ile Leu Leu Phe
                500                 505                 510

Val Thr Ser Phe Leu Gly Ile Thr Phe Leu Ile Ala Val Cys Cys Ile
            515                 520                 525

Ile Tyr Ile Lys Gln Ile Asp Glu Thr Glu Asp Glu Leu Glu Asn Tyr
        530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
            580                 585                 590

Thr Thr Asn Gln Ile Pro Val Phe Ile Val Met Gly Leu Tyr Ile Cys
        595                 600                 605

Met Tyr Ala Val Phe Ala Val Thr Ala Tyr Asn His Ser Lys Arg Thr
610                 615                 620

Ile Arg His Ser Ile
625

<210> SEQ ID NO 12
<211> LENGTH: 200
<212> TYPE: PRT
<213> ORGANISM: Staphylococcus aureus

<400> SEQUENCE: 12

Arg Ala Ser Leu Ser Ser Glu Ile Lys Tyr Thr Ala Pro His Asp Val
1               5                   10                  15

Thr Ile Lys Asp Gln Gln Lys Ala Asn Gln Leu Ala Ser Glu Leu Asn
                20                  25                  30

Asn Gln Lys Ile Pro His Phe Tyr Asn Tyr Lys Glu Val Ile His Thr
            35                  40                  45

Lys Leu Tyr Lys Asp Asn Leu Phe Asp Val Lys Ala Lys Glu Pro Tyr
```

```
                    50                  55                  60
Asn Val Thr Ile Thr Ser Asp Lys Tyr Ile Pro Asn Thr Asp Leu Lys
 65                  70                  75                  80

Arg Gly Gln Ala Asp Leu Phe Val Ala Glu Gly Ser Ile Lys Asp Leu
                     85                  90                  95

Val Lys His Lys Lys His Gly Lys Ala Ile Ile Gly Thr Lys Lys His
                100                 105                 110

His Val Asn Ile Lys Leu Arg Lys Asp Ile Asn Lys Ile Tyr Phe Met
                115                 120                 125

Thr Asp Val Asp Leu Gly Gly Pro Thr Phe Val Leu Asn Asp Lys Asp
            130                 135                 140

Tyr Gln Glu Ile Arg Lys Tyr Thr Lys Ala Lys His Ile Val Ser Gln
145                 150                 155                 160

Phe Gly Phe Asp Leu Lys His Lys Lys Asp Ala Leu Ala Leu Glu Lys
                165                 170                 175

Ala Lys Asn Lys Val Asp Lys Ser Ile Glu Thr Arg Ser Glu Ala Ile
                180                 185                 190

Ser Ser Ile Ser Ser Leu Thr Gly
            195                 200

<210> SEQ ID NO 13
<211> LENGTH: 199
<212> TYPE: PRT
<213> ORGANISM: Staphylococcus aureus

<400> SEQUENCE: 13

Ala Ser Leu Ser Ser Glu Ile Lys Tyr Thr Ala Pro His Asp Val Thr
 1               5                  10                  15

Ile Lys Asp Gln Gln Lys Ala Asn Gln Leu Ala Ser Glu Leu Asn Asn
                20                  25                  30

Gln Lys Ile Pro His Phe Tyr Asn Tyr Lys Glu Val Ile His Thr Lys
            35                  40                  45

Leu Tyr Lys Asp Asn Leu Phe Asp Val Lys Ala Lys Glu Pro Tyr Asn
 50                  55                  60

Val Thr Ile Thr Ser Asp Lys Tyr Ile Pro Asn Thr Asp Leu Lys Arg
 65                  70                  75                  80

Gly Gln Ala Asp Leu Phe Val Ala Glu Gly Ser Ile Lys Asp Leu Val
                 85                  90                  95

Lys His Lys Lys His Gly Lys Ala Ile Ile Gly Thr Lys Lys His His
                100                 105                 110

Val Asn Ile Lys Leu Arg Lys Asp Ile Asn Lys Ile Tyr Phe Met Thr
            115                 120                 125

Asp Val Asp Leu Gly Gly Pro Thr Phe Val Leu Asn Asp Lys Asp Tyr
130                 135                 140

Gln Glu Ile Arg Lys Tyr Thr Lys Ala Lys His Ile Val Ser Gln Phe
145                 150                 155                 160

Gly Phe Asp Leu Lys His Lys Lys Asp Ala Leu Ala Leu Glu Lys Ala
                165                 170                 175

Lys Asn Lys Val Asp Lys Ser Ile Glu Thr Arg Ser Glu Ala Ile Ser
                180                 185                 190

Ser Ile Ser Ser Leu Thr Gly
            195

<210> SEQ ID NO 14
<211> LENGTH: 146
```

```
<212> TYPE: PRT
<213> ORGANISM: Staphylococcus aureus

<400> SEQUENCE: 14

Ala Ser Leu Ser Ser Glu Ile Lys Tyr Thr Ala Pro His Asp Val Thr
1               5                   10                  15

Ile Lys Asp Gln Gln Lys Ala Asn Gln Leu Ala Ser Glu Leu Asn Asn
            20                  25                  30

Gln Lys Ile Pro His Phe Tyr Asn Tyr Lys Glu Val Ile His Thr Lys
        35                  40                  45

Leu Tyr Lys Asp Asn Leu Phe Asp Val Lys Ala Lys Glu Pro Tyr Asn
    50                  55                  60

Val Thr Ile Thr Ser Asp Lys Tyr Ile Pro Asn Thr Asp Leu Lys Arg
65                  70                  75                  80

Gly Gln Ala Asp Leu Phe Val Ala Glu Gly Ser Ile Lys Asp Leu Val
                85                  90                  95

Lys His Lys Lys His Gly Lys Ala Ile Ile Gly Thr Lys Lys His His
            100                 105                 110

Val Asn Ile Lys Leu Arg Lys Asp Ile Asn Lys Ile Tyr Phe Met Thr
        115                 120                 125

Asp Val Asp Leu Gly Gly Pro Thr Phe Val Leu Asn Asp Lys Asp Tyr
    130                 135                 140

Gln Glu
145

<210> SEQ ID NO 15
<211> LENGTH: 54
<212> TYPE: PRT
<213> ORGANISM: Staphylococcus aureus

<400> SEQUENCE: 15

Lys Asp Ile Asn Lys Ile Tyr Phe Met Thr Asp Val Asp Leu Gly Gly
1               5                   10                  15

Pro Thr Phe Val Leu Asn Asp Lys Asp Tyr Gln Glu Ile Arg Lys Tyr
            20                  25                  30

Thr Lys Ala Lys His Ile Val Ser Gln Phe Gly Phe Asp Leu Lys His
        35                  40                  45

Lys Lys Asp Ala Leu Ala
    50

<210> SEQ ID NO 16
<211> LENGTH: 25
<212> TYPE: PRT
<213> ORGANISM: Staphylococcus aureus

<400> SEQUENCE: 16

Lys Asp Ile Asn Lys Ile Tyr Phe Met Thr Asp Val Asp Leu Gly Gly
1               5                   10                  15

Pro Thr Phe Val Leu Asn Asp Lys Asp
            20                  25

<210> SEQ ID NO 17
<211> LENGTH: 26
<212> TYPE: PRT
<213> ORGANISM: Staphylococcus aureus

<400> SEQUENCE: 17

Lys Asp Ile Asn Lys Ile Tyr Phe Met Thr Asp Val Asp Leu Gly Gly
1               5                   10                  15
```

```
Pro Thr Phe Val Leu Asn Asp Lys Asp Tyr
            20                  25

<210> SEQ ID NO 18
<211> LENGTH: 15
<212> TYPE: PRT
<213> ORGANISM: Staphylococcus aureus

<400> SEQUENCE: 18

Ser Gln Phe Gly Phe Asp Leu Lys His Lys Lys Asp Ala Leu Ala
1               5                   10                  15

<210> SEQ ID NO 19
<211> LENGTH: 23
<212> TYPE: PRT
<213> ORGANISM: Staphylococcus aureus

<400> SEQUENCE: 19

Lys Asp Ile Asn Lys Ile Tyr Phe Met Thr Asp Val Asp Leu Gly Gly
1               5                   10                  15

Pro Thr Phe Val Leu Asn Asp
            20

<210> SEQ ID NO 20
<211> LENGTH: 19
<212> TYPE: PRT
<213> ORGANISM: Staphylococcus aureus

<400> SEQUENCE: 20

Lys His Ile Val Ser Gln Phe Gly Phe Asp Leu Lys His Lys Lys Asp
1               5                   10                  15

Ala Leu Ala

<210> SEQ ID NO 21
<211> LENGTH: 14
<212> TYPE: PRT
<213> ORGANISM: Staphylococcus aureus

<400> SEQUENCE: 21

Gln Phe Gly Phe Asp Leu Lys His Lys Lys Asp Ala Leu Ala
1               5                   10

<210> SEQ ID NO 22
<211> LENGTH: 13
<212> TYPE: PRT
<213> ORGANISM: Staphylococcus aureus

<400> SEQUENCE: 22

Thr Ile Lys Asp Gln Gln Lys Ala Asn Gln Leu Ala Ser
1               5                   10

<210> SEQ ID NO 23
<211> LENGTH: 14
<212> TYPE: PRT
<213> ORGANISM: Staphylococcus aureus

<400> SEQUENCE: 23

Lys Asp Ile Asn Lys Ile Tyr Phe Met Thr Asp Val Asp Leu
1               5                   10

<210> SEQ ID NO 24
<211> LENGTH: 13
<212> TYPE: PRT
```

<213> ORGANISM: Staphylococcus aureus

<400> SEQUENCE: 24

Asp Val Asp Leu Gly Gly Pro Thr Phe Val Leu Asn Asp
1               5                   10

<210> SEQ ID NO 25
<211> LENGTH: 153
<212> TYPE: PRT
<213> ORGANISM: Artificial sequence
<220> FEATURE:
<223> OTHER INFORMATION: synthetic sequence

<400> SEQUENCE: 25

Met His His His His His His Ala Ser Leu Ser Ser Glu Ile Lys Tyr
1               5                   10                  15

Thr Ala Pro His Asp Val Thr Ile Lys Asp Gln Gln Lys Ala Asn Gln
                20                  25                  30

Leu Ala Ser Glu Leu Asn Asn Gln Lys Ile Pro His Phe Tyr Asn Tyr
            35                  40                  45

Lys Glu Val Ile His Thr Lys Leu Tyr Lys Asp Asn Leu Phe Asp Val
        50                  55                  60

Lys Ala Lys Glu Pro Tyr Asn Val Thr Ile Thr Ser Asp Lys Tyr Ile
65                  70                  75                  80

Pro Asn Thr Asp Leu Lys Arg Gly Gln Ala Asp Leu Phe Val Ala Glu
                85                  90                  95

Gly Ser Ile Lys Asp Leu Val Lys His Lys His Gly Lys Ala Ile
            100                 105                 110

Ile Gly Thr Lys Lys His His Val Asn Ile Lys Leu Arg Lys Asp Ile
        115                 120                 125

Asn Lys Ile Tyr Phe Met Thr Asp Val Asp Leu Gly Gly Pro Thr Phe
    130                 135                 140

Val Leu Asn Asp Lys Asp Tyr Gln Glu
145                 150

<210> SEQ ID NO 26
<211> LENGTH: 158
<212> TYPE: PRT
<213> ORGANISM: Artificial sequence
<220> FEATURE:
<223> OTHER INFORMATION: synthetic sequence

<400> SEQUENCE: 26

Met Arg Gly Ser His His His His His His Gly Ser Ala Ser Leu Ser
1               5                   10                  15

Ser Glu Ile Lys Tyr Thr Ala Pro His Asp Val Thr Ile Lys Asp Gln
                20                  25                  30

Gln Lys Ala Asn Gln Leu Ala Ser Glu Leu Asn Asn Gln Lys Ile Pro
            35                  40                  45

His Phe Tyr Asn Tyr Lys Glu Val Ile His Thr Lys Leu Tyr Lys Asp
        50                  55                  60

Asn Leu Phe Asp Val Lys Ala Lys Glu Pro Tyr Asn Val Thr Ile Thr
65                  70                  75                  80

Ser Asp Lys Tyr Ile Pro Asn Thr Asp Leu Lys Arg Gly Gln Ala Asp
                85                  90                  95

Leu Phe Val Ala Glu Gly Ser Ile Lys Asp Leu Val Lys His Lys Lys
            100                 105                 110

His Gly Lys Ala Ile Ile Gly Thr Lys Lys His His Val Asn Ile Lys

```
                    115                 120                 125
Leu Arg Lys Asp Ile Asn Lys Ile Tyr Phe Met Thr Asp Val Asp Leu
                130                 135                 140

Gly Gly Pro Thr Phe Val Leu Asn Asp Lys Asp Tyr Gln Glu
145                 150                 155

<210> SEQ ID NO 27
<211> LENGTH: 50
<212> TYPE: PRT
<213> ORGANISM: Artificial sequence
<220> FEATURE:
<223> OTHER INFORMATION: synthetic sequence

<400> SEQUENCE: 27

Lys Asp Ile Asn Lys Ile Tyr Phe Met Thr Asp Val Asp Leu Gly Gly
1               5                   10                  15

Pro Thr Phe Val Leu Asn Asp Lys Asp Tyr Glu Arg Lys Tyr Lys Lys
                20                  25                  30

His Ile Val Ser Gln Phe Gly Phe Asp Leu Lys His Lys Lys Asp Ala
            35                  40                  45

Leu Ala
    50

<210> SEQ ID NO 28
<211> LENGTH: 612
<212> TYPE: DNA
<213> ORGANISM: Staphylococcus aureus

<400> SEQUENCE: 28
atgttcaaaa aatatgactc aaaaaattca atcgtattaa aatctattct atcgctaggt     60
atcatctatg ggggaacatt tggaatatat ccaaaagcag acgcgtcaac acaaaattcc    120
tcaagtgtac aagataaaca attacaaaaa gttgaagaag taccaaataa ttcagaaaaa    180
gctttggtta aaaaacttta cgatagatac agcaaggata caataaatgg aaaatctaat    240
aaatctagga attgggtttta ttcagagaga cctttaaatg aaaaccaagt tcgtatacat    300
ttagaaggaa catacacagt tgctggcaga gtgtatacac taagaggaa tattactctt     360 aataaagaag ttgtcacttt aaaagaattg gatcatatca taagatttgc tcatatttcc    420
tatggcttgt atatgggaga acatttgcct aaaggtaaca tcgtcataaa tacaaaagat    480
ggtggtaaat atacattaga gtcgcataaa gagctacaaa aagataggga aaatgtaaaa    540
attaatacag ccgatataaa aaatgtaact ttcaaacttg tgaaaagtgt taatgacatt    600
gaacaagttt ga                                                        612

<210> SEQ ID NO 29
<211> LENGTH: 203
<212> TYPE: PRT
<213> ORGANISM: Staphylococcus aureus

<400> SEQUENCE: 29

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
                20                  25                  30

Ala Asp Ala Ser Thr Gln Asn Ser Ser Val Gln Asp Lys Gln Leu
            35                  40                  45

Gln Lys Val Glu Glu Val Pro Asn Asn Ser Glu Lys Ala Leu Val Lys
        50                  55                  60
```

```
Lys Leu Tyr Asp Arg Tyr Ser Lys Asp Thr Ile Asn Gly Lys Ser Asn
 65                  70                  75                  80

Lys Ser Arg Asn Trp Val Tyr Ser Glu Arg Pro Leu Asn Glu Asn Gln
                 85                  90                  95

Val Arg Ile His Leu Glu Gly Thr Tyr Thr Val Ala Gly Arg Val Tyr
            100                 105                 110

Thr Pro Lys Arg Asn Ile Thr Leu Asn Lys Glu Val Val Thr Leu Lys
            115                 120                 125

Glu Leu Asp His Ile Ile Arg Phe Ala His Ile Ser Tyr Gly Leu Tyr
        130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
            195                 200
```

<210> SEQ ID NO 30
<211> LENGTH: 168
<212> TYPE: PRT
<213> ORGANISM: Staphylococcus aureus

<400> SEQUENCE: 30

```
Ser Thr Gln Asn Ser Ser Val Gln Asp Lys Gln Leu Gln Lys Val
  1               5                  10                  15

Glu Glu Val Pro Asn Asn Ser Glu Lys Ala Leu Val Lys Lys Leu Tyr
                 20                  25                  30

Asp Arg Tyr Ser Lys Asp Thr Ile Asn Gly Lys Ser Asn Lys Ser Arg
             35                  40                  45

Asn Trp Val Tyr Ser Glu Arg Pro Leu Asn Glu Asn Gln Val Arg Ile
         50                  55                  60

His Leu Glu Gly Thr Tyr Thr Val Ala Gly Arg Val Tyr Thr Pro Lys
 65                  70                  75                  80

Arg Asn Ile Thr Leu Asn Lys Glu Val Val Thr Leu Lys Glu Leu Asp
                 85                  90                  95

His Ile Ile Arg Phe Ala His Ile Ser Tyr Gly Leu Tyr Met Gly Glu
            100                 105                 110

His Leu Pro Lys Gly Asn Ile Val Ile Asn Thr Lys Asp Gly Gly Lys
            115                 120                 125

Tyr Thr Leu Glu Ser His Lys Glu Leu Gln Lys Asp Arg Glu Asn Val
        130                 135                 140

Lys Ile Asn Thr Ala Asp Ile Lys Asn Val Thr Phe Lys Leu Val Lys
145                 150                 155                 160

Ser Val Asn Asp Ile Glu Gln Val
                165
```

<210> SEQ ID NO 31
<211> LENGTH: 116
<212> TYPE: PRT
<213> ORGANISM: Staphylococcus aureus

<400> SEQUENCE: 31

```
Gln Asp Lys Gln Leu Gln Lys Val Glu Glu Val Pro Asn Asn Ser Glu
  1               5                  10                  15
```

Lys Ala Leu Val Lys Lys Leu Tyr Asp Arg Tyr Ser Lys Asp Thr Ile
            20                  25                  30

Asn Gly Lys Ser Asn Lys Ser Arg Asn Trp Val Tyr Ser Glu Arg Pro
        35                  40                  45

Leu Asn Glu Asn Gln Val Arg Ile His Leu Glu Gly Thr Tyr Thr Val
 50                  55                  60

Ala Gly Arg Val Tyr Thr Pro Lys Arg Asn Ile Thr Leu Asn Lys Glu
 65                  70                  75                  80

Val Val Thr Leu Lys Glu Leu Asp His Ile Ile Arg Phe Ala His Ile
                85                  90                  95

Ser Tyr Gly Leu Tyr Met Gly Glu His Leu Pro Lys Gly Asn Ile Val
            100                 105                 110

Ile Asn Thr Lys
        115

<210> SEQ ID NO 32
<211> LENGTH: 115
<212> TYPE: PRT
<213> ORGANISM: Staphylococcus aureus

<400> SEQUENCE: 32

Asp Lys Gln Leu Gln Lys Val Glu Glu Val Pro Asn Asn Ser Glu Lys
1               5                   10                  15

Ala Leu Val Lys Lys Leu Tyr Asp Arg Tyr Ser Lys Asp Thr Ile Asn
            20                  25                  30

Gly Lys Ser Asn Lys Ser Arg Asn Trp Val Tyr Ser Glu Arg Pro Leu
        35                  40                  45

Asn Glu Asn Gln Val Arg Ile His Leu Glu Gly Thr Tyr Thr Val Ala
 50                  55                  60

Gly Arg Val Tyr Thr Pro Lys Arg Asn Ile Thr Leu Asn Lys Glu Val
 65                  70                  75                  80

Val Thr Leu Lys Glu Leu Asp His Ile Ile Arg Phe Ala His Ile Ser
                85                  90                  95

Tyr Gly Leu Tyr Met Gly Glu His Leu Pro Lys Gly Asn Ile Val Ile
            100                 105                 110

Asn Thr Lys
        115

<210> SEQ ID NO 33
<211> LENGTH: 159
<212> TYPE: PRT
<213> ORGANISM: Staphylococcus aureus

<400> SEQUENCE: 33

Asp Lys Gln Leu Gln Lys Val Glu Glu Val Pro Asn Asn Ser Glu Lys
1               5                   10                  15

Ala Leu Val Lys Lys Leu Tyr Asp Arg Tyr Ser Lys Asp Thr Ile Asn
            20                  25                  30

Gly Lys Ser Asn Lys Ser Arg Asn Trp Val Tyr Ser Glu Arg Pro Leu
        35                  40                  45

Asn Glu Asn Gln Val Arg Ile His Leu Glu Gly Thr Tyr Thr Val Ala
 50                  55                  60

Gly Arg Val Tyr Thr Pro Lys Arg Asn Ile Thr Leu Asn Lys Glu Val
 65                  70                  75                  80

Val Thr Leu Lys Glu Leu Asp His Ile Ile Arg Phe Ala His Ile Ser
                85                  90                  95

```
Tyr Gly Leu Tyr Met Gly Glu His Leu Pro Lys Gly Asn Ile Val Ile
            100                 105                 110

Asn Thr Lys Asp Gly Lys Tyr Thr Leu Glu Ser His Lys Glu Leu
        115                 120                 125

Gln Lys Asp Arg Glu Asn Val Lys Ile Asn Thr Ala Asp Ile Lys Asn
130                 135                 140

Val Thr Phe Lys Leu Val Lys Ser Val Asn Asp Ile Glu Gln Val
145                 150                 155

<210> SEQ ID NO 34
<211> LENGTH: 14
<212> TYPE: PRT
<213> ORGANISM: Staphylococcus aureus

<400> SEQUENCE: 34

Lys Asp Thr Ile Asn Gly Lys Ser Asn Lys Ser Arg Asn Trp
1               5                   10

<210> SEQ ID NO 35
<211> LENGTH: 166
<212> TYPE: PRT
<213> ORGANISM: Artificial sequence
<220> FEATURE:
<223> OTHER INFORMATION: synthetic sequence

<400> SEQUENCE: 35

Met His His His His His His Asp Lys Gln Leu Gln Lys Val Glu Glu
1               5                   10                  15

Val Pro Asn Asn Ser Glu Lys Ala Leu Val Lys Lys Leu Tyr Asp Arg
            20                  25                  30

Tyr Ser Lys Asp Thr Ile Asn Gly Lys Ser Asn Lys Ser Arg Asn Trp
        35                  40                  45

Val Tyr Ser Glu Arg Pro Leu Asn Glu Asn Gln Val Arg Ile His Leu
    50                  55                  60

Glu Gly Thr Tyr Thr Val Ala Gly Arg Val Tyr Thr Pro Lys Arg Asn
65                  70                  75                  80

Ile Thr Leu Asn Lys Glu Val Val Thr Leu Lys Glu Leu Asp His Ile
                85                  90                  95

Ile Arg Phe Ala His Ile Ser Tyr Gly Leu Tyr Met Gly Glu His Leu
            100                 105                 110

Pro Lys Gly Asn Ile Val Ile Asn Thr Lys Asp Gly Lys Tyr Thr
        115                 120                 125

Leu Glu Ser His Lys Glu Leu Gln Lys Asp Arg Glu Asn Val Lys Ile
130                 135                 140

Asn Thr Ala Asp Ile Lys Asn Val Thr Phe Lys Leu Val Lys Ser Val
145                 150                 155                 160

Asn Asp Ile Glu Gln Val
                165

<210> SEQ ID NO 36
<211> LENGTH: 171
<212> TYPE: PRT
<213> ORGANISM: Artificial sequence
<220> FEATURE:
<223> OTHER INFORMATION: synthetic sequence

<400> SEQUENCE: 36

Met Arg Gly Ser His His His His His His Gly Ser Asp Lys Gln Leu
1               5                   10                  15
```

Gln Lys Val Glu Glu Val Pro Asn Asn Ser Glu Lys Ala Leu Val Lys
            20                  25                  30

Lys Leu Tyr Asp Arg Tyr Ser Lys Asp Thr Ile Asn Gly Lys Ser Asn
        35                  40                  45

Lys Ser Arg Asn Trp Val Tyr Ser Glu Arg Pro Leu Asn Glu Asn Gln
    50                  55                  60

Val Arg Ile His Leu Glu Gly Thr Tyr Thr Val Ala Gly Arg Val Tyr
65                  70                  75                  80

Thr Pro Lys Arg Asn Ile Thr Leu Asn Lys Glu Val Val Thr Leu Lys
                85                  90                  95

Glu Leu Asp His Ile Ile Arg Phe Ala His Ile Ser Tyr Gly Leu Tyr
            100                 105                 110

Met Gly Glu His Leu Pro Lys Gly Asn Ile Val Ile Asn Thr Lys Asp
        115                 120                 125

Gly Gly Lys Tyr Thr Leu Glu Ser His Lys Gly Leu Gln Lys Asp Arg
    130                 135                 140

Glu Asn Val Lys Ile Asn Thr Ala Asp Ile Lys Asn Val Thr Phe Lys
145                 150                 155                 160

Leu Val Lys Ser Val Asn Asp Ile Glu Gln Val
                165                 170

<210> SEQ ID NO 37
<211> LENGTH: 720
<212> TYPE: DNA
<213> ORGANISM: Staphylococcus aureus

<400> SEQUENCE: 37
atgaataaaa atatagtcat taaaagcatg gcagcattag ccattctaac ctcagtaact     60
ggaataaatg ctgcagtcgt tgaagagaca caacaaatag caaatgcaga gaagaatgtt    120
acgcaagtta aagatacaaa tattttttcca tataatggcg tcgtttcatt taaagatgcg   180
acaggttttg taattggaaa aaatacaatt atcaccaata acatgtatc aaaagattat     240
aaagttggcg atagaattac tgcccatcca acggtgaca aaggaaatgg tggtatatat     300
aaaattaaaa gcatttctga ttatccgggt gatgaagaca tctctgtcat gaatattgaa    360
gaacaagcag tcgaacgtgg accaaaaggc tttaatttta tgaaaatgt ccaagcattc     420
aattttgcga agatgctaa agttgatgac aaaattaaag ttattggtta cccattacct    480
gctcaaaata gttttaaaca gtttgaatct acaggaacta taaaagaat caaagacaat    540
attttaaatt ttgatgcata cattgaaccc gggaattcag atcaccagt tctaaattct    600
aacaatgagg tcataggtgt ggtgtatggc ggtattggaa aaattggttc tgaatataat   660
ggtgccgtat actttacgcc tcaaatcaaa gattttattc aaaagcacat tgaacaataa    720

<210> SEQ ID NO 38
<211> LENGTH: 239
<212> TYPE: PRT
<213> ORGANISM: Staphylococcus aureus

<400> SEQUENCE: 38

Met Asn Lys Asn Ile Val Ile Lys Ser Met Ala Ala Leu Ala Ile Leu
1               5                   10                  15

Thr Ser Val Thr Gly Ile Asn Ala Ala Val Val Glu Glu Thr Gln Gln
            20                  25                  30

Ile Ala Asn Ala Glu Lys Asn Val Thr Gln Val Lys Asp Thr Asn Ile
        35                  40                  45

```
Phe Pro Tyr Asn Gly Val Val Ser Phe Lys Asp Ala Thr Gly Phe Val
    50                  55                  60

Ile Gly Lys Asn Thr Ile Ile Thr Asn Lys His Val Ser Lys Asp Tyr
65                  70                  75                  80

Lys Val Gly Asp Arg Ile Thr Ala His Pro Asn Gly Asp Lys Gly Asn
                85                  90                  95

Gly Gly Ile Tyr Lys Ile Lys Ser Ile Ser Asp Tyr Pro Gly Asp Glu
            100                 105                 110

Asp Ile Ser Val Met Asn Ile Glu Glu Gln Ala Val Glu Arg Gly Pro
        115                 120                 125

Lys Gly Phe Asn Phe Asn Glu Asn Val Gln Ala Phe Asn Phe Ala Lys
    130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
            180                 185                 190

Ser Gly Ser Pro Val Leu Asn Ser Asn Asn Glu Val Ile Gly Val Val
        195                 200                 205

Tyr Gly Gly Ile Gly Lys Ile Gly Ser Glu Tyr Asn Gly Ala Val Tyr
    210                 215                 220

Phe Thr Pro Gln Ile Lys Asp Phe Ile Gln Lys His Ile Glu Gln
225                 230                 235

<210> SEQ ID NO 39
<211> LENGTH: 199
<212> TYPE: PRT
<213> ORGANISM: Staphylococcus aureus

<400> SEQUENCE: 39

Thr Gln Val Lys Asp Thr Asn Ile Phe Pro Tyr Asn Gly Val Val Ser
1               5                   10                  15

Phe Lys Asp Ala Thr Gly Phe Val Ile Gly Lys Asn Thr Ile Ile Thr
                20                  25                  30

Asn Lys His Val Ser Lys Asp Tyr Lys Val Gly Asp Arg Ile Thr Ala
            35                  40                  45

His Pro Asn Gly Asp Lys Gly Asn Gly Gly Ile Tyr Lys Ile Lys Ser
        50                  55                  60

Ile Ser Asp Tyr Pro Gly Asp Glu Asp Ile Ser Val Met Asn Ile Glu
65                  70                  75                  80

Glu Gln Ala Val Glu Arg Gly Pro Lys Gly Phe Asn Phe Asn Glu Asn
                85                  90                  95

Val Gln Ala Phe Asn Phe Ala Lys Asp Ala Lys Val Asp Asp Lys Ile
            100                 105                 110

Lys Val Ile Gly Tyr Pro Leu Pro Ala Gln Asn Ser Phe Lys Gln Phe
        115                 120                 125

Glu Ser Thr Gly Thr Ile Lys Arg Ile Lys Asp Asn Ile Leu Asn Phe
    130                 135                 140

Asp Ala Tyr Ile Glu Pro Gly Asn Ser Gly Ser Pro Val Leu Asn Ser
145                 150                 155                 160

Asn Asn Glu Val Ile Gly Val Val Tyr Gly Gly Ile Gly Lys Ile Gly
                165                 170                 175

Ser Glu Tyr Asn Gly Ala Val Tyr Phe Thr Pro Gln Ile Lys Asp Phe
```

Ile Gln Lys His Ile Glu Gln
         195

<210> SEQ ID NO 40
<211> LENGTH: 206
<212> TYPE: PRT
<213> ORGANISM: Artificial sequence
<220> FEATURE:
<223> OTHER INFORMATION: synthetic sequence

<400> SEQUENCE: 40

Met His His His His His His Thr Gln Val Lys Asp Thr Asn Ile Phe
1               5                   10                  15

Pro Tyr Asn Gly Val Val Ser Phe Lys Asp Ala Thr Gly Phe Val Ile
            20                  25                  30

Gly Lys Asn Thr Ile Ile Thr Asn Lys His Val Ser Lys Asp Tyr Lys
        35                  40                  45

Val Gly Asp Arg Ile Thr Ala His Pro Asn Gly Asp Lys Gly Asn Gly
    50                  55                  60

Gly Ile Tyr Lys Ile Lys Ser Ile Ser Asp Tyr Pro Gly Asp Glu Asp
65                  70                  75                  80

Ile Ser Val Met Asn Ile Glu Glu Gln Ala Val Glu Arg Gly Pro Lys
                85                  90                  95

Gly Phe Asn Phe Asn Glu Asn Val Gln Ala Phe Asn Phe Ala Lys Asp
            100                 105                 110

Ala Lys Val Asp Asp Lys Ile Lys Val Ile Gly Tyr Pro Leu Pro Ala
        115                 120                 125

Gln Asn Ser Phe Lys Gln Phe Glu Ser Thr Gly Thr Ile Lys Arg Ile
    130                 135                 140

Lys Asp Asn Ile Leu Asn Phe Asp Ala Tyr Ile Glu Pro Gly Asn Ser
145                 150                 155                 160

Gly Ser Pro Val Leu Asn Ser Asn Asn Glu Val Ile Gly Val Val Tyr
                165                 170                 175

Gly Gly Ile Gly Lys Ile Gly Ser Glu Tyr Asn Gly Ala Val Tyr Phe
            180                 185                 190

Thr Pro Gln Ile Lys Asp Phe Ile Gln Lys His Ile Glu Gln
        195                 200                 205

<210> SEQ ID NO 41
<211> LENGTH: 211
<212> TYPE: PRT
<213> ORGANISM: Artificial sequence
<220> FEATURE:
<223> OTHER INFORMATION: synthetic sequence

<400> SEQUENCE: 41

Met Arg Gly Ser His His His His His His Gly Ser Thr Gln Val Lys
1               5                   10                  15

Asp Thr Asn Ile Phe Pro Tyr Asn Gly Val Val Ser Phe Lys Asp Ala
            20                  25                  30

Thr Gly Phe Val Ile Gly Lys Asn Thr Ile Ile Thr Asn Lys His Val
        35                  40                  45

Ser Lys Asp Tyr Lys Val Gly Asp Arg Ile Thr Ala His Pro Asn Gly
    50                  55                  60

Asp Lys Gly Asn Gly Gly Ile Tyr Lys Ile Lys Ser Ile Ser Asp Tyr
65                  70                  75                  80

```
Pro Gly Asp Glu Asp Ile Ser Val Met Asn Ile Glu Glu Gln Ala Val
            85                  90                  95

Glu Arg Gly Pro Lys Gly Phe Asn Phe Asn Glu Asn Val Gln Ala Phe
        100                 105                 110

Asn Phe Ala Lys Asp Ala Lys Val Asp Asp Lys Ile Lys Val Ile Gly
            115                 120                 125

Tyr Pro Leu Pro Ala Gln Asn Ser Phe Lys Gln Phe Glu Ser Thr Gly
        130                 135                 140

Thr Ile Lys Arg Ile Lys Asp Asn Ile Leu Asn Phe Asp Ala Tyr Ile
145                 150                 155                 160

Glu Pro Gly Asn Ser Gly Ser Pro Val Leu Asn Ser Asn Asn Glu Val
                165                 170                 175

Ile Gly Val Val Tyr Gly Gly Ile Gly Lys Ile Gly Ser Glu Tyr Asn
            180                 185                 190

Gly Ala Val Tyr Phe Thr Pro Gln Ile Lys Asp Phe Ile Gln Lys His
        195                 200                 205

Ile Glu Gln
    210
```

<210> SEQ ID NO 42
<211> LENGTH: 600
<212> TYPE: DNA
<213> ORGANISM: Staphylococcus aureus

<400> SEQUENCE: 42

```
atggcaatga actttaaagt ctttgacaat agtcaacttg tagcagaata tgctgctgat     60
attattagaa agcaatttaa caataatcct actacaattg caggttttca tttagataca    120
gatcaagcgc cagttctaga tgaattaaag aaaaatgttg aaaaacatgc tgttgatttt    180
agccaaataa atattttaga ttatgacgat aaaaaatcat atttcgaagc gttaggtgta    240
ccagcaggtc aagtttatcc aattgcttat gaaaaagatg caatcgaatt aatcgctgat    300
aagattaaaa ctaagaaaaa taagggaaa ttaacattac aagttgtttc tatcgatgag    360
caaggtaagt taaatgttag tattcgtcaa ggactaatgg aagcaagaga aattttctta    420
gtagtgacag gtgctaataa acgagatgta gttgaaaaat tatatcaaga aaatggtaaa    480
acaagcttcg aaccagccga tttaaaagca catagaatgg taaatgttat tcttgataaa    540
gaagcggctg caggtttacc tgaagatgtt aaagcttact ttacgtcacg ctttgcttaa    600
```

<210> SEQ ID NO 43
<211> LENGTH: 199
<212> TYPE: PRT
<213> ORGANISM: Staphylococcus aureus

<400> SEQUENCE: 43

```
Met Ala Met Asn Phe Lys Val Phe Asp Asn Ser Gln Leu Val Ala Glu
1               5                   10                  15

Tyr Ala Ala Asp Ile Ile Arg Lys Gln Phe Asn Asn Asn Pro Thr Thr
            20                  25                  30

Ile Ala Gly Phe His Leu Asp Thr Asp Gln Ala Pro Val Leu Asp Glu
        35                  40                  45

Leu Lys Lys Asn Val Glu Lys His Ala Val Asp Phe Ser Gln Ile Asn
    50                  55                  60

Ile Leu Asp Tyr Asp Asp Lys Lys Ser Tyr Phe Glu Ala Leu Gly Val
65                  70                  75                  80

Pro Ala Gly Gln Val Tyr Pro Ile Ala Tyr Glu Lys Asp Ala Ile Glu
```

```
                    85                  90                  95
Leu Ile Ala Asp Lys Ile Lys Thr Lys Glu Asn Lys Gly Lys Leu Thr
                100                 105                 110

Leu Gln Val Val Ser Ile Asp Glu Gln Gly Lys Leu Asn Val Ser Ile
                115                 120                 125

Arg Gln Gly Leu Met Glu Ala Arg Glu Ile Phe Leu Val Val Thr Gly
            130                 135                 140

Ala Asn Lys Arg Asp Val Val Glu Lys Leu Tyr Gln Glu Asn Gly Lys
145                 150                 155                 160

Thr Ser Phe Glu Pro Ala Asp Leu Lys Ala His Arg Met Val Asn Val
                165                 170                 175

Ile Leu Asp Lys Glu Ala Ala Ala Gly Leu Pro Glu Asp Val Lys Ala
                180                 185                 190

Tyr Phe Thr Ser Arg Phe Ala
                195

<210> SEQ ID NO 44
<211> LENGTH: 206
<212> TYPE: PRT
<213> ORGANISM: Artificial sequence
<220> FEATURE:
<223> OTHER INFORMATION: synthetic sequence

<400> SEQUENCE: 44

Met His His His His His Met Ala Met Asn Phe Lys Val Phe Asp
1               5                   10                  15

Asn Ser Gln Leu Val Ala Glu Tyr Ala Ala Asp Ile Ile Arg Lys Gln
                20                  25                  30

Phe Asn Asn Pro Thr Thr Ile Ala Gly Phe His Leu Asp Thr Asp
            35                  40                  45

Gln Ala Pro Val Leu Asp Glu Leu Lys Lys Asn Val Glu Lys His Ala
        50                  55                  60

Val Asp Phe Ser Gln Ile Asn Ile Leu Asp Tyr Asp Lys Lys Ser
65                  70                  75                  80

Tyr Phe Glu Ala Leu Gly Val Pro Ala Gly Gln Val Tyr Pro Ile Ala
                85                  90                  95

Tyr Glu Lys Asp Ala Ile Glu Leu Ile Ala Asp Lys Ile Lys Thr Lys
                100                 105                 110

Glu Asn Lys Gly Lys Leu Thr Leu Gln Val Val Ser Ile Asp Glu Gln
                115                 120                 125

Gly Lys Leu Asn Val Ser Ile Arg Gln Gly Leu Met Glu Ala Arg Glu
            130                 135                 140

Ile Phe Leu Val Val Thr Gly Ala Asn Lys Arg Asp Val Val Glu Lys
145                 150                 155                 160

Leu Tyr Gln Glu Asn Gly Lys Thr Ser Phe Glu Pro Ala Asp Leu Lys
                165                 170                 175

Ala His Arg Met Val Asn Val Ile Leu Asp Lys Glu Ala Ala Ala Gly
            180                 185                 190

Leu Pro Glu Asp Val Lys Ala Tyr Phe Thr Ser Arg Phe Ala
                195                 200                 205

<210> SEQ ID NO 45
<211> LENGTH: 14
<212> TYPE: PRT
<213> ORGANISM: Staphylococcus aureus

<400> SEQUENCE: 45
```

Asp Ile Ile Arg Lys Gln Phe Asn Asn Asn Pro Thr Thr Ile
1               5                   10

<210> SEQ ID NO 46
<211> LENGTH: 14
<212> TYPE: PRT
<213> ORGANISM: Staphylococcus aureus

<400> SEQUENCE: 46

Tyr Phe Glu Ala Leu Gly Val Pro Ala Gly Gln Val Tyr Pro
1               5                   10

<210> SEQ ID NO 47
<211> LENGTH: 14
<212> TYPE: PRT
<213> ORGANISM: Staphylococcus aureus

<400> SEQUENCE: 47

Ala Asp Lys Ile Lys Thr Lys Glu Asn Lys Gly Lys Leu Thr
1               5                   10

<210> SEQ ID NO 48
<211> LENGTH: 14
<212> TYPE: PRT
<213> ORGANISM: Staphylococcus aureus

<400> SEQUENCE: 48

Gln Glu Asn Gly Lys Thr Ser Phe Glu Pro Ala Asp Leu Lys
1               5                   10

<210> SEQ ID NO 49
<211> LENGTH: 429
<212> TYPE: DNA
<213> ORGANISM: Staphylococcus aureus

<400> SEQUENCE: 49

```
atgatattga acttcaatca attcgagaat caaaactttt ttaacggtaa tccaagtgat      60
acatttaaag atttaggtaa acaagtattt aattactttt caacaccttc atttgtaacg     120
aatatatatg aaacagacga attatattac ttagaagctg aactagcagg tgtaaataaa     180
gaagatatta gtatcgattt caataataat acgctcacta ttcaagctac tagaagcgca     240
aaatacaaat ctgaacaact catttttagat gagcgtaact tcgaatcatt aatgcgtcaa     300
tttgattttg aagctgttga taagcaacat attactgcta gttttgaaaa tgggttatta     360
accattacct tgcctaaaat caaaccaagc aatgaaacta cttcatcaac atctattcca     420
atttcatag                                                             429
```

<210> SEQ ID NO 50
<211> LENGTH: 93
<212> TYPE: PRT
<213> ORGANISM: Staphylococcus aureus

<400> SEQUENCE: 50

Met Ile Leu Asn Phe Asn Gln Phe Glu Asn Gln Asn Phe Phe Asn Gly
1               5                   10                  15

Asn Pro Ser Asp Thr Phe Lys Asp Leu Gly Lys Gln Val Phe Asn Tyr
                20                  25                  30

Phe Ser Thr Pro Ser Phe Val Thr Asn Ile Tyr Glu Thr Asp Glu Leu
            35                  40                  45

Tyr Tyr Leu Glu Ala Glu Leu Ala Gly Val Asn Lys Glu Asp Ile Ser

```
                    50                  55                  60

Ile Asp Phe Asn Asn Thr Leu Thr Ile Gln Ala Thr Arg Ser Ala
 65                  70                  75                  80

Lys Tyr Lys Ser Glu Gln Leu Ile Leu Asp Glu Arg Asn
                 85                  90
```

<210> SEQ ID NO 51
<211> LENGTH: 100
<212> TYPE: PRT
<213> ORGANISM: Staphylococcus aureus

<400> SEQUENCE: 51

```
Met His His His His His His Met Ile Leu Asn Phe Asn Gln Phe Glu
  1               5                  10                  15

Asn Gln Asn Phe Phe Asn Gly Asn Pro Ser Asp Thr Phe Lys Asp Leu
                 20                  25                  30

Gly Lys Gln Val Phe Asn Tyr Phe Ser Thr Pro Ser Phe Val Thr Asn
             35                  40                  45

Ile Tyr Glu Thr Asp Glu Leu Tyr Tyr Leu Glu Ala Glu Leu Ala Gly
     50                  55                  60

Val Asn Lys Glu Asp Ile Ser Ile Asp Phe Asn Asn Thr Leu Thr
 65                  70                  75                  80

Ile Gln Ala Thr Arg Ser Ala Lys Tyr Lys Ser Glu Gln Leu Ile Leu
                 85                  90                  95

Asp Glu Arg Asn
            100
```

<210> SEQ ID NO 52
<211> LENGTH: 14
<212> TYPE: PRT
<213> ORGANISM: Staphylococcus aureus

<400> SEQUENCE: 52

```
Asn Gly Asn Pro Ser Asp Thr Phe Lys Asp Leu Gly Lys Gln
  1               5                  10
```

<210> SEQ ID NO 53
<211> LENGTH: 14
<212> TYPE: PRT
<213> ORGANISM: Staphylococcus aureus

<400> SEQUENCE: 53

```
Glu Asp Ile Ser Ile Asp Phe Asn Asn Asn Thr Leu Thr Ile
  1               5                  10
```

<210> SEQ ID NO 54
<211> LENGTH: 807
<212> TYPE: DNA
<213> ORGANISM: Artificial sequence
<220> FEATURE:
<223> OTHER INFORMATION: synthetic sequence

<400> SEQUENCE: 54

```
ctagaatcta gagagcaatt atcagtcgaa gaatacgaaa cattctttaa cagatttgat      60
aatcaagaat ttgatttcga acgtgaattg acacaagatc catattcaaa agtatactta     120
tacagtatag aagaccatat cagaacatat aagatagaga aaggaggtgg cggttcagga     180
ggtggaggat ctggaggcgg tggatcaacg caagttaaag atacaaatat ttttccatat     240
aatggcgtcg tttcatttaa agatgcgaca ggttttgtaa ttggaaaaaa tacaattatc     300
```

```
accaataaac atgtatcaaa agattataaa gttggcgata gaattactgc ccatccaaac    360
ggtgacaaag gaaatggtgg tatatataaa attaaaagca tttctgatta tccgggtgat    420
gaagacatct ctgtcatgaa tattgaagaa caagcagtcg aacgtggacc aaaaggcttt    480
aattttaatg aaaatgtcca agcattcaat tttgcgaaag atgctaaagt tgatgacaaa    540
attaaagtta ttggttaccc attacctgct caaaatagtt ttaaacagtt tgaatctaca    600
ggaactataa aaagaatcaa agacaatatt ttaaattttg atgcatacat tgaacccggg    660
aattcaggat caccagttct aaattctaac aatgaggtca taggtgtggt gtatggcggt    720
attggaaaaa ttggttctga atataatggt gccgtatact ttacgcctca aatcaaagat    780
tttattcaaa agcacattga acaataa                                       807
```

```
<210> SEQ ID NO 55
<211> LENGTH: 268
<212> TYPE: PRT
<213> ORGANISM: Artificial sequence
<220> FEATURE:
<223> OTHER INFORMATION: synthetic sequence

<400> SEQUENCE: 55
```

```
Leu Glu Ser Arg Glu Gln Leu Ser Val Glu Glu Tyr Glu Thr Phe Phe
1               5                   10                  15

Asn Arg Phe Asp Asn Gln Glu Phe Asp Phe Glu Arg Glu Leu Thr Gln
            20                  25                  30

Asp Pro Tyr Ser Lys Val Tyr Leu Tyr Ser Ile Glu Asp His Ile Arg
        35                  40                  45

Thr Tyr Lys Ile Glu Lys Gly Gly Gly Ser Gly Gly Gly Gly Ser
    50                  55                  60

Gly Gly Gly Gly Ser Thr Gln Val Lys Asp Thr Asn Ile Phe Pro Tyr
65                  70                  75                  80

Asn Gly Val Val Ser Phe Lys Asp Ala Thr Gly Phe Val Ile Gly Lys
                85                  90                  95

Asn Thr Ile Ile Thr Asn Lys His Val Ser Lys Asp Tyr Lys Val Gly
            100                 105                 110

Asp Arg Ile Thr Ala His Pro Asn Gly Asp Lys Gly Asn Gly Gly Ile
        115                 120                 125

Tyr Lys Ile Lys Ser Ile Ser Asp Tyr Pro Gly Asp Glu Asp Ile Ser
    130                 135                 140

Val Met Asn Ile Glu Glu Gln Ala Val Glu Arg Gly Pro Lys Gly Phe
145                 150                 155                 160

Asn Phe Asn Glu Asn Val Gln Ala Phe Asn Phe Ala Lys Asp Ala Lys
                165                 170                 175

Val Asp Asp Lys Ile Lys Val Ile Gly Tyr Pro Leu Pro Ala Gln Asn
            180                 185                 190

Ser Phe Lys Gln Phe Glu Ser Thr Gly Thr Ile Lys Arg Ile Lys Asp
        195                 200                 205

Asn Ile Leu Asn Phe Asp Ala Tyr Ile Glu Pro Gly Asn Ser Gly Ser
    210                 215                 220

Pro Val Leu Asn Ser Asn Asn Glu Val Ile Gly Val Val Tyr Gly Gly
225                 230                 235                 240

Ile Gly Lys Ile Gly Ser Glu Tyr Asn Gly Ala Val Tyr Phe Thr Pro
                245                 250                 255

Gln Ile Lys Asp Phe Ile Gln Lys His Ile Glu Gln
            260                 265
```

<210> SEQ ID NO 56
<211> LENGTH: 825
<212> TYPE: DNA
<213> ORGANISM: Artificial sequence
<220> FEATURE:
<223> OTHER INFORMATION: synthetic sequence

<400> SEQUENCE: 56

```
atgcaccacc accaccacca cctggaatcc cgtgaacaac tgtccgtcga agaatacgaa      60
accttcttta accgctttga taaccaagaa tttgatttcg aacgtgaact gacccaggat     120
ccgtattcta aagtgtatct gtacagtatc gaagatcata ttcgcacgta caaaatcgaa     180
aaaggcggtg gcggttctgg cggtggcggt agtggcggtg gcggtagcac ccaggtgaaa     240
gatacgaata tctttccgta taacggcgtg gtttcttta aagatgcgac cggcttcgtt      300
atcggtaaaa acaccatcat cacgaacaaa catgtgagca agattacaa agttggcgat      360
cgtattaccg cccacccgaa tggcgataag ggtaacggcg gtatctacaa aatcaaaagc     420
atctctgatt acccgggtga tgaagatatc agcgtgatga atattgaaga acaggcagtt     480
gaacgcggcc cgaaaggttt aacttcaat gaaaacgttc aggcgtttaa tttcgcgaaa      540
gatgccaaag tggatgataa aatcaaagtt attggctatc cgctgccggc ccagaacagc     600
tttaaacagt tcgaatctac cggtacgatc aaacgtatca agataacat cctgaacttc      660
gatgcatata ttgaaccggg caatagtggt agcccggtgc tgaacagtaa caatgaagtt     720
attggtgtgg tttatggcgg tatcggcaaa attggtagcg aatacaacgg tgctgtgtat     780
tttacgccgc agatcaaaga cttcatccag aaacatatcg aacaa                    825
```

<210> SEQ ID NO 57
<211> LENGTH: 275
<212> TYPE: PRT
<213> ORGANISM: Artificial sequence
<220> FEATURE:
<223> OTHER INFORMATION: synthetic sequence

<400> SEQUENCE: 57

Met His His His His His His Leu Glu Ser Arg Glu Gln Leu Ser Val
1               5                   10                  15

Glu Glu Tyr Glu Thr Phe Phe Asn Arg Phe Asp Asn Gln Glu Phe Asp
            20                  25                  30

Phe Glu Arg Glu Leu Thr Gln Asp Pro Tyr Ser Lys Val Tyr Leu Tyr
        35                  40                  45

Ser Ile Glu Asp His Ile Arg Thr Tyr Lys Ile Glu Lys Gly Gly Gly
    50                  55                  60

Gly Ser Gly Gly Gly Gly Ser Gly Gly Gly Gly Ser Thr Gln Val Lys
65                  70                  75                  80

Asp Thr Asn Ile Phe Pro Tyr Asn Gly Val Val Ser Phe Lys Asp Ala
                85                  90                  95

Thr Gly Phe Val Ile Gly Lys Asn Thr Ile Ile Thr Asn Lys His Val
            100                 105                 110

Ser Lys Asp Tyr Lys Val Gly Asp Arg Ile Thr Ala His Pro Asn Gly
        115                 120                 125

Asp Lys Gly Asn Gly Gly Ile Tyr Lys Ile Lys Ser Ile Ser Asp Tyr
    130                 135                 140

Pro Gly Asp Glu Asp Ile Ser Val Met Asn Ile Glu Glu Gln Ala Val
145                 150                 155                 160

Glu Arg Gly Pro Lys Gly Phe Asn Phe Asn Glu Asn Val Gln Ala Phe

```
                    165                 170                 175
Asn Phe Ala Lys Asp Ala Lys Val Asp Asp Lys Ile Lys Val Ile Gly
                180                 185                 190

Tyr Pro Leu Pro Ala Gln Asn Ser Phe Lys Gln Phe Glu Ser Thr Gly
                195                 200                 205

Thr Ile Lys Arg Ile Lys Asp Asn Ile Leu Asn Phe Asp Ala Tyr Ile
            210                 215                 220

Glu Pro Gly Asn Ser Gly Ser Pro Val Leu Asn Ser Asn Asn Glu Val
225                 230                 235                 240

Ile Gly Val Val Tyr Gly Gly Ile Gly Lys Ile Gly Ser Glu Tyr Asn
                245                 250                 255

Gly Ala Val Tyr Phe Thr Pro Gln Ile Lys Asp Phe Ile Gln Lys His
                260                 265                 270

Ile Glu Gln
        275

<210> SEQ ID NO 58
<211> LENGTH: 280
<212> TYPE: PRT
<213> ORGANISM: Artificial sequence
<220> FEATURE:
<223> OTHER INFORMATION: synthetic sequence

<400> SEQUENCE: 58

Met Arg Gly Ser His His His His His His Gly Ser Leu Glu Ser Arg
1               5                   10                  15

Glu Gln Leu Ser Val Glu Glu Tyr Glu Thr Phe Phe Asn Arg Phe Asp
            20                  25                  30

Asn Gln Glu Phe Asp Phe Glu Arg Glu Leu Thr Gln Asp Pro Tyr Ser
        35                  40                  45

Lys Val Tyr Leu Tyr Ser Ile Glu Asp His Ile Arg Thr Tyr Lys Ile
    50                  55                  60

Glu Lys Gly Gly Gly Gly Ser Gly Gly Gly Gly Ser Gly Gly Gly Gly
65                  70                  75                  80

Ser Thr Gln Val Lys Asp Thr Asn Ile Phe Pro Tyr Asn Gly Val Val
                85                  90                  95

Ser Phe Lys Asp Ala Thr Gly Phe Val Ile Gly Lys Asn Thr Ile Ile
            100                 105                 110

Thr Asn Lys His Val Ser Lys Asp Tyr Lys Val Gly Asp Arg Ile Thr
        115                 120                 125

Ala His Pro Asn Gly Asp Lys Gly Asn Gly Gly Ile Tyr Lys Ile Lys
    130                 135                 140

Ser Ile Ser Asp Tyr Pro Gly Asp Glu Asp Ile Ser Val Met Asn Ile
145                 150                 155                 160

Glu Glu Gln Ala Val Glu Arg Gly Pro Lys Gly Phe Asn Phe Asn Glu
                165                 170                 175

Asn Val Gln Ala Phe Asn Phe Ala Lys Asp Ala Lys Val Asp Asp Lys
            180                 185                 190

Ile Lys Val Ile Gly Tyr Pro Leu Pro Ala Gln Asn Ser Phe Lys Gln
        195                 200                 205

Phe Glu Ser Thr Gly Thr Ile Lys Arg Ile Lys Asp Asn Ile Leu Asn
    210                 215                 220

Phe Asp Ala Tyr Ile Glu Pro Gly Asn Ser Gly Ser Pro Val Leu Asn
225                 230                 235                 240

Ser Asn Asn Glu Val Ile Gly Val Val Tyr Gly Gly Ile Gly Lys Ile
```

245                 250                 255
Gly Ser Glu Tyr Asn Gly Ala Val Tyr Phe Thr Pro Gln Ile Lys Asp
            260                 265                 270

Phe Ile Gln Lys His Ile Glu Gln
        275                 280

<210> SEQ ID NO 59
<211> LENGTH: 45
<212> TYPE: DNA
<213> ORGANISM: Artificial sequence
<220> FEATURE:
<223> OTHER INFORMATION: synthetic sequence

<400> SEQUENCE: 59
ggaggtggcg gttcaggagg tggaggatct ggaggcggtg gatca            45

<210> SEQ ID NO 60
<211> LENGTH: 15
<212> TYPE: PRT
<213> ORGANISM: Artificial sequence
<220> FEATURE:
<223> OTHER INFORMATION: synthetic sequence

<400> SEQUENCE: 60

Gly Gly Gly Gly Ser Gly Gly Gly Gly Ser Gly Gly Gly Gly Ser
1               5                   10                  15

<210> SEQ ID NO 61
<211> LENGTH: 5
<212> TYPE: PRT
<213> ORGANISM: Artificial sequence
<220> FEATURE:
<223> OTHER INFORMATION: synthetic sequence

<400> SEQUENCE: 61

Glu Arg Lys Tyr Lys
1               5

<210> SEQ ID NO 62
<211> LENGTH: 10
<212> TYPE: PRT
<213> ORGANISM: Artificial sequence
<220> FEATURE:
<223> OTHER INFORMATION: synthetic sequence

<400> SEQUENCE: 62

Glu Ala Ala Ala Lys Glu Ala Ala Ala Lys
1               5                   10

<210> SEQ ID NO 63
<211> LENGTH: 5
<212> TYPE: PRT
<213> ORGANISM: Artificial sequence
<220> FEATURE:
<223> OTHER INFORMATION: synthetic sequence

<400> SEQUENCE: 63

Glu Ala Ala Ala Lys
1               5

<210> SEQ ID NO 64
<211> LENGTH: 15
<212> TYPE: PRT
<213> ORGANISM: Artificial sequence
<220> FEATURE:
<223> OTHER INFORMATION: synthetic sequence

```
<400> SEQUENCE: 64

Glu Ala Ala Ala Lys Glu Ala Ala Ala Lys Glu Ala Ala Ala Lys
1               5                   10                  15

<210> SEQ ID NO 65
<211> LENGTH: 10
<212> TYPE: PRT
<213> ORGANISM: Artificial sequence
<220> FEATURE:
<223> OTHER INFORMATION: synthetic sequence

<400> SEQUENCE: 65

Glu Arg Lys Tyr Lys Glu Arg Lys Tyr Lys
1               5                   10

<210> SEQ ID NO 66
<211> LENGTH: 15
<212> TYPE: PRT
<213> ORGANISM: Artificial sequence
<220> FEATURE:
<223> OTHER INFORMATION: synthetic sequence

<400> SEQUENCE: 66

Glu Arg Lys Tyr Lys Glu Arg Lys Tyr Lys Glu Arg Lys Tyr Lys
1               5                   10                  15

<210> SEQ ID NO 67
<211> LENGTH: 5
<212> TYPE: PRT
<213> ORGANISM: Artificial sequence
<220> FEATURE:
<223> OTHER INFORMATION: synthetic sequence

<400> SEQUENCE: 67

Gly Gly Gly Gly Ser
1               5

<210> SEQ ID NO 68
<211> LENGTH: 10
<212> TYPE: PRT
<213> ORGANISM: Artificial sequence
<220> FEATURE:
<223> OTHER INFORMATION: synthetic sequence

<400> SEQUENCE: 68

Gly Gly Gly Gly Ser Gly Gly Gly Gly Ser
1               5                   10

<210> SEQ ID NO 69
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 69
```

Xaa Pro Xaa Pro Xaa Pro
1               5

<210> SEQ ID NO 70
<211> LENGTH: 12
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 70

Xaa Pro Xaa Pro Xaa Pro Xaa Pro Xaa Pro Xaa Pro
1               5                   10

<210> SEQ ID NO 71
<211> LENGTH: 612
<212> TYPE: DNA
<213> ORGANISM: Staphylococcus aureus

<400> SEQUENCE: 71
atgttcaaaa aaaatgactc gaaaaattca attctattaa aatctattct atcgctaggt      60
atcatctatg ggggaacatt tggaatatat ccaaaagcag acgcgtcaac acaaaattcc     120
ccaagtgtac aagataaaca attccaaaaa gttgaagaag taccaaataa ttcagaaaaa     180
gctttggtta aaaaacttta cgatagatac agccaaaata caataaacgg aaaatctaat     240
aaatctagga attgggttta ttcagagaga cctttaaatg aaaaccaagt tcgtataaat     300
ttagaaggaa catacagagt tgctgataga gtatatacac taagagaaa tattactctt      360 aataaagaag ttgtcacttt aaaggaattg gatcatatca taagatttgc tcatatttct     420
tatggcttat atatgggaga acatttgcct aaaggtaaca tcgtcataaa tacaaaagat     480
ggcggtaaat atacattaga gtcgcataaa gagctacaaa aagatagga aaatgtaaaa      540 attaatacag ccgatataaa aaatgtaact ttcaaacttg tgaaaagtgt taatgacatt     600
gaacaagttt ga                                                        612

<210> SEQ ID NO 72
<211> LENGTH: 612
<212> TYPE: DNA
<213> ORGANISM: Staphylococcus aureus

<400> SEQUENCE: 72

```
atgttcaaaa aaaatgactc gaaaaattca attctattaa aatctattct atcgctaggt    60
atcatctatg ggggaacatt tggaatatat ccaaaagcag acgcgtcaac acaaaattcc   120
ccaagtgtac aagataaaca attccaaaaa gttgaagaag taccaaataa ttcagaaaaa   180
gctttggtta aaaaacttta cgatagatac agccaaaata caataaacgg aaaatctaat   240
aaatctagga attgggttta ttcagagaga cctttaaatg aaaaccaagt tcgtataaat   300
ttagaaggaa catacagagt tgctgataga gtatatacac taagagaaa tattactctt   360
aataaagaag ttgtcacttt aaaggaattg gatcatatca taagatttgc tcatatttct   420
tatggcttat atatgggaga acatttgcct aaaggtaaca tcgtcataaa tacaaaagat   480
ggcggtaaat atacattaga gtcgcataaa gagctacaaa aagataggga aaatgtaaaa   540
attaatacag ccgatataaa aaatgtaact ttcaaacttg tgaaaagtgt taatgacatt   600
gaacaagttt ga                                                      612
```

<210> SEQ ID NO 73
<211> LENGTH: 612
<212> TYPE: DNA
<213> ORGANISM: Staphylococcus aureus

<400> SEQUENCE: 73

```
atgttcaaaa aatatgactc aaaaaattca atcgtattaa aatctattct atcgctaggt    60
atcatctatg ggggaacatt tggaatatat ccaaaagcag acgcgtcaac acaaaattcc   120
tcaagtgtac aagataaaca attacaaaaa gttgaagaag taccaaataa ttcagaaaaa   180
gctttggtta aaaaacttta cgatagatac agcaaggata caataaatgg aaaatctaat   240
aaatctagga attgggttta ttcagagaga cctttaaatg aaaaccaagt tcgtatacat   300
ttagaaggaa catacacagt tgctggcaga gtgtatacac taagaggaa tattactctt   360
aataaagaag ttgtcacttt aaaagaattg gatcatatca taagatttgc tcatatttcc   420
tatggcttgt atatgggaga acatttgcct aaaggtaaca tcgtcataaa tacaaaagat   480
ggtggtaaat atacattaga gtcgcataaa gagctacaaa aagataggga aaatgtaaaa   540
attaatacag ccgatataaa aaatgtaact ttcaaacttg tgaaaagtgt taatgacatt   600
gaacaagttt ga                                                      612
```

<210> SEQ ID NO 74
<211> LENGTH: 612
<212> TYPE: DNA
<213> ORGANISM: Staphylococcus aureus

<400> SEQUENCE: 74

```
atgttcaaaa aatatgactc aaaaaattca atcgtattaa aatctattct atcgctaggt    60
atcatctatg ggggaacatt tggaatatat ccaaaagcag acgcgtcaac acaaaattcc   120
tcaagtgtac aagataaaca attcaaaaaa gttgaagaag taccaaataa ttcagaaaaa   180
gctttggtta aaaaacttta cgatagatac agcaaggata caataaatgg aaaatctaat   240
aaatctagga attgggttta ttcagagaga cctttaaatg aaaaccaagt tcgtatacat   300
ttagaaggaa catacacagt tgctggcaga gtgtatacac taagaggaa tattactctt   360
aataaagaag ttgtcacttt aaaagaattg gatcatatca taagatttgc tcatatttcc   420
tatggcttgt atatgggaga acatttgcct aaaggtaaca tcgtcataaa tacaaaagat   480
ggtggtaaat atacattaga gtcgcataaa gagctacaaa aagataggga aaatgtaaaa   540
attaatacag ccgatataaa aaatgtaact ttcaaacttg tgaaaagtgt taatgacatt   600
```

```
gaacaagttt ga                                                    612

<210> SEQ ID NO 75
<211> LENGTH: 612
<212> TYPE: DNA
<213> ORGANISM: Staphylococcus aureus

<400> SEQUENCE: 75
atgttcaaaa aatatgactc aaaaaattca atcgtattaa aatctattct atcgctaggt     60
atcatctatg ggggaacatt tggaatatat ccaaaagcag acgcgtcaac acaaaattcc    120
tcaagtgtac aagataaaca attacaaaaa gttgaagaag taccaaataa ttcagaaaaa    180
gctttggtta aaaaacttta cgatagatac agcaaggata caataaatgg aaaatctaat    240
aaatctagga attgggttta ttcagagaga cctttaaatg aaaaccaagt tcgtatacat    300
ttagaaggaa catacacagt tgctggcaga gtgtatacac ctaagaggaa tattactctt    360
aataaagaag ttgtcacttt aaaagaattg gatcatatca taagatttgc tcatatttcc    420
tatggcttgt atatgggaga acatttgcct aaaggtaaca tcgtcataaa tacaaaagat    480
ggtggtaaat atacattaga gtcgcataaa gagctacaaa aagataggga aaatgtaaaa    540
attaatacag ccgatataaa aaatgtaact ttcaaacttg tgaaagtgt taatgacatt    600 gaacaagttt ga                                                    612

<210> SEQ ID NO 76
<211> LENGTH: 612
<212> TYPE: DNA
<213> ORGANISM: Staphylococcus aureus

<400> SEQUENCE: 76
atgttcaaaa aatatgactc aaaaaattca atcgtattaa aatctattct atcgctaggt     60
atcatctatg ggggaacatt tggaatatat ccaaaagcag acgcgtcaac acaaaattcc    120
tcaagtgtac aagataaaca attacaaaaa gttgaagaag taccaaataa ttcagaaaaa    180
gctttggtta aaaaacttta cgatagatac agcaaggata caataaatgg aaaatctaat    240
aaatctagga attgggttta ttcagagaga cctttaaatg aaaaccaagt tcgtatacat    300
ttagaaggaa catacacagt tgctgataga gtatatacac ctaagagaaa tattactctt    360
aataaagaag ttgtcacttt aaaggaattg gatcatatca taagatttgc tcatatttct    420
tatggcttat atatgggaga acatttgcct aaaggtaaca tcgtcataaa tacaaaagat    480
ggcggtaaat atacattaga gtcgcataaa gagctacaaa aagataggga aaatgtaaaa    540
attaatacag ccgatataaa aaatgtaact ttcaaacttg tgaaagtgt taatgacatt    600 gaacaagttt ga                                                    612

<210> SEQ ID NO 77
<211> LENGTH: 612
<212> TYPE: DNA
<213> ORGANISM: Staphylococcus aureus

<400> SEQUENCE: 77
atgttcaaaa aatatgactc aaaaaattca atcgtattaa aatctattct atcgctaggt     60
atcatctatg ggggaacatt tggaatatat ccaaaagcag acgcgtcaac acaaaattcc    120
tcaagtgtac aagataaaca attacaaaaa gttgaagaag taccaaataa ttcagaaaaa    180
gctttggtta aaaaacttta cgatagatac agcaaggata caataaatgg aaaatctaat    240
```

```
aaatctagga attgggttta ttcagagaga ccttταaatg aaaaccaagt tcgtatacat    300
ttagaaggaa catacacagt tgctgataga gtatatacac ctaagagaaa tattactctt    360
aataaagaag ttgtcacttt aaaggaattg gatcatatca taagatttgc tcatatttct    420
tatggcttat atatgggaga acatttgcct aaaggtaaca tcgtcataaa tacaaaagat    480
ggcggtaaat atacattaga gtcgcataaa gagctacaaa aagataggga aaatgtaaaa    540
attaatacag ccgatataaa aaatgtaact ttcaaacttg tgaaaagtgt taatgacatt    600
gaacaagttt ga                                                        612

<210> SEQ ID NO 78
<211> LENGTH: 612
<212> TYPE: DNA
<213> ORGANISM: Staphylococcus aureus

<400> SEQUENCE: 78
atgttcaaaa aatatgactc aaaaaattca atcgtattaa aatctattct atcgctaggt     60
atcatctatg ggggaacatt tggaatatat ccaaaagcag acgcgtcaac acaaaattcc    120
tcaagtgtac aagataaaca attacaaaaa gttgaagaag taccaaataa ttcagaaaaa    180
gctttggtta aaaaacttta cgatagatac agcaaggata caataaatgg aaaatctaat    240
aaatctagga attgggttta ttcagagaga ccttταaatg aaaaccaagt tcgtatacat    300
ttagaaggaa catacacagt tgctgataga gtatatacac ctaagagaaa tattactctt    360
aataaagaag ttgtcacttt aaaggaattg gatcatatca taagatttgc tcatatttct    420
tatggcttat atatgggaga acatttgcct aaaggtaaca tcgtcataaa tacaaaagat    480
ggcggtaaat atacattaga gtcgcataaa gagctacaaa aagataggga aaatgtaaaa    540
attaatacag ccgatataaa aaatgtaact ttcaaacttg tgaaaagtgt taatgacatt    600
gaacaagttt ga                                                        612

<210> SEQ ID NO 79
<211> LENGTH: 612
<212> TYPE: DNA
<213> ORGANISM: Staphylococcus aureus

<400> SEQUENCE: 79
atgttcaaaa aatatgactc aaaaaattca atcgtattaa aatctattct atcgctaggt     60
atcatctatg ggggaacatt tggaatatat ccaaaagcag acgcgtcaac acaaaattcc    120
tcaagtgtac aagataaaca attacaaaaa gttgaagaag taccaaataa ttcagaaaaa    180
gctttggtta aaaaacttta cgatagatac agcaaggata caataaatgg aaaatctaat    240
aaatctagga attgggttta ttcagagaga ccttταaatg aaaaccaagt tcgtatacat    300
ttagaaggaa catacacagt tgctgataga gtatatacac ctaagagaaa tattactctt    360
aataaagaag ttgtcacttt aaaggaattg gatcatatca taagatttgc tcatatttct    420
tatggcttat atatgggaga acatttgcct aaaggtaaca tcgtcataaa tacaaaagat    480
ggcggtaaat atacattaga gtcgcataaa gagctacaaa aagataggga aaatgtaaaa    540
attaatacag ccgatataaa aaatgtaact ttcaaacttg tgaaaagtgt taatgacatt    600
gaacaagttt ga                                                        612

<210> SEQ ID NO 80
<211> LENGTH: 612
<212> TYPE: DNA
<213> ORGANISM: Staphylococcus aureus
```

<400> SEQUENCE: 80

```
atgttcaaaa aatatgactc aaaaaattca atcgtattaa atctattct atcgctaggt      60
atcatctatg ggggaacatt tggaatatat ccaaaagcag acgcgtcaac acaaaattcc    120
tcaagtgtac aagataaaca attacaaaaa gttgaagaag taccaaataa ttcagaaaaa    180
gctttggtta aaaaacttta cgatagatac agcaaggata caataaatgg aaaatctaat    240
aaatctagga attgggttta ttcagagaga cctttaaatg aaaaccaagt tcgtatacat    300
ttagaaggaa catacacagt tgctgataga gtatatacac taagagaaaa tattactctt    360
aataaagaag ttgtcacttt aaaggaattg gatcatatca taagatttgc tcatatttct    420
tatggcttat atatgggaga acatttgcct aaaggtaaca tcgtcataaa tacaaaagat    480
ggcggtaaat atacattaga gtcgcataaa gagctacaaa aagatagga  aaatgtaaaa    540
attaatacag ccgatataaa aaatgtaact ttcaaacttg tgaaaagtgt taatgacatt    600
gaacaagttt ga                                                         612
```

<210> SEQ ID NO 81
<211> LENGTH: 612
<212> TYPE: DNA
<213> ORGANISM: Staphylococcus aureus

<400> SEQUENCE: 81

```
atgttcaaaa aatatgactc aaaaaattca atcgtattaa atctattct atcgctaggt      60
atcatctatg ggggaacatt tggaatatat ccaaaagcag acgcgtcaac acaaaattcc    120
tcaagtgtac aagataaaca attccaaaaa gttgaagaag taccaaataa ttcagaaaaa    180
gctttggtta aaaaactgta cgatagatac agccaaaata caataaacgg aaaatctaat    240
aaagctagga attgggttta ttcagagaga cctttaaatg aaaatcaagt tcgcatacat    300
ttagaaggta catacagagt tgctgataga gtgtatacac taagaggaa  cattactctt    360
aataaagaag ttgtcacttt aaaagaattg gatcatatca taagatttgc tcatatttct    420
tatggcttat atatgggaga acatttgcct aaaggtaaca tcgtcataaa tacaaagaat    480
ggcggtaaat atacattaga gtcgcacaaa gagttacaaa agaatagga  aaatgtagaa    540
attaatactg atgatataaa aaatgtaact ttcgaacttg tgaaaagtgt taatgacatt    600
gaacaagttt ga                                                         612
```

<210> SEQ ID NO 82
<211> LENGTH: 203
<212> TYPE: PRT
<213> ORGANISM: Staphylococcus aureus

<400> SEQUENCE: 82

```
Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Val Gln Asp Lys Gln Leu
        35                  40                  45

Gln Lys Val Glu Glu Val Pro Asn Asn Ser Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
```

```
            85                  90                  95
Val Arg Ile His Leu Glu Gly Thr Tyr Thr Val Ala Gly Arg Val Tyr
            100                 105                 110

Thr Pro Lys Arg Asn Ile Thr Leu Asn Lys Glu Val Val Thr Leu Lys
            115                 120                 125

Glu Leu Asp His Ile Ile Arg Phe Ala His Ile Ser Tyr Gly Leu Tyr
            130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
            195                 200
```

<210> SEQ ID NO 83
<211> LENGTH: 203
<212> TYPE: PRT
<213> ORGANISM: Staphylococcus aureus

<400> SEQUENCE: 83

```
Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Val Gln Asp Lys Gln Leu
            35                  40                  45

Gln Lys Val Glu Glu Val Pro Asn Asn Ser Glu Lys Ala Leu Val Lys
50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
            85                  90                  95

Val Arg Ile His Leu Glu Gly Thr Tyr Thr Val Ala Gly Arg Val Tyr
            100                 105                 110

Thr Pro Lys Arg Asn Ile Thr Leu Asn Lys Glu Val Val Thr Leu Lys
            115                 120                 125

Glu Leu Asp His Ile Ile Arg Phe Ala His Ile Ser Tyr Gly Leu Tyr
            130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
            195                 200
```

<210> SEQ ID NO 84
<211> LENGTH: 203
<212> TYPE: PRT
<213> ORGANISM: Staphylococcus aureus

<400> SEQUENCE: 84

Met Phe Lys Lys Tyr Asp Ser Lys Asn Ser Ile Val Leu Lys Ser Ile

```
            1               5                  10                 15
Leu Ser Leu Gly Ile Ile Tyr Gly Gly Thr Phe Gly Ile Tyr Pro Lys
            20                 25                 30

Ala Asp Ala Ser Thr Gln Asn Ser Ser Val Gln Asp Lys Gln Leu
            35                 40                 45

Gln Lys Val Glu Glu Val Pro Asn Asn Ser Glu Lys Ala Leu Val Lys
            50                 55                 60

Lys Leu Tyr Asp Arg Tyr Ser Lys Asp Thr Ile Asn Gly Lys Ser Asn
65                  70                 75                  80

Lys Ser Arg Asn Trp Val Tyr Ser Glu Arg Pro Leu Asn Glu Asn Gln
                85                 90                  95

Val Arg Ile His Leu Glu Gly Thr Tyr Thr Val Ala Gly Arg Val Tyr
                100                105                 110

Thr Pro Lys Arg Asn Ile Thr Leu Asn Lys Glu Val Val Thr Leu Lys
                115                120                 125

Glu Leu Asp His Ile Ile Arg Phe Ala His Ile Ser Tyr Gly Leu Tyr
            130                135                 140

Met Gly Glu His Leu Pro Lys Gly Asn Ile Val Ile Asn Thr Lys Asp
145                 150                155                 160

Gly Gly Lys Tyr Thr Leu Glu Ser His Lys Glu Leu Gln Lys Asp Arg
                165                170                 175

Glu Asn Val Lys Ile Asn Thr Ala Asp Ile Lys Asn Val Thr Phe Lys
                180                185                 190

Leu Val Lys Ser Val Asn Asp Ile Glu Gln Val
                195                200
```

<210> SEQ ID NO 85
<211> LENGTH: 203
<212> TYPE: PRT
<213> ORGANISM: Staphylococcus aureus

<400> SEQUENCE: 85

```
Met Phe Lys Lys Tyr Asp Ser Lys Asn Ser Ile Val Leu Lys Ser Ile
1               5                  10                 15

Leu Ser Leu Gly Ile Ile Tyr Gly Gly Thr Phe Gly Ile Tyr Pro Lys
            20                 25                 30

Ala Asp Ala Ser Thr Gln Asn Ser Ser Val Gln Asp Lys Gln Leu
            35                 40                 45

Gln Lys Val Glu Glu Val Pro Asn Asn Ser Glu Lys Ala Leu Val Lys
            50                 55                 60

Lys Leu Tyr Asp Arg Tyr Ser Lys Asp Thr Ile Asn Gly Lys Ser Asn
65                  70                 75                  80

Lys Ser Arg Asn Trp Val Tyr Ser Glu Arg Pro Leu Asn Glu Asn Gln
                85                 90                  95

Val Arg Ile His Leu Glu Gly Thr Tyr Thr Val Ala Asp Arg Val Tyr
                100                105                 110

Thr Pro Lys Arg Asn Ile Thr Leu Asn Lys Glu Val Val Thr Leu Lys
                115                120                 125

Glu Leu Asp His Ile Ile Arg Phe Ala His Ile Ser Tyr Gly Leu Tyr
            130                135                 140

Met Gly Glu His Leu Pro Lys Gly Asn Ile Val Ile Asn Thr Lys Asp
145                 150                155                 160

Gly Gly Lys Tyr Thr Leu Glu Ser His Lys Glu Leu Gln Lys Asp Arg
                165                170                 175
```

Glu Asn Val Lys Ile Asn Thr Ala Asp Ile Lys Asn Val Thr Phe Lys
            180                 185                 190

Leu Val Lys Ser Val Asn Asp Ile Glu Gln Val
            195                 200

<210> SEQ ID NO 86
<211> LENGTH: 203
<212> TYPE: PRT
<213> ORGANISM: Staphylococcus aureus

<400> SEQUENCE: 86

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Val Gln Asp Lys Gln Leu
            35                  40                  45

Gln Lys Val Glu Glu Val Pro Asn Asn Ser Glu Lys Ala Leu Val Lys
50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
            85                  90                  95

Val Arg Ile His Leu Glu Gly Thr Tyr Thr Val Ala Ser Arg Val Tyr
            100                 105                 110

Thr Pro Lys Arg Asn Ile Thr Leu Asn Lys Glu Val Val Thr Leu Lys
            115                 120                 125

Glu Leu Asp His Ile Ile Arg Phe Ala His Ile Ser Tyr Gly Leu Tyr
            130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
            165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
            195                 200

<210> SEQ ID NO 87
<211> LENGTH: 203
<212> TYPE: PRT
<213> ORGANISM: Staphylococcus aureus

<400> SEQUENCE: 87

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Val Gln Asp Lys Gln Leu
            35                  40                  45

Gln Lys Val Glu Glu Val Pro Asn Asn Ser Glu Lys Ala Leu Val Lys
50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
            85                  90                  95

Val Arg Ile His Leu Glu Gly Thr Tyr Thr Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200

<210> SEQ ID NO 88
<211> LENGTH: 203
<212> TYPE: PRT
<213> ORGANISM: Staphylococcus aureus

<400> SEQUENCE: 88

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200

<210> SEQ ID NO 89
<211> LENGTH: 203
<212> TYPE: PRT
<213> ORGANISM: Staphylococcus aureus

<400> SEQUENCE: 89

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200

<210> SEQ ID NO 90
<211> LENGTH: 203
<212> TYPE: PRT
<213> ORGANISM: Staphylococcus aureus

<400> SEQUENCE: 90

Met Phe Lys Lys Asn Asp Ser Lys Asn Ser Ile Leu Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Pro Ser Val Gln Asp Lys Gln Phe
        35                  40                  45

Gln Lys Val Glu Glu Val Pro Asn Asn Ser Glu Lys Ala Leu Val Lys
    50                  55                  60

Lys Leu Tyr Asp Arg Tyr Ser Gln Asn Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile Asn Leu Glu Gly Thr Tyr Arg Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200

<210> SEQ ID NO 91
<211> LENGTH: 203
<212> TYPE: PRT
<213> ORGANISM: Staphylococcus aureus

<400> SEQUENCE: 91

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Val Gln Asp Lys Gln Phe
        35                  40                  45

Gln Lys Val Glu Glu Val Pro Asn Asn Ser Glu Lys Ala Leu Val Lys
    50                  55                  60

Lys Leu Tyr Asp Arg Tyr Ser Gln Asn Thr Ile Asn Gly Lys Ser Asn
65                  70                  75                  80

Lys Ala Arg Asn Trp Val Tyr Ser Glu Arg Pro Leu Asn Glu Asn Gln
                85                  90                  95

Val Arg Ile His Leu Glu Gly Thr Tyr Arg Val Ala Asp Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asn
145                 150                 155                 160

Gly Gly Lys Tyr Thr Leu Glu Ser His Lys Glu Leu Gln Lys Asn Arg
                165                 170                 175

Glu Asn Val Glu Ile Asn Thr Asp Asp Ile Lys Asn Val Thr Phe Glu
            180                 185                 190

Leu Val Lys Ser Val Asn Asp Ile Glu Gln Val
        195                 200

<210> SEQ ID NO 92
<211> LENGTH: 203
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:

```
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (201)..(203)
<223> OTHER INFORMATION: Xaa can be any naturally occurring amino acid

<400> SEQUENCE: 92

Met Phe Lys Lys Xaa Asp Ser Lys Asn Ser Ile Xaa Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Xaa Ser Val Gln Asp Lys Gln Xaa
        35                  40                  45

Gln Lys Val Glu Glu Val Pro Asn Asn Ser Glu Lys Ala Leu Val Lys
    50                  55                  60

Lys Leu Tyr Asp Arg Tyr Ser Xaa Xaa Thr Ile Asn Gly Lys Ser Asn
65                  70                  75                  80

Lys Xaa Arg Asn Trp Val Tyr Ser Glu Arg Pro Leu Asn Glu Asn Gln
                85                  90                  95

Val Arg Ile Xaa Leu Glu Gly Thr Tyr Xaa Val Ala Xaa Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Xaa
145                 150                 155                 160

Gly Gly Lys Tyr Thr Leu Glu Ser His Lys Glu Leu Gln Lys Xaa Arg
                165                 170                 175

Glu Asn Val Xaa Ile Asn Thr Xaa Asp Ile Lys Asn Val Thr Phe Xaa
            180                 185                 190

Leu Val Lys Ser Val Asn Asp Ile Xaa Xaa Xaa
```

-continued

```
            195                 200
```

<210> SEQ ID NO 93
<211> LENGTH: 14
<212> TYPE: PRT
<213> ORGANISM: Staphylococcus aureus

<400> SEQUENCE: 93

Gln Asn Thr Ile Asn Gly Lys Ser Asn Lys Ser Arg Asn Trp
1               5                   10

<210> SEQ ID NO 94
<211> LENGTH: 14
<212> TYPE: PRT
<213> ORGANISM: Staphylococcus aureus

<400> SEQUENCE: 94

Gln Asn Thr Ile Asn Gly Lys Ser Asn Lys Ala Arg Asn Trp
1               5                   10

<210> SEQ ID NO 95
<211> LENGTH: 15
<212> TYPE: PRT
<213> ORGANISM: Staphylococcus aureus

<400> SEQUENCE: 95

Lys Asn Gly Gly Lys Tyr Thr Leu Glu Ser His Lys Glu Leu Gln
1               5                   10                  15

<210> SEQ ID NO 96
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 96

Xaa Xaa Thr Ile Asn Gly Lys Ser Asn Lys Xaa Arg Asn Trp
1               5                   10

<210> SEQ ID NO 97
<211> LENGTH: 15
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 97

Lys Xaa Gly Gly Lys Tyr Thr Leu Glu Ser His Lys Glu Leu Gln
1               5                   10                  15

<210> SEQ ID NO 98
<211> LENGTH: 1755
<212> TYPE: DNA
<213> ORGANISM: Staphylococcus aureus

<400> SEQUENCE: 98

```
atgacagagt catatccaat tattaaggaa ggctcacaag tcggaagcta ctttctattt      60
ttcatcataa ttgcattttt gttatatgcc aatgtgttat ttattaaacg acgaagttat     120
gagcttgcat tatatcaaac attaggttta tctaaattca acattatttta tatactaatg    180
ctcgaacaat tactaatatt tataattacg gcaatattag gtattattat tggtattttt     240
ggttcaaaac tgttattaat gattgtcttt acattattag gaattaaaga aaaggttcca     300
attatttta gtttgagggc ggtatttgaa acattaatgt taatcggtgt cgcttatttt      360
ttaacctctg ctcaaaattt tatattagtg ttcaaacaat ctatttcaca gatgtcaaag     420
aataaccagg ttaaagaaac aaatcataat aaaattacat tgaagaggt tgttttaggc      480
atcttaggta tagtattgat tatcacagga tactatctat ctttgaacat tgttcaatat    540
tatgattcta tcggtatact tatgtttatt ttattgtcaa ctgtgattgg ggcatactta    600
ttttttaaaa gctctgtttc tctagttttt aaaatggtga agaagtttag aaaaggtgtt   660
ataagtgtaa atgatgtcat gttctcatca tctattatgt atcgtattaa gaaaaatgct  720
ttttcactta cggtcatggc aatcatttca gcgattactg tttcagttct ttgctttgct   780
gctataagta gagcgtcctt atcaagtgaa ataaaatata ctgcaccaca cgacgttaca  840
attaaagacc aacaaaaagc taatcaatta gcaagtgaat aaacaatca aaaaattcct    900
cattttata attataaaga agtaattcat acgaaattgt ataagataa tttatttgat   960
gtaaaagcga agaaccata caatgtaaca attactagtg ataaatatat ccctaatact   1020
gatttgaaac gtggacaagc tgatttgttt gtagcggaag gttctatcaa agatttagtg   1080
aaacataaga agcatggtaa ggcaattata ggaacgaaaa acatcatgt taatattaag   1140
ttacggaaag atattaataa aatctatttt atgacagatg ttgatttagg tggaccaacg   1200
tttgtcttaa atgacaaaga ctatcaagaa ataagaaagt atacaaaagc aaagcatatc   1260
gtctctcaat ttggattcga tttgaaacat aaaaaagatg ctttagcatt agaaaaagtg   1320
aaaaataaag ttgataaatc tattaaaaca agaagtgaag cgataagctc aatatcaagt   1380
ttaaccggaa tattattatt tgtaacatca tttttaggta ttacattctt gattgctgta   1440
tgttgcatta tatacattaa gcaaatagat gaaaccgaag atgagttaga gaattatagt   1500
atattgagaa agcttggatt tacacaaaaa gatatggcaa ggggactaaa gtttaaaatt   1560
atgtttaatt ttgggttacc tttagttatt gcactatcac atgcatattt tacatcatta   1620
gcatatatga aattaatggg tacaacgaat caaataccgg ttttcatagt aatgggatta   1680
tacatttgta tgtatgctgt ttttgcagtg acggcttata atcattccaa gcgaacaatt   1740
agacattcca tataa                                                   1755
```

<210> SEQ ID NO 99
<211> LENGTH: 1755
<212> TYPE: DNA
<213> ORGANISM: Staphylococcus aureus

<400> SEQUENCE: 99

```
atgacagagt catatccaat tattaaggaa ggctcacaag tcggaagcta ctttctattt      60
ttcatcataa ttgcattttt gttatatgcc aatgtgttat ttattaaacg acgaagttat     120
gagcttgcat tatatcaaac attaggttta tctaaattca acattatttta tatactaatg    180
ctcgaacaat tactaatatt tataattacg gcaatattag gtattattat tggtattttt     240
ggttcaaaac tgttattaat gattgtcttt acattattag gaattaaaga aaaggttcca     300
```

-continued

```
attattttta gtttgagggc ggtatttgaa acattaatgt taatcggtgt cgcttatttt      360
ttaacctctg ctcaaaattt tatattagtg ttcaaacaat ctatttcaca gatgtcaaag      420
aataaccagg ttaaagaaac aaatcataat aaaattacat tgaagaggt tgttttaggc       480
atcttaggta tagtattgat tatcacagga tactatctat ctttgaacat tgttcaatat      540
tatgattcta tcggtatact tatgtttatt ttattgtcaa ctgtgattgg ggcatactta      600
tttttaaaa gctctgtttc tctagttttt aaaatggtga agaagtttag aaaaggtgtt       660
ataagtgtaa atgatgtcat gttctcatca tctattatgt atcgtattaa gaaaaatgct      720
ttttcactta cggtcatggc aatcatttca gcgattactg tttcagttct ttgctttgct      780
gctataagta gagcgtcctt atcaagtgaa ataaaatata ctgcaccaca cgacgttaca      840
attaaagacc aacaaaaagc taatcaatta gcaagtgaat aaacaatca aaaaattcct       900
cattttata attataaaga agtaattcat acgaaattgt ataagataa tttatttgat        960
gtaaaagcga aagaaccata caatgtaaca attactagtg ataaatatat ccctaatact     1020
gatttgaaac gtggacaagc tgatttgttt gtagcggaag gttctatcaa agatttagtg     1080
aaacataaga agcatggtaa ggcaattata ggaacgaaaa aacatcatgt taatattaag     1140
ttacggaaag atattaataa aatctatttt atgacagatg ttgatttagg tggaccaacg     1200
tttgtcttaa atgacaaaga ctatcaagaa ataagaaagt atacaaaagc aaagcatatc     1260
gtctctcaat ttggattcga tttgaaacat aaaaaagatg ctttagcatt agaaaaagtg     1320
aaaaataaag ttgataaatc tattaaaaca agaagtgaag cgataagctc aatatcaagt     1380
ttaaccggaa tattattatt tgtaacatca ttttaggta ttacattctt gattgctgta      1440
tgttgcatta tatacattaa gcaaatagat gaaaccgaag atgagttaga gaattatagt     1500
atattgagaa agcttggatt tacacaaaaa gatatggcaa ggggactaaa gtttaaaatt     1560
atgtttaatt ttgggttacc tttagttatt gtactatcac atgcatattt tacatcatta     1620
gcatatatga aattaatggg tacaacgaat caaataccgg ttttcatagt aatgggatta     1680
tacatttgta tgtatgctgt ttttgcagtg acggcttata atcattccaa gcgaacaatt     1740
agacattcca tataa                                                      1755
```

<210> SEQ ID NO 100
<211> LENGTH: 1755
<212> TYPE: DNA
<213> ORGANISM: Staphylococcus aureus

<400> SEQUENCE: 100

```
atgacagagt catatccaat tattaaggaa ggctcacaag tcggaagcta ctttctattt       60
ttcatcataa ttgcattttt gttatatgcc aatgtgttat ttattaaacg acgaagttat      120
gagcttgcat tatatcaaac attaggttta tctaaattca acattattta tatactaatg      180
ctcgaacaat tactaatatt tataattacg gcaatattag gtattattat ggtattttt       240
ggttcaaaac tgttattaat gattgtcttt acattattag gaattaaaga aaaggttcca      300
attatttta gtttgagggc ggtatttgaa acattaatgt taatcggtgt cgcttatttt       360
ttaacctctg ctcaaaattt tatattagtg ttcaaacaat ctatttcaca gatgtcaaag      420
aataaccagg ttaaagaaac aaatcataat aaaattacat tgaagaggt tgttttaggc       480
atcttaggta tagtattgat taccacagga tactatctat ctttgaacat tgttcaatat      540
tatgattcta tcggtatact tatgtttatt ttattgtcaa ctgtgattgg ggcatactta      600
```

```
tttttttaaaa gctctgtttc tctagttttt aaaatggtga agaagtttag aaaaggtgtt    660
ataagtgtaa atgatgtcat gttctcatca tctattatgt atcgtattaa gaaaaatgct    720
ttttcactta cggtcatggc aatcatttca gcgattactg tttcagttct ttgctttgct    780
gctataagta gagcgtcctt atcaagtgaa ataaaatata ctgcaccaca cgacgttaca    840
attaaagacc aacaaaaagc taatcaatta gcaagtgaat taaacaatca aaaaattcct    900 cattttata attataaaga agtaattcat acgaaattgt ataaagataa tttatttgat    960
gtaaaagcga agaaccata caatgtaaca attactagtg ataaatatat ccctaatact   1020
gatttgaaac gtggacaagc tgatttgttt gtagcggaag gttctatcaa agatttagtg   1080
aaacataaga agcatggtaa ggcaattata ggaacgaaaa acatcatgt taatattaag    1140 ttacggaaag atattaataa aatctatttt atgacagatg ttgatttagg tggaccaacg   1200
tttgtcttaa atgacaaaga ctatcaagaa ataagaaagt atacaaaagc aaagcatatc   1260
gtctctcaat ttggattcga tttgaaacat aaaaaagatg ctttagcatt agaaaaagtg   1320
aaaaataaag ttgataaatc tattaaaaca agaagtgaag cgataagctc aatatcaagt   1380
ttaaccggaa tattattatt tgtaacatca ttttaggta ttacattctt gattgctgta    1440
tgttgcatta tatacattaa gcaaatagat gaaaccgaag atgagttaga gaattatagt   1500
atattgagaa agcttggatt tacacaaaaa gatatggcaa ggggactaaa gtttaaaatt   1560
atgtttaatt ttgggttacc tttagttatt gcactatcac atgcatattt tacatcatta   1620
gcatatatga aattaatggg tacaacgaat caaataccgg ttttcatagt aatgggatta   1680
tacatttgta tgtatgctgt ttttgcagtg acggcttata atcattccaa gcgaacaatt   1740
agacattcca tataa                                                    1755

<210> SEQ ID NO 101
<211> LENGTH: 1840
<212> TYPE: DNA
<213> ORGANISM: Staphylococcus aureus

<400> SEQUENCE: 101 atgacccttta acgagataat atttaaaaat ttccgtcaaa atttatcaca gctttgtagc     60
attaaaatac gcgcataaac taaacatgac agagtcatat ccaattatta aggaaggctc    120
acaagtcgga agctactttc tattttttcat cataattgca ttttttgttat atgccaatgt   180 gttatttatt aaacgacgaa gttatgagct tgcattatat caaacattag gtttatctaa    240
attcaacatt atttatatac taatgctcga acaattacta atatttataa ttacggcaat    300
attaggtatt attattggta ttttttggttc aaaactgtta ttaatgattg tctttacatt    360
attaggaatt aaagaaaagg ttccaattat ttttagtttg agggcggtat ttgaaacatt    420
aatgttaatc ggtgtcgctt attttttaac ctctgctcaa aatttatat tagtgttcaa    480 acaatctatt tcacagatgt caaagaataa ccaggttaaa gaaacaaatc ataataaaat   540
tacatttgaa gaggttgttt taggcatctt aggtatagta ttgattacca caggatacta    600
tctatctttg aacattgttc aatattatga ttctatcggt atacttatgt ttattttatt    660
gtcaactgtg attggggcat acttattttt taaaagctct gttctctag ttttttaaaat    720 ggtgaagaag tttagaaaag gtgttataag tgtaaatgat gtcatgttct catcatctat    780
tatgtatcgt attaagaaaa atgctttttc acttacggtc atggcaatca tttcagcgat    840
tactgtttca gttctttgct tgctgctat aagtagagcg tccttatcaa gtgaaataaa    900
atatactgca ccacacgacg ttacaattaa agaccaacaa aaagctaatc aattagcaag   960
```

| | |
|---|---:|
| tgaattaaac aatcaaaaaa ttcctcattt ttataattat aaagaagtaa ttcatacgaa | 1020 |
| attgtataaa gataatttat ttgatgtaaa agcgaaagaa ccatacaatg taacaattac | 1080 |
| tagtgataaa tatatcccta atactgattt gaaacgtgga caagctgatt tgtttgtagc | 1140 |
| ggaaggttct atcaaagatt tagtgaaaca taagaagcat ggtaaggcaa ttataggaac | 1200 |
| gaaaaaacat catgttaata ttaagttacg gaaagatatt aataaaatct attttatgac | 1260 |
| agatgttgat ttaggtggac caacgtttgt cttaaatgac aaagactatc aagaaataag | 1320 |
| aaagtataca aaagcaaagc atatcgtctc tcaatttgga ttcgatttga acataaaaa | 1380 |
| agatgcttta gcattagaaa aagtgaaaaa taagttgat aaatctatta aaacaagaag | 1440 |
| tgaagcgata agctcaatat caagtttaac cggaatatta ttatttgtaa catcattttt | 1500 |
| aggtattaca ttcttgattg ctgtatgttg cattatatac attaagcaaa tagatgaaac | 1560 |
| cgaagatgag ttagagaatt atagtatatt gagaaagctt ggatttacac aaaaagatat | 1620 |
| ggcaagggga ctaaagttta aaattatgtt taattttggg ttacctttag ttattgcact | 1680 |
| atcacatgca tattttacat cattagcata tatgaaatta atgggtacaa cgaatcaaat | 1740 |
| accggttttc atagtaatgg gattatacat ttgtatgtat gctgttttg cagtgacggc | 1800 |
| ttataatcat tccaagcgaa caattagaca ttccatataa | 1840 |

<210> SEQ ID NO 102
<211> LENGTH: 1890
<212> TYPE: DNA
<213> ORGANISM: Staphylococcus aureus

<400> SEQUENCE: 102

| | |
|---|---:|
| atgacccttta acgagataat atttaaaaat ttccgtcaaa atttatcaca ttatgccatc | 60 |
| tatcttttt cattaattac gagtgtagta ttgtatttta gctttgtagc attaaaatac | 120 |
| gcgcataaac taaacatgac agagtctatc ccaattatta aggaaggctc acaagtcgga | 180 |
| agctactttc tattttttcat cataattgca ttttttgttat atgccaatgt gttatttatt | 240 |
| aaacgacgaa gttatgagct tgcattatat caaacattag gtttatctaa attcaacatt | 300 |
| atttatatac taatgctcga acaattacta atatttataa ttacggcaat attaggtatt | 360 |
| attattggta ttttttggttc aaaactgtta ttaatgattg tctttacatt attaggaatt | 420 |
| aaagaaaagg ttccaattat ttttagtttg agggcggtat ttgaaacatt aatgttaatc | 480 |
| ggtgtcgctt attttttaac ctctgctcaa aattttatat tagtgttcaa acaatctatt | 540 |
| tcacagatgt caaagaataa ccaggttaaa gaaacaaatc ataataaaat tacatttgaa | 600 |
| gaggttgttt taggcatctt aggtatagta ttgattacca caggatacta tctatctttg | 660 |
| aacattgttc aatattatga ttctatcggt atacttatgt ttattttatt gtcaactgtg | 720 |
| attggggcat acttatttt taaaagctct gtttctctag tttttaaaat ggtgaagaag | 780 |
| tttagaaaag gtgttataag tgtaaatgat gtcatgttct catcatctat tatgtatcgt | 840 |
| attaagaaaa atgcttttc acttacggtc atggcaatca tttcagcgat tactgtttca | 900 |
| gttctttgct tgctgctat aagtagagcg tccttatcaa gtgaaataaa atatactgca | 960 |
| ccacacgacg ttacaattaa agaccaacaa aaagctaatc aattagcaag tgaattaaac | 1020 |
| aatcaaaaaa ttcctcattt ttataattat aaagaagtaa ttcatacgaa attgtataaa | 1080 |
| gataatttat ttgatgtaaa agcgaaagaa ccatacaatg taacaattac tagtgataaa | 1140 |
| tatatcccta atactgattt gaaacgtgga caagctgatt tgtttgtagc ggaaggttct | 1200 |

| | |
|---|---|
| atcaaagatt tagtgaaaca taagaagcat ggtaaggcaa ttataggaac gaaaaaacat | 1260 |
| catgttaata ttaagttacg gaaagatatt aataaaatct attttatgac agatgttgat | 1320 |
| ttaggtggac caacgtttgt cttaaatgac aaagactatc aagaaataag aaagtataca | 1380 |
| aaagcaaagc atatcgtctc tcaatttgga ttcgatttga aacataaaaa agatgcttta | 1440 |
| gcattagaaa aagtgaaaaa taaagttgat aaatctatta aacaagaag tgaagcgata | 1500 |
| agctcaatat caagtttaac cggaatatta ttatttgtaa catcattttt aggtattaca | 1560 |
| ttcttgattg ctgtatgttg cattatatac attaagcaaa tagatgaaac cgaagatgag | 1620 |
| ttagagaatt atagtatatt gagaaagctt ggatttacac aaaagatat ggcaagggga | 1680 |
| ctaaagttta aaattatgtt taattttggg ttacctttag ttattgcact atcacatgca | 1740 |
| tattttacat cattagcata tatgaaatta atgggtacaa cgaatcaaat accggttttc | 1800 |
| atagtaatgg gattatacat ttgtatgtat gctgttttg cagtgacggc ttataatcat | 1860 |
| tccaagcgaa caattagaca ttccatataa | 1890 |

<210> SEQ ID NO 103
<211> LENGTH: 1890
<212> TYPE: DNA
<213> ORGANISM: Staphylococcus aureus

<400> SEQUENCE: 103

| | |
|---|---|
| atgacctta acgagataat atttaaaaat ttccgtcaaa atttatcaca ttatgccatc | 60 |
| tatctttttt cattaattac gagtgtagta ttgtatttta gctttgtagc attaaaatac | 120 |
| gcgcataaac taaacatgac agagtcatat ccaattatta aggaaggctc acaagtcgga | 180 |
| agctactttc tattttttcat cataattgca ttttgttat atgccaatgt gttatttatt | 240 |
| aaacgacgaa gttatgagct tgcattatat caaacattag gttatctaa attcaacatt | 300 |
| atttatatac taatgctcga acaattacta atatttataa ttacggcaat attaggtatt | 360 |
| attattggta tttttggttc aaaactgtta ttaatgattg tctttacatt attaggaatt | 420 |
| aaagaaaagg ttccaattat ttttagtttg agggcggtat ttgaaacatt aatgttaatc | 480 |
| ggtgtcgctt attttttaac ctctgctcaa aattttatat tagtgttcaa acaatctatt | 540 |
| tcacagatgt caaagaataa ccaggttaaa gaaacaaatc ataataaaat tacatttgaa | 600 |
| gaggttgttt taggcatctt aggtatagta ttgattacca caggatacta tctatctttg | 660 |
| aacattgttc aatattatga ttctatcggt atacttatgt ttatttatt gtcaactgtg | 720 |
| attggggcat acttattttt taaaagctct gtttctctag tttttaaaat ggtgaagaag | 780 |
| tttagaaaag gtgttataag tgtaaatgat gtcatgttct catcatctat tatgtatcgt | 840 |
| attaagaaaa atgcttttc acttacggtc atggcaatca tttcagcgat tactgtttca | 900 |
| gttctttgct tgctgctat aagtagagcg tccttatcaa gtgaaataaa atatactgca | 960 |
| ccacacgacg ttacaattaa agaccaacaa aaagctaatc aattagcaag tgaattaaac | 1020 |
| aatcaaaaaa ttcctcattt ttataattat aaagaagtaa ttcatacgaa attgtataaa | 1080 |
| gataatttat ttgatgtaaa agcgaaagaa ccatacaatg taacaattac tagtgataaa | 1140 |
| tatatcccta atactgattt gaacgtggaa caagctgatt tgtttgtagc ggaaggttct | 1200 |
| atcaaagatt tagtgaaaca taagaagcat ggtaaagcag ttataggaac gaaaaaacat | 1260 |
| catgttaata ttaagttgcg gaaagatatt aataaaatct attttatgac agatgttgat | 1320 |
| ttaggtggac caacgtttgt cttaaatgac aaagactatc aagaaataag aaagtataca | 1380 |
| aaagcaaagc atatcgtctc tcaatttgga ttcgatttga aacataaaaa agatgcttta | 1440 |

```
gcattagaaa aagtgaaaaa taaagttgat aaatctatta aaacaagaag tgaagcgata    1500
agctcaatat caagtttaac cggaatatta ttatttgtaa catcattttt aggtattaca    1560
ttcttgattg ctgtatgttg cattatatac ataaagcaaa tagatgaaac cgaagatgag    1620
ttagagaatt atagtatttt gagaaagctt ggatttacac aaaaagatat ggcaagggga    1680
ctaaagttta aaattatgtt taattttggg ttacctttag ttattgcact atcacatgca    1740
tattttacat cattagcata tatgaaatta atgggtacaa cgaatcaaat accgttttc     1800 atagtaatgg gattatacat ttgtatgtat gctgtttttg cagtgacggc ttataatcat    1860
tccaagcgaa caattagaca ttccatataa                                     1890
```

<210> SEQ ID NO 104
<211> LENGTH: 1890
<212> TYPE: DNA
<213> ORGANISM: Staphylococcus aureus

<400> SEQUENCE: 104

```
atgacctta acgagataat atttaaaaat ttccgtcaaa atttatcaca ttatgccatc       60
tatctttttt cattaattac gagtgtagta ttgtatttta gctttgtagc attaaaaatac    120 gcgcataaac taaacatgac agagtcatat ccaattatta aggaaggctc acaagtcgga    180
agctactttc tattttttcat cataattgca ttttttgttat atgccaatgt gttatttatt    240
aaacgacgaa gttatgagct tgcattatat caaacattag gtttatctaa attcaacatt     300
atttatatac taatgctcga acaattacta atatttataa ttacggcaat attaggtatt    360
attattggta ttttttggttc aaaactgtta ttaatgattg tctttacatt attaggaatt    420
aaagaaaagg ttccaattat ttttagtttg agggcggtat ttgaaacatt aatgttaatc    480
ggtgtcgctt attttttaac ctctgctcaa aattttatat tagtgttcaa acaatctatt    540
tcacagatgt caaagaataa ccaggttaaa gaaacaaatc ataataaaat tacatttgaa    600
gaggttgttt taggcatctt aggtatagta ttgattacca caggatacta tctatctttg    660
aacattgttc aatattatga ttctatcggt atacttatgt ttatttatt gtcaactgtg     720 attgggggcat acttatttt taaaagctct gtttctctag ttttttaaaat ggtgaagaag    780 tttagaaaag gtgttataag tgtaaatgat gtcatgttct catcatctat tatgtatcgt    840
attaagaaaa atgcttttc acttacggtc atggcaatca tttcagcgat tactgtttca    900
gttctttgct ttgctgctat aagtagagcg tccttatcaa gtgaaataaa atatactgca    960
ccacacgacg ttacaattaa agaccaacaa aaagctaatc aattagcaag tgaattaaac    1020
aatcaaaaaa ttcctcattt ttataattat aaagaagtaa ttcatacgaa attgtataaa    1080
gataaattat ttgatgtaaa agcgaaagaa ccatacaatg taacaattac tagtgataaa    1140
tatatcccta atactgattt gaaacgtgga caagctgatt tgtttgtagc ggaaggttct    1200
atcaaagatt tagtgaaaca taagaagcat ggtaaagcag ttataggaac gaaaaaacat    1260
catgttaata ttaagttgcg gaaagatatt aataaaatct attttatgac agatgttgat    1320
ttaggtggac caacgtttgt cttaaatgac aaagactatc aagaaataag aaagtataca    1380
aaagcaaagc atatcgtctc tcaatttgga ttcgatttga acataaaaa agatgcttta     1440 gcattagaaa aagtgaaaaa taaagttgat aaatctatta aaacaagaag tgaagcgata    1500
agctcaatat caagtttaac cggaatatta ttatttgtaa catcattttt aggtattaca    1560
ttcttgattg ctgtatgttg cattatatac ataaagcaaa tagatgaaac cgaagatgag    1620
```

| | |
|---|---:|
| ttagagaatt atagtatttt gagaaagctt ggatttacac aaaaagatat ggcaagggga | 1680 |
| ctaaagttta aaattatgtt taattttggg ttacctttag ttattgcact atcacatgca | 1740 |
| tattttacat cattagcata tatgaaatta atgggtacaa cgaatcaaat accggttttc | 1800 |
| atagtaatgg gattatacat ttgtatgtat gctgttttg cagtgacggc ttataatcat | 1860 |
| tccaagcgaa caattagaca ttccatataa | 1890 |

<210> SEQ ID NO 105
<211> LENGTH: 1890
<212> TYPE: DNA
<213> ORGANISM: Staphylococcus aureus

<400> SEQUENCE: 105

| | |
|---|---:|
| atgacctttA acgagataat atttaaaaat ttccgtcaaa atttatcaca ttatgccatc | 60 |
| tatctttttt cgttaattac gagtgtagta ttgtatttta gctttgtagc attaaaatac | 120 |
| gctcataaac taaacatgac agagtctcat ccaattataa aggaaggctc acaagtcgga | 180 |
| agctactttc tattttcat cataattgca tttttgttat atgccaatgt gttatttatt | 240 |
| aaacgacgaa gttatgagct tgcattatat caaacattag gtttatctaa attcaacatt | 300 |
| atttatatac taatgctcga acaattacta atatttataa ttacggcaat attaggtatt | 360 |
| attattggta tttttggttc gaaactgtta ttaatgattg tctttacatt attaggaatt | 420 |
| aaagaaaagg ttccaattat ttttagtttg agggcggtat ttgaaacatt aatgttaatc | 480 |
| ggtgtcgctt attttttaac atctgctcaa aattttatat tagtgttcaa acaatctatt | 540 |
| tcacagatgt caagaataa ccaggttaaa gaaacaaatc ataataaaat tacatttgaa | 600 |
| gaggttgttt taggcatctt aggtatagta ttgattacca caggatacta tctatctttg | 660 |
| aacattgttc aatattatga ttctatcggt acacttatgt ttattttatt gtcaactgtg | 720 |
| attggggcat acttatttt taaaagctct gtttctctag tttttaaaat ggtgaagaag | 780 |
| tttagaaaag gtgttataag tgtaaatgat gtcatgttct catcatctat tatgtatcgt | 840 |
| attaagaaaa atgcttttc acttacggtc atggcaatca tttcagcgat tactgtttca | 900 |
| gttcttgct tgctgctat aagtagagcg tccttatcaa gtgaaataaa atatactgca | 960 |
| ccacacgacg ttacaattaa agaccaacaa aaagctaatc aattagcaag tgaattaaac | 1020 |
| aatcaaaaaa ttcctcattt ttataattat aaagaagtaa ttcatacgaa attgtataaa | 1080 |
| gataatttat ttgatgtaaa agcgaaagaa ccatacaatg taacaattac tagtgataaa | 1140 |
| tacatcccta atactgattt gaacgtgggg caagctgatt tatttgtagc ggaaggttct | 1200 |
| atcaaagatt tagtgaaaca taagaagcat ggtaaggcaa ttataggaac gaaaaaacat | 1260 |
| catgttaata ttaagttacg taaagatatt aataaaatct attttatgac agatgttgat | 1320 |
| ttaggtggac caacgtttgt cttaaatgac aaagactatc aagaaataag aaagtataca | 1380 |
| aaggcaaagc atatcgtctc tcaatttgga ttcgatttga acataaaaaa agatgcttta | 1440 |
| gcattagaaa aagcgaaaaa taagttgat aaatctattg aaacaagaag tgaagcgata | 1500 |
| agctcaatat caagtttaac cggaatatta ttatttgtaa catcattttt aggtattaca | 1560 |
| ttcttgattg ctgtatgttg cattatatac ataaagcaaa tagatgaaac cgaagatgag | 1620 |
| ttagagaatt atagtatttt gagaaagctt ggatttacac aaaaagatat ggcaagggga | 1680 |
| ctaaagttta aaattatgtt taattttggg ttacctttag ttattgcact atcacatgca | 1740 |
| tattttacat cattagcata tatgaaatta atgggtacaa cgaatcaaat accggttttc | 1800 |
| atagtaatgg gattatacat ttgtatgtat gctgttttg cagtgacggc ttataatcat | 1860 | tccaagcgaa caattagaca ttccatataa                                        1890

<210> SEQ ID NO 106
<211> LENGTH: 1800
<212> TYPE: DNA
<213> ORGANISM: Staphylococcus aureus

<400> SEQUENCE: 106

| | | | | | |
|---|---|---|---|---|---|
| ttgtatttta | gctttgtagc | attaaaatac | gctcataaac | taaacatgac | agagtcatat |   60 |
| ccaattataa | aggaaggctc | acaagtcgga | agctactttc | tatttttcat | cataattgca |  120 |
| tttttgttat | atgccaatgt | gttatttatt | aaacgacgaa | gttatgagct | tgcattatat |  180 |
| caaacattag | gtttatctaa | attcaacatt | atttatatac | taatgctcga | acaattacta |  240 |
| atatttataa | ttacggcaat | attaggtatt | attattggta | tttttggttc | gaaactgtta |  300 |
| ttaatgattg | tctttacatt | attaggaatt | aaagaaaagg | ttccaattat | ttttagtttg |  360 |
| agggcggtat | ttgaaacatt | aatgttaatc | ggtgtcgctt | attttttaac | atctgctcaa |  420 |
| aattttatat | tagtgttcaa | acaatctatt | tcacagatgt | caaagaataa | ccaggttaaa |  480 |
| gaaacaaatc | ataataaaat | tacatttgaa | gaggttgttt | taggcatctt | aggtatagta |  540 |
| ttgattacca | caggatacta | tctatctttg | aacattgttc | aatattatga | ttctatcggt |  600 |
| acacttatgt | ttatttttatt | gtcaactgtg | attgggggcat | acttattttt | taaaagctct |  660 |
| gtttctctag | tttttaaaat | ggtgaagaag | tttagaaaag | gtgttataag | tgtaaatgat |  720 |
| gtcatgttct | catcatctat | tatgtatcgt | attaagaaaa | atgcttttttc | acttacggtc |  780 |
| atggcaatca | tttcagcgat | tactgtttca | gttctttgct | ttgctgctat | aagtagagcg |  840 |
| tccttatcaa | gtgaaataaa | atatactgca | ccacacgacg | ttacaattaa | agaccaacaa |  900 |
| aaagctaatc | aattagcaag | tgaattaaac | aatcaaaaaa | ttcctcatttt | ttataattat |  960 |
| aaagaagtaa | ttcatacgaa | attgtataaa | gataatttat | ttgatgtaaa | agcgaaagaa | 1020 |
| ccatacaatg | taacaattac | tagtgataaa | tacatcccta | atactgattt | gaaacgtggg | 1080 |
| caagctgatt | tatttgtagc | ggaaggttct | atcaaagatt | tagtgaaaca | taagaagcat | 1140 |
| ggtaaggcaa | ttataggaac | gaaaaaacat | catgttaata | ttaagttacg | taaagatatt | 1200 |
| aataaaatct | attttatgac | agatgttgat | ttaggtggac | caacgtttgt | cttaaatgac | 1260 |
| aaagactatc | aagaaataag | aaagtataca | aaggcaaagc | atatcgtctc | tcaatttgga | 1320 |
| ttcgatttga | acataaaaaa | agatgcttta | gcattagaaa | aagcgaaaaa | taaagttgat | 1380 |
| aaatctattg | aaacaagaag | tgaagcgata | agctcaatat | caagtttaac | cggaatatta | 1440 |
| ttatttgtaa | catcattttt | aggtattaca | ttcttgattg | ctgtatgttg | cattatatac | 1500 |
| ataaagcaaa | tagatgaaac | cgaagatgag | ttagagaatt | atagtatttt | gagaaagctt | 1560 |
| ggatttacac | aaaaagatat | ggcaagggga | ctaaagttta | aaattatgtt | taattttggg | 1620 |
| ttacctttag | ttattgcact | atcacatgca | tattttacat | cattagcata | tatgaaatta | 1680 |
| atgggtacaa | cgaatcaaat | accggttttc | atagtaatgg | gattatacat | ttgtatgtat | 1740 |
| gctgtttttg | cagtgacggc | ttataatcat | tccaagcgaa | caattagaca | ttccatataa | 1800 |

<210> SEQ ID NO 107
<211> LENGTH: 1755
<212> TYPE: DNA
<213> ORGANISM: Staphylococcus aureus

<400> SEQUENCE: 107

| | | |
|---|---|---|
| atgacagagt catatccaat tataaaggaa ggctcacaag tcggaagcta ctttctattt | 60 | |
| ttcatcataa ttgcattttt gttatatgcc aatgtgttat ttattaaacg acgaagttat | 120 | |
| gagcttgcat tatatcaaac attaggttta tctaaattca acattattta tatactaatg | 180 | |
| ctcgaacaat tactaatatt tataattacg gcaatattag gtattattat tggtattttt | 240 | |
| ggttcgaaac tgttattaat gattgtcttt acattattag gaattaaaga aaaggttcca | 300 | |
| attattttta gtttgagggc ggtatttgaa acattaatgt taatcggtgt cgcttatttt | 360 | |
| ttaacatctg ctcaaaattt tatattagtg ttcaaacaat ctatttcaca gatgtcaaag | 420 | |
| aataaccagg ttaaagaaac aaatcataat aaaattacat tgaagaggt tgttttaggc | 480 | |
| atcttaggta tagtattgat taccacagga tactatctat ctttgaacat tgttcaatat | 540 | |
| tatgattcta tcggtacact tatgtttatt ttattgtcaa ctgtgattgg ggcatactta | 600 | |
| tttttttaaaa gctctgtttc tctagttttt aaaatggtga agaagtttag aaaaggtgtt | 660 | |
| ataagtgtaa atgatgtcat gttctcatca tctattatgt atcgtattaa gaaaaatgct | 720 | |
| ttttcactta cggtcatggc aatcatttca gcgattactg tttcagttct ttgctttgct | 780 | |
| gctataagta gagcgtcctt atcaagtgaa ataaaatata ctgcaccaca cgacgttaca | 840 | |
| attaaagacc aacaaaaagc taatcaatta gcaagtgaat taaacaatca aaaaattcct | 900 | |
| cattttata attataaaga agtaattcat acgaaattgt ataagataa tttatttgat | 960 | |
| gtaaaagcga aagaaccata caatgtaaca attactagtg ataaatacat ccctaatact | 1020 | |
| gatttgaaac gtgggcaagc tgatttattt gtagcggaag gttctatcaa agatttagtg | 1080 | |
| aaacataaga agcatggtaa ggcaattata ggaacgaaaa aacatcatgt taatattaag | 1140 | |
| ttacgtaaag atattaataa aatctatttt atgacagatg ttgatttagg tggaccaacg | 1200 | |
| tttgtcttaa atgacaaaga ctatcaagaa ataagaaagt atacaaaggc aaagcatatc | 1260 | |
| gtctctcaat ttggattcga tttgaaacat aaaaaagatg ctttagcatt agaaaaagcg | 1320 | |
| aaaaataaag ttgataaatc tattgaaaca agaagtgaag cgataagctc aatatcaagt | 1380 | |
| ttaaccggaa tattattatt tgtaacatca tttttaggta ttacattctt gattgctgta | 1440 | |
| tgttgcatta tatacataaa gcaaatagat gaaaccgaag atgagttaga gaattatagt | 1500 | |
| attttgagaa agcttggatt tacacaaaaa gatatggcaa ggggactaaa gtttaaaatt | 1560 | |
| atgtttaatt ttgggttacc tttagttatt gcactatcac atgcatattt tacatcatta | 1620 | |
| gcatatatga attaatggg tacaacgaat caaataccgg ttttcatagt aatgggatta | 1680 | |
| tacatttgta tgtatgctgt ttttgcagtg acggcttata atcattccaa gcgaacaatt | 1740 | |
| agacattcca tataa | 1755 | |

<210> SEQ ID NO 108
<211> LENGTH: 1890
<212> TYPE: DNA
<213> ORGANISM: Staphylococcus aureus

<400> SEQUENCE: 108

| | | |
|---|---|---|
| atgacccttta acgagataat atttaaaaat ttccgtcaaa atttatcaca ttatgccatc | 60 | |
| tatcttttt cattaattac gagtgtagta ttgtattttta gctttgtagc attaaaaatac | 120 | |
| gctcataaac taaacatgac agagtcatat ccaattataa aggaaggctc acaagtcgga | 180 | |
| agctactttc tattttttcat cataattgca ttttgttat atgccaatgt gttatttatt | 240 | |
| aaacgacgaa gttatgagct tgcattatat caaacattag gttatctaa attcaacatt | 300 | |
| atttatatac taatgctcga acaattacta atatttataa ttacggcaat attaggtatt | 360 | |

```
attattggta tttttggttc gaaactgtta ttaatgattg tctttacatt attaggaatt    420
aaagaaaagg ttccaattat ttttagtttg agggcggtat ttgaaacatt aatgttaatc    480
ggtgtcgctt atttttaac atctgctcaa aatttatat tagtgttcaa acaatctatt     540
tcacagatgt caaagaataa ccaggttaaa gaaacaaatc ataaaaat tacatttgaa     600 gaggttgttt taggcatctt aggtatagta ttgattacca caggatacta tctatctttg    660
aacattgttc aatattatga ttctatcggt acacttatgt ttatttatt gtcaactgtg    720 attgggcat acttattttt taaaagctct gtttctctag tttttaaaat ggtgaagaag    780
tttagaaaag gtgttataag tgtaaatgat gtcatgttct catcatctat tatgtatcgt    840
attaagaaaa atgctttttc acttacggtc atggcaatca tttcagcgat tactgtttca    900
gttctttgct ttgctgctat aagtagagcg tccttatcaa gtgaaataaa atatactgca    960
ccacacgacg ttacaattaa agaccaacaa aaagctaatc aattagcaag tgaattaaac   1020
aatcaaaaaa ttcctcattt ttataattat aaagaagtaa ttcatacgaa attgtataaa   1080
gataatttat ttgatgtaaa atcgaaacaa ccatacaatg taacaattac tagtgataaa   1140
tacatcccta gtactgattt gaaacgtggg caagctgatt tgtttgtagc ggaaggttct   1200
atcaaagatt tagtgaaaca taagaagcat ggtaaagcag ttataggaac gaaaaaacat   1260
catgttaata ttaagttacg taaagatatt aataaaatct attttatgac agatgttgat   1320
ttaggtggac caacgtttgt cttaaatgac aaagactatc aagaaataag aaagtataca   1380
aaggcaaagc atatcgtctc tcaatttgga ttcgatttga aacataaaaa agatgcttta   1440
gcattagaaa aagcgaaaaa taaagttgat aaatctattg agacaagaag tgaagcgata   1500
agctcaatat caagtttaac cggaatatta ttatttgtaa catcattttt aggtattaca   1560
ttcttgattg ctgtatgttg cattatatac attaagcaaa tagatgaaac cgaagatgag   1620
ttagagaatt atagtatatt gagaaagctt ggatttacac aaaagatat ggcaagggga   1680 ctaaagttta aaattatgtt taattttggg ttacctttag ttattgcact atcacatgca   1740
tattttacat cattagcata tatgaaatta atgggtacaa cgaatcaaat accggttttc   1800
atagtaatgg gattatacat ttgtatgtat gctgttttg cagtgacggc ttataatcat   1860
tccaagcgaa caattagaca ttccatataa                                    1890
```

<210> SEQ ID NO 109
<211> LENGTH: 629
<212> TYPE: PRT
<213> ORGANISM: Staphylococcus aureus

<400> SEQUENCE: 109

Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

```
Lys Phe Asn Ile Ile Tyr Ile Leu Met Leu Glu Gln Leu Leu Ile Phe
            100                 105                 110

Ile Ile Thr Ala Ile Leu Gly Ile Ile Gly Ile Phe Gly Ser Lys
            115                 120                 125

Leu Leu Leu Met Ile Val Phe Thr Leu Leu Gly Ile Lys Glu Lys Val
            130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                    165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
            195                 200                 205

Ile Val Leu Ile Thr Thr Gly Tyr Tyr Leu Ser Leu Asn Ile Val Gln
            210                 215                 220

Tyr Tyr Asp Ser Ile Gly Thr Leu Met Phe Ile Leu Leu Ser Thr Val
225                 230                 235                 240

Ile Gly Ala Tyr Leu Phe Phe Lys Ser Ser Val Ser Leu Val Phe Lys
                    245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
            275                 280                 285

Thr Val Met Ala Ile Ile Ser Ala Ile Thr Val Ser Val Leu Cys Phe
            290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                    325                 330                 335

Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Ala
            355                 360                 365

Lys Glu Pro Tyr Asn Val Thr Ile Thr Ser Asp Lys Tyr Ile Pro Asn
            370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Ile Ile Gly
                    405                 410                 415

Thr Lys Lys His His Val Asn Ile Lys Leu Arg Lys Asp Ile Asn Lys
            420                 425                 430

Ile Tyr Phe Met Thr Asp Val Asp Leu Gly Gly Pro Thr Phe Val Leu
            435                 440                 445

Asn Asp Lys Asp Tyr Gln Glu Ile Arg Lys Tyr Thr Lys Ala Lys His
450                 455                 460

Ile Val Ser Gln Phe Gly Phe Asp Leu Lys His Lys Lys Asp Ala Leu
465                 470                 475                 480

Ala Leu Glu Lys Ala Lys Asn Lys Val Asp Lys Ser Ile Glu Thr Arg
                    485                 490                 495

Ser Glu Ala Ile Ser Ser Ile Ser Ser Leu Thr Gly Ile Leu Leu Phe
            500                 505                 510

Val Thr Ser Phe Leu Gly Ile Thr Phe Leu Ile Ala Val Cys Cys Ile
```

```
                515                 520                 525
Ile Tyr Ile Lys Gln Ile Asp Glu Thr Glu Asp Glu Leu Glu Asn Tyr
530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
                580                 585                 590

Thr Thr Asn Gln Ile Pro Val Phe Ile Val Met Gly Leu Tyr Ile Cys
                595                 600                 605

Met Tyr Ala Val Phe Ala Val Thr Ala Tyr Asn His Ser Lys Arg Thr
610                 615                 620

Ile Arg His Ser Ile
625

<210> SEQ ID NO 110
<211> LENGTH: 599
<212> TYPE: PRT
<213> ORGANISM: Staphylococcus aureus

<400> SEQUENCE: 110

Met Tyr Phe Ser Phe Val Ala Leu Lys Tyr Ala His Lys Leu Asn Met
1               5                   10                  15

Thr Glu Ser Tyr Pro Ile Ile Lys Glu Gly Ser Gln Val Gly Ser Tyr
                20                  25                  30

Phe Leu Phe Phe Ile Ile Ile Ala Phe Leu Leu Tyr Ala Asn Val Leu
            35                  40                  45

Phe Ile Lys Arg Arg Ser Tyr Glu Leu Ala Leu Tyr Gln Thr Leu Gly
    50                  55                  60

Leu Ser Lys Phe Asn Ile Ile Tyr Ile Leu Met Leu Glu Gln Leu Leu
65                  70                  75                  80

Ile Phe Ile Ile Thr Ala Ile Leu Gly Ile Ile Gly Ile Phe Gly
                85                  90                  95

Ser Lys Leu Leu Leu Met Ile Val Phe Thr Leu Gly Ile Lys Glu
                100                 105                 110

Lys Val Pro Ile Ile Phe Ser Leu Arg Ala Val Phe Glu Thr Leu Met
            115                 120                 125

Leu Ile Gly Val Ala Tyr Phe Leu Thr Ser Ala Gln Asn Phe Ile Leu
    130                 135                 140

Val Phe Lys Gln Ser Ile Ser Gln Met Ser Lys Asn Asn Gln Val Lys
145                 150                 155                 160

Glu Thr Asn His Asn Lys Ile Thr Phe Glu Glu Val Val Leu Gly Ile
                165                 170                 175

Leu Gly Ile Val Leu Ile Thr Thr Gly Tyr Tyr Leu Ser Leu Asn Ile
            180                 185                 190

Val Gln Tyr Tyr Asp Ser Ile Gly Thr Leu Met Phe Ile Leu Leu Ser
    195                 200                 205

Thr Val Ile Gly Ala Tyr Leu Phe Phe Lys Ser Ser Val Ser Leu Val
210                 215                 220

Phe Lys Met Val Lys Lys Phe Arg Lys Gly Val Ile Ser Val Asn Asp
225                 230                 235                 240

Val Met Phe Ser Ser Ser Ile Met Tyr Arg Ile Lys Lys Asn Ala Phe
                245                 250                 255
```

```
Ser Leu Thr Val Met Ala Ile Ile Ser Ala Ile Thr Val Ser Val Leu
            260                 265                 270

Cys Phe Ala Ala Ile Ser Arg Ala Ser Leu Ser Ser Glu Ile Lys Tyr
            275                 280                 285

Thr Ala Pro His Asp Val Thr Ile Lys Asp Gln Gln Lys Ala Asn Gln
        290                 295                 300

Leu Ala Ser Glu Leu Asn Asn Gln Lys Ile Pro His Phe Tyr Asn Tyr
305                 310                 315                 320

Lys Glu Val Ile His Thr Lys Leu Tyr Lys Asp Asn Leu Phe Asp Val
                325                 330                 335

Lys Ala Lys Glu Pro Tyr Asn Val Thr Ile Thr Ser Asp Lys Tyr Ile
            340                 345                 350

Pro Asn Thr Asp Leu Lys Arg Gly Gln Ala Asp Leu Phe Val Ala Glu
        355                 360                 365

Gly Ser Ile Lys Asp Leu Val Lys His Lys His Gly Lys Ala Ile
    370                 375                 380

Ile Gly Thr Lys Lys His His Val Asn Ile Lys Leu Arg Lys Asp Ile
385                 390                 395                 400

Asn Lys Ile Tyr Phe Met Thr Asp Val Asp Leu Gly Gly Pro Thr Phe
                405                 410                 415

Val Leu Asn Asp Lys Asp Tyr Gln Glu Ile Arg Lys Tyr Thr Lys Ala
            420                 425                 430

Lys His Ile Val Ser Gln Phe Gly Phe Asp Leu Lys His Lys Lys Asp
        435                 440                 445

Ala Leu Ala Leu Glu Lys Ala Lys Asn Lys Val Asp Lys Ser Ile Glu
    450                 455                 460

Thr Arg Ser Glu Ala Ile Ser Ser Ile Ser Ser Leu Thr Gly Ile Leu
465                 470                 475                 480

Leu Phe Val Thr Ser Phe Leu Gly Ile Thr Phe Leu Ile Ala Val Cys
                485                 490                 495

Cys Ile Ile Tyr Ile Lys Gln Ile Asp Glu Thr Glu Asp Glu Leu Glu
            500                 505                 510

Asn Tyr Ser Ile Leu Arg Lys Leu Gly Phe Thr Gln Lys Asp Met Ala
        515                 520                 525

Arg Gly Leu Lys Phe Lys Ile Met Phe Asn Phe Gly Leu Pro Leu Val
    530                 535                 540

Ile Ala Leu Ser His Ala Tyr Phe Thr Ser Leu Ala Tyr Met Lys Leu
545                 550                 555                 560

Met Gly Thr Thr Asn Gln Ile Pro Val Phe Ile Val Met Gly Leu Tyr
                565                 570                 575

Ile Cys Met Tyr Ala Val Phe Ala Val Thr Ala Tyr Asn His Ser Lys
            580                 585                 590

Arg Thr Ile Arg His Ser Ile
        595

<210> SEQ ID NO 111
<211> LENGTH: 584
<212> TYPE: PRT
<213> ORGANISM: Staphylococcus aureus

<400> SEQUENCE: 111

Met Thr Glu Ser Tyr Pro Ile Ile Lys Glu Gly Ser Gln Val Gly Ser
1               5                   10                  15

Tyr Phe Leu Phe Phe Ile Ile Ile Ala Phe Leu Leu Tyr Ala Asn Val
            20                  25                  30
```

```
Leu Phe Ile Lys Arg Arg Ser Tyr Glu Leu Ala Leu Tyr Gln Thr Leu
            35                  40                  45

Gly Leu Ser Lys Phe Asn Ile Ile Tyr Ile Leu Met Leu Glu Gln Leu
 50                  55                  60

Leu Ile Phe Ile Ile Thr Ala Ile Leu Gly Ile Ile Gly Ile Phe
 65                  70                  75                  80

Gly Ser Lys Leu Leu Leu Met Ile Val Phe Thr Leu Leu Gly Ile Lys
                     85                  90                  95

Glu Lys Val Pro Ile Ile Phe Ser Leu Arg Ala Val Phe Glu Thr Leu
                 100                 105                 110

Met Leu Ile Gly Val Ala Tyr Phe Leu Thr Ser Ala Gln Asn Phe Ile
            115                 120                 125

Leu Val Phe Lys Gln Ser Ile Ser Gln Met Ser Lys Asn Asn Gln Val
        130                 135                 140

Lys Glu Thr Asn His Asn Lys Ile Thr Phe Glu Val Val Leu Gly
145                 150                 155                 160

Ile Leu Gly Ile Val Leu Ile Thr Thr Gly Tyr Tyr Leu Ser Leu Asn
                165                 170                 175

Ile Val Gln Tyr Tyr Asp Ser Ile Gly Thr Leu Met Phe Ile Leu Leu
            180                 185                 190

Ser Thr Val Ile Gly Ala Tyr Leu Phe Phe Lys Ser Ser Val Ser Leu
        195                 200                 205

Val Phe Lys Met Val Lys Lys Phe Arg Lys Gly Val Ile Ser Val Asn
    210                 215                 220

Asp Val Met Phe Ser Ser Ile Met Tyr Arg Ile Lys Lys Asn Ala
225                 230                 235                 240

Phe Ser Leu Thr Val Met Ala Ile Ile Ser Ala Ile Thr Val Ser Val
                245                 250                 255

Leu Cys Phe Ala Ala Ile Ser Arg Ala Ser Leu Ser Ser Glu Ile Lys
            260                 265                 270

Tyr Thr Ala Pro His Asp Val Thr Ile Lys Asp Gln Gln Lys Ala Asn
        275                 280                 285

Gln Leu Ala Ser Glu Leu Asn Asn Gln Lys Ile Pro His Phe Tyr Asn
    290                 295                 300

Tyr Lys Glu Val Ile His Thr Lys Leu Tyr Lys Asp Asn Leu Phe Asp
305                 310                 315                 320

Val Lys Ala Lys Glu Pro Tyr Asn Val Thr Ile Thr Ser Asp Lys Tyr
                325                 330                 335

Ile Pro Asn Thr Asp Leu Lys Arg Gly Gln Ala Asp Leu Phe Val Ala
            340                 345                 350

Glu Gly Ser Ile Lys Asp Leu Val Lys His Lys Lys His Gly Lys Ala
        355                 360                 365

Ile Ile Gly Thr Lys Lys His His Val Asn Ile Lys Leu Arg Lys Asp
    370                 375                 380

Ile Asn Lys Ile Tyr Phe Met Thr Asp Val Asp Leu Gly Gly Pro Thr
385                 390                 395                 400

Phe Val Leu Asn Asp Lys Asp Tyr Gln Glu Ile Arg Lys Tyr Thr Lys
                405                 410                 415

Ala Lys His Ile Val Ser Gln Phe Gly Phe Asp Leu Lys His Lys Lys
            420                 425                 430

Asp Ala Leu Ala Leu Glu Lys Ala Lys Asn Lys Val Asp Lys Ser Ile
        435                 440                 445
```

```
Glu Thr Arg Ser Glu Ala Ile Ser Ser Ile Ser Ser Leu Thr Gly Ile
    450                 455                 460

Leu Leu Phe Val Thr Ser Phe Leu Gly Ile Thr Phe Leu Ile Ala Val
465                 470                 475                 480

Cys Cys Ile Ile Tyr Ile Lys Gln Ile Asp Glu Thr Glu Asp Glu Leu
                485                 490                 495

Glu Asn Tyr Ser Ile Leu Arg Lys Leu Gly Phe Thr Gln Lys Asp Met
            500                 505                 510

Ala Arg Gly Leu Lys Phe Lys Ile Met Phe Asn Phe Gly Leu Pro Leu
            515                 520                 525

Val Ile Ala Leu Ser His Ala Tyr Phe Thr Ser Leu Ala Tyr Met Lys
530                 535                 540

Leu Met Gly Thr Thr Asn Gln Ile Pro Val Phe Ile Val Met Gly Leu
545                 550                 555                 560

Tyr Ile Cys Met Tyr Ala Val Phe Ala Val Thr Ala Tyr Asn His Ser
                565                 570                 575

Lys Arg Thr Ile Arg His Ser Ile
            580
```

```
<210> SEQ ID NO 112
<211> LENGTH: 584
<212> TYPE: PRT
<213> ORGANISM: Staphylococcus aureus

<400> SEQUENCE: 112

Met Thr Glu Ser Tyr Pro Ile Ile Lys Glu Gly Ser Gln Val Gly Ser
1               5                   10                  15

Tyr Phe Leu Phe Phe Ile Ile Ala Phe Leu Leu Tyr Ala Asn Val
            20                  25                  30

Leu Phe Ile Lys Arg Arg Ser Tyr Glu Leu Ala Leu Tyr Gln Thr Leu
            35                  40                  45

Gly Leu Ser Lys Phe Asn Ile Ile Tyr Ile Leu Met Leu Glu Gln Leu
        50                  55                  60

Leu Ile Phe Ile Ile Thr Ala Ile Leu Gly Ile Ile Gly Ile Phe
65              70                  75                  80

Gly Ser Lys Leu Leu Leu Met Ile Val Phe Thr Leu Leu Gly Ile Lys
                85                  90                  95

Glu Lys Val Pro Ile Ile Phe Ser Leu Arg Ala Val Phe Glu Thr Leu
            100                 105                 110

Met Leu Ile Gly Val Ala Tyr Phe Leu Thr Ser Ala Gln Asn Phe Ile
        115                 120                 125

Leu Val Phe Lys Gln Ser Ile Ser Gln Met Ser Lys Asn Asn Gln Val
130                 135                 140

Lys Glu Thr Asn His Asn Lys Ile Thr Phe Glu Glu Val Val Leu Gly
145                 150                 155                 160

Ile Leu Gly Ile Val Leu Ile Ile Thr Gly Tyr Tyr Leu Ser Leu Asn
                165                 170                 175

Ile Val Gln Tyr Tyr Asp Ser Ile Gly Ile Leu Met Phe Ile Leu Leu
            180                 185                 190

Ser Thr Val Ile Gly Ala Tyr Leu Phe Lys Ser Ser Val Ser Leu
        195                 200                 205

Val Phe Lys Met Val Lys Lys Phe Arg Lys Gly Val Ile Ser Val Asn
    210                 215                 220

Asp Val Met Phe Ser Ser Ser Ile Met Tyr Arg Ile Lys Lys Asn Ala
225                 230                 235                 240
```

```
Phe Ser Leu Thr Val Met Ala Ile Ile Ser Ala Ile Thr Val Ser Val
                245                 250                 255

Leu Cys Phe Ala Ala Ile Ser Arg Ala Ser Leu Ser Ser Glu Ile Lys
            260                 265                 270

Tyr Thr Ala Pro His Asp Val Thr Ile Lys Asp Gln Gln Lys Ala Asn
        275                 280                 285

Gln Leu Ala Ser Glu Leu Asn Asn Gln Lys Ile Pro His Phe Tyr Asn
    290                 295                 300

Tyr Lys Glu Val Ile His Thr Lys Leu Tyr Lys Asp Asn Leu Phe Asp
305                 310                 315                 320

Val Lys Ala Lys Glu Pro Tyr Asn Val Thr Ile Thr Ser Asp Lys Tyr
                325                 330                 335

Ile Pro Asn Thr Asp Leu Lys Arg Gly Gln Ala Asp Leu Phe Val Ala
            340                 345                 350

Glu Gly Ser Ile Lys Asp Leu Val Lys His Lys His Gly Lys Ala
        355                 360                 365

Ile Ile Gly Thr Lys Lys His His Val Asn Ile Lys Leu Arg Lys Asp
    370                 375                 380

Ile Asn Lys Ile Tyr Phe Met Thr Asp Val Asp Leu Gly Gly Pro Thr
385                 390                 395                 400

Phe Val Leu Asn Asp Lys Asp Tyr Gln Glu Ile Arg Lys Tyr Thr Lys
                405                 410                 415

Ala Lys His Ile Val Ser Gln Phe Gly Phe Asp Leu Lys His Lys Lys
            420                 425                 430

Asp Ala Leu Ala Leu Glu Lys Val Lys Asn Lys Val Asp Lys Ser Ile
        435                 440                 445

Lys Thr Arg Ser Glu Ala Ile Ser Ser Ile Ser Ser Leu Thr Gly Ile
    450                 455                 460

Leu Leu Phe Val Thr Ser Phe Leu Gly Ile Thr Phe Leu Ile Ala Val
465                 470                 475                 480

Cys Cys Ile Ile Tyr Ile Lys Gln Ile Asp Glu Thr Glu Asp Glu Leu
                485                 490                 495

Glu Asn Tyr Ser Ile Leu Arg Lys Leu Gly Phe Thr Gln Lys Asp Met
            500                 505                 510

Ala Arg Gly Leu Lys Phe Lys Ile Met Phe Asn Phe Gly Leu Pro Leu
        515                 520                 525

Val Ile Ala Leu Ser His Ala Tyr Phe Thr Ser Leu Ala Tyr Met Lys
    530                 535                 540

Leu Met Gly Thr Thr Asn Gln Ile Pro Val Phe Ile Val Met Gly Leu
545                 550                 555                 560

Tyr Ile Cys Met Tyr Ala Val Phe Ala Val Thr Ala Tyr Asn His Ser
                565                 570                 575

Lys Arg Thr Ile Arg His Ser Ile
            580

<210> SEQ ID NO 113
<211> LENGTH: 584
<212> TYPE: PRT
<213> ORGANISM: Staphylococcus aureus

<400> SEQUENCE: 113

Met Thr Glu Ser Tyr Pro Ile Ile Lys Glu Gly Ser Gln Val Gly Ser
1               5                   10                  15

Tyr Phe Leu Phe Phe Ile Ile Ile Ala Phe Leu Leu Tyr Ala Asn Val
```

-continued

```
                20                  25                  30
Leu Phe Ile Lys Arg Arg Ser Tyr Glu Leu Ala Leu Tyr Gln Thr Leu
            35                  40                  45
Gly Leu Ser Lys Phe Asn Ile Ile Tyr Ile Leu Met Leu Glu Gln Leu
        50                  55                  60
Leu Ile Phe Ile Ile Thr Ala Ile Leu Gly Ile Ile Gly Ile Phe
65                  70                  75                  80
Gly Ser Lys Leu Leu Leu Met Ile Val Phe Thr Leu Leu Gly Ile Lys
                85                  90                  95
Glu Lys Val Pro Ile Ile Phe Ser Leu Arg Ala Val Phe Glu Thr Leu
            100                 105                 110
Met Leu Ile Gly Val Ala Tyr Phe Leu Thr Ser Ala Gln Asn Phe Ile
        115                 120                 125
Leu Val Phe Lys Gln Ser Ile Ser Gln Met Ser Lys Asn Asn Gln Val
    130                 135                 140
Lys Glu Thr Asn His Asn Lys Ile Thr Phe Glu Glu Val Val Leu Gly
145                 150                 155                 160
Ile Leu Gly Ile Val Leu Ile Ile Thr Gly Tyr Tyr Leu Ser Leu Asn
                165                 170                 175
Ile Val Gln Tyr Tyr Asp Ser Ile Gly Ile Leu Met Phe Ile Leu Leu
            180                 185                 190
Ser Thr Val Ile Gly Ala Tyr Leu Phe Phe Lys Ser Ser Val Ser Leu
        195                 200                 205
Val Phe Lys Met Val Lys Lys Phe Arg Lys Gly Val Ile Ser Val Asn
    210                 215                 220
Asp Val Met Phe Ser Ser Ile Met Tyr Arg Ile Lys Lys Asn Ala
225                 230                 235                 240
Phe Ser Leu Thr Val Met Ala Ile Ile Ser Ala Ile Thr Val Ser Val
                245                 250                 255
Leu Cys Phe Ala Ala Ile Ser Arg Ala Ser Leu Ser Ser Glu Ile Lys
            260                 265                 270
Tyr Thr Ala Pro His Asp Val Thr Ile Lys Asp Gln Gln Lys Ala Asn
        275                 280                 285
Gln Leu Ala Ser Glu Leu Asn Asn Gln Lys Ile Pro His Phe Tyr Asn
    290                 295                 300
Tyr Lys Glu Val Ile His Thr Lys Leu Tyr Lys Asp Asn Leu Phe Asp
305                 310                 315                 320
Val Lys Ala Lys Glu Pro Tyr Asn Val Thr Ile Thr Ser Asp Lys Tyr
                325                 330                 335
Ile Pro Asn Thr Asp Leu Lys Arg Gly Gln Ala Asp Leu Phe Val Ala
            340                 345                 350
Glu Gly Ser Ile Lys Asp Leu Val Lys His Lys His Gly Lys Ala
        355                 360                 365
Ile Ile Gly Thr Lys Lys His His Val Asn Ile Lys Leu Arg Lys Asp
    370                 375                 380
Ile Asn Lys Ile Tyr Phe Met Thr Asp Val Asp Leu Gly Gly Pro Thr
385                 390                 395                 400
Phe Val Leu Asn Asp Lys Asp Tyr Gln Glu Ile Arg Lys Tyr Thr Lys
                405                 410                 415
Ala Lys His Ile Val Ser Gln Phe Gly Phe Asp Leu Lys His Lys Lys
            420                 425                 430
Asp Ala Leu Ala Leu Glu Lys Val Lys Asn Lys Val Asp Lys Ser Ile
        435                 440                 445
```

```
Lys Thr Arg Ser Glu Ala Ile Ser Ser Ile Ser Ser Leu Thr Gly Ile
    450                 455                 460

Leu Leu Phe Val Thr Ser Phe Leu Gly Ile Thr Phe Leu Ile Ala Val
465                 470                 475                 480

Cys Cys Ile Ile Tyr Ile Lys Gln Ile Asp Glu Thr Glu Asp Glu Leu
                    485                 490                 495

Glu Asn Tyr Ser Ile Leu Arg Lys Leu Gly Phe Thr Gln Lys Asp Met
                500                 505                 510

Ala Arg Gly Leu Lys Phe Lys Ile Met Phe Asn Phe Gly Leu Pro Leu
            515                 520                 525

Val Ile Val Leu Ser His Ala Tyr Phe Thr Ser Leu Ala Tyr Met Lys
        530                 535                 540

Leu Met Gly Thr Thr Asn Gln Ile Pro Val Phe Ile Val Met Gly Leu
545                 550                 555                 560

Tyr Ile Cys Met Tyr Ala Val Phe Ala Val Thr Ala Tyr Asn His Ser
                565                 570                 575

Lys Arg Thr Ile Arg His Ser Ile
            580

<210> SEQ ID NO 114
<211> LENGTH: 584
<212> TYPE: PRT
<213> ORGANISM: Staphylococcus aureus

<400> SEQUENCE: 114

Met Thr Glu Ser Tyr Pro Ile Ile Lys Glu Gly Ser Gln Val Gly Ser
1               5                   10                  15

Tyr Phe Leu Phe Phe Ile Ile Ala Phe Leu Leu Tyr Ala Asn Val
                20                  25                  30

Leu Phe Ile Lys Arg Arg Ser Tyr Glu Leu Ala Leu Tyr Gln Thr Leu
            35                  40                  45

Gly Leu Ser Lys Phe Asn Ile Ile Tyr Ile Leu Met Leu Glu Gln Leu
        50                  55                  60

Leu Ile Phe Ile Ile Thr Ala Ile Leu Gly Ile Ile Ile Gly Ile Phe
65                  70                  75                  80

Gly Ser Lys Leu Leu Leu Met Ile Val Phe Thr Leu Gly Ile Lys
                85                  90                  95

Glu Lys Val Pro Ile Ile Phe Ser Leu Arg Ala Val Phe Glu Thr Leu
                100                 105                 110

Met Leu Ile Gly Val Ala Tyr Phe Leu Thr Ser Ala Gln Asn Phe Ile
            115                 120                 125

Leu Val Phe Lys Gln Ser Ile Ser Gln Met Ser Lys Asn Asn Gln Val
        130                 135                 140

Lys Glu Thr Asn His Asn Lys Ile Thr Phe Glu Glu Val Val Leu Gly
145                 150                 155                 160

Ile Leu Gly Ile Val Leu Ile Thr Thr Gly Tyr Tyr Leu Ser Leu Asn
                165                 170                 175

Ile Val Gln Tyr Tyr Asp Ser Ile Gly Ile Leu Met Phe Ile Leu Leu
                180                 185                 190

Ser Thr Val Ile Gly Ala Tyr Leu Phe Lys Ser Ser Val Ser Leu
            195                 200                 205

Val Phe Lys Met Val Lys Lys Phe Arg Lys Gly Val Ile Ser Val Asn
        210                 215                 220

Asp Val Met Phe Ser Ser Ser Ile Met Tyr Arg Ile Lys Lys Asn Ala
```

```
            225                 230                 235                 240
    Phe Ser Leu Thr Val Met Ala Ile Ile Ser Ala Ile Thr Val Ser Val
                        245                 250                 255

Leu Cys Phe Ala Ala Ile Ser Arg Ala Ser Leu Ser Ser Glu Ile Lys
                        260                 265                 270

Tyr Thr Ala Pro His Asp Val Thr Ile Lys Asp Gln Gln Lys Ala Asn
                        275                 280                 285

Gln Leu Ala Ser Glu Leu Asn Asn Gln Lys Ile Pro His Phe Tyr Asn
                        290                 295                 300

Tyr Lys Glu Val Ile His Thr Lys Leu Tyr Lys Asp Asn Leu Phe Asp
    305                 310                 315                 320

Val Lys Ala Lys Glu Pro Tyr Asn Val Thr Ile Thr Ser Asp Lys Tyr
                        325                 330                 335

Ile Pro Asn Thr Asp Leu Lys Arg Gly Gln Ala Asp Leu Phe Val Ala
                        340                 345                 350

Glu Gly Ser Ile Lys Asp Leu Val Lys His Lys His Gly Lys Ala
                        355                 360                 365

Ile Ile Gly Thr Lys Lys His His Val Asn Ile Lys Leu Arg Lys Asp
    370                 375                 380

Ile Asn Lys Ile Tyr Phe Met Thr Asp Val Asp Leu Gly Gly Pro Thr
    385                 390                 395                 400

Phe Val Leu Asn Asp Lys Asp Tyr Gln Glu Ile Arg Lys Tyr Thr Lys
                        405                 410                 415

Ala Lys His Ile Val Ser Gln Phe Gly Phe Asp Leu Lys His Lys Lys
                        420                 425                 430

Asp Ala Leu Ala Leu Glu Lys Val Lys Asn Lys Val Asp Lys Ser Ile
                        435                 440                 445

Lys Thr Arg Ser Glu Ala Ile Ser Ser Ile Ser Ser Leu Thr Gly Ile
                        450                 455                 460

Leu Leu Phe Val Thr Ser Phe Leu Gly Ile Thr Phe Leu Ile Ala Val
    465                 470                 475                 480

Cys Cys Ile Ile Tyr Ile Lys Gln Ile Asp Glu Thr Glu Asp Glu Leu
                        485                 490                 495

Glu Asn Tyr Ser Ile Leu Arg Lys Leu Gly Phe Thr Gln Lys Asp Met
                        500                 505                 510

Ala Arg Gly Leu Lys Phe Lys Ile Met Phe Asn Phe Gly Leu Pro Leu
                        515                 520                 525

Val Ile Ala Leu Ser His Ala Tyr Phe Thr Ser Leu Ala Tyr Met Lys
    530                 535                 540

Leu Met Gly Thr Thr Asn Gln Ile Pro Val Phe Ile Val Met Gly Leu
    545                 550                 555                 560

Tyr Ile Cys Met Tyr Ala Val Phe Ala Val Thr Ala Tyr Asn His Ser
                        565                 570                 575

Lys Arg Thr Ile Arg His Ser Ile
                        580

<210> SEQ ID NO 115
<211> LENGTH: 629
<212> TYPE: PRT
<213> ORGANISM: Staphylococcus aureus

<400> SEQUENCE: 115

Met Thr Phe Asn Glu Ile Ile Phe Lys Asn Phe Arg Gln Asn Leu Ser
1               5                   10                  15
```

-continued

His Tyr Ala Ile Tyr Leu Phe Ser Leu Ile Thr Ser Val Val Leu Tyr
            20                      25                      30

Phe Ser Phe Val Ala Leu Lys Tyr Ala His Lys Leu Asn Met Thr Glu
        35                      40                      45

Ser Tyr Pro Ile Ile Lys Glu Gly Ser Gln Val Gly Ser Tyr Phe Leu
    50                      55                      60

Phe Phe Ile Ile Ile Ala Phe Leu Leu Tyr Ala Asn Val Leu Phe Ile
65                      70                      75                  80

Lys Arg Arg Ser Tyr Glu Leu Ala Leu Tyr Gln Thr Leu Gly Leu Ser
                85                      90                      95

Lys Phe Asn Ile Ile Tyr Ile Leu Met Leu Glu Gln Leu Leu Ile Phe
            100                     105                     110

Ile Ile Thr Ala Ile Leu Gly Ile Ile Gly Ile Phe Gly Ser Lys
            115                     120                     125

Leu Leu Leu Met Ile Val Phe Thr Leu Leu Gly Ile Lys Glu Lys Val
        130                     135                     140

Pro Ile Ile Phe Ser Leu Arg Ala Val Phe Glu Thr Leu Met Leu Ile
145                     150                     155                 160

Gly Val Ala Tyr Phe Leu Thr Ser Ala Gln Asn Phe Ile Leu Val Phe
                165                     170                     175

Lys Gln Ser Ile Ser Gln Met Ser Lys Asn Asn Gln Val Lys Glu Thr
            180                     185                     190

Asn His Asn Lys Ile Thr Phe Glu Glu Val Val Leu Gly Ile Leu Gly
            195                     200                     205

Ile Val Leu Ile Thr Thr Gly Tyr Tyr Leu Ser Leu Asn Ile Val Gln
210                     215                     220

Tyr Tyr Asp Ser Ile Gly Ile Leu Met Phe Ile Leu Leu Ser Thr Val
225                     230                     235                 240

Ile Gly Ala Tyr Leu Phe Phe Lys Ser Ser Val Ser Leu Val Phe Lys
                245                     250                     255

Met Val Lys Lys Phe Arg Lys Gly Val Ile Ser Val Asn Asp Val Met
            260                     265                     270

Phe Ser Ser Ile Met Tyr Arg Ile Lys Lys Asn Ala Phe Ser Leu
            275                     280                     285

Thr Val Met Ala Ile Ile Ser Ala Ile Thr Val Ser Val Leu Cys Phe
290                     295                     300

Ala Ala Ile Ser Arg Ala Ser Leu Ser Ser Glu Ile Lys Tyr Thr Ala
305                     310                     315                 320

Pro His Asp Val Thr Ile Lys Asp Gln Gln Lys Ala Asn Gln Leu Ala
            325                     330                     335

Ser Glu Leu Asn Asn Gln Lys Ile Pro His Phe Tyr Asn Tyr Lys Glu
            340                     345                     350

Val Ile His Thr Lys Leu Tyr Lys Asp Asn Leu Phe Asp Val Lys Ala
            355                     360                     365

Lys Glu Pro Tyr Asn Val Thr Ile Thr Ser Asp Lys Tyr Ile Pro Asn
    370                     375                     380

Thr Asp Leu Lys Arg Gly Gln Ala Asp Leu Phe Val Ala Glu Gly Ser
385                     390                     395                 400

Ile Lys Asp Leu Val Lys His Lys Lys His Gly Lys Ala Ile Ile Gly
                405                     410                     415

Thr Lys Lys His His Val Asn Ile Lys Leu Arg Lys Asp Ile Asn Lys
            420                     425                     430

Ile Tyr Phe Met Thr Asp Val Asp Leu Gly Gly Pro Thr Phe Val Leu

```
                435                 440                 445
Asn Asp Lys Asp Tyr Gln Glu Ile Arg Lys Tyr Thr Lys Ala Lys His
450                 455                 460

Ile Val Ser Gln Phe Gly Phe Asp Leu Lys His Lys Lys Asp Ala Leu
465                 470                 475                 480

Ala Leu Glu Lys Val Lys Asn Lys Val Asp Lys Ser Ile Lys Thr Arg
                485                 490                 495

Ser Glu Ala Ile Ser Ser Ile Ser Ser Leu Thr Gly Ile Leu Leu Phe
                500                 505                 510

Val Thr Ser Phe Leu Gly Ile Thr Phe Leu Ile Ala Val Cys Cys Ile
                515                 520                 525

Ile Tyr Ile Lys Gln Ile Asp Glu Thr Glu Asp Glu Leu Glu Asn Tyr
                530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
                580                 585                 590

Thr Thr Asn Gln Ile Pro Val Phe Ile Val Met Gly Leu Tyr Ile Cys
                595                 600                 605

Met Tyr Ala Val Phe Ala Val Thr Ala Tyr Asn His Ser Lys Arg Thr
                610                 615                 620

Ile Arg His Ser Ile
625

<210> SEQ ID NO 116
<211> LENGTH: 629
<212> TYPE: PRT
<213> ORGANISM: Staphylococcus aureus

<400> SEQUENCE: 116

Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
                20                  25                  30

Phe Ser Phe Val Ala Leu Lys Tyr Ala His Lys Leu Asn Met Thr Glu
            35                  40                  45

Ser Tyr Pro Ile Ile Lys Glu Gly Ser Gln Val Gly Ser Tyr Phe Leu
        50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
                100                 105                 110

Ile Ile Thr Ala Ile Leu Gly Ile Ile Gly Ile Phe Gly Ser Lys
                115                 120                 125

Leu Leu Leu Met Ile Val Phe Thr Leu Gly Ile Lys Glu Lys Val
130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175
```

-continued

```
Lys Gln Ser Ile Ser Gln Met Ser Lys Asn Asn Gln Val Lys Glu Thr
                180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
210                 215                 220

Tyr Tyr Asp Ser Ile Gly Ile Leu Met Phe Ile Leu Leu Ser Thr Val
225                 230                 235                 240

Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
                260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
        290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                325                 330                 335

Ser Glu Leu Asn Asn Gln Lys Ile Pro His Phe Tyr Asn Tyr Lys Glu
                340                 345                 350

Val Ile His Thr Lys Leu Tyr Lys Asp Asn Leu Phe Asp Val Lys Ala
        355                 360                 365

Lys Glu Pro Tyr Asn Val Thr Ile Thr Ser Asp Lys Tyr Ile Pro Asn
370                 375                 380

Thr Asp Leu Lys Arg Gly Gln Ala Asp Leu Phe Val Ala Glu Gly Ser
385                 390                 395                 400

Ile Lys Asp Leu Val Lys His Lys His Gly Lys Ala Ile Gly
                405                 410                 415

Thr Lys Lys His His Val Asn Ile Lys Leu Arg Lys Asp Ile Asn Lys
                420                 425                 430

Ile Tyr Phe Met Thr Asp Val Asp Leu Gly Gly Pro Thr Phe Val Leu
        435                 440                 445

Asn Asp Lys Asp Tyr Gln Glu Ile Arg Lys Tyr Thr Lys Ala Lys His
450                 455                 460

Ile Val Ser Gln Phe Gly Phe Asp Leu Lys His Lys Lys Asp Ala Leu
465                 470                 475                 480

Ala Leu Glu Lys Val Lys Asn Lys Val Asp Lys Ser Ile Lys Thr Arg
                485                 490                 495

Ser Glu Ala Ile Ser Ser Ile Ser Ser Leu Thr Gly Ile Leu Leu Phe
                500                 505                 510

Val Thr Ser Phe Leu Gly Ile Thr Phe Leu Ile Ala Val Cys Cys Ile
        515                 520                 525

Ile Tyr Ile Lys Gln Ile Asp Glu Thr Glu Asp Glu Leu Glu Asn Tyr
        530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
                580                 585                 590

Thr Thr Asn Gln Ile Pro Val Phe Ile Val Met Gly Leu Tyr Ile Cys
```

Met Tyr Ala Val Phe Ala Val Thr Ala Tyr Asn His Ser Lys Arg Thr
            595                 600                 605
Met Tyr Ala Val Phe Ala Val Thr Ala Tyr Asn His Ser Lys Arg Thr
            610                 615                 620
Ile Arg His Ser Ile
625

<210> SEQ ID NO 117
<211> LENGTH: 629
<212> TYPE: PRT
<213> ORGANISM: Staphylococcus aureus

<400> SEQUENCE: 117

Met Thr Phe Asn Glu Ile Ile Phe Lys Asn Phe Arg Gln Asn Leu Ser
1               5                   10                  15
His Tyr Ala Ile Tyr Leu Phe Ser Leu Ile Thr Ser Val Val Leu Tyr
                20                  25                  30
Phe Ser Phe Val Ala Leu Lys Tyr Ala His Lys Leu Asn Met Thr Glu
            35                  40                  45
Ser Tyr Pro Ile Ile Lys Glu Gly Ser Gln Val Gly Ser Tyr Phe Leu
        50                  55                  60
Phe Phe Ile Ile Ile Ala Phe Leu Leu Tyr Ala Asn Val Leu Phe Ile
65                  70                  75                  80
Lys Arg Arg Ser Tyr Glu Leu Ala Leu Tyr Gln Thr Leu Gly Leu Ser
                85                  90                  95
Lys Phe Asn Ile Ile Tyr Ile Leu Met Leu Glu Gln Leu Leu Ile Phe
            100                 105                 110
Ile Ile Thr Ala Ile Leu Gly Ile Ile Gly Ile Phe Gly Ser Lys
        115                 120                 125
Leu Leu Leu Met Ile Val Phe Thr Leu Gly Ile Lys Glu Lys Val
            130                 135                 140
Pro Ile Ile Phe Ser Leu Arg Ala Val Phe Glu Thr Leu Met Leu Ile
145                 150                 155                 160
Gly Val Ala Tyr Phe Leu Thr Ser Ala Gln Asn Phe Ile Leu Val Phe
                165                 170                 175
Lys Gln Ser Ile Ser Gln Met Ser Lys Asn Asn Gln Val Lys Glu Thr
            180                 185                 190
Asn His Asn Lys Ile Thr Phe Glu Glu Val Val Leu Gly Ile Leu Gly
        195                 200                 205
Ile Val Leu Ile Thr Thr Gly Tyr Tyr Leu Ser Leu Asn Ile Val Gln
    210                 215                 220
Tyr Tyr Asp Ser Ile Gly Ile Leu Met Phe Ile Leu Leu Ser Thr Val
225                 230                 235                 240
Ile Gly Ala Tyr Leu Phe Phe Lys Ser Ser Val Ser Leu Val Phe Lys
                245                 250                 255
Met Val Lys Lys Phe Arg Lys Gly Val Ile Ser Val Asn Asp Val Met
            260                 265                 270
Phe Ser Ser Ser Ile Met Tyr Arg Ile Lys Lys Asn Ala Phe Ser Leu
        275                 280                 285
Thr Val Met Ala Ile Ile Ser Ala Ile Thr Val Ser Val Leu Cys Phe
    290                 295                 300
Ala Ala Ile Ser Arg Ala Ser Leu Ser Ser Glu Ile Lys Tyr Thr Ala
305                 310                 315                 320
Pro His Asp Val Thr Ile Lys Asp Gln Gln Lys Ala Asn Gln Leu Ala
                325                 330                 335

```
Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Ala
        355                 360                 365

Lys Glu Pro Tyr Asn Val Thr Ile Thr Ser Asp Lys Tyr Ile Pro Asn
370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Val Ile Gly
                405                 410                 415

Thr Lys Lys His His Val Asn Ile Lys Leu Arg Lys Asp Ile Asn Lys
                420                 425                 430

Ile Tyr Phe Met Thr Asp Val Asp Leu Gly Gly Pro Thr Phe Val Leu
            435                 440                 445

Asn Asp Lys Asp Tyr Gln Glu Ile Arg Lys Tyr Thr Lys Ala Lys His
        450                 455                 460

Ile Val Ser Gln Phe Gly Phe Asp Leu Lys His Lys Asp Ala Leu
465                 470                 475                 480

Ala Leu Glu Lys Val Lys Asn Lys Val Asp Lys Ser Ile Lys Thr Arg
                485                 490                 495

Ser Glu Ala Ile Ser Ser Ile Ser Ser Leu Thr Gly Ile Leu Leu Phe
                500                 505                 510

Val Thr Ser Phe Leu Gly Ile Thr Phe Leu Ile Ala Val Cys Cys Ile
            515                 520                 525

Ile Tyr Ile Lys Gln Ile Asp Glu Thr Glu Asp Glu Leu Glu Asn Tyr
        530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
            580                 585                 590

Thr Thr Asn Gln Ile Pro Val Phe Ile Val Met Gly Leu Tyr Ile Cys
        595                 600                 605

Met Tyr Ala Val Phe Ala Val Thr Ala Tyr Asn His Ser Lys Arg Thr
        610                 615                 620

Ile Arg His Ser Ile
625

<210> SEQ ID NO 118
<211> LENGTH: 629
<212> TYPE: PRT
<213> ORGANISM: Staphylococcus aureus

<400> SEQUENCE: 118

Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80
```

-continued

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Gly Ile Phe Gly Ser Lys
        115                 120                 125

Leu Leu Leu Met Ile Val Phe Thr Leu Leu Gly Ile Lys Glu Lys Val
130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
                195                 200                 205

Ile Val Leu Ile Thr Thr Gly Tyr Tyr Leu Ser Leu Asn Ile Val Gln
        210                 215                 220

Tyr Tyr Asp Ser Ile Gly Ile Leu Met Phe Ile Leu Leu Ser Thr Val
225                 230                 235                 240

Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
        275                 280                 285

Thr Val Met Ala Ile Ile Ser Ala Ile Thr Val Ser Val Leu Cys Phe
290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                325                 330                 335

Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Ala
        355                 360                 365

Lys Glu Pro Tyr Asn Val Thr Ile Thr Ser Asp Lys Tyr Ile Pro Asn
370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Val Ile Gly
                405                 410                 415

Thr Lys Lys His His Val Asn Ile Lys Leu Arg Lys Asp Ile Asn Lys
            420                 425                 430

Ile Tyr Phe Met Thr Asp Val Asp Leu Gly Gly Pro Thr Phe Val Leu
        435                 440                 445

Asn Asp Lys Asp Tyr Gln Glu Ile Arg Lys Tyr Thr Lys Ala Lys His
450                 455                 460

Ile Val Ser Gln Phe Gly Phe Asp Leu Lys His Lys Lys Asp Ala Leu
465                 470                 475                 480

Ala Leu Glu Lys Val Lys Asn Lys Val Asp Lys Ser Ile Lys Thr Arg
                485                 490                 495

Ser Glu Ala Ile Ser Ser Ile Ser Ser Leu Thr Gly Ile Leu Leu Phe
                500                 505                 510

Val Thr Ser Phe Leu Gly Ile Thr Phe Leu Ile Ala Val Cys Cys Ile
            515                 520                 525

Ile Tyr Ile Lys Gln Ile Asp Glu Thr Glu Asp Glu Leu Glu Asn Tyr
        530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Ala
                565                 570                 575

Leu Ser His Ala Tyr Phe Thr Ser Leu Ala Tyr Met Lys Leu Met Gly
            580                 585                 590

Thr Thr Asn Gln Ile Pro Val Phe Ile Val Met Gly Leu Tyr Ile Cys
        595                 600                 605

Met Tyr Ala Val Phe Ala Val Thr Ala Tyr Asn His Ser Lys Arg Thr
610                 615                 620

Ile Arg His Ser Ile
625

<210> SEQ ID NO 119
<211> LENGTH: 629
<212> TYPE: PRT
<213> ORGANISM: Staphylococcus aureus

<400> SEQUENCE: 119

Met Thr Phe Asn Glu Ile Ile Phe Lys Asn Phe Arg Gln Asn Leu Ser
1               5                   10                  15

His Tyr Ala Ile Tyr Leu Phe Ser Leu Ile Thr Ser Val Val Leu Tyr
            20                  25                  30

Phe Ser Phe Val Ala Leu Lys Tyr Ala His Lys Leu Asn Met Thr Glu
        35                  40                  45

Ser Tyr Pro Ile Ile Lys Glu Gly Ser Gln Val Gly Ser Tyr Phe Leu
    50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Gly Ile Phe Gly Ser Lys
        115                 120                 125

Leu Leu Leu Met Ile Val Phe Thr Leu Leu Gly Ile Lys Glu Lys Val
    130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175

Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
        195                 200                 205

Ile Val Leu Ile Thr Thr Gly Tyr Tyr Leu Ser Leu Asn Ile Val Gln
    210                 215                 220

Tyr Tyr Asp Ser Ile Gly Thr Leu Met Phe Ile Leu Leu Ser Thr Val
225                 230                 235                 240

```
Ile Gly Ala Tyr Leu Phe Phe Lys Ser Ser Val Ser Leu Val Phe Lys
                245                 250                 255
Met Val Lys Lys Phe Arg Lys Gly Val Ile Ser Val Asn Asp Val Met
            260                 265                 270
Phe Ser Ser Ser Ile Met Tyr Arg Ile Lys Lys Asn Ala Phe Ser Leu
        275                 280                 285
Thr Val Met Ala Ile Ile Ser Ala Ile Thr Val Ser Val Leu Cys Phe
    290                 295                 300
Ala Ala Ile Ser Arg Ala Ser Leu Ser Ser Glu Ile Lys Tyr Thr Ala
305                 310                 315                 320
Pro His Asp Val Thr Ile Lys Asp Gln Gln Lys Ala Asn Gln Leu Ala
                325                 330                 335
Ser Glu Leu Asn Asn Gln Lys Ile Pro His Phe Tyr Asn Tyr Lys Glu
            340                 345                 350
Val Ile His Thr Lys Leu Tyr Lys Asp Asn Leu Phe Asp Val Lys Ser
        355                 360                 365
Lys Gln Pro Tyr Asn Val Thr Ile Thr Ser Asp Lys Tyr Ile Pro Ser
    370                 375                 380
Thr Asp Leu Lys Arg Gly Gln Ala Asp Leu Phe Val Ala Glu Gly Ser
385                 390                 395                 400
Ile Lys Asp Leu Val Lys His Lys Lys His Gly Lys Ala Val Ile Gly
                405                 410                 415
Thr Lys Lys His His Val Asn Ile Lys Leu Arg Lys Asp Ile Asn Lys
            420                 425                 430
Ile Tyr Phe Met Thr Asp Val Asp Leu Gly Gly Pro Thr Phe Val Leu
        435                 440                 445
Asn Asp Lys Asp Tyr Gln Glu Ile Arg Lys Tyr Thr Lys Ala Lys His
    450                 455                 460
Ile Val Ser Gln Phe Gly Phe Asp Leu Lys His Lys Lys Asp Ala Leu
465                 470                 475                 480
Ala Leu Glu Lys Ala Lys Asn Lys Val Asp Lys Ser Ile Glu Thr Arg
                485                 490                 495
Ser Glu Ala Ile Ser Ser Ile Ser Ser Leu Thr Gly Ile Leu Leu Phe
            500                 505                 510
Val Thr Ser Phe Leu Gly Ile Thr Phe Leu Ile Ala Val Cys Cys Ile
        515                 520                 525
Ile Tyr Ile Lys Gln Ile Asp Glu Thr Glu Asp Glu Leu Glu Asn Tyr
    530                 535                 540
Ser Ile Leu Arg Lys Leu Gly Phe Thr Gln Lys Asp Met Ala Arg Gly
545                 550                 555                 560
Leu Lys Phe Lys Ile Met Phe Asn Phe Gly Leu Pro Leu Val Ile Ala
                565                 570                 575
Leu Ser His Ala Tyr Phe Thr Ser Leu Ala Tyr Met Lys Leu Met Gly
            580                 585                 590
Thr Thr Asn Gln Ile Pro Val Phe Ile Val Met Gly Leu Tyr Ile Cys
        595                 600                 605
Met Tyr Ala Val Phe Ala Val Thr Ala Tyr Asn His Ser Lys Arg Thr
    610                 615                 620
Ile Arg His Ser Ile
625

<210> SEQ ID NO 120
<211> LENGTH: 629
```

```
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(45)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (370)..(370)
<223> OTHER INFORMATION: Xaa can be any naturally occurring amino acid
<220> FEATURE:
<221> NAME/KEY: misc_feature
<222> LOCATION: (384)..(384)
<223> OTHER INFORMATION: Xaa can be any naturally occurring amino acid
<220> FEATURE:
<221> NAME/KEY: misc_feature
<222> LOCATION: (414)..(414)
<223> OTHER INFORMATION: Xaa can be any naturally occurring amino acid
<220> FEATURE:
<221> NAME/KEY: misc_feature
<222> LOCATION: (486)..(486)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (576)..(576)
<223> OTHER INFORMATION: Xaa can be any naturally occurring amino acid

<400> SEQUENCE: 120

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Met Thr Glu
        35                  40                  45

Ser Tyr Pro Ile Ile Lys Glu Gly Ser Gln Val Gly Ser Tyr Phe Leu
50                  55                  60

Phe Phe Ile Ile Ile Ala Phe Leu Leu Tyr Ala Asn Val Leu Phe Ile
65                  70                  75                  80

Lys Arg Arg Ser Tyr Glu Leu Ala Leu Tyr Gln Thr Leu Gly Leu Ser
                85                  90                  95

Lys Phe Asn Ile Ile Tyr Ile Leu Met Leu Glu Gln Leu Leu Ile Phe
            100                 105                 110

Ile Ile Thr Ala Ile Leu Gly Ile Ile Ile Gly Ile Phe Gly Ser Lys
        115                 120                 125

Leu Leu Leu Met Ile Val Phe Thr Leu Leu Gly Ile Lys Glu Lys Val
    130                 135                 140

Pro Ile Ile Phe Ser Leu Arg Ala Val Phe Glu Thr Leu Met Leu Ile
145                 150                 155                 160

Gly Val Ala Tyr Phe Leu Thr Ser Ala Gln Asn Phe Ile Leu Val Phe
                165                 170                 175
```

```
Lys Gln Ser Ile Ser Gln Met Ser Lys Asn Asn Gln Val Lys Glu Thr
            180                 185                 190

Asn His Asn Lys Ile Thr Phe Glu Glu Val Val Leu Gly Ile Leu Gly
            195                 200                 205

Ile Val Leu Ile Xaa Thr Gly Tyr Tyr Leu Ser Leu Asn Ile Val Gln
210                 215                 220

Tyr Tyr Asp Ser Ile Gly Xaa Leu Met Phe Ile Leu Leu Ser Thr Val
225                 230                 235                 240

Ile Gly Ala Tyr Leu Phe Phe Lys Ser Ser Val Ser Leu Val Phe Lys
                245                 250                 255

Met Val Lys Lys Phe Arg Lys Gly Val Ile Ser Val Asn Asp Val Met
            260                 265                 270

Phe Ser Ser Ser Ile Met Tyr Arg Ile Lys Lys Asn Ala Phe Ser Leu
                275                 280                 285

Thr Val Met Ala Ile Ile Ser Ala Ile Thr Val Ser Val Leu Cys Phe
            290                 295                 300

Ala Ala Ile Ser Arg Ala Ser Leu Ser Ser Glu Ile Lys Tyr Thr Ala
305                 310                 315                 320

Pro His Asp Val Thr Ile Lys Asp Gln Gln Lys Ala Asn Gln Leu Ala
                325                 330                 335

Ser Glu Leu Asn Asn Gln Lys Ile Pro His Phe Tyr Asn Tyr Lys Glu
            340                 345                 350

Val Ile His Thr Lys Leu Tyr Lys Asp Asn Leu Phe Asp Val Lys Xaa
            355                 360                 365

Lys Xaa Pro Tyr Asn Val Thr Ile Thr Ser Asp Lys Tyr Ile Pro Xaa
        370                 375                 380

Thr Asp Leu Lys Arg Gly Gln Ala Asp Leu Phe Val Ala Glu Gly Ser
385                 390                 395                 400

Ile Lys Asp Leu Val Lys His Lys Lys His Gly Lys Ala Xaa Ile Gly
                405                 410                 415

Thr Lys Lys His His Val Asn Ile Lys Leu Arg Lys Asp Ile Asn Lys
                420                 425                 430

Ile Tyr Phe Met Thr Asp Val Asp Leu Gly Gly Pro Thr Phe Val Leu
            435                 440                 445

Asn Asp Lys Asp Tyr Gln Glu Ile Arg Lys Tyr Thr Lys Ala Lys His
450                 455                 460

Ile Val Ser Gln Phe Gly Phe Asp Leu Lys His Lys Lys Asp Ala Leu
465                 470                 475                 480

Ala Leu Glu Lys Ala Xaa Asn Lys Val Asp Lys Ser Ile Xaa Thr Arg
                485                 490                 495

Ser Glu Ala Ile Ser Ser Ile Ser Ser Leu Thr Gly Ile Leu Leu Phe
            500                 505                 510

Val Thr Ser Phe Leu Gly Ile Thr Phe Leu Ile Ala Val Cys Cys Ile
            515                 520                 525

Ile Tyr Ile Lys Gln Ile Asp Glu Thr Glu Asp Glu Leu Glu Asn Tyr
            530                 535                 540

Ser Ile Leu Arg Lys Leu Gly Phe Thr Gln Lys Asp Met Ala Arg Gly
545                 550                 555                 560

Leu Lys Phe Lys Ile Met Phe Asn Phe Gly Leu Pro Leu Val Ile Xaa
                565                 570                 575

Leu Ser His Ala Tyr Phe Thr Ser Leu Ala Tyr Met Leu Met Gly
            580                 585                 590
```

Thr Thr Asn Gln Ile Pro Val Phe Ile Val Met Gly Leu Tyr Ile Cys
            595                 600                 605

Met Tyr Ala Val Phe Ala Val Thr Ala Tyr Asn His Ser Lys Arg Thr
            610                 615                 620

Ile Arg His Ser Ile
625

<210> SEQ ID NO 121
<211> LENGTH: 55
<212> TYPE: PRT
<213> ORGANISM: Staphylococcus aureus

<400> SEQUENCE: 121

Met Leu Glu Ser Arg Glu Gln Leu Ser Val Glu Glu Tyr Glu Thr Phe
1               5                   10                  15

Phe Asn Arg Phe Asp Asn Gln Glu Phe Asp Phe Glu Arg Glu Leu Thr
            20                  25                  30

Gln Asp Pro Tyr Ser Lys Val Tyr Leu Tyr Ser Ile Glu Asp His Ile
        35                  40                  45

Arg Thr Tyr Lys Ile Glu Lys
    50                  55

<210> SEQ ID NO 122
<211> LENGTH: 55
<212> TYPE: PRT
<213> ORGANISM: Staphylococcus aureus

<400> SEQUENCE: 122

Met Leu Glu Ser Arg Glu Gln Leu Ser Val Glu Glu Tyr Glu Thr Phe
1               5                   10                  15

Phe Asn Arg Phe Asp Asn Gln Glu Phe Asp Phe Glu Arg Glu Leu Thr
            20                  25                  30

Gln Asp Pro Tyr Ser Lys Val Tyr Leu Tyr Ser Ile Glu Asp His Ile
        35                  40                  45

Arg Thr Tyr Lys Ile Glu Lys
    50                  55

<210> SEQ ID NO 123
<211> LENGTH: 88
<212> TYPE: PRT
<213> ORGANISM: Staphylococcus aureus

<400> SEQUENCE: 123

Cys Leu Phe Ser Tyr Gly Ser Gly Ala Val Gly Glu Ile Phe Ser Gly
1               5                   10                  15

Ser Ile Val Lys Gly Tyr Asp Lys Ala Leu Asp Lys Glu Lys His Leu
            20                  25                  30

Asn Met Leu Glu Ser Arg Glu Gln Leu Ser Val Glu Glu Tyr Glu Thr
        35                  40                  45

Phe Phe Asn Arg Phe Asp Asn Gln Glu Phe Asp Phe Glu Arg Glu Leu
    50                  55                  60

Thr Gln Asp Pro Tyr Ser Lys Val Tyr Leu Tyr Ser Ile Glu Asp His
65                  70                  75                  80

Ile Arg Thr Tyr Lys Ile Glu Lys
                85

<210> SEQ ID NO 124
<211> LENGTH: 88
<212> TYPE: PRT

<213> ORGANISM: Staphylococcus aureus

<400> SEQUENCE: 124

Cys Leu Phe Ser Tyr Gly Ser Gly Ala Val Gly Glu Ile Phe Ser Gly
1               5                   10                  15

Ser Ile Val Lys Gly Tyr Asp Lys Ala Leu Asp Lys Glu Lys His Leu
            20                  25                  30

Asn Met Leu Glu Ser Arg Glu Gln Leu Ser Val Glu Glu Tyr Glu Thr
        35                  40                  45

Phe Phe Asn Arg Phe Asp Asn Gln Glu Phe Phe Glu Arg Glu Leu
    50                  55                  60

Thr Gln Asp Pro Tyr Ser Lys Val Tyr Leu Tyr Ser Ile Glu Asp His
65                  70                  75                  80

Ile Arg Thr Tyr Lys Ile Glu Lys
                85

<210> SEQ ID NO 125
<211> LENGTH: 88
<212> TYPE: PRT
<213> ORGANISM: Staphylococcus aureus

<400> SEQUENCE: 125

Cys Leu Phe Ser Tyr Gly Ser Gly Ala Val Gly Glu Ile Phe Ser Gly
1               5                   10                  15

Ser Ile Val Lys Gly Tyr Asp Lys Ala Leu Asp Lys Glu Lys His Leu
            20                  25                  30

Asn Met Leu Glu Ser Arg Glu Gln Leu Ser Val Glu Glu Tyr Glu Thr
        35                  40                  45

Phe Phe Asn Arg Phe Asp Asn Gln Glu Phe Phe Glu Arg Glu Leu
    50                  55                  60

Thr Gln Asp Pro Tyr Ser Lys Val Tyr Leu Tyr Ser Ile Glu Asp His
65                  70                  75                  80

Ile Arg Thr Tyr Lys Ile Glu Lys
                85

<210> SEQ ID NO 126
<211> LENGTH: 78
<212> TYPE: PRT
<213> ORGANISM: Staphylococcus aureus

<400> SEQUENCE: 126

Gly Glu Phe Tyr Ser Ala Thr Leu Val Glu Gly Tyr Lys Asp His Leu
1               5                   10                  15

Asp Gln Ala Ala His Lys Ala Leu Leu Asn Asn Arg Thr Glu Val Ser
            20                  25                  30

Val Asp Ala Tyr Glu Thr Phe Phe Lys Arg Phe Asp Asp Val Asp Phe
        35                  40                  45

Asp Glu Gln Gln Asp Ala Val His Glu Asp Arg Arg Ile Phe Tyr Leu
    50                  55                  60

Ser Asn Ile Glu Asn Asn Val Arg Glu Tyr His Arg Pro Glu
65                  70                  75

<210> SEQ ID NO 127
<211> LENGTH: 88
<212> TYPE: PRT
<213> ORGANISM: Staphylococcus aureus

<400> SEQUENCE: 127

Gly Leu Phe Ser Tyr Gly Ser Gly Ser Val Gly Glu Phe Tyr Ser Ala
1               5                   10                  15

Thr Leu Val Glu Gly Tyr Lys Asp His Leu Asp Gln Ala Ala His Lys
            20                  25                  30

Ala Leu Leu Asn Asn Arg Thr Glu Val Ser Val Asp Ala Tyr Glu Thr
            35                  40                  45

Phe Phe Lys Arg Phe Asp Asp Val Asp Phe Glu Gln Gln Asp Ala
            50                  55                  60

Val His Glu Asp Arg Arg Ile Phe Tyr Leu Ser Asn Ile Glu Asn Asn
65                  70                  75                  80

Val Arg Glu Tyr His Arg Pro Glu
                85

<210> SEQ ID NO 128
<211> LENGTH: 78
<212> TYPE: PRT
<213> ORGANISM: Staphylococcus aureus

<400> SEQUENCE: 128

Gly Glu Phe Tyr Ser Ala Thr Leu Val Glu Gly Tyr Lys Asp His Leu
1               5                   10                  15

Asp Gln Ala Ala His Lys Ala Leu Leu Asn Asn Arg Thr Glu Val Ser
            20                  25                  30

Val Asp Ala Tyr Glu Thr Phe Phe Lys Arg Phe Asp Asp Val Asp Phe
            35                  40                  45

Asp Glu Glu Gln Asp Ala Val His Glu Asp Arg His Ile Phe Tyr Leu
            50                  55                  60

Ser Asn Ile Glu Asn Asn Val Arg Glu Tyr His Arg Pro Glu
65                  70                  75

<210> SEQ ID NO 129
<211> LENGTH: 88
<212> TYPE: PRT
<213> ORGANISM: Staphylococcus aureus

<400> SEQUENCE: 129

Gly Leu Phe Ser Tyr Gly Ser Gly Ser Val Gly Glu Phe Tyr Ser Ala
1               5                   10                  15

Thr Leu Val Glu Gly Tyr Lys Asp His Leu Asp Gln Ala Ala His Lys
            20                  25                  30

Ala Leu Leu Asn Asn Arg Thr Glu Val Ser Val Asp Ala Tyr Glu Thr
            35                  40                  45

Phe Phe Lys Arg Phe Asp Asp Val Glu Phe Asp Glu Gln Asp Ala
            50                  55                  60

Val His Glu Asp Arg His Ile Phe Tyr Leu Ser Asn Ile Glu Asn Asn
65                  70                  75                  80

Val Arg Glu Tyr His Arg Pro Glu
                85

<210> SEQ ID NO 130
<211> LENGTH: 88
<212> TYPE: PRT
<213> ORGANISM: Staphylococcus aureus

<400> SEQUENCE: 130

Gly Leu Phe Ser Tyr Gly Ser Gly Ser Val Gly Glu Phe Tyr Ser Ala
1               5                   10                  15

Thr Leu Val Glu Gly Tyr Lys Asp His Leu Asp Gln Ala Ala His Lys

```
                20                  25                  30
Ala Leu Leu Asn Asn Arg Thr Glu Val Ser Val Asp Ala Tyr Glu Thr
            35                  40                  45

Phe Phe Lys Arg Phe Asp Asp Val Glu Phe Asp Glu Glu Gln Asp Ala
        50                  55                  60

Val His Glu Asp Arg His Ile Phe Tyr Leu Ser Asn Ile Glu Asn Asn
65                  70                  75                  80

Val Arg Glu Tyr His Arg Pro Glu
                85

<210> SEQ ID NO 131
<211> LENGTH: 88
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(34)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (39)..(41)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (55)..(57)
<223> OTHER INFORMATION: Xaa can be any naturally occurring amino acid
<220> FEATURE:
<221> NAME/KEY: misc_feature
<222> LOCATION: (60)..(72)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (79)..(81)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(88)
<223> OTHER INFORMATION: Xaa can be any naturally occurring amino acid

<400> SEQUENCE: 131

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Leu Xaa Xaa Arg Xaa Xaa Xaa Ser Val Xaa Xaa Tyr Glu Thr
        35                  40                  45

Phe Phe Xaa Arg Phe Asp Xaa Xaa Xaa Phe Asp Xaa Xaa Xaa Xaa Xaa
    50                  55                  60
```

Xaa Xaa Xaa Xaa Xaa Xaa Xaa Tyr Leu Xaa Xaa Ile Glu Xaa Xaa
65                  70                  75                  80

Xaa Arg Xaa Tyr Xaa Xaa Xaa Xaa
            85

<210> SEQ ID NO 132
<211> LENGTH: 14
<212> TYPE: PRT
<213> ORGANISM: Staphylococcus aureus

<400> SEQUENCE: 132

Glu Ser Arg Glu Gln Leu Ser Val Glu Glu Tyr Glu Thr Phe
1               5                   10

<210> SEQ ID NO 133
<211> LENGTH: 14
<212> TYPE: PRT
<213> ORGANISM: Staphylococcus aureus

<400> SEQUENCE: 133

Asn Asn Arg Thr Glu Val Ser Val Asp Ala Tyr Glu Thr Phe
1               5                   10

<210> SEQ ID NO 134
<211> LENGTH: 14
<212> TYPE: PRT
<213> ORGANISM: Staphylococcus aureus

<400> SEQUENCE: 134

Asn Gln Glu Phe Asp Phe Glu Arg Glu Leu Thr Gln Asp Pro
1               5                   10

<210> SEQ ID NO 135
<211> LENGTH: 14
<212> TYPE: PRT
<213> ORGANISM: Staphylococcus aureus

<400> SEQUENCE: 135

Asp Val Asp Phe Asp Glu Gln Gln Asp Ala Val His Glu Asp
1               5                   10

<210> SEQ ID NO 136
<211> LENGTH: 14
<212> TYPE: PRT
<213> ORGANISM: Staphylococcus aureus

<400> SEQUENCE: 136

Asp Val Asp Phe Asp Glu Glu Gln Asp Ala Val His Glu Asp
1               5                   10

<210> SEQ ID NO 137
<211> LENGTH: 14
<212> TYPE: PRT
<213> ORGANISM: Staphylococcus aureus

<400> SEQUENCE: 137

Asp Val Glu Phe Asp Glu Glu Gln Asp Ala Val His Glu Asp
1               5                   10

<210> SEQ ID NO 138
<211> LENGTH: 14
<212> TYPE: PRT
<213> ORGANISM: Artificial sequence
<220> FEATURE:

```
<223> OTHER INFORMATION: synthetic sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 138

Xaa Xaa Arg Xaa Xaa Xaa Ser Val Xaa Xaa Tyr Glu Thr Phe
 1               5                  10

<210> SEQ ID NO 139
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(14)
<223> OTHER INFORMATION: Xaa can be any naturally occurring amino acid

<400> SEQUENCE: 139

Xaa Xaa Xaa Phe Asp Xaa Xaa Xaa Xaa Xaa Xaa Xaa Xaa Xaa
 1               5                  10

<210> SEQ ID NO 140
<211> LENGTH: 720
<212> TYPE: DNA
<213> ORGANISM: Staphylococcus aureus

<400> SEQUENCE: 140
ttattgttca atgtgctttt gaataaaatc tttgatttga ggcgtaaagt atacggcacc      60
attatattca gaaccaattt ttccaatacc gccatacacc acacctatga cctcattgtt     120
agaatttaga actggtgatc ctgaattccc gggttcaatg tatgcatcaa aatttaaaat     180
attgtctttg attctttta tagttcctgt agattcaaac tgtttaaaac tattttgagc      240
aggtaatggg taaccaataa ctttaatttt gtcatcaact ttagcatctt tcgcaaaatt     300
taatgcttgg acatttcat taaaattaaa gccttttggt ccacgttcaa ctgcttgttc      360
ttcaatattc atgacagaga tgtcttcatc acccggataa tcagaaatgc ttttaatttt     420
atatatacca ccatttcctt tgtcaccgtc tggatgggca gtaattctat cgccaacttt     480
ataatctttt gatacatgtt tattggtgat aattgtattt tttccaatta caaaacctgt     540
cgcatcttta aatgaaacga cgccattata tggaaaaata tttgtatctt taacttgcgt     600
aacattcttc tctgcatttg ctatttgttg tgtctcttca acgactgcag catttattcc     660
agttactgag gttagaatgg ctaatgctgc catgctttta atgactatat ttttattcat     720

<210> SEQ ID NO 141
<211> LENGTH: 720
<212> TYPE: DNA
<213> ORGANISM: Staphylococcus aureus

<400> SEQUENCE: 141
```

| | |
|---|---|
| ttattgttca atgtgctttt gaataaaatc tttgatttga ggcgtaaagt atacggcacc | 60 |
| attatattca gaaccaattt ttccaatacc gccatacacc acacctatga cctcattgtt | 120 |
| agaatttaga actggtgatc ctgaattccc gggttcaatg tatgcatcaa aatttaaaat | 180 |
| attgtctttg attcttttta tagttcctgt agattcaaac tgtttaaaac tattttgagc | 240 |
| aggtaatggg taaccaataa ctttaatttt gtcatcaact ttagcatctt tcgcaaaatt | 300 |
| taatgcttgg acattttcat taaaattaaa gccttttggt ccacgttcaa ctgcttgttc | 360 |
| ttcaatattc atgacagaga tgtcttcatc acccggataa tcagaaatgc ttttaatttt | 420 |
| atatatacca ccatttcctt tgtcaccgtc tggatgggca gtaattctat cgccaacttt | 480 |
| ataatctttt gatacatgtt tattggtgat aattgtattt tttccaatta caaaacctgt | 540 |
| cgcatcttta aatgaaacga cgccattata tggaaaaata tttgtatctt taacttgcgt | 600 |
| aacattcttc tctgcatttg ctatttgttg tgtctcttca acgactgcag catttattcc | 660 |
| agttgctgag gttagaatgg ctaatgctgc catgctttta atgactatat ttttattcat | 720 |

<210> SEQ ID NO 142
<211> LENGTH: 740
<212> TYPE: DNA
<213> ORGANISM: Staphylococcus aureus

<400> SEQUENCE: 142

| | |
|---|---|
| ttattgttca atgtgctttt gaataaaatc tttgatttga ggcgtaaagt atacggcacc | 60 |
| attatattca gaaccaattt ttccaatacc gccatacacc acacctatga cctcattgtt | 120 |
| agaatttaga actggtgatc ctgaattccc gggttcaatg tatgcatcaa aatttaaaat | 180 |
| attgtctttg attcttttta tagttcctgt agattcaaac tgtttaaaac tattttgagc | 240 |
| aggtaatggg taaccaataa ctttaatttt gtcatcaact ttagcatctt tcgcaaaatt | 300 |
| gaatgcttgg acattttcat taaaattaaa gccttttggt ccacgttcga ctgcttgttc | 360 |
| ttcaatattc atgacagaga tgtcttcatc acccggataa tcagaaatgc ttttaatttt | 420 |
| atatatacca ccatttcctt tgtcaccgtt tggatgggca gtaattctat cgccaacttt | 480 |
| ataatctttt gatacatgtt tattggtgat aattgtattt tttccaatta caaaacctgt | 540 |
| cgcatcttta aatgaaacga cgccattata tggaaaaata tttgtatctt taacttgcgt | 600 |
| aacattcttc tctgcatttg ctatttgttg tgtctcttca acgactgcag catttattcc | 660 |
| agttactgag gttagaatgg ctaatgctgc catgctttta atgactatat ttttattcat | 720 |
| aaaagcacat tgaacaataa | 740 |

<210> SEQ ID NO 143
<211> LENGTH: 720
<212> TYPE: DNA
<213> ORGANISM: Staphylococcus aureus

<400> SEQUENCE: 143

| | |
|---|---|
| ttattgttca atgtgctttt gaataaaatc tttgatttga ggcgtaaagt atacggcacc | 60 |
| attatattca gaaccaattt ttccaatacc gccatacacc acacctatga cctcattgtt | 120 |
| agaatttaga actggtgatc ctgaattccc gggttcaatg tatgcatcaa aatttaaaat | 180 |
| attgtctttg attcttttta tagttcctgt agattcaaac tgtttaaaac tattttgagc | 240 |
| aggtaatggg taaccaataa ctttaatttt gtcatcaact ttagcatctt tcgcaaaatt | 300 |
| gaatgcttgg acattttcat taaaattaaa gccttttggt ccacgttcga ctgcttgttc | 360 |

| | |
|---|---|
| ttcaatattc atgacagaga tgtcttcatc acccggataa tcagaaatgc tttttaatttt | 420 |
| atatatacca ccatttcctt tgtcaccgtt tggatgggca gtaattctat cgccaacttt | 480 |
| ataatctttt gatacatgtt tattggtgat aattgtattt tttccaatta caaaacctgt | 540 |
| cgcatcttta aatgaaacga cgccattata tggaaaaata tttgtatctt taacttgcgt | 600 |
| aacattcttc tctgcatttg ctatttgttg tgtctcttca acgactgcag catttattcc | 660 |
| agttactgag gttagaatgg ctaatgctgc catgctttta atgactatat ttttattcat | 720 |

<210> SEQ ID NO 144
<211> LENGTH: 720
<212> TYPE: DNA
<213> ORGANISM: Staphylococcus aureus

<400> SEQUENCE: 144

| | |
|---|---|
| ttattgttca atgtgctttt gaataaaatc tttgatttga ggcgtaaagt atacggcacc | 60 |
| attatattca gaaccaattt ttccaatacc gccatacacc acacctatga cctcattgtt | 120 |
| agaatttaga actggtgatc ctgaattccc gggttcaatg tatgcatcaa aatttaaaat | 180 |
| attgtctttg attcttttta tagttcctgt agattcaaac tgtttaaaac tattttgagc | 240 |
| aggtaatggg taaccaataa ctttaatttt gtcatcaact ttagcatctt tcgcaaaatt | 300 |
| taatgcttgg acattttcat taaaattaaa gccttttggt ccacgttcga ctgcttgttc | 360 |
| ttcaatattc atgacagaga tgtcttcatc acccggataa tcagaaatgc tttttaatttt | 420 |
| atatatacca ccatttcctt tgtcaccgtt tggatgggca gtaattctat cgccaacttt | 480 |
| ataatctttt gatacatgtt tattggtgat aattgtattt tttccaatta caaaacctgt | 540 |
| cgcatcttta aatgaaacga cgccattata tggaaaaata tttgtatctt taacttgcgt | 600 |
| aacattcttc tctgcatttg ctatttgttg tgtctcttca acgactgcag catttattcc | 660 |
| agttactgag gttagaatgg ctaatgctgc catgctttta atgactatat ttttattcat | 720 |

<210> SEQ ID NO 145
<211> LENGTH: 720
<212> TYPE: DNA
<213> ORGANISM: Staphylococcus aureus

<400> SEQUENCE: 145

| | |
|---|---|
| ttattgttca atgtgctttt gaataaaatc tttgatttga ggcgtaaagt atacggcacc | 60 |
| attatattca gaaccaattt ttccaatacc gccatacacc acacctatga cctcattgtt | 120 |
| agaatttaga actggtgatc ctgaattccc gggttcaatg tatgcatcaa aatttaaaat | 180 |
| attgtctttg attcttttta tagttcctgt agattcaaac tgtttaaaac tattttgagc | 240 |
| aggtaatggg taaccaataa ctttaatttt gtcatcaact ttagcatctt tcgcaaaatt | 300 |
| gaatgcttgg acattttcat taaaattaaa gccttttggt ccacgttcga ctgcttgttc | 360 |
| ttcaatattc atgacagaga tgtcttcatc acccggataa tcagaaatgc tttttaatttt | 420 |
| atatatacca ccatttcctt tgtcaccgtt tggatgggca gtaattctat cgccaacttt | 480 |
| ataatctttt gatacatgtt tattggtgat aattgtattt tttccaatta caaaacctgt | 540 |
| cgcatcttta aatgaaacga cgccattata tggaaaaata tttgtatctt taacttgcgt | 600 |
| aacattcttc tctgcatttg ctatttgttg tgtctcttca acgactgcag catttattcc | 660 |
| agttactgag gttagaatgg ctaatgctgc catgctttta atgactatat ttttattcat | 720 |

<210> SEQ ID NO 146
<211> LENGTH: 720

<212> TYPE: DNA
<213> ORGANISM: Staphylococcus aureus

<400> SEQUENCE: 146

```
ttattgttca atgtgctttt gaataaaatc tttgatttga ggcgtaaagt atacggcacc      60
attatattca gaaccaattt ttccaatacc gccatacacc acacctatga cctcattgtt     120
agaatttaga actggtgatc ctgaattccc gggttcaatg tatgcatcaa aatttaaaat     180
attgtctttg attcttttta tagttcctgt agattcaaac tgtttaaaac tattttgagc     240
aggtaatggg taaccaataa ctttaatttt gtcatcaact ttagcatctt tcgcaaaatt     300
gaatgcttgg acattttcat taaaattaaa gccttttggt ccacgttcaa ctgcttgttc     360
ttcaatattc atgacagaga tgtcttcatc acccggataa tcagaaatgc ttttaatttt     420
atatatacca ccatttcctt tgtcaccgtt tggatgggca gtaattctat cgccaacttt     480
ataatctttt gatacatgtt tattggtgat aattgtattt tttccaatta caaaacctgt     540
cgcatcctta aatgaaacga cgccattata tggaaaatta tttgtatctt taacttgcgt     600
aacattcttc tctgcatttg ctatttgttg tgtctcttca acgactgcag catttattcc     660
agttactgag gttagaatgg ctaatgctgc catgctttta atgactatat ttttattcat     720
```

<210> SEQ ID NO 147
<211> LENGTH: 720
<212> TYPE: DNA
<213> ORGANISM: Staphylococcus aureus

<400> SEQUENCE: 147

```
ttattgttca atgtgctttt gaataaaatc tttgatttga ggcgtaaagt atacggcacc      60
attatattca gaaccaattt ttccaatacc gccatacacc acacctatga cctcattgtt     120
agaatttaga actggtgatc ctgaattccc gggttcaatg tatgcatcaa aatttaaaat     180
attgtctttg attcttttta tagttcctgt agattcaaac tgtttaaaac tattttgagc     240
aggtaatggg taaccaataa ctttaatttt gtcatcaact ttagcatctt tcgcaaaatt     300
gaatgcttgg acattttcat taaaattaaa gccttttggt ccacgttcaa ctgcttgttc     360
ttcaatattc atgacagaga tgtcttcatc acccggataa tcagaaatgc ttttaatttt     420
atatatacca ccatttcctt tgtcaccgtt tggatgggca gtaattctat cgccaacttt     480
ataatctttt gatacatgtt tattggtgat aattgtattt tttccaatta caaaacctgt     540
cgcatcctta aatgaaacga cgccattata tggaaaatta tttgtatctt taacttgcgt     600
aacattcttc tctgcatttg ctatttgttg tgtctcttca acgactgcag catttattcc     660
agttactgag gttagaatgg ctaatgctgc catgctttta atgactatat ttttattcat     720
```

<210> SEQ ID NO 148
<211> LENGTH: 720
<212> TYPE: DNA
<213> ORGANISM: Staphylococcus aureus

<400> SEQUENCE: 148

```
ttattgttca atgtgctttt gaataaaatc tttgatttga ggcgtaaagt atacggcacc      60
attatattca gaaccaattt ttccaatacc gccatacacc acacctatga cctcattgtt     120
agaatttaga actggtgatc ctgaattccc gggttcaatg tatgcatcaa aatttaaaat     180
attgtctttg attcttttta tagttcctgt agattcaaac tgtttaaaac tattttgagc     240
aggtaatggg taaccaataa ctttaatttt gtcatcaact ttagcatctt tcgcaaaatt     300
```

| | |
|---|---|
| gaatgcttgg acattttcat taaaattaaa gccttttggt ccacgttcaa ctgcttgttc | 360 |
| ttcaatattc atgacagaga tgtcttcatc acccggataa tcagaaatgc ttttaatttt | 420 |
| atatatacca ccatttcctt tgtcaccgtt tggatgggca gtaattctat cgccaacttt | 480 |
| ataatctttt gatacatgtt tattggtgat aattgtattt tttccaatta caaaacctgt | 540 |
| cgcatcctta aatgaaacga cgccattata tggaaaatta tttgtatctt taacttgcgt | 600 |
| aacattcttc tctgcatttg ctatttgttg tgtctcttca acgactgcag catttattcc | 660 |
| agttactgag gttagaatgg ctaatgctgc catgctttta atgactatat ttttattcat | 720 |

<210> SEQ ID NO 149
<211> LENGTH: 720
<212> TYPE: DNA
<213> ORGANISM: Staphylococcus aureus

<400> SEQUENCE: 149

| | |
|---|---|
| ttattgttca atgtgctttt gaataaaatc tttgatttga ggcgtaaagt atacggcacc | 60 |
| attatattca gaaccaattt ttccaatacc gccatacacc acacctatga cctcattgtt | 120 |
| agaatttaga actggtgatc ctgaattccc gggttcaatg tatgcatcaa aatttaaaat | 180 |
| attgtctttg attcttttta tagttcctgt agattcaaac tgtttaaaac tatttttgagc | 240 |
| aggtaatggg taaccaataa ctttaatttt gtcatcaact ttagcatctt tcgcaaaatt | 300 |
| gaatgcttgg acattttcat taaaattaaa gccttttggt ccacgttcaa ctgcttgttc | 360 |
| ttcaatattc atgacagaga tgtcttcatc acccggataa tcagaaatgc ttttaatttt | 420 |
| atatatacca ccatttcctt tgtcaccgtt tggatgggca gtaattctat cgccaacttt | 480 |
| ataatctttt gatacatgtt tattggtgat aattgtattt tttccaatta caaaacctgt | 540 |
| cgcatcctta aatgaaacga cgccattata tggaaaatta tttgtatctt taacttgcgt | 600 |
| aacattcttc tctgcatttg ctatttgttg tgtctcttca acgactgcag catttattcc | 660 |
| agttactgag gttagaatgg ctaatgctgc catgctttta atgactatat ttttattcat | 720 |

<210> SEQ ID NO 150
<211> LENGTH: 720
<212> TYPE: DNA
<213> ORGANISM: Staphylococcus aureus

<400> SEQUENCE: 150

| | |
|---|---|
| ttattgttca atgtgctttt gaataaaatc tttgatttga ggcgtaaagt atacggcacc | 60 |
| attatattca gaaccaattt ttccaatacc gccatacacc acacctatga cctcattgtt | 120 |
| agaatttaga actggtgatc ctgaattccc gggttcaatg tatgcatcaa aatttaaaat | 180 |
| attgtctttg attcttttta tagttcctgt agattcaaac tgtttaaaac tatttttgagc | 240 |
| aggtaatggg taaccaataa ctttaatttt gtcatcaact ttagcatctt tcgcaaaatt | 300 |
| gaatgcttgg acattttcat taaaattaaa gccttttggt ccacgttcaa ctgcttgttc | 360 |
| ttcaatattc atgacagaga tgtcttcatc acccggataa tcagaaatgc ttttaatttt | 420 |
| atatatacca ccatttcctt tgtcaccgtt tggatgggca gtaattctat cgccaacttt | 480 |
| ataatctttt gatacatgtt tattggtgat aattgtattt tttccaatta caaaacctgt | 540 |
| cgcatcctta aatgaaacga cgccattata tggaaaatta tttgtatctt taacttgcgt | 600 |
| aacattcttc tctgcatttg ctatttgttg tgtctcttca acgactgcag catttattcc | 660 |
| agttactgag gttagaatgg ctaatgctgc catgctttta atgactatat ttttattcat | 720 |

<210> SEQ ID NO 151
<211> LENGTH: 720
<212> TYPE: DNA
<213> ORGANISM: Staphylococcus aureus

<400> SEQUENCE: 151

```
ttattgttca atgtgctttt gaataaattc tttgatttga ggcgtaaaat aaactgcacc    60
attgtattct gatccgattt ttccaatacc tccatacaca actcctacga cttcattatt   120
taaatttaaa actggggatc ctgaatttcc aggctcgata tatgcatcaa aatttaaatt   180
attatcttta atacttttta cagttccagt tgattcaaat tgtttgaatg tattttgagc   240
tggtaaaggg tatccaataa ctttaatttt gtcgtcaact ttagcatctt tcgcaaaatt   300
gaatgcttgg acattttcat taaaattata accatttgct ccacgttcaa cagcattttc   360
ttcaacgttc attactgata tatcctcatt acctggataa tcagaaatat ttttaatttt   420
ataaattcca ccgttgcctt tgtcaccatt tgggtgggca gtaattctat cgccaacttt   480
atagtccttt gatacatgtt tattggtgat aattgtattt ttttcaattg caaaacctgt   540
cgcatcttta aatgaaacga cgccattata tggaaaaaca tttgtatctt taacttgcgt   600
aacattcttc tctgcatttg ctatttgttg tgtctcatca acgactgcag catttattcc   660
agttactgag gttagaatgg ctaatgctgc catgcttta atgactatat ttttattcat   720
```

<210> SEQ ID NO 152
<211> LENGTH: 239
<212> TYPE: PRT
<213> ORGANISM: Staphylococcus aureus

<400> SEQUENCE: 152

```
Met Asn Lys Asn Ile Val Ile Lys Ser Met Ala Ala Leu Ala Ile Leu
1               5                   10                  15

Thr Ser Val Thr Gly Ile Asn Ala Ala Val Glu Glu Thr Gln Gln
            20                  25                  30

Ile Ala Asn Ala Glu Lys Asn Val Thr Gln Val Lys Asp Thr Asn Ile
        35                  40                  45

Phe Pro Tyr Asn Gly Val Val Ser Phe Lys Asp Ala Thr Gly Phe Val
    50                  55                  60

Ile Gly Lys Asn Thr Ile Ile Thr Asn Lys His Val Ser Lys Asp Tyr
65                  70                  75                  80

Lys Val Gly Asp Arg Ile Thr Ala His Pro Asp Gly Asp Lys Gly Asn
                85                  90                  95

Gly Gly Ile Tyr Lys Ile Lys Ser Ile Ser Asp Tyr Pro Gly Asp Glu
            100                 105                 110

Asp Ile Ser Val Met Asn Ile Glu Glu Gln Ala Val Glu Arg Gly Pro
        115                 120                 125

Lys Gly Phe Asn Phe Asn Glu Asn Val Gln Ala Leu Asn Phe Ala Lys
    130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
            180                 185                 190

Ser Gly Ser Pro Val Leu Asn Ser Asn Asn Glu Val Ile Gly Val Val
        195                 200                 205

Tyr Gly Gly Ile Gly Lys Ile Gly Ser Glu Tyr Asn Gly Ala Val Tyr
```

```
                210                 215                 220
Phe Thr Pro Gln Ile Lys Asp Phe Ile Gln Lys His Ile Glu Gln
225                 230                 235

<210> SEQ ID NO 153
<211> LENGTH: 239
<212> TYPE: PRT
<213> ORGANISM: Staphylococcus aureus

<400> SEQUENCE: 153

Met Asn Lys Asn Ile Val Ile Lys Ser Met Ala Ala Leu Ala Ile Leu
1               5                   10                  15

Thr Ser Ala Thr Gly Ile Asn Ala Ala Val Val Glu Glu Thr Gln Gln
                20                  25                  30

Ile Ala Asn Ala Glu Lys Asn Val Thr Gln Val Lys Asp Thr Asn Ile
            35                  40                  45

Phe Pro Tyr Asn Gly Val Val Ser Phe Lys Asp Ala Thr Gly Phe Val
        50                  55                  60

Ile Gly Lys Asn Thr Ile Ile Thr Asn Lys His Val Ser Lys Asp Tyr
65                  70                  75                  80

Lys Val Gly Asp Arg Ile Thr Ala His Pro Asp Gly Asp Lys Gly Asn
                85                  90                  95

Gly Gly Ile Tyr Lys Ile Lys Ser Ile Ser Asp Tyr Pro Gly Asp Glu
            100                 105                 110

Asp Ile Ser Val Met Asn Ile Glu Glu Gln Ala Val Glu Arg Gly Pro
        115                 120                 125

Lys Gly Phe Asn Phe Asn Glu Asn Val Gln Ala Leu Asn Phe Ala Lys
    130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
            180                 185                 190

Ser Gly Ser Pro Val Leu Asn Ser Asn Asn Glu Val Ile Gly Val Val
        195                 200                 205

Tyr Gly Gly Ile Gly Lys Ile Gly Ser Glu Tyr Asn Gly Ala Val Tyr
    210                 215                 220

Phe Thr Pro Gln Ile Lys Asp Phe Ile Gln Lys His Ile Glu Gln
225                 230                 235

<210> SEQ ID NO 154
<211> LENGTH: 239
<212> TYPE: PRT
<213> ORGANISM: Staphylococcus aureus

<400> SEQUENCE: 154

Met Asn Lys Asn Ile Val Ile Lys Ser Met Ala Ala Leu Ala Ile Leu
1               5                   10                  15

Thr Ser Val Thr Gly Ile Asn Ala Ala Val Val Glu Glu Thr Gln Gln
                20                  25                  30

Ile Ala Asn Ala Glu Lys Asn Val Thr Gln Val Lys Asp Thr Asn Ile
            35                  40                  45

Phe Pro Tyr Asn Gly Val Val Ser Phe Lys Asp Ala Thr Gly Phe Val
        50                  55                  60

Ile Gly Lys Asn Thr Ile Ile Thr Asn Lys His Val Ser Lys Asp Tyr
```

```
            65                  70                  75                  80
Lys Val Gly Asp Arg Ile Thr Ala His Pro Asn Gly Asp Lys Gly Asn
                85                  90                  95

Gly Gly Ile Tyr Lys Ile Lys Ser Ile Ser Asp Tyr Pro Gly Asp Glu
                100                 105                 110

Asp Ile Ser Val Met Asn Ile Glu Glu Gln Ala Val Glu Arg Gly Pro
                115                 120                 125

Lys Gly Phe Asn Phe Asn Glu Asn Val Gln Ala Phe Asn Phe Ala Lys
        130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
                180                 185                 190

Ser Gly Ser Pro Val Leu Asn Ser Asn Asn Glu Val Ile Gly Val Val
                195                 200                 205

Tyr Gly Gly Ile Gly Lys Ile Gly Ser Glu Tyr Asn Gly Ala Val Tyr
        210                 215                 220

Phe Thr Pro Gln Ile Lys Asp Phe Ile Gln Lys His Ile Glu Gln
225                 230                 235

<210> SEQ ID NO 155
<211> LENGTH: 239
<212> TYPE: PRT
<213> ORGANISM: Staphylococcus aureus

<400> SEQUENCE: 155

Met Asn Lys Asn Ile Val Ile Lys Ser Met Ala Ala Leu Ala Ile Leu
1               5                   10                  15

Thr Ser Val Thr Gly Ile Asn Ala Ala Val Glu Glu Thr Gln Gln
                20                  25                  30

Ile Ala Asn Ala Glu Lys Asn Val Thr Gln Val Lys Asp Thr Asn Ile
        35                  40                  45

Phe Pro Tyr Asn Gly Val Val Ser Phe Lys Asp Ala Thr Gly Phe Val
    50                  55                  60

Ile Gly Lys Asn Thr Ile Ile Thr Asn Lys His Val Ser Lys Asp Tyr
65                  70                  75                  80

Lys Val Gly Asp Arg Ile Thr Ala His Pro Asn Gly Asp Lys Gly Asn
                85                  90                  95

Gly Gly Ile Tyr Lys Ile Lys Ser Ile Ser Asp Tyr Pro Gly Asp Glu
                100                 105                 110

Asp Ile Ser Val Met Asn Ile Glu Glu Gln Ala Val Glu Arg Gly Pro
                115                 120                 125

Lys Gly Phe Asn Phe Asn Glu Asn Val Gln Ala Phe Asn Phe Ala Lys
        130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
                180                 185                 190

Ser Gly Ser Pro Val Leu Asn Ser Asn Asn Glu Val Ile Gly Val Val
                195                 200                 205
```

Tyr Gly Gly Ile Gly Lys Ile Gly Ser Glu Tyr Asn Gly Ala Val Tyr
210                 215                 220

Phe Thr Pro Gln Ile Lys Asp Phe Ile Gln Lys His Ile Glu Gln
225                 230                 235

<210> SEQ ID NO 156
<211> LENGTH: 239
<212> TYPE: PRT
<213> ORGANISM: Staphylococcus aureus

<400> SEQUENCE: 156

Met Asn Lys Asn Ile Val Ile Lys Ser Met Ala Ala Leu Ala Ile Leu
1               5                   10                  15

Thr Ser Val Thr Gly Ile Asn Ala Ala Val Val Glu Glu Thr Gln Gln
                20                  25                  30

Ile Ala Asn Ala Glu Lys Asn Val Thr Gln Val Lys Asp Thr Asn Ile
            35                  40                  45

Phe Pro Tyr Asn Gly Val Val Ser Phe Lys Asp Ala Thr Gly Phe Val
50                  55                  60

Ile Gly Lys Asn Thr Ile Ile Thr Asn Lys His Val Ser Lys Asp Tyr
65                  70                  75                  80

Lys Val Gly Asp Arg Ile Thr Ala His Pro Asn Gly Asp Lys Gly Asn
                85                  90                  95

Gly Gly Ile Tyr Lys Ile Lys Ser Ile Ser Asp Tyr Pro Gly Asp Glu
            100                 105                 110

Asp Ile Ser Val Met Asn Ile Glu Glu Gln Ala Val Glu Arg Gly Pro
        115                 120                 125

Lys Gly Phe Asn Phe Asn Glu Asn Val Gln Ala Phe Asn Phe Ala Lys
130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
            180                 185                 190

Ser Gly Ser Pro Val Leu Asn Ser Asn Asn Glu Val Ile Gly Val Val
        195                 200                 205

Tyr Gly Gly Ile Gly Lys Ile Gly Ser Glu Tyr Asn Gly Ala Val Tyr
210                 215                 220

Phe Thr Pro Gln Ile Lys Asp Phe Ile Gln Lys His Ile Glu Gln
225                 230                 235

<210> SEQ ID NO 157
<211> LENGTH: 239
<212> TYPE: PRT
<213> ORGANISM: Staphylococcus aureus

<400> SEQUENCE: 157

Met Asn Lys Asn Ile Val Ile Lys Ser Met Ala Ala Leu Ala Ile Leu
1               5                   10                  15

Thr Ser Val Thr Gly Ile Asn Ala Ala Val Val Glu Glu Thr Gln Gln
                20                  25                  30

Ile Ala Asn Ala Glu Lys Asn Val Thr Gln Val Lys Asp Thr Asn Ile
            35                  40                  45

Phe Pro Tyr Asn Gly Val Val Ser Phe Lys Asp Ala Thr Gly Phe Val
50                  55                  60

```
Ile Gly Lys Asn Thr Ile Ile Thr Asn Lys His Val Ser Lys Asp Tyr
 65                  70                  75                  80

Lys Val Gly Asp Arg Ile Thr Ala His Pro Asn Gly Asp Lys Gly Asn
                 85                  90                  95

Gly Gly Ile Tyr Lys Ile Lys Ser Ile Ser Asp Tyr Pro Gly Asp Glu
                100                 105                 110

Asp Ile Ser Val Met Asn Ile Glu Glu Gln Ala Val Glu Arg Gly Pro
            115                 120                 125

Lys Gly Phe Asn Phe Asn Glu Asn Val Gln Ala Phe Asn Phe Ala Lys
        130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
                180                 185                 190

Ser Gly Ser Pro Val Leu Asn Ser Asn Asn Glu Val Ile Gly Val Val
            195                 200                 205

Tyr Gly Gly Ile Gly Lys Ile Gly Ser Glu Tyr Asn Gly Ala Val Tyr
        210                 215                 220

Phe Thr Pro Gln Ile Lys Asp Phe Ile Gln Lys His Ile Glu Gln
225                 230                 235

<210> SEQ ID NO 158
<211> LENGTH: 239
<212> TYPE: PRT
<213> ORGANISM: Staphylococcus aureus

<400> SEQUENCE: 158

Met Asn Lys Asn Ile Val Ile Lys Ser Met Ala Ala Leu Ala Ile Leu
  1               5                  10                  15

Thr Ser Val Thr Gly Ile Asn Ala Ala Val Glu Glu Thr Gln Gln
             20                  25                  30

Ile Ala Asn Ala Glu Lys Asn Val Thr Gln Val Lys Asp Thr Asn Asn
        35                  40                  45

Phe Pro Tyr Asn Gly Val Val Ser Phe Lys Asp Ala Thr Gly Phe Val
 50                  55                  60

Ile Gly Lys Asn Thr Ile Ile Thr Asn Lys His Val Ser Lys Asp Tyr
 65                  70                  75                  80

Lys Val Gly Asp Arg Ile Thr Ala His Pro Asn Gly Asp Lys Gly Asn
                 85                  90                  95

Gly Gly Ile Tyr Lys Ile Lys Ser Ile Ser Asp Tyr Pro Gly Asp Glu
                100                 105                 110

Asp Ile Ser Val Met Asn Ile Glu Glu Gln Ala Val Glu Arg Gly Pro
            115                 120                 125

Lys Gly Phe Asn Phe Asn Glu Asn Val Gln Ala Phe Asn Phe Ala Lys
        130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
                180                 185                 190

Ser Gly Ser Pro Val Leu Asn Ser Asn Asn Glu Val Ile Gly Val Val
            195                 200                 205
```

```
Tyr Gly Gly Ile Gly Lys Ile Gly Ser Glu Tyr Asn Gly Ala Val Tyr
            210                 215                 220

Phe Thr Pro Gln Ile Lys Asp Phe Ile Gln Lys His Ile Glu Gln
225                 230                 235

<210> SEQ ID NO 159
<211> LENGTH: 239
<212> TYPE: PRT
<213> ORGANISM: Staphylococcus aureus

<400> SEQUENCE: 159

Met Asn Lys Asn Ile Val Ile Lys Ser Met Ala Ala Leu Ala Ile Leu
1               5                   10                  15

Thr Ser Val Thr Gly Ile Asn Ala Ala Val Val Glu Glu Thr Gln Gln
            20                  25                  30

Ile Ala Asn Ala Glu Lys Asn Val Thr Gln Val Lys Asp Thr Asn Asn
        35                  40                  45

Phe Pro Tyr Asn Gly Val Val Ser Phe Lys Asp Ala Thr Gly Phe Val
    50                  55                  60

Ile Gly Lys Asn Thr Ile Ile Thr Asn Lys His Val Ser Lys Asp Tyr
65                  70                  75                  80

Lys Val Gly Asp Arg Ile Thr Ala His Pro Asn Gly Asp Lys Gly Asn
                85                  90                  95

Gly Gly Ile Tyr Lys Ile Lys Ser Ile Ser Asp Tyr Pro Gly Asp Glu
            100                 105                 110

Asp Ile Ser Val Met Asn Ile Glu Glu Gln Ala Val Glu Arg Gly Pro
        115                 120                 125

Lys Gly Phe Asn Phe Asn Glu Asn Val Gln Ala Phe Asn Phe Ala Lys
    130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
            180                 185                 190

Ser Gly Ser Pro Val Leu Asn Ser Asn Asn Glu Val Ile Gly Val Val
        195                 200                 205

Tyr Gly Gly Ile Gly Lys Ile Gly Ser Glu Tyr Asn Gly Ala Val Tyr
    210                 215                 220

Phe Thr Pro Gln Ile Lys Asp Phe Ile Gln Lys His Ile Glu Gln
225                 230                 235

<210> SEQ ID NO 160
<211> LENGTH: 239
<212> TYPE: PRT
<213> ORGANISM: Staphylococcus aureus

<400> SEQUENCE: 160

Met Asn Lys Asn Ile Val Ile Lys Ser Met Ala Ala Leu Ala Ile Leu
1               5                   10                  15

Thr Ser Val Thr Gly Ile Asn Ala Ala Val Val Glu Glu Thr Gln Gln
            20                  25                  30

Ile Ala Asn Ala Glu Lys Asn Val Thr Gln Val Lys Asp Thr Asn Asn
        35                  40                  45

Phe Pro Tyr Asn Gly Val Val Ser Phe Lys Asp Ala Thr Gly Phe Val
    50                  55                  60
```

```
Ile Gly Lys Asn Thr Ile Ile Thr Asn Lys His Val Ser Lys Asp Tyr
 65                  70                  75                  80

Lys Val Gly Asp Arg Ile Thr Ala His Pro Asn Gly Asp Lys Gly Asn
                 85                  90                  95

Gly Gly Ile Tyr Lys Ile Lys Ser Ile Ser Asp Tyr Pro Gly Asp Glu
            100                 105                 110

Asp Ile Ser Val Met Asn Ile Glu Glu Gln Ala Val Glu Arg Gly Pro
            115                 120                 125

Lys Gly Phe Asn Phe Asn Glu Asn Val Gln Ala Phe Asn Phe Ala Lys
            130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
                180                 185                 190

Ser Gly Ser Pro Val Leu Asn Ser Asn Asn Glu Val Ile Gly Val Val
            195                 200                 205

Tyr Gly Gly Ile Gly Lys Ile Gly Ser Glu Tyr Asn Gly Ala Val Tyr
210                 215                 220

Phe Thr Pro Gln Ile Lys Asp Phe Ile Gln Lys His Ile Glu Gln
225                 230                 235
```

<210> SEQ ID NO 161
<211> LENGTH: 239
<212> TYPE: PRT
<213> ORGANISM: Staphylococcus aureus

<400> SEQUENCE: 161

```
Met Asn Lys Asn Ile Val Ile Lys Ser Met Ala Ala Leu Ala Ile Leu
 1               5                  10                  15

Thr Ser Val Thr Gly Ile Asn Ala Ala Val Val Glu Glu Thr Gln Gln
             20                  25                  30

Ile Ala Asn Ala Glu Lys Asn Val Thr Gln Val Lys Asp Thr Asn Asn
             35                  40                  45

Phe Pro Tyr Asn Gly Val Val Ser Phe Lys Asp Ala Thr Gly Phe Val
 50                  55                  60

Ile Gly Lys Asn Thr Ile Ile Thr Asn Lys His Val Ser Lys Asp Tyr
 65                  70                  75                  80

Lys Val Gly Asp Arg Ile Thr Ala His Pro Asn Gly Asp Lys Gly Asn
                 85                  90                  95

Gly Gly Ile Tyr Lys Ile Lys Ser Ile Ser Asp Tyr Pro Gly Asp Glu
            100                 105                 110

Asp Ile Ser Val Met Asn Ile Glu Glu Gln Ala Val Glu Arg Gly Pro
            115                 120                 125

Lys Gly Phe Asn Phe Asn Glu Asn Val Gln Ala Phe Asn Phe Ala Lys
            130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
                180                 185                 190

Ser Gly Ser Pro Val Leu Asn Ser Asn Asn Glu Val Ile Gly Val Val
```

```
                195                 200                 205
Tyr Gly Gly Ile Gly Lys Ile Gly Ser Glu Tyr Asn Gly Ala Val Tyr
    210                 215                 220

Phe Thr Pro Gln Ile Lys Asp Phe Ile Gln Lys His Ile Glu Gln
225                 230                 235

<210> SEQ ID NO 162
<211> LENGTH: 239
<212> TYPE: PRT
<213> ORGANISM: Staphylococcus aureus

<400> SEQUENCE: 162

Met Asn Lys Asn Ile Val Ile Lys Ser Met Ala Ala Leu Ala Ile Leu
1               5                   10                  15

Thr Ser Val Thr Gly Ile Asn Ala Ala Val Glu Glu Thr Gln Gln
            20                  25                  30

Ile Ala Asn Ala Glu Lys Asn Val Thr Gln Val Lys Asp Thr Asn Asn
        35                  40                  45

Phe Pro Tyr Asn Gly Val Val Ser Phe Lys Asp Ala Thr Gly Phe Val
    50                  55                  60

Ile Gly Lys Asn Thr Ile Ile Thr Asn Lys His Val Ser Lys Asp Tyr
65                  70                  75                  80

Lys Val Gly Asp Arg Ile Thr Ala His Pro Asn Gly Asp Lys Gly Asn
                85                  90                  95

Gly Gly Ile Tyr Lys Ile Lys Ser Ile Ser Asp Tyr Pro Gly Asp Glu
            100                 105                 110

Asp Ile Ser Val Met Asn Ile Glu Glu Gln Ala Val Glu Arg Gly Pro
        115                 120                 125

Lys Gly Phe Asn Phe Asn Glu Asn Val Gln Ala Phe Asn Phe Ala Lys
130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
            180                 185                 190

Ser Gly Ser Pro Val Leu Asn Ser Asn Asn Glu Val Ile Gly Val Val
        195                 200                 205

Tyr Gly Gly Ile Gly Lys Ile Gly Ser Glu Tyr Asn Gly Ala Val Tyr
    210                 215                 220

Phe Thr Pro Gln Ile Lys Asp Phe Ile Gln Lys His Ile Glu Gln
225                 230                 235

<210> SEQ ID NO 163
<211> LENGTH: 239
<212> TYPE: PRT
<213> ORGANISM: Staphylococcus aureus

<400> SEQUENCE: 163

Met Asn Lys Asn Ile Val Ile Lys Ser Met Ala Ala Leu Ala Ile Leu
1               5                   10                  15

Thr Ser Val Thr Gly Ile Asn Ala Ala Val Asp Glu Thr Gln Gln
            20                  25                  30

Ile Ala Asn Ala Glu Lys Asn Val Thr Gln Val Lys Asp Thr Asn Val
        35                  40                  45

Phe Pro Tyr Asn Gly Val Val Ser Phe Lys Asp Ala Thr Gly Phe Ala
```

```
                50                  55                  60
Ile Glu Lys Asn Thr Ile Ile Thr Asn Lys His Val Ser Lys Asp Tyr
 65                  70                  75                  80

Lys Val Gly Asp Arg Ile Thr Ala His Pro Asn Gly Asp Lys Gly Asn
                 85                  90                  95

Gly Gly Ile Tyr Lys Ile Lys Asn Ile Ser Asp Tyr Pro Gly Asn Glu
                100                 105                 110

Asp Ile Ser Val Met Asn Val Glu Glu Asn Ala Val Glu Arg Gly Ala
                115                 120                 125

Asn Gly Tyr Asn Phe Asn Glu Asn Val Gln Ala Phe Asn Phe Ala Lys
            130                 135                 140

Asp Ala Lys Val Asp Asp Lys Ile Lys Val Ile Gly Tyr Pro Leu Pro
145                 150                 155                 160

Ala Gln Asn Thr Phe Lys Gln Phe Glu Ser Thr Gly Thr Val Lys Ser
                165                 170                 175

Ile Lys Asp Asn Asn Leu Asn Phe Asp Ala Tyr Ile Glu Pro Gly Asn
                180                 185                 190

Ser Gly Ser Pro Val Leu Asn Leu Asn Asn Glu Val Val Gly Val Val
            195                 200                 205

Tyr Gly Gly Ile Gly Lys Ile Gly Ser Glu Tyr Asn Gly Ala Val Tyr
            210                 215                 220

Phe Thr Pro Gln Ile Lys Glu Phe Ile Gln Lys His Ile Glu Gln
225                 230                 235

<210> SEQ ID NO 164
<211> LENGTH: 239
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
```

```
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (128)..(129)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid

<400> SEQUENCE: 164

Met Asn Lys Asn Ile Val Ile Lys Ser Met Ala Ala Leu Ala Ile Leu
1               5                   10                  15

Thr Ser Xaa Thr Gly Ile Asn Ala Ala Val Val Xaa Glu Thr Gln Gln
            20                  25                  30

Ile Ala Asn Ala Glu Lys Asn Val Thr Gln Val Lys Asp Thr Asn Xaa
        35                  40                  45

Phe Pro Tyr Asn Gly Val Val Ser Phe Lys Asp Ala Thr Gly Phe Xaa
    50                  55                  60

Ile Xaa Lys Asn Thr Ile Ile Thr Asn Lys His Val Ser Lys Asp Tyr
65                  70                  75                  80

Lys Val Gly Asp Arg Ile Thr Ala His Pro Xaa Gly Asp Lys Gly Asn
                85                  90                  95

Gly Gly Ile Tyr Lys Ile Lys Xaa Ile Ser Asp Tyr Pro Gly Xaa Glu
            100                 105                 110

Asp Ile Ser Val Met Asn Xaa Glu Glu Xaa Ala Val Glu Arg Gly Xaa
        115                 120                 125

Xaa Gly Xaa Asn Phe Asn Glu Asn Val Gln Ala Xaa Asn Phe Ala Lys
    130                 135                 140

Asp Ala Lys Val Asp Asp Lys Ile Lys Val Ile Gly Tyr Pro Leu Pro
145                 150                 155                 160

Ala Gln Asn Xaa Phe Lys Gln Phe Glu Ser Thr Gly Thr Xaa Lys Xaa
                165                 170                 175
```

Ile Lys Asp Asn Xaa Leu Asn Phe Asp Ala Tyr Ile Glu Pro Gly Asn
            180                 185                 190

Ser Gly Ser Pro Val Leu Asn Xaa Asn Asn Glu Val Xaa Gly Val Val
        195                 200                 205

Tyr Gly Gly Ile Gly Lys Ile Gly Ser Glu Tyr Asn Gly Ala Val Tyr
        210                 215                 220

Phe Thr Pro Gln Ile Lys Xaa Phe Ile Gln Lys His Ile Glu Gln
225                 230                 235

<210> SEQ ID NO 165
<211> LENGTH: 14
<212> TYPE: PRT
<213> ORGANISM: Staphylococcus aureus

<400> SEQUENCE: 165

Pro Tyr Asn Gly Val Val Ser Phe Lys Asp Ala Thr Gly Phe
1               5                   10

<210> SEQ ID NO 166
<211> LENGTH: 14
<212> TYPE: PRT
<213> ORGANISM: Staphylococcus aureus

<400> SEQUENCE: 166

Ala His Pro Asp Gly Asp Lys Gly Asn Gly Gly Ile Tyr Lys
1               5                   10

<210> SEQ ID NO 167
<211> LENGTH: 14
<212> TYPE: PRT
<213> ORGANISM: Staphylococcus aureus

<400> SEQUENCE: 167

Ala His Pro Asn Gly Asp Lys Gly Asn Gly Gly Ile Tyr Lys
1               5                   10

<210> SEQ ID NO 168
<211> LENGTH: 14
<212> TYPE: PRT
<213> ORGANISM: artificial sequence
<220> FEATURE:
<223> OTHER INFORMATION: synthetic sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 168

Ala His Pro Xaa Gly Asp Lys Gly Asn Gly Gly Ile Tyr Lys
1               5                   10

<210> SEQ ID NO 169
<211> LENGTH: 14
<212> TYPE: PRT
<213> ORGANISM: Staphylococcus aureus

<400> SEQUENCE: 169

Ser Ile Ser Asp Tyr Pro Gly Asp Glu Asp Ile Ser Val Met
1               5                   10

<210> SEQ ID NO 170
<211> LENGTH: 14
<212> TYPE: PRT
<213> ORGANISM: Staphylococcus aureus

```
<400> SEQUENCE: 170

Asn Ile Ser Asp Tyr Pro Gly Asn Glu Asp Ile Ser Val Met
1               5                   10

<210> SEQ ID NO 171
<211> LENGTH: 14
<212> TYPE: PRT
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 171

Xaa Ile Ser Asp Tyr Pro Gly Xaa Glu Asp Ile Ser Val Met
1               5                   10

<210> SEQ ID NO 172
<211> LENGTH: 14
<212> TYPE: PRT
<213> ORGANISM: Staphylococcus aureus

<400> SEQUENCE: 172

Arg Gly Pro Lys Gly Phe Asn Phe Asn Glu Asn Val Gln Ala
1               5                   10

<210> SEQ ID NO 173
<211> LENGTH: 14
<212> TYPE: PRT
<213> ORGANISM: Staphylococcus aureus

<400> SEQUENCE: 173

Arg Gly Ala Asn Gly Tyr Asn Phe Asn Glu Asn Val Gln Ala
1               5                   10

<210> SEQ ID NO 174
<211> LENGTH: 14
<212> TYPE: PRT
<213> ORGANISM: artificial sequence
<220> FEATURE:
<223> OTHER INFORMATION: synthetic sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 174

Arg Gly Xaa Xaa Gly Xaa Asn Phe Asn Glu Asn Val Gln Ala
1               5                   10

<210> SEQ ID NO 175
<211> LENGTH: 14
<212> TYPE: PRT
<213> ORGANISM: Staphylococcus aureus

<400> SEQUENCE: 175

Gln Phe Glu Ser Thr Gly Thr Ile Lys Arg Ile Lys Asp Asn
1               5                   10
```

<210> SEQ ID NO 176
<211> LENGTH: 14
<212> TYPE: PRT
<213> ORGANISM: Staphylococcus aureus

<400> SEQUENCE: 176

Gln Phe Glu Ser Thr Gly Thr Val Lys Ser Ile Lys Asp Asn
1               5                   10

<210> SEQ ID NO 177
<211> LENGTH: 14
<212> TYPE: PRT
<213> ORGANISM: artificial sequence
<220> FEATURE:
<223> OTHER INFORMATION: synthetic sequence
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 177

Gln Phe Glu Ser Thr Gly Thr Xaa Lys Xaa Ile Lys Asp Asn
1               5                   10

<210> SEQ ID NO 178
<211> LENGTH: 14
<212> TYPE: PRT
<213> ORGANISM: Staphylococcus aureus

<400> SEQUENCE: 178

Gly Asn Ser Gly Ser Pro Val Leu Asn Ser Asn Asn Glu Val
1               5                   10

<210> SEQ ID NO 179
<211> LENGTH: 14
<212> TYPE: PRT
<213> ORGANISM: Staphylococcus aureus

<400> SEQUENCE: 179

Gly Asn Ser Gly Ser Pro Val Leu Asn Leu Asn Asn Glu Val
1               5                   10

<210> SEQ ID NO 180
<211> LENGTH: 14
<212> TYPE: PRT
<213> ORGANISM: artificial sequence
<220> FEATURE:
<223> OTHER INFORMATION: synthetic sequence
<220> FEATURE:
<221> NAME/KEY: misc_feature
<222> LOCATION: (10)..(10)
<223> OTHER INFORMATION: Xaa can be any naturally occurring amino acid

<400> SEQUENCE: 180

Gly Asn Ser Gly Ser Pro Val Leu Asn Xaa Asn Asn Glu Val
1               5                   10

<210> SEQ ID NO 181
<211> LENGTH: 975
<212> TYPE: DNA
<213> ORGANISM: Staphylococcus aureus

<400> SEQUENCE: 181

-continued

```
atgaaatttg atagacatag aagattgaga tcatcagcga caatgagaga tatggttaga      60
gagaatcatg taagaaaaga agatttaata tatccaattt ttgtagttga aaaagacgat     120
gtgaaaaaag aaattaagtc attgccaggt gtataccaaa tcagtttgaa tttacttgaa     180
agtgaattaa aagaagctta tgacttaggc atacgtgcca ttatgttttt cggtgttcca     240
aactcaaaag atgatatagg tactggtgca tacattcacg atggtgttat tcaacaggca     300
acacgtattg ctaaaaaaat gtatgatgac ttattaattg ttgcagacac ttgtttatgt     360
gaatatactg atcatggtca ttgtggcgtg attgatgacc atacacatga cgttgacaat     420
gataaatcat tgccactact tgttaaaaca gcaatttctc aagtggaagc tggtgctgat     480
attattgcgc caagtaatat gatggatggt tttgttgctg aaattcgtcg tggattagat     540
gaagccggct attacaatat tcctataatg agttatggtg tcaagtatgc atcaagtttc     600
tttggacctt ttagagatgc agcagattca gcgccatcat ttggggatag aaaaacgtat     660
cagatggacc ctgctaaccg tttggaagca cttcgtgaat tagaaagtga tcttaaagaa     720
gggtgcgaca tgatgattgt taaacctgct ctaagttatt tagatatagt tcgagatgtt     780
aaaaatcata cgaatgttcc agttgttgca tataatgtga gtggagaata tagtatgact     840
aaagcagcgg cacaaaatgg ttggatagat gaagaacgtg tcgttatgga acaaatggtt     900
tcaatgaaac gtgcaggtgc tgatatgatt attacgtatt ttgcaaagga catttgtcgc     960
tatttagata ataa                                                      975
```

<210> SEQ ID NO 182
<211> LENGTH: 324
<212> TYPE: PRT
<213> ORGANISM: Staphylococcus aureus

<400> SEQUENCE: 182

```
Met Lys Phe Asp Arg His Arg Leu Arg Ser Ser Ala Thr Met Arg
1               5                   10                  15

Asp Met Val Arg Glu Asn His Val Arg Lys Glu Asp Leu Ile Tyr Pro
            20                  25                  30

Ile Phe Val Val Glu Lys Asp Val Lys Lys Glu Ile Lys Ser Leu
        35                  40                  45

Pro Gly Val Tyr Gln Ile Ser Leu Asn Leu Leu Glu Ser Glu Leu Lys
    50                  55                  60

Glu Ala Tyr Asp Leu Gly Ile Arg Ala Ile Met Phe Phe Gly Val Pro
65                  70                  75                  80

Asn Ser Lys Asp Asp Ile Gly Thr Gly Ala Tyr Ile His Asp Gly Val
                85                  90                  95

Ile Gln Gln Ala Thr Arg Ile Ala Lys Lys Met Tyr Asp Asp Leu Leu
            100                 105                 110

Ile Val Ala Asp Thr Cys Leu Cys Glu Tyr Thr Asp His Gly His Cys
        115                 120                 125

Gly Val Ile Asp Asp His Thr His Asp Val Asp Asn Asp Lys Ser Leu
    130                 135                 140

Pro Leu Leu Val Lys Thr Ala Ile Ser Gln Val Glu Ala Gly Ala Asp
145                 150                 155                 160

Ile Ile Ala Pro Ser Asn Met Met Asp Gly Phe Val Ala Glu Ile Arg
                165                 170                 175

Arg Gly Leu Asp Glu Ala Gly Tyr Tyr Asn Ile Pro Ile Met Ser Tyr
            180                 185                 190
```

```
Gly Val Lys Tyr Ala Ser Ser Phe Phe Gly Pro Phe Arg Asp Ala Ala
            195                 200                 205

Asp Ser Ala Pro Ser Phe Gly Asp Arg Lys Thr Tyr Gln Met Asp Pro
210                 215                 220

Ala Asn Arg Leu Glu Ala Leu Arg Glu Leu Glu Ser Asp Leu Lys Glu
225                 230                 235                 240

Gly Cys Asp Met Met Ile Val Lys Pro Ala Leu Ser Tyr Leu Asp Ile
                245                 250                 255

Val Arg Asp Val Lys Asn His Thr Asn Val Pro Val Val Ala Tyr Asn
            260                 265                 270

Val Ser Gly Glu Tyr Ser Met Thr Lys Ala Ala Ala Gln Asn Gly Trp
        275                 280                 285

Ile Asp Glu Glu Arg Val Val Met Glu Gln Met Val Ser Met Lys Arg
290                 295                 300

Ala Gly Ala Asp Met Ile Ile Thr Tyr Phe Ala Lys Asp Ile Cys Arg
305                 310                 315                 320

Tyr Leu Asp Lys

<210> SEQ ID NO 183
<211> LENGTH: 2802
<212> TYPE: DNA
<213> ORGANISM: Staphylococcus aureus

<400> SEQUENCE: 183
atgaatatga agaaaaaga aaaacacgca attcggaaaa aatcgattgg cgtggcttca      60
gtgcttgtag gtacgttaat cggttttgga ctactcagca gtaaagaagc agatgcaagt     120
gaaaatagtg ttacgcaatc tgatagcgca agtaacgaaa gcaaaagtaa tgattcaagt     180
agcgttagtc ctgcacctaa acagacgac acaaacgtga gtgatactaa acatcgtca      240 aacactaata atggcgaaac gagtgtggcg caaaatccag cacaacagga acgacacaa      300 tcatcatcaa caaatgcaac tacggaagaa acgccggtaa ctggtgaagc tactactacg     360
acaacgaatc aagctaatac accggcaaca actcaatcaa gcaatacaaa tgcggaggaa     420
ttagtgaatc aaacaagtaa tgaaacgact tttaatgata ctaatacagt atcatctgta     480
aattcacctc aaaattctac aaatgcggaa atgtttcaa caacgcaaga tacttcaact      540
gaagcaacac cttcaaacaa tgaatcagct ccacagagta cagatgcaag taataaagat     600
gtagttaatc aagcggttaa tacaagtgcg cctagaatga gagcatttag tttagcggca     660
gtagctgcag atgcaccggc agctggcaca gatattacga atcagttgac gaatgtgaca     720
gttggtattg actctggtac gactgtgtat ccgcaccaag caggttatgt caaactgaat     780
tatggttttt cagtgcctaa ttctgctgtt aaaggtgaca cattcaaaat aactgtacct     840
aaagaattaa acttaaatgg tgtaacttca actgctaaag tgccaccaat tatggctgga     900
gatcaagtat tggcaaatgg tgtaatcgat agtgatggta atgttatta cacatttaca     960 gactatgtaa atactaaaga tgatgtaaaa gcaactttga ccatgcccgc ttatattgac    1020
cctgaaaatg ttaaaaagac aggtaatgtg acattggcta ctggcatagg tagtacaaca    1080
gcaaacaaaa cagtattagt agattatgaa aaatatggta agttttataa cttatctatt    1140
aaaggtacaa ttgaccaaat cgataaaaca ataatacgt atcgtcagac aatttatgtc     1200
aatccaagtg gagataacgt tattgcgccg gttttaacag gtaatttaaa accaaatacg    1260
gatagtaatg cattaataga tcagcaaaat acaagtatta agtatataa agtagataat      1320 gcagctgatt tatctgaaag ttactttgtg aatccagaaa actttgagga tgtcactaat    1380
```

```
agtgtgaata ttacattccc aaatccaaat caatataaag tagagtttaa tacgcctgat    1440
gatcaaatta caacaccgta tatagtagtt gttaatggtc atattgatcc gaatagcaaa    1500
ggtgatttag ctttacgttc aactttatat gggtataact cgaatataat ttggcgctct    1560
atgtcatggg acaacgaagt agcatttaat aacggatcag gttctggtga cggtatcgat    1620
aaaccagttg ttcctgaaca acctgatgag cctggtgaaa ttgaaccaat tccagaggat    1680
tcagattctg acccaggttc agattctggc agcgattcta attcagatag cggtcagat     1740 tcgggtagtg attctacatc agatagtggt tcagattcag cgagtgattc agattcagca    1800
agtgattcag actcagcgag tgattcagat tcagcaagcg attccgactc agcgagcgat    1860
tccgactcag acaatgactc ggattcagat agcgattctg actcagacag tgactcagat    1920
tccgacagtg actcagattc agatagcgat tctgactcag acagtgactc agattcagat    1980
agcgattcag attcagatag cgattcagat tccgacagtg attccgactc agacagcgat    2040
tctgactccg acagtgattc cgactcagac agcgattcag attccgacag tgattccgac    2100
tcagatagcg attccgactc agatagcgac tcagattcag acagcgattc agattcagac    2160
agcgattcag attcagatag cgattcagat tccgacagtg actcagattc cgacagtgac    2220
tcggattcag atagcgattc agattccgac agtgactcag attccgacag tgactcagac    2280
tcagacagtg attcggattc agcgagtgat tcggattcag atagtgattc cgactccgac    2340
agtgactcgg attcagatag cgactcagac tcggatagcg actcggattc agatagcgat    2400
tcggactcag atagcgattc agaatcagac agcgattcag aatcagacag cgattcagat    2460
tcagacagcg actcagacag tgactcagat tcagatagtg actcggattc agcgagtgat    2520
tcagactcag gtagtgactc cgattcatca agtgattccg actcagaaag tgattcaaat    2580
agcgattccg agtcaggttc taacaataat gtagttccgc taattcacc taaaaatggt     2640 actaatgctt ctaataaaaa tgaggctaaa gatagtaaag aaccattacc agatacaggt    2700
tctgaagatg aagcaaatac gtcactaatt tggggattat tagcatcaat aggttcatta    2760 ctactttca gaagaaaaaa agaaaataaa gataagaaat aa                         2802
```

<210> SEQ ID NO 184
<211> LENGTH: 933
<212> TYPE: PRT
<213> ORGANISM: Staphylococcus aureus

<400> SEQUENCE: 184

Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Glu Glu Thr Pro
            100                 105                 110

Val Thr Gly Glu Ala Thr Thr Thr Thr Thr Asn Gln Ala Asn Thr Pro

-continued

```
            115                 120                 125
Ala Thr Thr Gln Ser Ser Asn Thr Asn Ala Glu Glu Leu Val Asn Gln
130                 135                 140

Thr Ser Asn Glu Thr Thr Phe Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
530                 535                 540
```

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
            580                 585                 590

Ser Ala Ser Asp Ser Asp Ser Ala Ser Asp Ser Asp Ser Ala Ser Asp
        595                 600                 605

Ser Asp Ser Ala Ser Asp Ser Asp Ser Ala Ser Asp Ser Asp Ser Asp
    610                 615                 620

Asn Asp Ser Asp Ser Asp Ser Asp Ser Asp Ser Asp Ser Asp Ser Asp
625                 630                 635                 640

Ser Asp Ser Asp Ser Asp Ser Asp Ser Asp Ser Asp Ser Asp Ser Asp
                645                 650                 655

Ser Asp Ser Asp Ser Asp Ser Asp Ser Asp Ser Asp Ser Asp Ser Asp
            660                 665                 670

Ser Asp Ser Asp Ser Asp Ser Asp Ser Asp Ser Asp Ser Asp Ser Asp
        675                 680                 685

Ser Asp Ser Asp Ser Asp Ser Asp Ser Asp Ser Asp Ser Asp Ser Asp
    690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
                725                 730                 735

Ser Asp Ser Asp Ser Asp Ser Asp Ser Asp Ser Asp Ser Asp Ser Asp
            740                 745                 750

Ser Asp Ser Asp Ser Asp Ser Asp Ser Asp Ser Asp Ser Asp Ser Ala
        755                 760                 765

Ser Asp Ser Asp Ser Asp Ser Asp Ser Asp Ser Asp Ser Asp Ser Asp
    770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Glu Ser Asp Ser Asp Ser Glu Ser Asp
                805                 810                 815

Ser Asp Ser Asp Ser Asp Ser Asp Ser Asp Ser Asp Ser Asp Ser Asp
            820                 825                 830

Ser Asp Ser Asp Ser Ala Ser Asp Ser Asp Ser Gly Ser Asp Ser Asp
        835                 840                 845

Ser Ser Ser Asp Ser Asp Ser Glu Ser Asp Ser Asn Ser Asp Ser Glu
    850                 855                 860

Ser Gly Ser Asn Asn Val Val Pro Pro Asn Ser Pro Lys Asn Gly
865                 870                 875                 880

Thr Asn Ala Ser Asn Lys Asn Glu Ala Lys Asp Ser Lys Glu Pro Leu
                885                 890                 895

Pro Asp Thr Gly Ser Glu Asp Glu Ala Asn Thr Ser Leu Ile Trp Gly
            900                 905                 910

Leu Leu Ala Ser Ile Gly Ser Leu Leu Leu Phe Arg Arg Lys Lys Glu
        915                 920                 925

Asn Lys Asp Lys Lys
    930

<210> SEQ ID NO 185
<211> LENGTH: 219

```
<212> TYPE: PRT
<213> ORGANISM: Staphylococcus aureus

<400> SEQUENCE: 185

Met Ile Glu Ile Asn Asn Leu Ser Lys Arg Tyr Arg Asn Lys Gln Ile
1               5                   10                  15

Phe Asn His Leu Thr Met Ser Phe Asp Ser Asn Arg Leu Thr Val Leu
            20                  25                  30

Leu Gly Asp Asn Gly Ala Gly Lys Ser Thr Leu Leu Arg Met Ile Ala
        35                  40                  45

Gly Ile Glu Lys Ala Asn Asp Gly Thr Ile Asn Tyr Phe Gly Glu Lys
    50                  55                  60

Trp Asn Gln Arg Gln Ile Gln Asn His Ile Gly Tyr Val Pro Gln Asp
65                  70                  75                  80

Ile Ala Leu Phe Glu His Met Thr Val Ala Glu Asn Ile Lys Phe Phe
                85                  90                  95

Lys Ser Leu Cys Lys Asn Pro Ile Asn Asp Thr Thr Ile Asn Glu Tyr
            100                 105                 110

Leu Gln Gln Leu Asn Phe Asp Asp Thr Ser Ala Lys Val Ser Thr Leu
        115                 120                 125

Ser Gly Gly Asn Lys Arg Lys Ile Asn Ile Leu Val Gly Leu Leu Gly
    130                 135                 140

Gln Pro Arg Ile Leu Ile Leu Asp Glu Pro Thr Val Gly Ile Asp Leu
145                 150                 155                 160

Lys Ser Arg His Asp Ile His Gln Leu Leu Asn Ile Met Lys Ser Lys
                165                 170                 175

Cys Leu Ile Ile Leu Thr Thr His His Leu Asp Glu Val Glu Ala Leu
            180                 185                 190

Ala Asp Asp Ile Lys Leu Ile Gly Gln Asp Pro Phe Tyr Gln His Val
        195                 200                 205

Leu Glu Asp Lys Gln Trp Thr Tyr Thr Tyr Tyr
    210                 215

<210> SEQ ID NO 186
<211> LENGTH: 253
<212> TYPE: PRT
<213> ORGANISM: Staphylococcus aureus

<400> SEQUENCE: 186

Met Ala Ile Leu Glu Val Lys Gln Leu Thr Lys Ile Tyr Gly Thr Lys
1               5                   10                  15

Lys Met Ala Gln Glu Val Leu Arg Asp Ile Asn Met Ser Ile Glu Glu
            20                  25                  30

Gly Glu Phe Ile Ala Ile Met Gly Pro Ser Gly Ser Gly Lys Thr Thr
        35                  40                  45

Leu Leu Asn Val Leu Ser Ser Ile Asp Tyr Ile Ser Gln Gly Ser Ile
    50                  55                  60

Thr Leu Lys Gly Lys Lys Leu Glu Lys Leu Ser Asn Lys Glu Leu Ser
65                  70                  75                  80

Asp Ile Arg Lys His Asp Ile Gly Phe Ile Phe Gln Glu Tyr Asn Leu
                85                  90                  95

Leu His Thr Leu Thr Val Lys Glu Asn Ile Met Leu Pro Leu Thr Val
            100                 105                 110

Gln Lys Leu Asp Lys Glu His Met Leu Asn Arg Tyr Glu Lys Val Ala
        115                 120                 125
```

```
Glu Ala Leu Asn Ile Leu Asp Ile Ser Asp Lys Tyr Pro Ser Glu Leu
            130                 135                 140

Ser Gly Gly Gln Arg Gln Arg Thr Ser Ala Ala Arg Ala Phe Ile Thr
145                 150                 155                 160

Leu Pro Ser Ile Ile Phe Ala Asp Glu Pro Thr Gly Ala Leu Asp Ser
                165                 170                 175

Lys Ser Thr Gln Asp Leu Leu Lys Arg Leu Thr Arg Met Asn Glu Ala
                180                 185                 190

Phe Lys Ser Thr Ile Ile Met Val Thr His Asp Pro Val Ala Ala Ser
            195                 200                 205

Tyr Ala Asn Arg Val Val Met Leu Lys Asp Gly Gln Ile Phe Thr Glu
        210                 215                 220

Leu Tyr Gln Gly Asp Asp Asp Lys His Thr Phe Phe Lys Glu Ile Ile
225                 230                 235                 240

Arg Val Gln Ser Val Leu Gly Gly Val Asn Tyr Asp Leu
                245                 250

<210> SEQ ID NO 187
<211> LENGTH: 243
<212> TYPE: PRT
<213> ORGANISM: Staphylococcus aureus

<400> SEQUENCE: 187

Met Ile Leu Ser Tyr Leu Lys Ile Glu Phe Lys Val Ile Met Arg Lys
1               5                   10                  15

Lys Thr Thr Leu Ile Leu Ser Ile Leu Phe Pro Val Ile Phe Tyr Ile
                20                  25                  30

Leu Phe Thr Ser Ile Leu Glu Leu Pro Glu Asp Val Lys Pro Lys Phe
            35                  40                  45

Tyr Lys Glu Tyr Met Tyr Ser Met Thr Val Tyr Ser Leu Leu Ser Phe
        50                  55                  60

Ser Leu Leu Thr Phe Pro Leu Asp Ile Ile Asn Glu Lys Gln Asn Glu
65                  70                  75                  80

Trp Arg Gln Arg Leu Met Val Thr Pro Phe Thr Phe Thr Ser Tyr Tyr
                85                  90                  95

Ile Ser Lys Val Val Lys Thr Met Leu Gln Phe Ala Ile Ala Ile Leu
                100                 105                 110

Val Ile Phe Met Val Gly His Phe Tyr Lys Gly Val Ala Met Ser Ala
            115                 120                 125

Val Gln Trp Leu Glu Ser Gly Ile Phe Leu Trp Leu Gly Ala Ser Leu
        130                 135                 140

Leu Ile Thr Phe Gly Ile Leu Phe Ser Leu Leu Asn Asp Ile Gln Lys
145                 150                 155                 160

Thr Ser Ala Leu Ala Asn Ile Val Thr Ile Gly Leu Ala Val Leu Gly
                165                 170                 175

Gly Leu Trp Phe Pro Ile Asn Thr Phe Pro Asn Trp Leu Gln His Val
            180                 185                 190

Ala His Val Leu Pro Ser Tyr His Leu Arg Lys Leu Gly Val Asp Ile
        195                 200                 205

Ala Ser Asn His His Ile Asn Leu Ile Ser Phe Ala Ile Ile Leu Leu
    210                 215                 220

Tyr Ala Leu Gly Ser Ile Ile Ala Val Tyr Cys Ile Ser His Phe Lys
225                 230                 235                 240

Arg Ala Glu
```

<210> SEQ ID NO 188
<211> LENGTH: 276
<212> TYPE: PRT
<213> ORGANISM: Staphylococcus aureus

<400> SEQUENCE: 188

Met His Lys Ile Phe Ser Lys Asn Asn Leu Ile Phe Val Phe Val
1               5                   10                  15

Ala Phe Ile Phe Val Val Ile Val Leu Gln Phe Phe Val Ser Ser Glu
        20                  25                  30

Asn Ala Thr Lys Val Asn Leu Ser Gln Thr Phe Glu Pro Ile Ser Trp
            35                  40                  45

Leu His Leu Leu Gly Thr Asp Asp Tyr Gly Arg Asp Leu Phe Thr Arg
    50                  55                  60

Ile Ile Ile Gly Ala Arg Ser Thr Leu Phe Val Thr Val Leu Thr Leu
65                  70                  75                  80

Ile Ala Ile Val Val Ile Gly Val Thr Leu Gly Leu Phe Ala Gly Tyr
                85                  90                  95

Lys Lys Gly Trp Ile Glu Arg Leu Val Leu Arg Phe Ile Asp Val Gly
            100                 105                 110

Leu Ser Ile Pro Glu Phe Ile Ile Met Ile Ala Leu Ala Ser Phe Phe
        115                 120                 125

Gln Pro Ser Leu Trp Asn Leu Val Ile Ser Ile Thr Leu Ile Lys Trp
    130                 135                 140

Met Asn Tyr Thr Arg Leu Thr Arg Ser Ile Val Asn Ser Glu Met Asn
145                 150                 155                 160

Lys Pro Tyr Ile Lys Met Ala Gln Leu Phe His Val Pro Thr Arg Thr
                165                 170                 175

Ile Leu Ile Arg His His Leu Thr Pro Lys Ile Ile Pro Ala Ile Ile Val
            180                 185                 190

Leu Met Val Val Asp Phe Gly Lys Ile Ile Leu Tyr Ile Ser Ser Leu
        195                 200                 205

Ser Phe Ile Gly Leu Gly Ala Gln Pro Pro Thr Pro Glu Trp Gly Ala
    210                 215                 220

Met Leu Gln Gln Gly Arg Asp Phe Ile Ser Ser His Pro Ile Met Leu
225                 230                 235                 240

Ile Ala Pro Ala Ser Val Ile Ala Ile Thr Leu Ile Phe Asn Leu
                245                 250                 255

Thr Gly Asp Ala Leu Arg Asp Arg Leu Leu Lys Gln Arg Gly Glu Tyr
            260                 265                 270

Asp Glu Ser His
        275

<210> SEQ ID NO 189
<211> LENGTH: 136
<212> TYPE: PRT
<213> ORGANISM: Staphylococcus aureus

<400> SEQUENCE: 189

Met Asn Thr Asn Asp Ala Ile Lys Ile Leu Lys Glu Asn Gly Leu Lys
1               5                   10                  15

Tyr Thr Asp Lys Arg Lys Asp Met Leu Asp Ile Phe Val Glu Glu Asp
        20                  25                  30

Lys Tyr Ile Asn Ala Lys Tyr Ile Gln Gln Val Met Asp Glu Asn Tyr
    35                  40                  45

```
Pro Gly Ile Ser Phe Asp Thr Ile Tyr Arg Asn Leu His Leu Phe Lys
    50                  55                  60

Asp Leu Gly Ile Ile Glu Asn Thr Glu Leu Asp Gly Glu Met Lys Phe
 65                  70                  75                  80

Arg Ile Ala Cys Thr Asn His His His His Phe Ile Cys Glu Lys
                85                  90                  95

Cys Gly Asp Thr Lys Val Ile Asp Tyr Cys Pro Ile Asp Gln Ile Lys
            100                 105                 110

Leu Ser Leu Pro Gly Val Asn Ile His Lys His Lys Leu Glu Val Tyr
        115                 120                 125

Gly Val Cys Glu Ser Cys Gln Asp
    130                 135
```

<210> SEQ ID NO 190
<211> LENGTH: 233
<212> TYPE: PRT
<213> ORGANISM: Staphylococcus aureus

<400> SEQUENCE: 190

```
Met Thr His Lys Tyr Ile Ser Thr Gln Met Leu Ile Ile Phe Thr Ala
 1               5                  10                  15

Leu Met Ile Ile Ala Asn Phe Tyr Tyr Ile Phe Glu Lys Ile Gly
                20                  25                  30

Phe Leu Leu Val Leu Leu Gly Cys Val Leu Val Tyr Val Gly Tyr
            35                  40                  45

Leu Tyr Phe His Lys Ile Arg Gly Leu Leu Ala Phe Trp Ile Gly Ala
    50                  55                  60

Leu Leu Ile Ala Phe Thr Leu Leu Ser Asn Lys Tyr Thr Ile Ile Ile
 65                  70                  75                  80

Leu Phe Val Phe Leu Leu Leu Ile Val Arg Tyr Leu Ile His Lys
                85                  90                  95

Phe Lys Pro Lys Lys Val Val Ala Thr Asp Glu Val Met Thr Ser Pro
            100                 105                 110

Ser Phe Ile Lys Gln Lys Trp Phe Gly Glu Gln Arg Thr Pro Val Tyr
        115                 120                 125

Val Tyr Lys Trp Glu Asp Val Gln Ile Gln His Gly Ile Gly Asp Leu
    130                 135                 140

His Ile Asp Leu Thr Lys Ala Ala Asn Ile Lys Glu Asn Asn Thr Ile
145                 150                 155                 160

Val Val Arg His Ile Leu Gly Lys Val Gln Val Ile Leu Pro Val Asn
                165                 170                 175

Tyr Asn Ile Asn Leu His Val Ala Ala Phe Tyr Gly Ser Thr Tyr Val
            180                 185                 190

Asn Glu Lys Ser Tyr Lys Val Glu Asn Asn Ile His Ile Glu Glu
        195                 200                 205

Met Met Lys Pro Asp Asn Tyr Thr Val Asn Ile Tyr Val Ser Thr Phe
    210                 215                 220

Ile Gly Asp Val Glu Val Ile Tyr Arg
225                 230
```

<210> SEQ ID NO 191
<211> LENGTH: 260
<212> TYPE: PRT
<213> ORGANISM: Staphylococcus aureus

<400> SEQUENCE: 191

```
Met Leu Ile Gln Leu Asp Gln Ile Gly Arg Met Lys Gln Gly Lys Thr
1               5                   10                  15

Ile Leu Lys Lys Ile Ser Trp Gln Ile Ala Lys Gly Asp Lys Trp Ile
            20                  25                  30

Leu Tyr Gly Leu Asn Gly Ala Gly Lys Thr Thr Leu Leu Asn Ile Leu
        35                  40                  45

Asn Ala Tyr Glu Pro Ala Thr Ser Gly Thr Val Asn Leu Phe Gly Lys
    50                  55                  60

Met Pro Gly Lys Val Gly Tyr Ser Ala Glu Thr Val Arg Gln His Ile
65                  70                  75                  80

Gly Phe Val Ser His Ser Leu Leu Glu Lys Phe Gln Glu Gly Glu Arg
                85                  90                  95

Val Ile Asp Val Val Ile Ser Gly Ala Phe Lys Ser Ile Gly Val Tyr
            100                 105                 110

Gln Asp Ile Asp Asp Glu Ile Arg Asn Glu Ala His Gln Leu Leu Lys
        115                 120                 125

Leu Val Gly Met Ser Ala Lys Ala Gln Gln Tyr Ile Gly Tyr Leu Ser
    130                 135                 140

Thr Gly Glu Lys Gln Arg Val Met Ile Ala Arg Ala Leu Met Gly Gln
145                 150                 155                 160

Pro Gln Val Leu Ile Leu Asp Glu Pro Ala Ala Gly Leu Asp Phe Ile
                165                 170                 175

Ala Arg Glu Ser Leu Leu Ser Ile Leu Asp Ser Leu Ser Asp Ser Tyr
            180                 185                 190

Pro Thr Leu Ala Met Ile Tyr Val Thr His Phe Ile Glu Glu Ile Thr
        195                 200                 205

Ala Asn Phe Ser Lys Ile Leu Leu Leu Lys Asp Gly Gln Ser Ile Gln
    210                 215                 220

Gln Gly Ala Val Glu Asp Ile Leu Thr Ser Glu Asn Met Ser Arg Phe
225                 230                 235                 240

Phe Gln Lys Asn Val Ala Val Gln Arg Trp Asn Asn Arg Phe Ser Met
                245                 250                 255

Ala Met Leu Glu
            260

<210> SEQ ID NO 192
<211> LENGTH: 209
<212> TYPE: PRT
<213> ORGANISM: Staphylococcus aureus

<400> SEQUENCE: 192

Met Lys Arg Leu Val Thr Gly Leu Leu Ala Leu Ser Leu Phe Leu Ala
1               5                   10                  15

Ala Cys Gly Gln Asp Ser Asp Gln Gln Lys Asp Gly Asn Lys Glu Lys
            20                  25                  30

Asp Asp Lys Ala Lys Thr Glu Gln Gln Asp Lys Lys Thr Asn Asp Ser
        35                  40                  45

Ser Lys Asp Lys Lys Asp Asn Lys Asp Ser Lys Asp Val Asn Lys
    50                  55                  60

Asp Asn Lys Asp Asn Ser Ala Asn Asp Gln Gln Gln Ser Asn Ser
65                  70                  75                  80

Asn Ala Thr Asn Asn Asp Gln Asn Gln Thr Asn Asn Asn Gln Ser Ser
                85                  90                  95

Asn Asn Gln Ala Asn Asn Asn Gln Lys Ser Ser Tyr Val Ala Pro Tyr
            100                 105                 110
```

```
Tyr Gly Gln Asn Ala Ala Pro Val Ala Arg Gln Ile Tyr Pro Phe Asn
            115                 120                 125
Gly Asn Lys Asn Gln Ala Leu Gln Gln Leu Pro Asn Phe Gln Thr Ala
        130                 135                 140
Leu Asn Ala Ala Asn Asn Glu Ala Asn Lys Phe Gly Ser Asn Asn Lys
145                 150                 155                 160
Val Tyr Asn Asp Tyr Ser Ile Glu Glu His Asn Gly Asn Tyr Lys Tyr
                165                 170                 175
Val Phe Ser Phe Lys Asp Pro Asn Ala Asn Gly Lys Tyr Ser Ile Val
            180                 185                 190
Thr Val Asp Tyr Thr Gly Gln Ala Met Val Thr Asp Pro Asn Tyr Gln
        195                 200                 205
Gln

<210> SEQ ID NO 193
<211> LENGTH: 439
<212> TYPE: PRT
<213> ORGANISM: Staphylococcus aureus

<400> SEQUENCE: 193

Met Arg Thr Gly His Tyr Thr Pro Ile Pro Asn Glu Pro His Tyr Leu
1               5                   10                  15
Val Ile Ser His Ala Asp Lys Leu Thr Ala Thr Glu Lys Ala Lys Leu
            20                  25                  30
Arg Leu Leu Ile Ile Lys Gln Lys Leu Asp Ile Ser Leu Ala Glu Ser
        35                  40                  45
Val Val Ser Ser Pro Ile Ala Ser Glu His Val Ile Glu Gln Leu Thr
    50                  55                  60
Leu Phe Gln His Glu Arg Arg His Leu Arg Pro Lys Ile Ser Ala Thr
65                  70                  75                  80
Phe Leu Ala Trp Leu Leu Ile Phe Leu Met Phe Ala Leu Pro Ile Gly
                85                  90                  95
Ile Ala Tyr Gln Phe Ser Asp Trp Phe Gln Asn Gln Tyr Val Ser Ala
            100                 105                 110
Trp Ile Glu Tyr Leu Thr Gln Thr Thr Leu Leu Asn His Asp Ile Leu
        115                 120                 125
Gln His Ile Leu Phe Gly Asp Tyr Gly Val Leu Ser Leu Gly Thr Tyr
    130                 135                 140
Ser Leu Val Trp Ala Leu Pro Val Val Ile Leu Ile Ser Leu Ser Thr
145                 150                 155                 160
Ala Ile Ile Asp Gln Thr Gly Leu Lys Ser Trp Met Ile Trp Ala Ile
                165                 170                 175
Glu Pro Ser Met Leu Trp Ile Gly Leu Gln Gly Asn Asp Ile Val Pro
            180                 185                 190
Leu Leu Glu Gly Phe Gly Cys Asn Ala Ala Ile Ser Gln Ala Ala
        195                 200                 205
His Gln Cys His Thr Cys Thr Lys Thr Gln Cys Met Ser Leu Ile Ser
    210                 215                 220
Phe Gly Ser Ser Cys Ser Tyr Gln Ile Gly Ala Thr Leu Ser Ile Phe
225                 230                 235                 240
Ser Val Ala Gly Lys Ser Trp Leu Phe Met Pro Tyr Leu Ile Leu Val
                245                 250                 255
Leu Leu Gly Gly Ile Leu His Asn Arg Ile Trp Leu Lys Lys Asn Asp
            260                 265                 270
```

```
Gln Gln Leu Ser Val Pro Leu Pro Tyr Asp Arg Gln Leu His Met Pro
            275                 280                 285

Asn Ile Arg Gln Met Leu Leu Gln Met Trp Gln Asn Ile Gln Met Phe
        290                 295                 300

Ile Val Gln Ala Leu Pro Ile Phe Ile Thr Ile Cys Leu Ile Val Ser
305                 310                 315                 320

Ile Leu Ser Leu Thr Pro Ile Leu Asn Val Leu Ser Gln Ile Phe Thr
                325                 330                 335

Pro Ile Leu Ser Leu Leu Gly Ile Ser Ser Glu Leu Ser Pro Gly Ile
            340                 345                 350

Leu Phe Ser Met Ile Arg Lys Asp Gly Met Leu Leu Phe Asn Leu His
            355                 360                 365

Gln Gly Ala Leu Leu Gln Gly Met Thr Ala Thr Gln Leu Leu Leu Leu
        370                 375                 380

Val Phe Phe Ser Ser Thr Phe Thr Ala Cys Ser Val Thr Met Thr Met
385                 390                 395                 400

Leu Leu Lys His Leu Gly Gly Gln Ser Ala Leu Lys Leu Ile Gly Lys
                405                 410                 415

Gln Met Val Thr Ser Leu Ser Leu Val Ile Gly Val Gly Ile Ile Val
            420                 425                 430

Lys Ile Val Met Leu Ile Ile
            435

<210> SEQ ID NO 194
<211> LENGTH: 22
<212> TYPE: DNA
<213> ORGANISM: Artificial sequence
<220> FEATURE:
<223> OTHER INFORMATION: synthetic sequence

<400> SEQUENCE: 194
tcgtcgttgt cgttttgtcg tt                                           22

<210> SEQ ID NO 195
<211> LENGTH: 13
<212> TYPE: PRT
<213> ORGANISM: Artificial sequence
<220> FEATURE:
<223> OTHER INFORMATION: synthetic sequence

<400> SEQUENCE: 195

Ile Leu Pro Trp Lys Trp Pro Trp Trp Pro Trp Arg Arg
1               5                   10

<210> SEQ ID NO 196
<211> LENGTH: 13
<212> TYPE: PRT
<213> ORGANISM: Artificial sequence
<220> FEATURE:
<223> OTHER INFORMATION: synthetic sequence

<400> SEQUENCE: 196

Lys Asp Tyr Glu Arg Lys Tyr Lys Lys His Ile Val Ser
1               5                   10
```

VACCINE CONSTRUCTS AND USES THEREOF AGAINST *STAPHYLOCOCCUS* INFECTIONS

CROSS-REFERENCE TO RELATED APPLICATIONS

This application is a National Entry Application of PCT application No. PCT/CA2017/051253 filed on Oct. 20, 2017 and published in English under PCT Article 21(2), which itself claims benefit of U.S. provisional application Ser. No. 62/411,120, filed on Oct. 21, 2016. All documents above are incorporated herein in their entirety by reference.

STATEMENT REGARDING FEDERALLY SPONSORED RESEARCH OR DEVELOPMENT

N.A.

FIELD OF THE INVENTION

The present invention relates to vaccine constructs and uses thereof against *Staphylococcus* infections. More specifically, the present invention is concerned with vaccine constructs combining antigens and their uses against *Staphylococcus* infections such as bovine intramammary infections (IMI).

REFERENCE TO SEQUENCE LISTING

Pursuant to 37 C.F.R. 1.821(c), a sequence listing is submitted herewith as an ASCII compliant text file named SEQUENCE LISTING USP62411120_ST25, created on Oct. 5, 2017 and having a size of 278 kilobytes. The content of the aforementioned file is hereby incorporated by reference in its entirety.

BACKGROUND OF THE INVENTION

Bovine mastitis is the most frequent and costly disease for dairy producers and *Staphylococcus aureus* is considered to be the transmittable bacterium that is the most often responsible for the development of the disease (Sears et al., 2003). Staphylococcal IMIs, which may lead to mastitis, are difficult to treat and frequent relapses are common (Sandholm et al., 1990).

The development of vaccines for the prevention and control of *S. aureus* IMIs has been extensively investigated although no formulation has demonstrated protective efficacy to date. This is probably because of inadequate vaccine targets (Middleton, 2008; Middleton 2009), high diversity among strains capable of provoking mastitis (Buzzola, 2007; Kerro-Dego, 2006; Middleton, 2008) or the failure to elicit an appropriate immune response (Bharathan, 2011; Ferens, 2000; Fowler, 2014; Proctor, 2012). It is increasingly understood that immunity solely based on vaccine-induced antibodies may be important but is however insufficient for inducing protection against *S. aureus* (Middleton 2008; Middleton 2009). It appears that cell mediated immunity (CMI) based on Th1 and Th17 type responses may be necessary to complete the protection (Fowler, 2014; Lin, 2009; Proctor, 2012; Spellberg, 2012).

Bacterial susceptibility to antibiotics in vitro is a poor predictor of therapeutic efficacy in chronically infected cows (Owens et al., 1997). Although infections that follow treatment of mastitis can be due to newly acquired strains, they are often the result of the persistence of the original infective organism (Sandholm et al., 1990; Myllys et al., 1997). Existing therapies thus often fail to eliminate the infection and it would be highly desirable to find novel approaches to prevent or treat staphylococcal IMI.

A lack of vaccine efficacy and protective ability has been noted for commercially available *S. aureus* vaccines (Middleton, 2008). Thus, it would be highly desirable to use highly efficient *S. aureus* antigens that are known to be expressed during IMI as vaccine components for protection against IMI and mastitis.

The present invention seeks to meet these and other needs.

The present description refers to a number of documents, the content of which is herein incorporated by reference in their entirety.

SUMMARY OF THE INVENTION

In a first aspect, the present invention provides fusion polypeptides displaying increased immunogenicity and their use as vaccine against staphylococcal IMI.

A characteristic of staphylococcal such as *S. aureus* IMI is the ability of *S. aureus* to persist within host cells. In particular, *S. aureus* small colony variants (SCVs) do not generally generate invasive infections and can be internalized in host cells. In a further aspect therefore, the present invention provides live-attenuated *S. aureus* strains for vaccine purposes based on the phenotypic aspects of SCVs to provide an immune response against such strains and increase the vaccine protective efficacy.

In an aspect, the present invention provides the following items:

Item 1: A fusion construct of formula (I): X-A-linker-B-Z (I) wherein: (1) A and B are identical or different and are independently: (a) a polypeptide comprising a SACOL0029 polypeptide as set forth in any one of the sequences depicted in FIG. 24 (SEQ ID NOs: 5 and 121 to 131), a SACOL0264 polypeptide (SEQ ID NO: 185), a SACOL0442 polypeptide as set forth in any one of the sequences depicted in FIG. 22D (SEQ ID NOs: 29 and 82 to 92), a SACOL0718 polypeptide (SEQ ID NO: 186), a SACOL0720 polypeptide as set forth in any one of the sequences depicted in FIGS. 23I-K (SEQ ID NOs: 11 and 109 to 120), a SACOL1353 polypeptide (SEQ ID NO: 187), a SACOL1416 polypeptide (SEQ ID NO: 188), a SACOL1611 polypeptide (SEQ ID NO: 189), a SACOL1867 polypeptide as set forth in any one of the sequences depicted in FIG. 25D (SEQ ID NOs: 152 to 164), a SACOL1912 polypeptide (SEQ ID NO: 43), a SACOL1944 polypeptide (SEQ ID NO: 190), a SACOL2144 polypeptide (SEQ ID NO: 191), a SACOL2365 polypeptide (SEQ ID NO: 192), a SACOL2385 polypeptide (SEQ ID NO: 50) or a SACOL2599 polypeptide (SEQ ID NO: 193), based on the gene nomenclature from the *Staphylococcus aureus* COL (SACOL) genome set forth in NCBI Reference Sequence NC_002951.2; (b) a polypeptide encoded by a gene from a same operon as a gene encoding the polypeptide of (a); (c) a polypeptide comprising an immunogenic fragment of at least 13 consecutive amino acids of (a) or (b); (d) a polypeptide comprising an amino acid sequence at least 60% identical overall to the sequence of the polypeptide of any one of (a) to (c); or (e) a polypeptide comprising an immunogenic variant comprising at least 13 consecutive amino acids of any one of (a) to (c); (2) the linker is an amino acid sequence of at least one amino acid or is absent; (3) X is absent or is an amino acid sequence of at least one amino acid; and (4) Z is absent or is an amino acid sequence of at least one amino acid.

Item 2: The construct of item 1, wherein (1) (a) is a polypeptide comprising a SACOL0029 polypeptide as set forth in any one of the sequences depicted in FIG. 24 (SEQ ID NOs: 5 and 121 to 131), a SACOL0442 polypeptide as set forth in any one of the sequences depicted in FIG. 22D (SEQ ID NOs: 29 and 82 to 92), a SACOL0720 polypeptide as set forth in any one of the sequences depicted in FIGS. 23I-K (SEQ ID NOs: 11 and 109 to 120), or a SACOL1867 polypeptide as set forth in any one of the sequences depicted in FIG. 25D (SEQ ID NOs: 152 to 164).

Item 3: The construct of item 2, wherein at least one of A and B is (a) a polypeptide comprising a SACOL0029 polypeptide as set forth in any one of the sequences depicted in FIG. 24 (SEQ ID NOs: 5 and 121 to 131); (b) a polypeptide encoded by a gene from a same operon as a gene encoding the polypeptide of (a); (c) a polypeptide comprising an immunogenic fragment of at least 13 consecutive amino acids of (a) or (b); (d) a polypeptide comprising an amino acid sequence at least 60% identical overall to the sequence of the polypeptide of any one of (a) to (c); or (e) a polypeptide comprising an immunogenic variant comprising at least 13 consecutive amino acids of any one of (a) to (d); and the other one of A and B is (a') a polypeptide comprising a SACOL1867 polypeptide as set forth in any one of the sequences depicted in FIG. 25D (SEQ ID NOs: 152 to 164); (b') a polypeptide encoded by a gene from a same operon as a gene encoding the polypeptide of (a'); (c') a polypeptide comprising an immunogenic fragment of at least 13 consecutive amino acids of (a') or (b'); (d') a polypeptide comprising an amino acid sequence at least 60% identical overall to the sequence of the polypeptide of any one of (a') to (c'); or (e') a polypeptide comprising an immunogenic variant comprising at least 12 consecutive amino acids of any one of (a') to (d').

Item 4: The construct of item 2, wherein at least one of A and B is (a) a polypeptide comprising a SACOL0442 polypeptide as set forth in any one of the sequences depicted in FIG. 22D (SEQ ID NOs: 29 and 82 to 92); (b) a polypeptide encoded by a gene from a same operon as a gene encoding the polypeptide of (a); (c) a polypeptide comprising an immunogenic fragment of at least 13 consecutive amino acids of (a) or (b); (d) a polypeptide comprising an amino acid sequence at least 60% identical overall to the sequence of the polypeptide of any one of (a) to (c); or (e) a polypeptide comprising an immunogenic variant comprising at least 13 consecutive amino acids of any one of (a) to (d); and the other one of A and B is (a') a polypeptide comprising a SACOL0720 polypeptide as set forth in any one of the sequences depicted in FIGS. 23I-K (SEQ ID NOs: 11 and 109 to 120); (b') a polypeptide encoded by a gene from a same operon as a gene encoding the polypeptide of (a'); (c') a polypeptide comprising an immunogenic fragment of at least 13 consecutive amino acids of (a') or (b'); (d') a polypeptide comprising an amino acid sequence at least 60% identical overall to the sequence of the polypeptide of any one of (a') to (c'); or (e') a polypeptide comprising an immunogenic variant comprising at least 12 consecutive amino acids of any one of (a') to (d').

Item 5: The construct of item 2, wherein A and B are identical or different and are (a) a polypeptide comprising a SACOL0720 polypeptide as set forth in any one of the sequences depicted in FIGS. 23I-K (SEQ ID NOs: 11 and 109 to 120); (b) a polypeptide encoded by a gene from a same operon as a gene encoding the polypeptide of (a); (c) a polypeptide comprising an immunogenic fragment of at least 13 consecutive amino acids of (a) or (b); (d) a polypeptide comprising an amino acid sequence at least 60% identical overall to the sequence of the polypeptide of any one of (a) to (c); or (e) a polypeptide comprising an immunogenic variant comprising at least 13 consecutive amino acids of any one of (a) to (d).

Item 6: The construct of any one of items 1-2 and 4, wherein said immunogenic fragment (d) comprises one or more of the following amino acid sequences: KDTINGKSNKSRNW (SEQ ID NO: 34); and KDGGKYTLESHKELQ (SEQ ID NO: 1).

Item 7: The construct of item 6, wherein said immunogenic fragment (d) comprises one or more of the following amino acid sequences:

```
                                          (SEQ ID NO: 30)
STQNSSSVQDKQLQKVEEVPNNSEKALVKKLYDRYSKDTINGKSNKSRNW

VYSERPLNENQVRIHLEGTYTVAGRVYTPKRNITLNKEVVTLKELDHIIR

FAHISYGLYMGEHLPKGNIVINTKDGGKYTLESHKELQKDRENVKINTAD

IKNVTFKLVKSVNDIEQV;

(SEQ ID NO: 32)
DKQLQKVEEVPNNSEKALVKKLYDRYSKDTINGKSNKSRNWVYSERPLNE

NQVRIHLEGTYTVAGRVYTPKRNITLNKEVVTLKELDHIIRFAHISYGLY

MGEHLPKGNIVINTK;
and
                                          (SEQ ID NO: 33)
DKQLQKVEEVPNNSEKALVKKLYDRYSKDTINGKSNKSRNWVYSERPLNE

NQVRIHLEGTYTVARVYTPKRNITLNKEVVTLKELDHIIRFAHISYGLYM

GEHLPKGNIVINTKDGGKYTLESHKELQKDRENVKINTADIKNVTFKLVK

SVNDIEQV.
```

Item 8: The construct of any one of items 1-2 and 4-5, wherein said immunogenic fragment (d) comprises one or more of the following amino acid sequences: QFGFDLKHKKDALA (SEQ ID NO: 21); TIKDQQ-KANQLAS (SEQ ID NO: 22); KDINKIYFMTDVDL (SEQ ID NO: 23); and DVDLGGPTFVLND (SEQ ID NO: 24).

Item 9: The construct of item 8, wherein said immunogenic fragment (d) comprises one or more of the following amino acid sequences:

```
                                          (SEQ ID NO: 12)
RASLSSEIKYTAPHDVTIKDQQKANQLASELNNQKIPHFYNYKEVIHTKL

YKDNLFDVKAKEPYNVTITSDKYIPNTDLKRGQADLFVAEGSIKDLVKHK

KHGKAIIGTKKHHVNIKLRKDINKIYFMTDVDLGGPTFVLNDKDYQEIRK

YTKAKHIVSQFGFDLKHKKDALALEKAKNKVDKSIETRSEAISSISSLT

G;
                                          (SEQ ID NO: 13)
ASLSSEIKYTAPHDVTIKDQQKANQLASELNNQKIPHFYNYKEVIHTKLY

KDNLFDVKAKEPYNVTITSDKYIPNTDLKRGQADLFVAEGSIKDLVKHKK

HGKAIIGTKKHHVNIKLRKDINKIYFMTDVDLGGPTFVLNDKDYQEIRKY

TKAKHIVSQFGFDLKHKKDALALEKAKNKVDKSIETRSEAISSISSLTG;
```

-continued (SEQ ID NO: 14)
ASLSSEIKYTAPHDVTIKDQQKANQLASELNNQKIPHFYNYKEVIHTKLY

KDNLFDVKAKEPYNVTITSDKYIPNTDLKRGQADLFVAEGSIKDLVKHKK

HGKAIIGTKKHHVNIKLRKDINKIYFMTDVDLGGPTFVLNDKDYQE;

(SEQ ID NO: 15)
KDINKIYFMTDVDLGGPTFVLNDKDYQEIRKYTKAKHIVSQFGFDLKHKK

DALA;

(SEQ ID NO: 16)
KDINKIYFMTDVDLGGPTFVLNDKD;

(SEQ ID NO: 17)
KDINKIYFMTDVDLGGPTFVLNDKDY;

(SEQ ID NO: 19)
KDINKIYFMTDVDLGGPTFVLND;

(SEQ ID NO: 18)
SQFGFDLKHKKDALA;
and (SEQ ID NO: 20)
KHIVSQFGFDLKHKKDALA.

Item 10: The construct of any one of items 1-3, wherein said immunogenic fragment (c') comprises one or more of the following amino acid sequences: PYNGWSFKDATGF (SEQ ID NO: 165); AHPNGDKGNGGIYK (SEQ ID NO: 167); SISDYPGDEDISVM (SEQ ID NO: 169); RGPKGFNFNENVQA (SEQ ID NO: 172); QFESTGTIKRIKDN (SEQ ID NO: 175); and GNSGSPVLNSNNEV (SEQ ID NO: 178).

Item 11: The construct of item 10, wherein said immunogenic fragment (d) comprises the following amino acid sequence:

(SEQ ID NO: 39)
TQVKDTNIFPYNGVVSFKDATGFVIGKNTIITNKHVSKDYKVGDRITAHP

NGDKGNGGIYKIKSISDYPGDEDISVMNIEEQAVERGPKGFNFNENVQAF

NFAKDAKVDDKIKVIGYPLPAQNSFKQFESTGTIKRIKDNILNFDAYIEP

GNSGSPVLNSNNEVIGVVYGGIGKIGSEYNGAVYFTPQIKDFIQKHIEQ.

Item 12: The construct of any one of items 1 to 11, wherein the linker comprises at least four identical or different amino acids selected from the group consisting of glycine, serine, alanine, aspartate, glutamate and lysine.

Item 13: The construct of any one of items 1 to 12, wherein the linker comprises (GGGGS)n (SEQ ID NO: 67), (ERKYK)n (SEQ ID NO: 61); or (EAAAK)n (SEQ ID NO: 63), wherein n=1 to 5.

Item 14: The construct of any one of items 1 to 13, wherein said X comprises a polyhistidine of 6 to 10 amino acids.

Item 15: The construct of any one of items 1 to 13, wherein said X is absent.

Item 16: The construct of any one of items 1 to 15, wherein said Z is absent.

Item 17: An isolated nucleic acid molecule encoding the construct defined in any one of items 1 to 16.

Item 18: A vector comprising the isolated nucleic acid defined in item 17.

Item 19: A host cell comprising the vector defined in item 18.

Item 20: The cell of item 19, which is a live attenuated form of Staphylococcus aureus.

Item 21: The cell of item 20, wherein the live attenuated form of Staphylococcus aureus has a stabilized small colony variant (SCV) phenotype.

Item 22: The cell of item 21, wherein the live attenuated form of Staphylococcus aureus having a stabilized SCV phenotype is a ΔhemBΔ720 S. aureus.

Item 23: A composition comprising: (A) at least one of the constructs defined in any one of items 1 to 16; at least one of the nucleic acid molecules defined in item 17; at least one of the vectors defined in item 18; or at least one of the cells defined in any one of items 19 to 22; and (B) (i) the polypeptide defined in any one of items 1 to 11; (ii) a live attenuated Staphylococcus aureus; (iii) a pharmaceutically acceptable excipient; (iv) an adjuvant; or (v) a combination of at least two of (i) to (iv).

Item 24: The composition of item 23, wherein the live attenuated form of Staphylococcus aureus expresses: (a) a polypeptide comprising a SACOL0029 polypeptide as set forth in any one of the sequences depicted in FIG. 24 (SEQ ID NOs: 5 and 121 to 131), a SACOL0264 polypeptide (SEQ ID NO: 185), a SACOL0442 polypeptide as set forth in any one of the sequences depicted in FIG. 22D (SEQ ID NOs: 29 and 82 to 92), a SACOL0718 polypeptide (SEQ ID NO: 186), a SACOL0720 polypeptide as set forth in any one of the sequences depicted in FIGS. 23I-K (SEQ ID NOs: 11 and 109 to 120), a SACOL1353 polypeptide (SEQ ID NO: 187), a SACOL1416 polypeptide (SEQ ID NO: 188), SACOL1611 (SEQ ID NO: 189), a SACOL1867 polypeptide as set forth in any one of the sequences depicted in FIG. 25D (SEQ ID NOs: 152 to 164), a SACOL1912 polypeptide (SEQ ID NO: 43), SACOL1944 (SEQ ID NO: 190), a SACOL2144 polypeptide (SEQ ID NO: 191), a SACOL2365 polypeptide (SEQ ID NO: 192), a SACOL2385 polypeptide (SEQ ID NO: 50) or a SACOL2599 polypeptide (SEQ ID NO: 193) based on the gene nomenclature from the Staphylococcus aureus COL (SACOL) genome set forth in NCBI Reference Sequence NC_002951.2; (b) a polypeptide encoded by a gene from a same operon as a gene encoding the polypeptide of (a); (c) a polypeptide comprising an immunogenic fragment of at least 13 consecutive amino acids of (a) or (b); (d) a polypeptide comprising an amino acid sequence at least 60% identical overall to the sequence of the polypeptide of any one of (a) to (c); or (e) a polypeptide comprising an immunogenic variant comprising at least 13 consecutive amino acids of any one of (a) to (c).

Item 25: The composition of item 23 or 24, wherein the live attenuated form of Staphylococcus aureus has a stabilized small colony variant (SCV) phenotype.

Item 26: The composition of any one of items 23 to 25, wherein the adjuvant comprises alum, an oil (e.g., emulsified oil, mineral oil), saponin (e.g., Quil-A™), cyclic-diguanosine-5'-monophosphate (c-di-GMP), polyphosphasine, indolicidin, pathogen-associated molecular patterns (PAMPS) or a combination of at least two thereof.

Item 27: A method for preventing and/or treating a Staphylococcal intramammary infection (IMI) in a mammal, said method comprising administrating to said mammal an effective amount of the construct defined in any one of items 1 to 16; of the nucleic acid molecule defined in item 17; of the vector defined in item 18; of the cell defined in any one of items 19 to 22; or of the composition defined in any one of items 23 to 26.

Item 28: The method of item 27, wherein said Staphylococcal IMI is caused by one or more Staphylococcus aureus strains.

Item 29: The method of item 27 or 28, wherein said mammal is a cow.

Item 30: A use of an effective amount of (i) the construct defined in any one of items 1 to 16; (ii) the nucleic acid molecule defined in item 17; (iii) the vector defined in item 18; of the cell defined in any one of items 19 to 22; (iv) the composition defined in any one of items 23 to 26; or (v) a combination of at least two of (i) to (iv), for preventing and/or treating a Staphylococcal intramammary infection (IMI) in a mammal.

Item 31: The use of item 30, wherein said Staphylococcal IMI is caused by one or more *Staphylococcus aureus* strains.

Item 32: The use of item 30 or 31, wherein said mammal is a cow.

Item 33: The construct defined in any one of items 1 to 16; the nucleic acid molecule defined in item 17; the vector defined in item 18; the cell defined in any one of items 19 to 22; the composition defined in any one of items 23 to 26 or a combination of at least two thereof, for use in the prevention and/or treatment of a Staphylococcal intramammary infection (IMI) in a mammal.

Item 34: The construct, nucleic acid molecule, vector, cell, composition or combination of item 33, wherein said Staphylococcal IMI is caused by one or more *Staphylococcus aureus* strains.

Item 35: The construct, nucleic acid molecule, vector, cell or composition of item 33 or 34, wherein said mammal is a cow.

Item 36: A kit for preventing and/or treating a Staphylococcal intramammary infection (IMI) in a mammal comprising: (A) (i) at least one of the constructs defined in any one of items 1 to 16; (ii) at least one of the nucleic acid molecules defined in item 17; (iii) at least one of the vectors defined in items 18; (iv) at least one of the cells defined in any one of items 19 to 22; or (v) a combination of at least two of (i) to (iv), and (B) (i) the polypeptide defined in any one of items 1 to 11; (ii) a live attenuated *Staphylococcus aureus*; (iii) a pharmaceutically acceptable excipient; (iv) an adjuvant; (v) instructions for using the kit for preventing and/or treating a Staphylococcal intramammary infection (IMI) in a mammal; or (vi) a combination of at least two of (i) to (v).

BRIEF DESCRIPTION OF THE DRAWINGS

In the appended drawings:

In FIG. 1D, the IgG2/IgG1 ratio is represented for the vaccinated cows. In FIGS. 1A, B and C, open circles (○) represent data for the vaccinated cows, black squares (■) represent data for the placebo cows. Each symbol represents the titer for one cow. Horizontal lines represent the medians: dashed lines represent the medians for the vaccinated cows while continuous lines represent the medians for the placebo cows. In FIGS. 1A, B and C, titers for the vaccinated cows are higher than the titers for the placebo cows ($P<0.0001$). In FIG. 1D, symbols represent the ratio IgG2/IgG1 for each cow. Horizontal lines represent the medians. The different letters show statistical differences. ***, $P<0.001$.

FIGS. 4A-C. FIG. 4A shows the correlation between CFU and the SCC for each cow, and FIG. 4B shows the correlation between serum IgG1 titer against SACOL0442 and SCC for each cow. Each symbol represents data for one cow. In FIG. 4A, it represents the mean of SCC and CFU for the 3 infected quarters from the beginning to the end of the infection. In FIG. 4B, it represents the mean of SCC for the 3 infected quarters from the beginning to the end of the infection and the serum IgG1 titer against SACOL0442 four weeks after the second immunization and just before the experimental infection. Open circles represent data for the vaccinated cows and black squares represent data for the placebo cows. There is a strong correlation between the SCC/ml and the CFU/ml and a negative correlation between the SCC and the IgG1 titer against SACOL0442. In FIG. 4C, the correlation between SCC or CFU relative to milk IgG2 titer against SACOL0029 is shown for each cow ten days after experimental infection (6 weeks after the second immunization). Each symbol represents data for one cow ten days after the experimental infection. Aseptic milk samples were taken at morning milking and the viable counts of *S. aureus* were determined by 10-fold dilutions and plating on tryptic soy agar (TSA) plates while SCC were determined by Valacta (Ste-Anne-de-Bellevue, QC). SCC and CFU data for each cow is the mean of the data for the 3 infected quarters ten days after the experimental infection. Milk samples for the determination of milk IgG2 titers are the mix of an equivalent volume of milk from the 4 quarters of each cow 10 days after the experimental infection (6 weeks after the second immunization). Black squares (■) represent data for the placebo cows, open circles (○) represent data for the vaccinated cows.

FIG. 5. shows serum total IgG titers for the vaccinated cows for each antigen of a vaccine comprising the fused antigens SACOL0029 and SACOL1867 (shown as SACOL0029-1867) and the antigens SACOL0442 and SACOL0720. In the ELISA, the targeted antigens were SACOL0029-1867, SACOL0029, SACOL1867, SACOL0442 and SACOL0720. Each open circle represents the titer four weeks after the second immunization for each of the 11 cows whereas each black diamond represents the preimmune titer. Horizontal lines represent the medians: solid line for the preimmune serums, dotted line for the samples taken four weeks after immunization. Titers for the vaccinated cows are higher than the titers of the preimmune serums (, P<0.01; *, P<0.001 for the other antigens tested).

(FIG. 8A) The hemB gene in the wild-type (WT) strain ATCC29213 and its isogenic mutant Δ720 was deleted by homologous recombination and replacement with an ermA cassette to create the mutant strains ΔhemB and Δ720ΔhemB, respectively. Thick lines and numbers denote the PCR-amplified regions depicted in B for parental (1) and hemB deleted (2) strains. (FIG. 8B) PCR products of the WT strain and its isogenic ΔhemB mutant (similar results were obtained with Δ720 and Δ720ΔhemB strains).

(FIG. 9A) Relative recovery of the initial inoculum found within cells at t 3 h for Δ720, and (FIG. 9B) for ΔhemBΔ720 mutants. Results are normalized according to that obtained for ATCC 29213 (WT) or ΔhemB, respectively, and are expressed as means with SD (, P≤0.01; *, P≤0.001; unpaired t test). (FIG. 9C) Means and SD of intracellular CFUs for WT and mutants at 12 h (left) and 24 h (right). A two-way ANOVA and Tukey's multiple comparisons test was used (*: P≤0.05; ***: P≤0.001). All values indicate the mean of three independent experiments, each performed in triplicate.

FIG. 15B. IgG titers rise with increasing doses of the live-attenuated strain Δ720GΔhemB: each dot represents the total IgG titer of one mouse against a Δ720GΔhemB whole cell extract. Medians are represented by thick lines for Immune titers and dashed lines for Preimmune titers. Titers were compared to their corresponding preimmune titers (Two-way ANOVA and Tukey's multiple comparisons test: ****: $P \leq 0.0001$). FIG. 15C. Immunization with the live-attenuated mutant Δ720GΔhemB confers IgG titers against components that are shared by mastitis strains of commonly found spa types. Each dot represents the total IgG titer of one mouse against the whole cell extract of the indicated strain. Medians are represented by thick lines for Immune titers and dashed lines for Preimmune titers. All immune titers were compared to their corresponding preimmune titer ($P \leq 0.0001$) and between clinical strains (Two-way ANOVA and Sidak's multiple comparisons test: NS: no significant difference).

FIGS. 21A-J. I. SACOL0029 polynucleotides (full length sequence SEQ ID NO: 4) and polypeptides (full length, fragment(s) and variant(s) sequences SEQ ID NOs: 5 to 9). Selected epitopes are shown shaded and/or bolded; II. SACOL0720 polynucleotides (full length sequence SEQ ID NO: 10) and polypeptides (full length, fragments and variant(s) sequences SEQ ID NOs: 11 to 27). Selected epitopes are shown shaded; III. SACOL0442 polynucleotides (full length sequence SEQ ID NO: 28) and polypeptides (full length, fragments and variant(s) sequences SEQ ID NOs: 29 to 36 and 1). Selected epitopes are shown shaded; IV. SACOL1867 polynucleotides (full length sequence SEQ ID NO: 37) and polypeptides (full length, fragment(s) and variant(s) sequences SEQ ID NOs: 38 to 41). Selected epitopes are shown shaded. Predicted transmembrane (enzim.hu/hmmtop/html/submit.html) domain shown bolded; V. SACOL1912 polynucleotide (full length sequence SEQ ID NO: 42) and polypeptides (full length and variant(s) sequences SEQ ID NOs: 43 to 44). Selected epitopes are shown shaded (see e.g., SEQ ID NOs: 45-48); VI. SACOL2385 polynucleotide (full length SEQ ID NO: 49) and polypeptides (full length and variant(s) sequences SEQ ID NOs: 50 to 51). Selected epitopes are shown shaded (see e.g., SEQ ID NOs: 52-53); VII. Fusions: (i) SACOL0029-1867 fusion polynucleotide sequences (SEQ ID NOs: 54 and 56) and polypeptide sequences (SEQ ID NOs: 55, 57-58). In the polynucleotide and polypeptide sequences, the double underlined sequence, if any, is that of the polyhistidine, the italicized sequence is the sequence of the SACOL0029 fragment, the single underlined sequence is the sequence of the linker and the bolded sequence is the sequence of the SACOL1867 fragment; (ii) SACOL0720-720 fusion polypeptide sequence (SEQ ID NO: 27 In the polypeptide sequence, the double underlined sequence, if any, is that of the polyhistidine, the italicized sequences are the sequences of the SACOL0720 fragments and the single underlined sequence is the sequence of the linker; (iii) SACOL0442-720 fusion polypeptide sequence (SEQ ID NO: 3). In the polynucleotide and polypeptide sequences, the double underlined sequence, if any, is that of the polyhistidine, the italicized sequence is the sequence of the SACOL0442 fragment, the single underlined sequence is the sequence of the linker and the bolded sequence is the sequence of the SACOL0720 fragment; and VIII. Sequences of linkers (SEQ ID NOs: 59 to 70).

FIGS. 22A-D I. Multiple polynucleotide sequences (SEQ ID NOs: 71-72, 28, 73 to 81) alignment for full length SACOL0442 and orthologues; II. Multiple polypeptide sequences (SEQ ID NOs: 29 and 82 to 92) alignment for full length SACOL0442, orthologues and consensus sequences derived therefrom are presented. In these sequences, "*" denotes that the residues in that column are identical in all sequences of the alignment, ":" denotes that conserved substitutions have been observed, and "." denotes that semi-conserved substitutions have been observed. Consensus sequences derived from these alignments are also presented wherein X is any amino acid. In the polypeptide sequences, selected epitopes are shown shaded (see e.g., SEQ ID NOs: 1, 34, 93-97).

FIGS. 23A-K I. Multiple polynucleotide sequences (SEQ ID NOs: 98 to 104, 10, and 105 to 108) alignment for full length SACOL0720 and orthologues; II. Multiple polypeptide sequences (SEQ ID NOs: 11 and 109 to 120) alignment for full length SACOL0720, orthologues. and consensus sequences derived therefrom are presented. In these sequences, "*" denotes that the residues in that column are identical in all sequences of the alignment, ":" denotes that conserved substitutions have been observed, and "." denotes that semi-conserved substitutions have been observed. Consensus sequences derived from these alignments are also presented wherein X is any amino acid. In the polypeptide sequences, selected epitopes are shown shaded (see e.g., SEQ ID NOs: 22, 19 and 21).

FIG. 24 Multiple polypeptide sequences (SEQ ID NOs: 5 and 121 to 131) alignment for full length SACOL0029, orthologues. and consensus sequences derived therefrom are presented. In these sequences, "*" denotes that the residues in that column are identical in all sequences of the alignment, ":" denotes that conserved substitutions have been observed, and "." denotes that semi-conserved substitutions have been observed. Consensus sequences derived from these alignments are also presented wherein X is any amino acid. In the polypeptide sequences, selected epitopes are shown shaded (see e.g., SEQ ID NOs: 132-139). Bolded epitope identified by BCPred™. Shaded epitopes identified by AAp predictions.

FIGS. 25A-D. I-Multiple polynucleotide sequences (SEQ ID NOs: 140 to 151) alignment for full length SACOL1867 and orthologues; II-Multiple polypeptide sequences (SEQ ID NOs: 152 to 164) alignment for full length SACOL1867, orthologues. and consensus sequences derived therefrom are presented. In these sequences, "*" denotes that the residues in that column are identical in all sequences of the alignment, ":" denotes that conserved substitutions have been observed, and "." denotes that semi-conserved substitutions have been observed. Consensus sequences derived from these alignments are also presented wherein X is any amino acid. In the polypeptide sequences, selected epitopes are shown shaded (see e.g., SEQ ID NOs: 165-180) and the end of the signal peptide domain and/or transmembrane domain is marked with a line (separates signal peptide and/or transmembrane domain from secreted form).

FIG. 26. I-polynucleotide sequence (SEQ ID NO: 181) for full length SACOL1715 (hemB); and II-amino acid sequence (SEQ ID NO: 182) for full length SACOL1715 (hemB).

FIG. 27. I-polynucleotide sequence (SEQ ID NO: 183) for full length ClfA (NWMN_0756, newman); and II-amino acid sequence (SEQ ID NO: 184) for full length ClfA.

DESCRIPTION OF ILLUSTRATIVE EMBODIMENTS

Figure 1A:
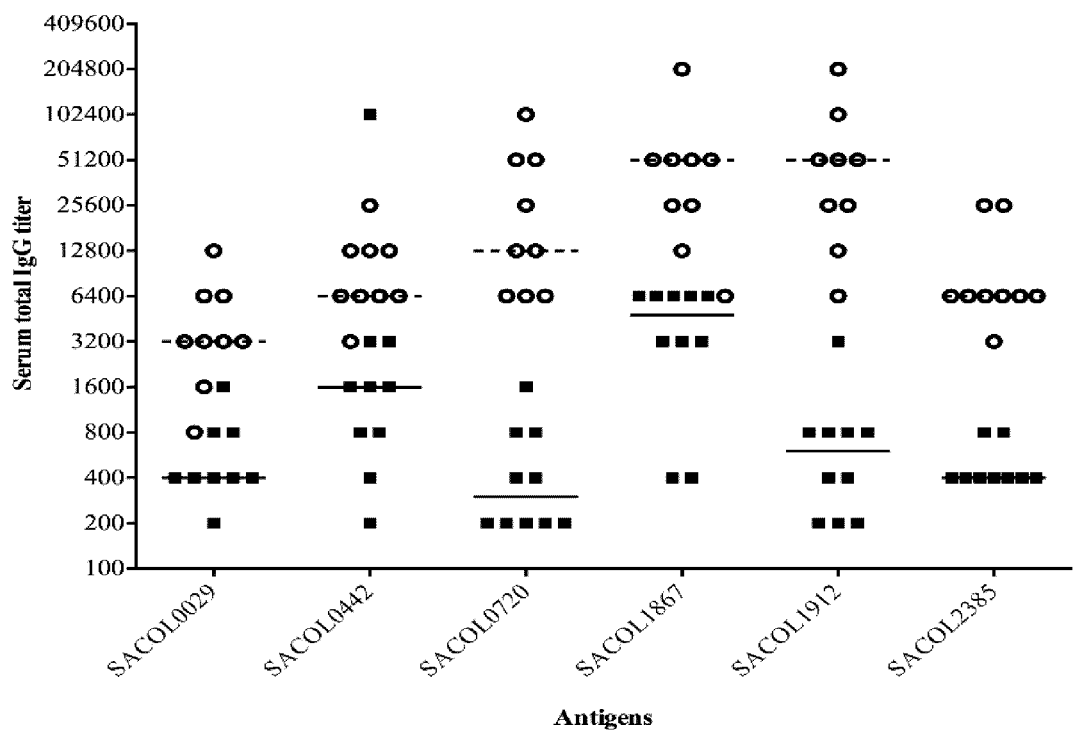
FIGS. 1A-D. shows serum total IgG (FIG. 1A), IgG1 (FIG. 1B), and IgG2 (FIG. 1C) titers for the vaccinated (9) and placebo (10) cows for each antigen of the vaccine, namely SACOL0029, SACOL0442, SACOL0720, SACOL1867, SACOL1912, and SACOL2385, four weeks after the second immunization (just before the experimental infection).

The present invention showed that a fusion of two antigens created an unexpected synergy in the immune response.

In addition, the present invention also stabilized the SCV phenotype of a *Staphylococcus* via hemB (complete deletion thus impairing the possibility of reversion to an invasive phenotype (Tuchscherr, 2011)) enabling its use as a vaccine delivery system. HemB is coding for the HemB protein/monomer, which combines to create the porphobilinogen synthase or aminolevulinate dehydratase enzyme [EC 4.2.1.24]. In addition, further attenuation was brought about by inactivation of an antigen of the present invention, namely gene SACOL0720, which has been previously shown to be important for *S. aureus* in cationic peptide resistance (Falord, 2012; Kawada-Matsuo, 2011; Meehl, 2007) and in vivo during IMI (Allard, 2013). Hence, this attenuated double mutant strain expressing constructs of the present invention is usable for immunization and protection against IMIs.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

In the present description, a number of terms are extensively utilized. In order to provide a clear and consistent understanding of the specification and claims, including the scope to be given such terms, the following definitions are provided.

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the term "consists of" or "consisting of" means including only the elements, steps, or ingredients specifically recited in the particular claimed embodiment or claim.

Polypeptides, Nucleic Acids and Delivery Systems

As used herein, the term "vaccine" refers to any compound/agent ("vaccine component"), or combinations thereof, capable of inducing/eliciting an immune response in a host and which permits to treat and/or prevent an infection and/or a disease. Therefore, non-limiting examples of such agent include proteins, polypeptides, protein/polypeptide fragments, immunogens, antigens, peptide epitopes, epitopes, mixtures of proteins, peptides or epitopes as well as nucleic acids, genes or portions of genes (encoding a polypeptide or protein of interest or a fragment thereof) added separately or in a contiguous sequence such as in nucleic acid vaccines, and the like.

In an aspect of the present invention, there is provided a fusion construct of formula I:

X-A-linker-B-Z         (formula (I),

Wherein A and B are identical or different and are each independently an antigenic polypeptide (i.e. native, fragment or variant thereof) of the present invention.

In a specific embodiment, A and/or Bis (a) a polypeptide comprising a SACOL0029 polypeptide as set forth in any one of the sequences depicted in FIG. 24 (SEQ ID NOs: 5 and 121 to 131), a SACOL0264 polypeptide (SEQ ID NO: 185), a SACOL0442 polypeptide as set forth in any one of the sequences depicted in FIG. 22D (SEQ ID NOs: 29 and 82 to 92), a SACOL0718 polypeptide (SEQ ID NO: 186), a SACOL0720 polypeptide as set forth in any one of the sequences depicted in FIGS. 23I-J (SEQ ID NOs: 11 and 109 to 120), a SACOL1353 polypeptide (SEQ ID NO: 187), a SACOL1416 polypeptide (SEQ ID NO: 188), SACOL1611 (SEQ ID NO: 189), a SACOL1867 polypeptide as set forth in any one of the sequences depicted in FIG. 25D (SEQ ID NOs: 152 to 164), a SACOL1912 polypeptide as set forth in FIG. 21G-V (SEQ ID NO: 43), SACOL1944 (SEQ ID NO: 190), a SACOL2144 polypeptide (SEQ ID NO: 191), a SACOL2365 polypeptide (SEQ ID NO: 192), a SACOL2385 polypeptide as set forth in VI on FIG. 21H (SEQ ID NO: 50) or a SACOL2599 polypeptide (SEQ ID NO: 193). In a specific embodiment, the above polypeptide (a) is the secreted or extracellular fragment of the polypeptide defined above. Transmembrane domains can be predicted using, for example, the software TMpredrM (ExPASy) ch.embnet.org/software/TMPRED_form.html, psort.org/psortb/index.html enzim.hu/hmmtop/html/submit.html and/or Sign/P4.1 (cbs.dtu.dk/services/SignalP). TMpred™ and Signal/P 4.1 predicted extracellular domain for: SACOL0720: AA 310-508; SACOL0442 AA 36 to 203. Enzim predicted a transmembrane domain SACOL1867 (1-40) so that extracellular domain was: AA 41-239 while psort.org/psortb/index.html predicted that SACOL1867 was an extracellular protein. Since the above-mentioned transmembrane and/or signal peptide domains are putative, the present invention encompasses cases where the antigens presented herein (e.g., SACOL1867) have or not a signal peptide and/or transmembrane domain and encompasses the corresponding extracellular fragments. In an embodiment, the above-mentioned polypeptide is a polypeptide normally secreted or expressed at the surface of the bacteria (e.g., *Staphylococcus aureus*).

The Genbank™ accession numbers for *S. aureus* genes listed herein and their encoded antigenic polypeptides encompassed by the present invention are depicted in Table I below:

TABLE I

Genbank™ accession numbers for the IMI-associated *S. aureus* genes and encoded polypeptides described herein

| Gene name | GenBank™ Gene ID No. | GenBank™ protein No. |
|---|---|---|
| SACOL0029 | 3236748 | YP_184940.1 (SEQ ID NO: 5) |
| SACOL0100 | 3236858 | YP_185004.1 |
| SACOL0101 | 3236840 | YP_185005.1 |
| SACOL0105 | 3236844 | YP_185009.1 |
| SACOL0148 | 3236734 | YP_185048.1 |
| SACOL0154 | 3238707 | YP_185054.1 |
| SACOL0204 | 3236774 | YP_185103.1 |
| SACOL0205 | 3236775 | YP_185104.1 |
| SACOL0264 | 3236683 | YP_185159.1 WP_000570071 (SEQ ID NO: 185) |
| SACOL0442 | 3236485 | YP_185332.1 (SEQ ID NO: 29) |
| SACOL0461 | 3236475 | YP_185351.1 |
| SACOL0608 | 3236353 | YP_185493.1 |
| SACOL0660 | 3238251 | YP_185544.1 |
| SACOL0688 | 3236721 | YP_185570.1 |
| SACOL0690 | 3236723 | YP_185572.1 |
| SACOL0704 | 3236241 | YP_185586.1 |
| SACOL0718 | 3236599 | YP_185600.1 WP_000985996 (SEQ ID NO: 186) |
| SACOL0720 | 3236600 | YP_185601.1 (SEQ ID NO: 11) |
| SACOL0829 | 3238649 | YP_185703.1 |
| SACOL1054 | 3236163 | YP_185919.1 |
| SACOL1142 | 3236098 | YP_186005.1 |
| SACOL1145 | 3237661 | YP_186008.1 |
| SACOL1320 | 3236394 | YP_186175.1 |
| SACOL1353 | 3236077 | YP_186206.1 WP_000603968 (SEQ ID NO: 187) |
| SACOL1416 | 3236563 | YP_186268.1 WP_000548932 (SEQ ID NO: 188) |
| SACOL1611 | 3236575 | YP_186451.1 WP_001095260 (SEQ ID NO: 189) |
| SACOL1637 | 3238018 | YP_186477.1 |
| SACOL1680 | 3238476 | YP_186520.1 |
| SACOL1781 | 3236594 | YP_186614.1 |
| SACOL1812 | 3238705 | YP_186645.1 |
| SACOL1867 | 3236101 | YP_186695.1 (SEQ ID NO: 38) |
| SACOL1912 | 3236086 | YP_186737.1 (SEQ ID NO: 43) |
| SACOL1944 | 3237515 | YP_186769.1 WP_000149064 (SEQ ID NO: 190) |
| SACOL2092 | 3238693 | YP_186907.1 |
| SACOL2144 | 3237436 | YP_186957.1 WP_000908177 (SEQ ID NO: 191) |
| SACOL2169 | 3237416 | YP_186981.1 |
| SACOL2171 | 3237418 | YP_186983.1 |
| SACOL2321 | 3238070 | YP_187128.1 |
| SACOL2325 | 3238483 | YP_187132.1 |
| SACOL2342 | 3235997 | YP_187148.1 |
| SACOL2365 | 3238203 | YP_187170.1 WP_000827000 (SEQ ID NO: 192) |
| SACOL2379 | 3237628 | YP_187183.1 |
| SACOL2385 | 3238646 | YP_187189.1 (SEQ ID NO: 50) |

TABLE I-continued

Genbank™ accession numbers for the IMI-associated *S. aureus* genes and encoded polypeptides described herein

| Gene name | GenBank ™ Gene ID No. | GenBank ™ protein No. |
|---|---|---|
| SACOL2599 | 3237186 | YP_187390.1 |
| | | AAW38600 |
| | | (SEQ ID NO: 193) |

Consensuses derived from the alignments of certain the above listed polypeptides are presented in FIGS. 21-25. In specific embodiment of these consensuses, each X in the consensus sequences (e.g., consensuses in FIGS. 21-25) is defined as being any amino acid, or absent when this position is absent in one or more of the orthologues presented in the alignment. In specific embodiment of these consensuses, each X in the consensus sequences is defined as being any amino acid that constitutes a conserved or semi-conserved substitution of any of the amino acid in the corresponding position in the orthologues presented in the alignment, or absent when this position is absent in one or more of the orthologues presented in the alignment. In FIGS. 21-25, conservative substitutions are denoted by the symbol ":" and semi-conservative substitutions are denoted by the symbol ".". In another embodiment, each X refers to any amino acid belonging to the same class as any of the amino acid residues in the corresponding position in the orthologues presented in the alignment, or absent when this position is absent in one or more of the orthologues presented in the alignment. In another embodiment, each X refers to any amino acid in the corresponding position of the orthologues presented in the alignment, or absent when this position is absent in one or more of the orthologues presented in the alignment. In a specific embodiment, A and/or B is a polypeptide satisfying any one of these consensuses or a fragment thereof.

Conservative amino acid mutation may include addition, deletion, or substitution of an amino acid; a conservative amino acid substitution is defined herein as the substitution of an amino acid residue for another amino acid residue with similar chemical properties (e.g., size, charge, or polarity). Such a conservative amino acid substitution may be a basic, neutral, hydrophobic, or acidic amino acid for another of the same group (see e.g., Table II below). By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (He or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

A semi-conserved amino acid replaces one residue with another one that has similar steric conformation, but does not share chemical properties. Examples of semi-conservative substitutions would include substituting cysteine for alanine or leucine; substituting serine for asparagine; substituting valine for threonine; or substituting proline for alanine.

The Table II below indicates which amino acid belongs to each amino acid class.

| Class | Name of the amino acids |
|---|---|
| Aliphatic | Glycine, Alanine, Valine, Leucine, Isoleucine |
| Hydroxyl or Sulfur/Selenium-containing | Serine, Cysteine, Selenocysteine, Threonine, Methionine |
| Cyclic | Proline |
| Aromatic | Phenylalanine, Tyrosine, Tryptophan |
| Basic | Histidine, Lysine, Arginine |
| Acidic and their Amide | Aspartate, Glutamate, Asparagine, Glutamine |

The similarity and identity between amino acid or nucleotide sequences can be determined by comparing each position in the aligned sequences. Optimal alignment of sequences for comparisons of similarity and/or identity may be conducted using a variety of algorithms, for example using a multiple sequence alignment program/software well known in the art such as ClustalW™, SAGA™, UGENE™ or T-Coffee™. Examples of multiple sequence alignments are described in the examples below and depicted in FIGS. 21A to 25.

Gene Operon

In another embodiment, A and/or B is (b) a polypeptide encoded by a gene from a same operon as a gene encoding the polypeptide of (a) as defined above. For example, SACOL0718 is a gene from the same operon as SACOL0720.

Fragment

In another embodiment, A and/or B is (c) a polypeptide comprising an immunogenic fragment of at least 13 consecutive amino acids of (a) or (b) as defined above.

An immunogenic fragment of a protein/polypeptide is defined as a part of a protein/polypeptide which is capable of inducing/eliciting an immune response in a host. In an embodiment, the immunogenic fragment is capable of eliciting the same immune response in kind, albeit not necessarily in amount, as the protein/polypeptide. An immunogenic fragment of a protein/polypeptide preferably comprises one or more epitopes of said protein/polypeptide. An epitope of a protein/polypeptide is defined as a fragment of said protein/polypeptide of at least about 4 or 5 amino acids in length, capable of eliciting a specific antibody and/or an immune cell (e.g., a T cell or B cell) bearing a receptor capable of specifically binding said epitope. Two different kinds of epitopes exist: linear epitopes and conformational epitopes. A linear epitope comprises a stretch of consecutive amino acids. A conformational epitope is typically formed by several stretches of consecutive amino acids that are folded in position and together form an epitope in a properly folded protein. An immunogenic fragment as used herein refers to either one, or both, of said types of epitopes. In an embodiment where immunogenic fragments are used alone (i.e. not fused in a larger polypeptide construct (e.g., fusion with other antigenic fragment)), the immunogenic fragment of a protein/polypeptide comprises at least 16 amino acid residues. In a further embodiment, the immunogenic fragment comprises at least 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 110, 120, 130, 140, 150, or 160 consecutive amino acids of the native protein/polypeptide. In a specific embodiment, the fragment has at least 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 50 or more consecutive amino acids of the native protein/polypeptide. In an embodiment where the at least one immunogenic fragment forms part of a larger polypeptide construct (e.g., fusion with other antigenic polypeptide, fragment or variant thereof), the immunogenic fragment comprises at least 13 consecutive amino acid residues of the polypeptide. Without being so limited, fragments encompassed by the present invention comprise immunogenic fragments of at least 13 consecutive amino acids of SACOL029 as shown in FIG. 21 (and corresponding fragments in SACOL029 orthologues (e.g., depicted in FIG. 24); of SACOL0442 as shown in FIG. 21 (and corresponding fragments in SACOL0442 orthologues (e.g., depicted in FIG. 22); of SACOL0720 as shown in FIG. 21, (and corresponding fragments in SACOL0720 orthologues (e.g., depicted in FIG. 23); and of SACOL1867 as shown in FIG. 21 (and corresponding fragments in SACOL1867 orthologues (e.g., depicted in FIG. 25). In another embodiment, fragments encompassed by the present invention include immunogenic fragments comprising at least one epitope of antigenic proteins/polypeptides of the present invention (polypeptide (a) defined above). In another embodiment, fragments encompassed by the present invention include immunogenic fragments comprising at least one epitope as depicted (shaded) in any one of the antigenic proteins/polypeptides depicted in any one of FIGS. 21 to 25. Without being so limited, epitopes in a sequence may be predicted with softwares such as BCPred™, AAP™, FBCPred™ and ABCPred™.

In an embodiment, the above-mentioned immunogenic fragment comprises a sequence that is conserved (i.e. identical) in at least two different strains of *Staphylococcus aureus*. In further embodiments, the above-mentioned immunogenic fragment comprises a sequence that is conserved (i.e. identical) in at least 3, 4, 5, 6, 7, 8, 9 or 10 different strains of *Staphylococcus aureus*. In another embodiment, the above-mentioned strains of *Staphylococcus aureus* are COL, RF122, NCTC 8325, JH1, JH9, Newman, Mu3, Mu50, USA300-FPR3757, N315, MW2 or MSSA476. In an embodiment, the above-mentioned strains of *Staphylococcus aureus* are associated with bovine mastitis (e.g., RF122).

Variants

In another embodiment, the above-mentioned polypeptide, or a polypeptide substantially identical to said polypeptide, is expressed in at least two different strains of *Staphylococcus aureus*. Substantially identical as used herein refers to polypeptides having at least 60% of identity, in embodiments at least 65%, 70%, 75%, 80%, 85%, 90%, 91%, 92%, 93%, 94%, 95%, 96%, 97%, 98% or 99% of identity in their amino acid sequences. In further embodiments, the polypeptides have at least 60%, 65%, 70%, 71%, 72%, 73%, 74%, 75%, 80%, 81%, 82%, 83%, 84%, 85%, 86%, 87%, 88%, 89%, 90%, 91%, 92%, 93%, 94%, 95%, 96%, 97%, 98% or 99% of identity in their amino acid sequences with other polypeptides to which they are compared.

In another embodiment, A and/or B is (d) a polypeptide comprising an amino acid sequence at least 60% identical overall to the sequence of the polypeptide of any one of (a) to (c) defined above. In other embodiments, the amino acid is at least 65%, 70%, 75%, 80%, 85%, 90%, 91%, 92%, 93%, 94%, 95%, 96%, 97%, 98% or 99% identical to (a) (e.g., over their full length). In further embodiments, the amino acid is at least 60%, 65%, 70%, 71%, 72%, 73%, 74%, 75%, 80%, 81%, 82%, 83%, 84%, 85%, 86%, 87%, 88%, 89%, 90%, 91%, 92%, 93%, 94%, 95%, 96%, 97%, 98% or 99% to (a). For example, antigens orthologues presented in alignments of FIGS. 21-25 are not identical but present a certain identity with the antigens or fragments to which they are compared. Consensuses presented in these FIGs embody such percent identities.

In another embodiment, A and/or B is (e) a polypeptide comprising an immunogenic variant comprising at least 13 consecutive amino acids of any one of (a) to (d). An immunogenic variant of a protein/polypeptide is defined as a part of a protein/polypeptide which is capable of inducing/eliciting an immune response in a host. As will be understood by the person of ordinary skill, agents (proteins/polypeptides, fragments thereof) having non-naturally occurring modifications (e.g., immunogenic variants) and which are capable of inducing an immune response specific for the unmodified agent (e.g., capable of inducing the production of antibodies capable of recognizing the unmodified agent) are also within the scope of the term "vaccine component". For example, the vaccine components of the present invention can be modified to enhance their activity, stability, and/or bioavailability, and/or to reduce their toxicity. Conservative amino acid substitutions may be made, like for example replacement of an amino acid comprising an acidic side chain by another amino acid comprising an acidic side chain, replacement of a bulky amino acid by another bulky amino acid, replacement of an amino acid comprising a basic side chain by another amino acid comprising a basic side chain, and the like. A person skilled in the art is well able to generate variants of a protein/polypeptide. This is for instance done through screening of a peptide library or by peptide changing programs. An immunogenic variant according to the invention has essentially the same immunogenic properties of said protein in kind, not necessarily in amount. An immunogenic variant of a protein/polypeptide of the invention may for instance comprise a fusion protein and/or chimeric protein. For example, the biological function of a protein identified herein predicted to be an exotoxin, enterotoxin or superantigen (e.g., SACOL0442) could potentially interfere with the mammalian immune system and antibody production, and/or show some toxicity in the host. Although such interference was not observed when the SACOL0442 polypeptide was used in combination with for example SACOL0720 during immunization, it may be useful to modify the protein or polypeptide used for vaccination so that the biological activity of the exotoxin is decreased. For such a purpose, it is possible to inactivate the exotoxin with chemicals (e.g., formaldehyde). It is also possible to use molecular biology techniques to delete or mutate the putative region(s) involved in exotoxin activity without losing immunogenicity (Chang et al., 2008). Another example is the conjugation or mixture of amino acid-based components with nucleic acids (e.g., genes or portions of genes added separately or in a contiguous sequence) carbohydrates such as those found in microbial polysaccharide capsules or biofilms. Other examples of variants include antigens described herein or fragments thereof comprising at either of their N or C terminus or inserted within their antigen sequence, an oligopeptide useful for purification (e.g., affinity purification)

or useful as a spacer or linker. Examples of oligopeptides useful for affinity purification include polyhistidine tags (e.g., 6-10 histidine residues including or not RGS tags (e.g. HHHHHH, RGSHHHHHH, or RGSHHHHHGS). The his-tag may also be followed by an amino acid sequence suitable to facilitate a removal of the polyhistidine-tag using endopeptidases. The "X" and/or "Z" segments as recited in formula (I) also may comprise such oligopeptide useful for purification and/or sequence suitable to facilitate removal of such oligopeptide useful for purification.

In specific embodiments, the immunogenic fragment comprises at least one epitope of the polypeptide (a). Without being so limited, in certain embodiments, the immunogenic fragment comprises at least one epitope of the polypeptide (a) as depicted (shaded) in the sequences presented in FIGS. 21-25, In other specific embodiments, the variants are as disclosed in FIGS. 21-25.

Linker

Insertion of linkers between fusion protein domains can increase bioactivity by augmenting distance between domains alleviating potential repulsive forces between different segments (e.g., antigenic fragments) of the construct resulting in improved and/or restored protein folding. Different sequences of polypeptide linkers can be used and are known to have distinct properties, such as flexible, rigid or cleavable linkers. The present invention encompasses the use of any such linkers including any one of those listed in Chen et. al, Adv Drug Deliv Rev. (2013), 65(10):1357-69 for example. Examples herein provide illustrations of specific linkers that were used (i.e. GGGGSGGGGSGGGGS (SEQ ID NO: 60), ERKYK (SEQ ID NO: 61), or and EAAAKEAAAK (SEQ ID NO: 62)), i.e. flexible linker structures, rich in small hydrophilic amino acids that maintain distance between the two connected domains and improve their folding.

In another specific embodiment, the Fc comprises a CH2 domain, a CH3 domain and a hinge region. In another specific embodiment, the Fc is a constant domain of an immunoglobulin selected from the group consisting of IgG-1, IgG-2, IgG-3, IgG-3 and IgG-4. In another specific embodiment, the Fc is a constant domain of an immunoglobulin IgG-1.

Linkers may be included between contiguous antigens of the fusion (e.g., 1 linker in fusion comprising two antigens, 2 linkers in fusions comprising three antigens, three linkers in fusions comprising four antigens, etc.). In fusions where large protein domains are used, linker may be larger and may comprise a fragment crystallizable region (Fc).

In a specific embodiment, the linker is an amino acid sequence of at least one amino acid or is absent. In a specific embodiment, the linker comprises at least three (at least 4, 5, 6, 7, 8, 9 or 10) amino acids selected from the group consisting of glycine, serine, alanine, aspartate, glutamate and lysine. In a specific embodiment, the linker is (EAAAK)n (SEQ ID NO: 63); (GGGGS)n (SEQ ID NO: 67); or (XPXPXP)n (SEQ ID NO: 69) wherein x is any amino acid; wherein n is any one of 1 to 5, more specifically 1, 2, 3, 4 or 5; EAAAKEAAAK (SEQ ID NO: 62); EAAAKEAAAKEAAAK (SEQ ID NO: 64); GGGGS (SEQ ID NO: 67); GGGGSGGGGS (SEQ ID NO: 68); GGGGSGGGGSGGGGS (SEQ ID NO: 60); XPXPXP (SEQ ID NO: 69), wherein x is any amino acid; XPXPXPXPXP (SEQ ID NO: 70), wherein x is any amino acid; ERKYK (SEQ ID NO: 61); ERKYKERKYK (SEQ ID NO: 65); ERKYKERKYKERKYK (SEQ ID NO: 66). In a more specific embodiment, the linker is GGGGSGGGGSGGGGS (SEQ ID NO: 60), ERKYK (SEQ ID NO: 61), or EAAAKEAAAK (SEQ ID NO: 62).

N and C Terminal of Construct

X and Z are each independently absent or an amino acid sequence of at least one amino acid. Without being so limited, they may be one or more of amino acids resulting from cloning strategy, amino acids used to facilitate purification of the construct (e.g. polyhistidine), amino acids suitable to facilitate a removal of the purification-tag using endopeptidases. In specific embodiments, where the fusion construct comprises three or more antigen polypeptides, any one of X and/or Z may also include the sequence of a further antigen (antigen C, antigen D, etc.) and, optionally that of at least one further linker. Such embodiments wherein X and/or Z comprise one or more further antigen(s) and optionally linker(s), could be more specifically illustrated as e.g., formula (II) or (III) as follows X'-C-linker$_1$-A-linker$_2$-B-Z' (II) when the fusion comprises at least 3 antigens; or X'-C-linker$_1$-A-linker$_2$-B-linker$_3$-D-Z' (III) when the fusion comprises at least 4 antigens. In both formula (II) and (III) X', Z', linker, linker$_2$, and, the case being, linker$_3$, are identical or different and are independently defined as are X, Z and linker in formula (I) defined herein.

Hence, in specific embodiments, the fusion construct comprises 2, 3, 4 or more antigen polypeptides (and, the case being further linkers). In a more specific embodiment, and without being so limited the fusion construct may be SACOL0029_SACOL0442; SACOL0029_SACOL0720; SACOL0029_SACOL1867; SACOL0029_SACOL0720_ SACOL1867; SACOL0029_SACOL1867_SACOL0442; SACOL0029_SACOL0720_SACOL0442; SACOL0442_ SACOL0029_SACOL0720; SACOL0442_SACOL0029_ SACOL1867; SACOL0442_SACOL1867_SACOL0720; SACOL0720_SACOL0442_SACOL1867; or SACOL0029_SACOL1867_SACOL0720_SACOL0442, or any of the foregoing constructs wherein the antigen polypeptides are in any other order.

Combination

The constructs of the present invention may be used as sole immunogenic component of a composition (e.g., vaccine) of the present invention or in combination with one or more further fusion construct(s), immunogenic polypeptide(s), fragment(s) or variant(s) thereof and/or live attenuated bacteria (e.g., S. aureus) (expressing or not fusion constructs and/or polypeptide(s), fragment(s) or variant(s) thereof).

The one or more fusion constructs may be any immunogenic fusion construct including a further fusion construct as defined above (see e.g., Example 14).

The one or more immunogenic polypeptide(s), fragment(s) or variant(s) thereof for use in compositions of the present invention may be any polypeptide(s), fragment(s) or variant(s) that contribute to the immunogenicity of the compositions of the present invention as defined herein. Without being so limited, such polypeptide(s), fragment(s) or variant(s) includes (a) a polypeptide comprising a SACOL0029 polypeptide as set forth in any one of the sequences depicted in FIG. 24 (SEQ ID NOs: 5 and 121 to 131), a SACOL0264 polypeptide (SEQ ID NO: 185), a SACOL0442 polypeptide as set forth in any one of the sequences depicted in FIG. 22D (SEQ ID NOs: 29 and 82 to 92), a SACOL0718 polypeptide (SEQ ID NO: 186), a SACOL0720 polypeptide as set forth in any one of the sequences depicted in FIGS. 23I-K (SEQ ID NOs: 11 and 109 to 120), a SACOL1353 polypeptide (SEQ ID NO: 187), a SACOL1416 polypeptide (SEQ ID NO: 188), SACOL1611 (SEQ ID NO: 189), a SACOL1867 polypeptide as set forth in any one of the sequences depicted in FIG. 25D (SEQ ID NOs: 152 to 164), a SACOL1912 polypeptide (SEQ ID NO: 43), a SACOL1944 polypeptide (SEQ ID NO: 190), a SACOL2144 polypeptide (SEQ ID NO: 191), a SACOL2365 polypeptide (SEQ ID NO: 192), a SACOL2385 polypeptide (SEQ ID NO: 50) or a SACOL2599 polypeptide (SEQ ID NO: 193); (b) a polypeptide encoded by a gene from a same operon as a gene encoding the polypeptide of (a); (c) a polypeptide comprising an immunogenic fragment of at least 13 consecutive amino acids of (a) or (b); (d) a polypeptide comprising an amino acid sequence at least 60% identical overall to the sequence of the polypeptide of any one of (a) to (c); or (e) a polypeptide comprising an immunogenic variant comprising at least 13 consecutive amino acids of any one of (a) to (c), as defined above. Without being so limited, any such polypeptide(s), fragment(s) or variant(s) encompasses those included in compositions (e.g., vaccines #1 to #8) exemplified in Examples 1 to 14 and 21-26.

Live Attenuated Bacteria

The live attenuated bacteria (e.g. *S. aureus*) for use in compositions of the present invention may be independent from the fusions constructs and/or polypeptide(s), fragment(s) or variant(s) thereof of the present invention, or be the vessel for (i.e. may express) such fusion constructs and/or polypeptide(s), fragment(s) or variant(s) thereof of the present invention.

Without being so limited, as illustrated herein, useful live attenuated bacteria in the context of combinations of the present invention include *Staphylococcus* (e.g., *aureus*) bacteria having at least one gene contributing to virulence (e.g., Δ720) or contributing to fitness in the host (e.g., a metabolic gene) mutated or deleted. Without being so limited, such gene may be any one of the genes identified in Novick 2003, Novick 2008, or Maresso and Schneewind 2008.

In a further embodiment, the live attenuated bacteria may be further attenuated by having a stabilized SCV phenotype. As used herein the terms "SCV phenotype" refers to bacteria having a dysfunctional oxidative metabolism causing a slow growth, an alteration in the expression of virulence factors, and an ability to be internalized in host cells. As used herein the term «stabilized SCV phenotype» is used to denote an SCV strain retaining the SCV phenotype i.e. unable to produce invasive revertants (i.e., a reversion to the normal growth phenotype). Such stabilized SCV *S. aureus* may be produced by mutating or deleting any one of the genes (e.g., ΔhemB) listed in Table III below. Without being limited, the present invention encompasses the use of the stabilized SCV *S. aureus* exemplified in Examples 15 to 25. Mutation as used herein includes a substitution, a deletion and/or an insertion of one or more nucleotides that prevents expression of the polypeptide encoded by a gene of the present invention or that prevents expression of a functional polypeptide. In a preferred embodiment, the mutation prevents expression of the polypeptide. In another specific embodiment, the two mutations in the same attenuated live or inactivated strain of *S. aureus* are a deletion or an insertion. It is expected that a mutated strain of *S. aureus* having a mutation at any position of one of the genes of the present invention that prevents expression of the polypeptide can be used as an attenuated live vaccine in accordance with the present invention. Attenuated live vaccines, i.e. vaccines comprising the bacterium according to the invention in a live attenuated form, have the advantage over inactivated vaccines that they best mimic the natural way of infection. In addition, their replicating abilities allow vaccination with low amounts of bacteria; their number will automatically increase until it reaches the trigger level of the immune system. From that moment on, the immune system will be triggered and will finally eliminate the bacteria. A minor disadvantage of the use of live attenuated bacteria however might be that inherently there is a certain level of virulence left. This need not be a real disadvantage as long as the level of virulence is acceptable, i.e. as long as the vaccine at least decreases the bacterial infection (e.g., IMI) symptoms. Of course, the lower the remaining virulence of the live attenuated vaccine is, the less influence the vaccination has on weight gain during/after vaccination.

TABLE III

Genbank ™ accession numbers for *S. aureus* genes associated with SCV phenotype (Kahl, 2014)

| Gene Name | GenBank ™ Gene ID No. | GenBank ™ Protein No. |
| --- | --- | --- |
| hemB | 3238571 (SACOL1715) | AAW36820.1<br>WP_000667126.1<br>GI: 446589780<br>EC: 4.2.1.24 |
| menB | 3236546 (SACOL1052) | AAW36517.1<br>WP_000526687.1<br>GI: 446448832<br>EC: 2.2.1.9 |
| thyA | 3238178 (SACOL1462) | AAW36663.1<br>WP_000667126.1<br>GI: 446589780<br>EC: 2.1.1.45 |
| fusA | 3236183 (SACOL0593) | AAW37703.1<br>GI: 57285609 |
| FusE (gene: rp1F) | 3238328 (SACOL2224) | AAW37099.1<br>GI: 57285005 |
| relA (relA2) | 3238211 (SACOL1689) | AAW36795.1<br>GI: 57284701<br>EC: 2.7.6.5 |
| cspB | 3238398 (SACO12731) | AAW37379.1<br>GI: 57285285 |
| hemH | 3236274 (SACO11888) | AAW36901.1<br>GI: 57284807<br>EC: 4.99.1.1 |
| ctaA | 3237823 (SACOL1124) | AAW38004.1<br>GI: 57285910 |

Nucleic Acids

The nucleic acid of the present invention preferably comprises a nucleotide sequence that encodes one or more proteins/polypeptides noted above (or fragments thereof) operably linked to regulatory elements needed for gene expression, such as a promoter, an initiation codon, a stop codon, enhancers, and a polyadenylation signal. Regulatory elements are preferably selected that are operable in the species to which they are to be administered. In specific embodiments, the nucleic acid is as depicted in FIGS. 21 to 25.

Within the context of the present invention is the in vivo administration of a nucleic acid of the invention to a mammal so that one or more proteins/polypeptides (or a fragment thereof) of interest is/are expressed in the mammal (e.g., nucleic acid vaccine, DNA or RNA vaccine).

Delivery Systems

The nucleic acid of the present vaccine can be "naked" DNA or can be operably incorporated in a vector. Nucleic acids may be delivered to cells in vivo using methods well known in the art such as direct injection of DNA, receptor-mediated DNA uptake, viral-mediated transfection or non-viral transfection and lipid-based transfection, all of which may involve the use of vectors. Direct injection has been used to introduce naked DNA into cells in vivo (see e.g., Acsadi et al. (1991) *Nature* 332:815-818; Wolff et al. (1990) *Science* 247:1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) *J. Biol. Chem.* 263: 14621; Wilson et al. (1992) *J. Biol. Chem.* 267: 963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) *Proc. Natl. Acad. Sci. USA* 88: 8850; Cristiano et al. (1993) *Proc. Natl. Acad. Sci. USA* 90:2122-2126).

Useful delivery vectors include biodegradable microcapsules, immuno-stimulating complexes (ISCOMs) or liposomes, and genetically engineered attenuated live vectors such as cells, viruses or bacteria.

Liposome vectors are unilamellar or multilamellar vesicles, having a membrane portion formed of lipophilic material and an interior aqueous portion. The aqueous portion is used in the present invention to contain the polynucleotide material to be delivered to the target cell. It is generally preferred that the liposome forming materials have a cationic group, such as a quaternary ammonium group, and one or more lipophilic groups, such as saturated or unsaturated alkyl groups having about 6 to about 30 carbon atoms. One group of suitable materials is described in European Patent Publication No. 0187702, and further discussed in U.S. Pat. No. 6,228,844 to Wolff et al., the pertinent disclosures of which are incorporated by reference. Many other suitable liposome-forming cationic lipid compounds are described in the literature. See, e.g., L. Stamatatos, et al., Biochemistry 27:3917 3925 (1988); and H. Eibl, et al., Biophysical Chemistry 10:261 271 (1979). Alternatively, a microsphere such as a polylactide-coglycolide biodegradable microsphere can be utilized. A nucleic acid construct is encapsulated or otherwise complexed with the liposome or microsphere for delivery of the nucleic acid to a tissue, as is known in the art.

Preferred viral vectors include Bacteriophages, Herpes virus, Adenovirus, Polio virus, Vaccinia virus, defective retroviruses, adeno-associated virus (AAV) and Avipox. Methods of transforming viral vector with an exogenous DNA construct are also well described in the art. See Sambrook and Russell, above.

As indicated above, the nucleic acid (e.g., DNA or RNA) may be incorporated in a host such as a host cell in vitro or ex vivo (e.g., an immune cell such as a dendritic cell) or, as indicated above, in an attenuated microbial host (e.g., attenuated *S. aureus*, SCV, etc., see e.g., Examples 25-26 for instance) by transfection or transformation, and the transfected or transformed cell or microorganism, which expresses the polypeptide (e.g. fusion of multiple antigens or fragments therefor and/or single antigens or fragments thereof) of interest, may be administered to the subject. Following administration, the cell will express the protein or polypeptide of interest (or a variant or fragment thereof) in the subject, which will in turn lead to the induction of an immune response directed against the protein, polypeptide or fragment thereof.

The use of attenuated live bacteria to immunize and/or to deliver specific constructs or antigen mixture of the present invention represents an interesting approach to improve immune responses (Griffiths and Khader, 2014). Live attenuated organisms that mimic natural infection stimulate the immune system in a powerful manner, eliciting broad and robust immune responses that produce both serum and mucosal antibodies, and effector and memory T cells which act synergistically to protect against disease (Detmer and Glenting, 2006; Kollaritsch et al, 2000; Pasetti et al., 2011). Examples of suitable attenuated live bacterial vectors include *S. aureus, Salmonella typhimurium, Salmonella typhi, Shigella, Bacillus, Lactobacillus*, Bacille Calmette-Guerin (BCG), *Escherichia coli, Vibrio cholerae, Campylobacter*, or any other suitable bacterial vector, as is known in the art. Methods of transforming live bacterial vectors with an exogenous DNA construct are well described in the art. See, for example, Joseph Sambrook and David W. Russell, Molecular Cloning, A Laboratory Manual, 3rd Ed., Cold Spring Harbor Laboratory Press, Cold Spring Harbor, N.Y. (2001). The present invention encompasses the use of a composition comprising an attenuated live bacterium (e.g., ΔhemBΔ720 *S. aureus* expressing the construct of the present invention as sole immunogenic component or in combination with other attenuated live bacteria each expressing another polypeptide, fragment or variant of the present invention (e.g., SACOL0442, SACOL0720 or fragments or variants thereof).

Compositions

The polypeptides, nucleic acids and delivery systems (e.g., host cells comprising said nucleic acids or vectors) described herein can be formulated into compositions. As used herein, the term "pharmaceutically acceptable" refers to vaccine components (e.g., excipients, carriers, adjuvants) and compositions that are physiologically tolerable and do not typically produce an allergic or similar untoward reaction, such as gastric upset, dizziness and the like, when administered to a subject. Preferably, as used herein, the term "pharmaceutically acceptable" means approved by regulatory agency of the federal or state government or listed in the U.S. Pharmacopeia or other generally recognized pharmacopeia for use in animals, and in humans. The term "excipient" refers to a diluent, carrier, or vehicle with which the vaccine components of the present invention may be administered. Sterile water or aqueous saline solutions and aqueous dextrose and glycerol solutions may be employed as carriers, particularly for injectable solutions.

In an embodiment, the agent of the present invention is administered in combination with an adjuvant or immunostimulant. Suitable adjuvant or immunostimulant that may improve the efficacy of components to raise an immune response include but is not limited to oils (e.g., mineral oils, emulsified oil such as MONTANIDE™ or EMULSIGEN™-D), metallic salts (e.g., alum, aluminum hydroxide or aluminum phosphate), cationic peptides (Bowdish et al., 2005; Hancock, et al., 2000) such as indolicidin, a cationic peptide produced by the cow's immune cells (Falla et al., 1996), natural and artificial microbial components (e.g., bacterial liposaccharides, Freund's adjuvants, muramyl dipeptide (MDP), cyclic-diguanosine-5'-monophosphate (c-di-GMP), pathogen-associated molecular patterns (PAMPS) such as surface polysaccharides, lipopolysaccharides, glycans, peptidoglycan or microbial DNA (e.g., CpG), plant components such as saponins (e.g., Quil-A™), and/or one or more substances that have a carrier effect (e.g., bentonite, latex particles, liposomes, ISCOM™, DNA and polyphosphazine (PCPP) copolymers). Immunization with synthetic nanoparticles (such as those made from a biodegradable synthetic polymer like poly(D,L-lacticco-glycolic acid)) containing antigens plus ligands that signal through TLR to stimulate proinflammatory cytokines is also possible (Kasturi et al, 2011).

Vaccine components of the invention may be administered in a pharmaceutical composition. Pharmaceutical compositions may be administered in unit dosage form. Any appropriate route of administration may be employed, for example, parenteral, subcutaneous, intramuscular, intramammary, intracranial, intraorbital, ophthalmic, intraventricular, intracapsular, intraarticular, intraspinal, intracisternal, intraperitoneal, intranasal, aerosol, or oral administration. Examples of specific routes of administration include parenteral, e.g., intravenous, intradermal, subcutaneous, intramammary; oral (e.g., inhalation); transdermal (topical); transmucosal, and rectal administration.

Conventional pharmaceutical practice may be employed to provide suitable formulations or compositions to administer such vaccine components with or without adjuvants to subjects. Methods well known in the art for making pharmaceutical compositions and formulations are found in, for example, Remington: The Science and Practice of Pharmacy, (20$^{th}$ ed.) ed. A. R. Gennaro A R., 2000, Lippincott: Philadelphia. Formulations for parenteral administration may, for example, contain excipients, sterile water, or saline, polyalkylene glycols such as polyethylene glycol, miglyol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds of the invention include ethylenevinyl acetate copolymer particles, osmotic pumps, implantable infusion systems, and liposomes. Formulations for inhalation or intramammary injection may contain excipients, for example, lactose, or may be aqueous solutions containing, for example, polyoxyethylene-9-lauryl ether, miglyol, glycocholate and deoxycholate, or may be oily solutions (e.g., paraffin oil) for administration in the form of nasal drops, or as a gel.

Therapeutic formulations may be in the form of liquid solutions or suspension; for oral administration, formulations may be in the form of tablets or capsules; and for intranasal formulations, in the form of powders, nasal drops, or aerosols. Solutions or suspensions used for parenteral, intradermal, intramammary or subcutaneous application can include the following components: a sterile diluent such as water for injection, saline solution, fixed oils (e.g., paraffin oil), polyethylene glycols, glycerin, propylene glycol, miglyol or other synthetic solvents; antibacterial agents such as benzyl alcohol or methyl parabens; antioxidants such as ascorbic acid or sodium bisulfite; chelating agents such as ethylenediaminetetraacetic acid; reducing agents such dithiothreitol, buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous or intramammary administration, suitable carriers include physiological saline, bacteriostatic water, Cremophor™ EL™ (BASF, Parsippany, N.J.) or phosphate buffered saline (PBS).

Oral compositions generally include an inert diluent or an edible carrier. They can be enclosed in gelatin capsules or compressed into tablets or feed. For the purpose of oral vaccine administration, the active components can be incorporated with excipients and used in the form of tablets, troches, capsules or in feed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the vaccine components are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Liposomal suspensions (including liposomes targeted to specific cell types) can also be used as pharmaceutically acceptable carriers.

The pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically valuable agents.

Intravenous, intramuscular, subcutaneous, intramammary or oral administration is a preferred form of use. The dosages in which the components of the present invention are administered in effective amounts depend on the nature of the specific active ingredient, the host and the requirements of the subject and the mode of application.

Microbial Targets

Polypeptides, nucleic acids and delivery systems of the present invention may be used as antimicrobial agents against Staphylococcal infections including those causing intramammary infection (IMI). In a preferred embodiment, the Staphylococcal infections are caused by *Staphylococcus aureus*.

Methods of Immunizing with Polypeptides, Nucleic Acids, Vectors, Cells, Compositions and Delivery Systems Encompassed by the methods, uses, pharmaceutical compositions and kits of the present invention is passive and active immunization.

Passive immunization is the injection of antibodies or antiserum, previously generated against the pathogen (or antigens described herein), in order to protect or cure a recipient animal of an infection or future infection. Protection fades over the course of a few weeks during which time the active immunization with polypeptides, nucleic acids or delivery systems (e.g., as described above) will have time to generate a lasting protective response. Serum for passive immunization can be generated by immunization of donor animals using the polypeptides, nucleic acids or delivery systems, as described herein. This serum, which contains antibodies against the antigens, can be used immediately or stored under appropriate conditions. It can be used to combat acute infections (e.g., IMI) or as a prophylactic (Tuchscherr et al., 2008). Use of antibodies or serums in a passive immunization can be combined with other agents such as an antibiotic to increase the cure rate of an infection currently in progress or to increase protection against an imminent infection.

Active immunization is administration of the polypeptides, nucleic acids or delivery systems as described herein to a subject.

The components identified in accordance with the teachings of the present invention have a prophylactic and/or therapeutic value such as they can be used to raise an immune response to prevent and/or combat diseases or conditions, and more particularly diseases or conditions related to microbial infections.

The terms "prevent/preventing/prevention" or "treat/treating/treatment" as used herein, refer to eliciting the desired biological response, i.e., a prophylactic and therapeutic effect, respectively in a subject. In accordance with the present invention, the therapeutic effect comprises one or more of a decrease/reduction in the severity, intensity and/or duration of the microbial infection (e.g., staphylococcal infection) or any symptom thereof following administration of the polypeptide, nucleic acid or delivery system (agent/composition of the present invention) of the present invention when compared to its severity, intensity and/or duration in the subject prior to treatment or as compared to that/those in a non-treated control subject having the infection or any symptom thereof. In accordance with the invention, a prophylactic effect may comprise a delay in the onset of the microbial infection (e.g., staphylococcal infection) or any symptom thereof in an asymptomatic subject at risk of experiencing the microbial infection (e.g., staphylococcal infection) or any symptom thereof at a future time; or a decrease/reduction in the severity, intensity and/or duration of a microbial infection (e.g., staphylococcal infection) or any symptom thereof occurring following administration of the agent/composition of the present invention, when compared to the timing of their onset or their severity, intensity and/or duration in a non-treated control subject (i.e. asymptomatic subject at risk of experiencing the microbial (e.g., bacterial) infection (e.g., staphylococcal infection) or any symptom thereof); and/or a decrease/reduction in the progression of any pre-existing microbial infection (e.g., staphylococcal infection) or any symptom thereof in a subject following administration of the agent/composition of the present invention when compared to the progression of microbial infection (e.g., staphylococcal infection) or any symptom thereof in a non-treated control subject having such pre-existing microbial infection (e.g., staphylococcal infection) or any symptom thereof. As used herein, in a therapeutic treatment, the agent/composition of the present invention is administered after the onset of the microbial infection (e.g., staphylococcal infection) or any symptom thereof. As used herein, in a prophylactic treatment, the agent/composition of the present invention is administered before the onset of the microbial infection (e.g., staphylococcal infection) or any symptom thereof or after the onset thereof but before the progression thereof.

As used herein, "decrease" or "reduction" of microbial infection (e.g., staphylococcal infection) or any symptom thereof refers to a reduction in a symptom of at least 10% as compared to a control subject (a subject not treated with the agent/composition present invention), in an embodiment of at least 20% lower, in a further embodiment of at least 30% lower, in a further embodiment of at least 40% lower, in a further embodiment of at least 50% lower, in a further embodiment of at least 60% lower, in a further embodiment of at least 70% lower, in a further embodiment of at least 80% lower, in a further embodiment of at least 90% lower, in a further embodiment of 100% (complete inhibition).

As used herein, the term "symptom" in reference to a staphylococcal infection refers to any staphylococcal infection symptom such as pain, inflammation, fever, vomiting, diarrhea, fatigue muscle aches, anorexia, dehydration, low blood pressure, cellulitis, impetigo, boil and scalded skin syndrome. More particularly, in reference to a staphylococcal IMI, a staphylococcal IMI symptom refers for example to visual abnormalities in milk (e.g., such as a watery appearance, flakes, clots, malodourous, presence of blood), redness of the udder, swelling in the udder, tenderness in the udder, elevated rectal temperature (>39.0° C.), anorexia, decreased rumen motility and fatigue. An increase in milk somatic cell counts (SCC) is another staphylococcal IMI. Milk somatic cells include white blood cells such as leukocytes or neutrophils as well as epithelial cells. It is generally agreed that a SCC of >200,000/mL may represent a staphylococcal IMI symptom or is indicative of a staphylococcal IMI.

Dosage

Toxicity or efficacy of vaccine components to elicit an immune response can be determined by standard procedures in cell cultures or experimental animals. The dose ratio between toxic and immune stimulatory effects can be measured. Components that exhibit large ratios are preferred. While components that exhibit toxic side effects may be used, care should be taken to design a delivery system in order to minimize potential damage to cells and, thereby, reduce side effects.

Data obtained from cell culture assays and laboratory animal studies can be used in formulating a range of dosage for use in large animals and humans. The dosage of such components lies preferably within a range of administered concentrations that include efficacy with little or no toxicity. The dosage may vary within this range depending upon the dosage form employed and the route of administration utilized.

Any suitable amount of the pharmaceutical composition may be administered to a subject. The dosages will depend on many factors. Typically, the amount of active ingredient contained within a single dose will be an amount that effectively prevents, or treats IMI without inducing significant toxicity. The skilled artisan will appreciate that certain factors may influence the dosage required to effectively raise an immune response in a subject. Moreover, the therapeutically effective amount of the antigens (e.g., fusion construct) of the present invention may require a series of doses. In general, an amount of about 0.01 mg-500 mg of antigens including the fusion construct per dose, come into consideration. In a specific embodiment, an amount of about 0.1 mg-1 mg of antigens including the fusion construct per dose, come into consideration. Generally, one, two or three doses of the vaccine may favor optimal development of immunity. The time between two doses may be as short as three or four weeks but it may be preferred to separate the priming dose (first dose) and the booster dose (second dose) by five, six, seven, eight, nine or ten weeks before stimulating the immune system with the booster shot. A subsequent booster shot (a recall shot) may also be optimal to provide a sustainable immunity. This recall could for example occur every half year (6 months), yearly, every two years, every three or every five years.

"Sample" or "biological sample" refers to any solid or liquid sample isolated from a live being. In a particular embodiment, it refers to any solid (e.g., tissue sample) or liquid sample isolated from a mammal, such as milk, a biopsy material (e.g., solid tissue sample), blood (e.g., plasma, serum or whole blood), saliva, synovial fluid, urine, amniotic fluid and cerebrospinal fluid. Such sample may be, for example, fresh, fixed (e.g., formalin-, alcohol- or acetone-fixed), paraffin-embedded or frozen prior to analysis of the infectious agent's expression level.

Patients

As used herein the term "subject" or "patient" refers to an animal, preferably a mammal such as but not limited to a human, cow (e.g., heifer, multiparous, primiparous, calf), goat, sheep, ewe, ass, horse, pig, chicken, cat, dog, etc. who is the object of treatment, observation or experiment. In a specific embodiment, it is a cow (e.g., at risk of experiencing staphylococcal (e.g., IMI) infection).

As used herein the terms "subject at risk of experiencing a staphylococcal infection (e.g., staphylococcal infection (e.g., IMI) or any symptom thereof at a future time" refers to a mammal (e.g., a cow (e.g., heifer, multiparous, primiparous, calf), goat, sheep) that is used for milk or meat production.

In an embodiment, the above-mentioned mammal is a cow.

Method of Detection

Examples of methods to measure the amount/level of selected proteins/polypeptides include, but are not limited to: Western blot, immunoblot, enzyme-linked immunosorbent assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, flow cytometry, and assays based on a property of the protein including but not limited to DNA binding, ligand binding, interaction with other protein partners or enzymatic activity.

In an embodiment, the amount of the polypeptide/protein within the methods of the present invention is detected using antibodies that are directed specifically against the polypeptide/protein. The term "antibody" as used herein encompasses monoclonal antibodies, polyclonal antibodies, multispecific antibodies (e.g., bispecific antibodies), and antibody fragments, so long as they exhibit the desired biological activity or specificity. "Antibody fragments" comprise a portion of a full-length antibody, generally the antigen binding or variable region thereof. Interactions between antibodies and a target polypeptide are detected by radiometric, colorimetric, or fluorometric means. Detection of antigen-antibody complexes may be accomplished by addition of a secondary antibody that is coupled to a detectable tag, such as for example, an enzyme, fluorophore, or chromophore.

Methods for making antibodies are well known in the art. Polyclonal antibodies can be prepared by immunizing a suitable subject (e.g., rabbit, goat, mouse, or other mammal) with the polypeptide/protein of interest or a fragment thereof as an immunogen. A polypeptide/protein "fragment" "portion" or "segment" is a stretch of amino acid residues of at least about 5, 7, 10, 14, 15, 20, 21 or more amino acids of the polypeptide noted above. The antibody titer in the immunized subject can be monitored over time by standard techniques, such as with an enzyme linked immunosorbent assay (ELISA) using immobilized exosomal marker polypeptide or a fragment thereof. At an appropriate time after immunization, e.g., when the antibody titers are highest, antibody-producing cells can be obtained from the animal, usually a mouse, and can be used to prepare monoclonal antibodies by standard techniques, such as the hybridoma technique originally described by Kohler and Milstein (1975) Nature 256: 495-497, the human B cell hybridoma technique (Kozbor et al. (1983) Immunol. Today 4: 72), the EBV-hybridoma technique (Cole et al. (1985) in Monoclonal Antibodies and Cancer Therapy, ed. Reisfeld and Sell (Alan R. Liss, Inc., New York, N.Y.), pp. 77-96) or trioma techniques. The technology for producing hybridomas is well known (see generally Coligan et al., eds. (1994) Current Protocols in Immunology, John Wiley & Sons, Inc., New York, N.Y.).

Alternatively, to preparing monoclonal antibody-secreting hybridomas, a monoclonal antibody can be identified and isolated by screening a recombinant combinatorial immunoglobulin library (e.g., an antibody phage display library) with a polypeptide or a fragment thereof to thereby isolate immunoglobulin library members that bind the polypeptide. Kits for generating and screening phage display libraries are commercially available (e.g., the Pharmacia Recombinant Phage Antibody System™, Catalog No. 27-9400-01; and the Stratagene SurfZAP™ Phage Display Kit, Catalog No. 240612).

Furthermore, antibodies directed against one or more of the polypeptides/proteins described herein may be obtained from commercial sources.

The use of immobilized antibodies specific for the polypeptides/proteins is also contemplated by the present invention and is well known by one of ordinary skill in the art. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality (2 or more) of polypeptides/proteins may be carried out separately or simultaneously with one test sample. Several polypeptides/proteins may be combined into one test for efficient processing of a multiple of samples.

The analysis of polypeptides/proteins could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion. Particularly useful physical formats comprise surfaces having a plurality of discrete, addressable locations for the detection of a plurality of different analytes. Such formats include protein microarrays, or "protein chips" (see, e.g., Ng and Ilag, J. Cell Mol. Med. 6: 329-340, 2002) and capillary devices.

In an embodiment, the above-mentioned level of expression is determined by measuring the level of expression of a mRNA transcribed from said one or more genes.

Methods to determine nucleic acid (mRNA) levels are known in the art, and include for example polymerase chain reaction (PCR), reverse transcriptase-PCR (RT-PCR), SAGE, quantitative PCR (q-PCR), Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the nucleic acids encoding the protein/polypeptide of this invention; amplification of mRNA expressed from one or more of the nucleic acids encoding the proteins/polypeptides of this invention using specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the biological sample, which is then labeled and used to probe cDNAs or oligonucleotides encoding all or part of the nucleic acids encoding the proteins/polypeptides of this invention, arrayed on any of a variety of surfaces.

Kits

The present invention also encompasses kits comprising the components of the present invention. For example, the kit can comprise one or more components. The components can be packaged in a suitable container and device for administration. The kit can further comprise instructions for using the kit.

The present invention also provides a kit or package comprising reagents useful for administering one or more construct, polypeptide, nucleic acid, vector, host, compositions of the present invention, or a combination of at least two thereof, to a subject in need thereof for treating and/or preventing Staphylococcal IMI. Such kit may further comprise, for example, instructions for the prevention and/or treatment of Staphylococcal IMI, containers, reagents useful for performing the methods. The kit may further include where necessary agents for reducing background interference in a test, agents for increasing signal, software and algorithms for combining and interpolating marker values to produce a prediction of clinical outcome of interest, apparatus for conducting a test, calibration curves and charts, standardization curves and charts, and the like.

MODE(S) FOR CARRYING OUT THE INVENTION

The present invention is illustrated in further details by the following non-limiting examples.

Example 1: Materials and Methods for Vaccine Including SACOL0029, SACOL0442, SACOL0720, SACOL1867, SACOL1912 and SACOL2385 (Vaccine #1)

Production of the Antigens.

Six antigens that are highly expressed during *S. aureus* bovine intramammary infection were selected for inclusion in a first bovine vaccine (Vaccine #1). These antigens are: SACOL0029 (GenBank™ accession No.: YP_184940.1) (SEQ ID NO: 5), SACOL0442 (YP_185332.1) (SEQ ID NO: 29), SACOL0720 (YP_185601.1) (SEQ ID NO: 11), SACOL1867 (GenBank™ accession No.: YP_186695.1) (SEQ ID NO: 38), SACOL1912 (GenBank™ accession No.: YP_186737.1) (SEQ ID NO: 43), and SACOL2385 (GenBank™ accession No.: YP_187189.1) (SEQ ID NO: 50). His-tagged recombinant proteins of SACOL0029, SACOL1867, SACOL1912, and SACOL2385 were engineered and produced by GenScript, Inc. (Piscataway, N.J.). His-tagged recombinant proteins of SACOL0442 and SACOL0720 were engineered and produced using QIA expression technology (pQE30 plasmid) from Qiagen Inc. (Mississauga, ON, Canada), according to the manufacturers' recommendations. See, FIG. 21 I to VI for the his-tagged sequences of the antigens. Examples 2-5 and FIGS. 1-4 relate to this vaccine #1.

Immunization of Dairy Cows.

Nineteen healthy multiparous Holstein cows in mid-lactation were housed in a level II biosafety barn at the Dairy and Swine Research and Development Centre of Agriculture and Agri-Food Canada (Sherbrooke, QC). Cows were randomly divided into 2 groups: one group (10 cows) received saline (placebo group); the other group (9 cows) received the vaccine #1 (vaccinated group). The vaccine was composed of 300 µg of each of six antigens (SACOL0029, SACOL0720, SACOL1867, SACOL1912, and SACOL2385) combined with Emulsigen™-D (MVP Technologies, Omaha, Nebr.), CpG ODN 2007 (TCGTCGTTGTCGTTTTGTCGTT (SEQ ID NO: 194), a pathogen-associated molecular pattern (PAMP), VIDO, Saskatoon, SW) and the cationic peptide indolicidin (IL-PWKWPWWPWRR (SEQ ID NO: 195), used to induce the cow's immune response, (Chemprep Inc., Miami, Fla.). Two immunizations were performed 10 weeks apart, subcutaneously in the neck. No adverse side effects were observed. Blood from the caudal vein and milk samples were taken before the first immunization (preimmune serums) and then every two weeks for the detection of total IgG, IgG1 and IgG2. Larger volumes of blood from the jugular vein (150 mL was taken before the first immunization and 14 weeks after the first immunization (i.e., 4 weeks after the second immunization) for peripheral blood mononuclear cells (PBMCs) isolation and analysis of the cellular immune responses.

Detection of Total IgG, IgG1 and IgG2 by ELISA.

Detection of total IgG, IgG1 and IgG2 against each of the antigens in serum and milk was performed as previously described with some modifications (Ster et al., *Vet. Immunol. Immunopathol.* (2010), 136: 311-318). Nunc MaxiSorp™ 96-well plates (Thermo Fisher Scientific Inc., Rochester, N.Y.) were coated with the test antigen (5 µg/mL diluted in carbonate/bicarbonate buffer, Sigma Aldrich, Oakville, ON) and incubated overnight at 37° C. The plates were then saturated with the PBS containing 0.5% gelatin (BD, Franklin Lakes, N.J.) for 1 h at 37° C. One hundred microliters of two-fold serial dilutions of the sera in PBS containing 0.5% gelatin and 0.1% Tween™ 20 were loaded into the plates and incubated for 1 h at 37° C. The plates were washed three times with PBS containing 0.1% Tween™ 20. One hundred microliters of horseradish peroxidase (HRP)-conjugated secondary antibody were added to the plate. The secondary antibodies used were a goat anti-bovine IgG (Jackson ImmunoResearch Laboratories Inc., West Grove, Pa.), a sheep anti-bovine IgG1 (AbD Serotec, Raleigh, N.C.) or a sheep anti-bovine IgG2 (AbD Serotec), diluted 1/50,000 1/20,000 and 1/20,000 respectively in PBS containing 0.5% gelatin and 0.1% Tween™ 20. After 1 h of incubation at 37° C. followed by 3 washes, peroxidase activity was detected with 3,3',5,5'-tetramethylbenzidine (TMB) reagent (KPL Inc., Gaithersburg, Md.) according to the manufacturer's recommendations.

Detection of total IgG, IgG1 and IgG2 in milk was carried out using the same procedure with few modifications. Milk samples were diluted into PBS containing 0.5% gelatin. The sheep anti-bovine IgG2 was diluted 1/10,000 into PBS containing 0.5% gelatin and 0.1% Tween™ 20.

Evaluation of the Cellular Immune Response.

PBMCs were isolated from jugular vein blood and labelled with carboxyfluoroscein diacetate, succinimidyl ester (CFDA-SE; Molecular Probes Inc., Eugene, Oreg.) as previously described (Loiselle et al., J. Dairy. Sci. (2009), 92:1900-1912). At the end of the CFDA-SE labelling procedure, the PBMCs were suspended in RPMI medium containing 5% FBS and 1× antibiotic/antimycotic (A5955, Sigma Chemical Aldrich). The PBMCs ($5 \times 10^6$ cells per well) were stimulated with the mitogen concanavalin A (ConA; positive control; Sigma Aldrich) at a final concentration of 1 µg/mL, or each antigen (5 µg per well) and incubated for 7 days at 37° C. As a negative control, the PBMCs were incubated without any mitogen. Stimulations were performed in duplicate (Ster et al., 2010).

The proliferation of CD4+ and CD8+ cells was evaluated after incubation with the different mitogens. The cells were centrifuged at 300×g for 5 min, suspended in PBS containing 0.5% BSA. The mouse anti-bovine CD8 coupled with Alexa Fluor™ 647 (diluted 1/20, AbD Serotec) and the mouse anti-bovine CD4 coupled with rPE (diluted 1/20, AbD Serotec) were then added. After 20 min of incubation on ice, the cells were washed three times with PBS containing 0.5% BSA. The cells were then suspended in PBS with 0.5% formaldehyde. The percentages of the proliferative populations were determined by flow cytometry on a BD FACS Canto II flow cytometer using the BD FACS Diva software.

Experimental S. aureus in IMI in Dairy Cows.

Before their use in experimental IMI, the relationship between the absorbance of the bacterial cultures (Δ600 nm) and CFU was determined. The day of the challenge, a volume of the overnight culture of S. aureus in Mueller Hinton broth (MHB; BD) was transferred to 200 mL of fresh MHB to obtain an Δ600 nm of 0.1 and subsequently grown at 35° C. until the Δ600 nm reached a value corresponding to $10^8$ CFU/mL in the exponential phase of growth. The strain to be used in this experimental infection (CLJ08-3) had previously been characterized in the co-inventor's lab (Allard et al., Vet. Microbiol. (2013) 162: 761-770). For intramammary infusions, bacteria were routinely diluted in sterile PBS (Sigma Aldrich) to obtain approximately 50 CFU in 3 mL. In this experiment, the inoculum was plated on TSA and found to contain 63 cfu in 3 mL.

Somatic cell count (SCC) determinations and bacterial analysis of aseptic quarter milk samples were carried out prior to experimental IMI to ensure that all cows were free of IMI. Experimental infusion of mammary quarters with bacteria was performed in three (randomly chosen) of the four quarters of each cow after the evening milking according to a procedure previously described (Petitclerc et al., J. Dairy. Sci. (2007), 90: 2778-2787) with few modifications. Briefly, before inoculation, teats were scrubbed with gauze soaked in 70% ethanol. Teats were allowed to air-dry before intramammary infusion of 3 mL of bacterial suspension (containing 63 CFU) into three of the four quarters. Immediately after infusion, all quarters were thoroughly massaged and teats were dipped in an iodophore-based teat sanitizer. Disposable gloves were worn throughout the procedure and disinfected before proceeding to the next animal. All quarters infused with S. aureus became infected and all cows showed clinical signs (inflammation, and/or poor milk appearance) of mastitis at some time during the first few days after infusion of S. aureus.

Evaluation of the S. aureus Viable Counts after Experimental Infections.

Aseptic milk samples were taken before the morning milking three times a week during the 3 first weeks following the experimental infection and then twice a week for the 2 remaining weeks. After foremilk was discarded and the teats were disinfected with 70% ethanol, a 10-mL milk sample was aseptically collected in a 50-mL sterile vial for each individual quarter. Milk samples were serially diluted and 100 µL of each dilution were plated on both tryptic soy agar (Becton Dickinson) and mannitol salt agar plates (Becton Dickinson) for CFU determinations and S. aureus identification. Plates were then incubated for 24 h at 35° C. before the colonies were counted. The dilutions that showed between 30 and 300 colonies were used to calculate the bacterial concentration. Each dilution was plated in duplicate.

Evaluation of the Somatic Cell Counts.

At the same frequency as for aseptic milk samples, milk was harvested using individual quarter milking units at morning milking and weighed for the determination of quarter milk production. A non-aseptic 50-mL sample was also taken from each quarter milking units for the determination of the SCC by a commercial laboratory (Valacta Inc., Ste-Anne-de-Bellevue, QC, Canada). The milking units were thoroughly washed and disinfected with an iodine-based germicide detergent (K.O. Dyne®, GEA Farm Technologies, Westmoreland, N.Y.) between their uses on each cow. All other materials in contact with milk were disinfected with 70% ethanol.

Statistical Analysis.

Statistical analyses of the experimental infection data were performed using the MIXED procedure of SAS (SAS Institute Inc., Cary, N.C.) as repeated measurements. For the analysis of SCC and CFU, data were log 10 transformed prior to analysis. Statistical analysis of the antibody titers and of the correlation between CFU and SCC was performed using GraphPad Prism™ v6.05.

Ethics Statement.

All animal experiments were approved by the Agriculture and Agri-Food Canada local institutional animal care committee and conducted in accordance with the guidelines of the Canadian Council on Animal Care.

Example 2: Serum Total IgG1 Titers Following Vaccination—Vaccine #1

Recombinant His-tagged antigens for SACOL0029 (GenBank™ accession No.: YP_184940.1) (SEQ ID NO: 5), SACOL0442 (SEQ ID NO: 29), SACOL0720 (SEQ ID NO: 11), SACOL1867 (GenBank™ accession No.: YP_186695.1) (SEQ ID NO: 38), SACOL1912 (GenBank™ accession No.: YP_186737.1) (SEQ ID NO: 43), and SACOL2385 (GenBank™ accession No.: YP_187189.1) (SEQ ID NO: 50), were prepared and administered to healthy cows as described in Example 1 (Production of the antigens and Immunization of dairy cows). Nine dairy cows received the vaccine and 10 cows received saline (placebo). Total serum IgG, IgG1 and IgG2 titers were detected as described in Example 1 (Detection of total IgG, IgG1 and IgG2 by ELISA).

Figure 1B:
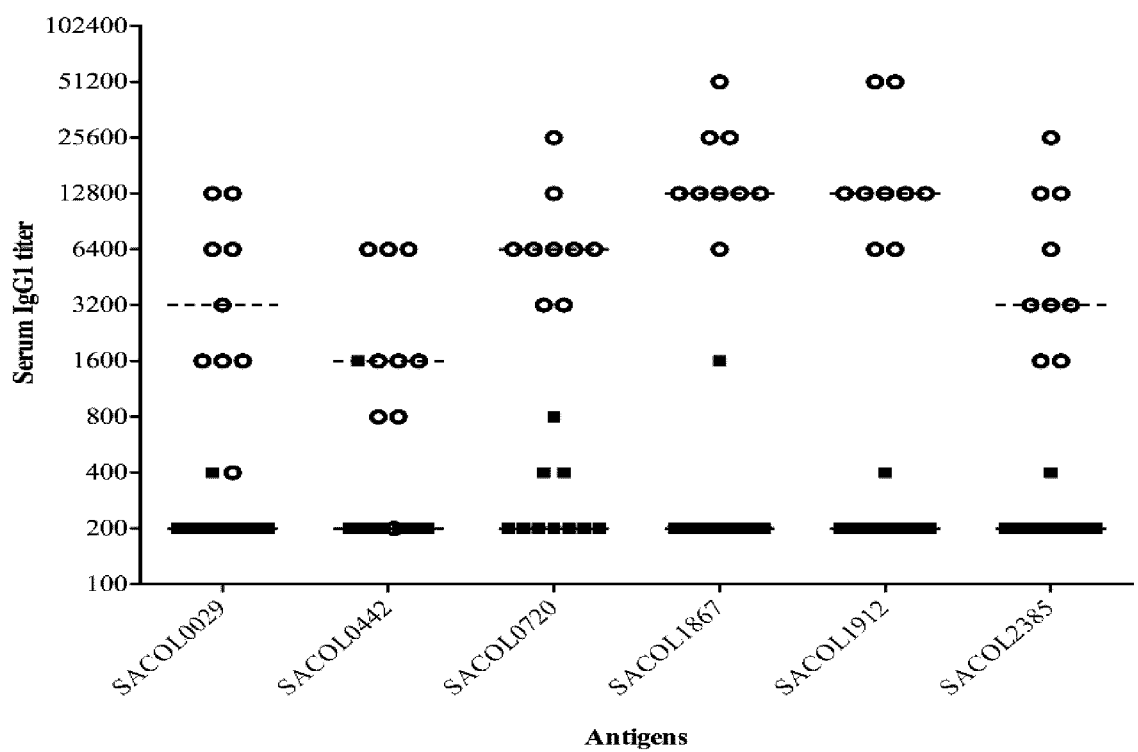
Figure 1C:
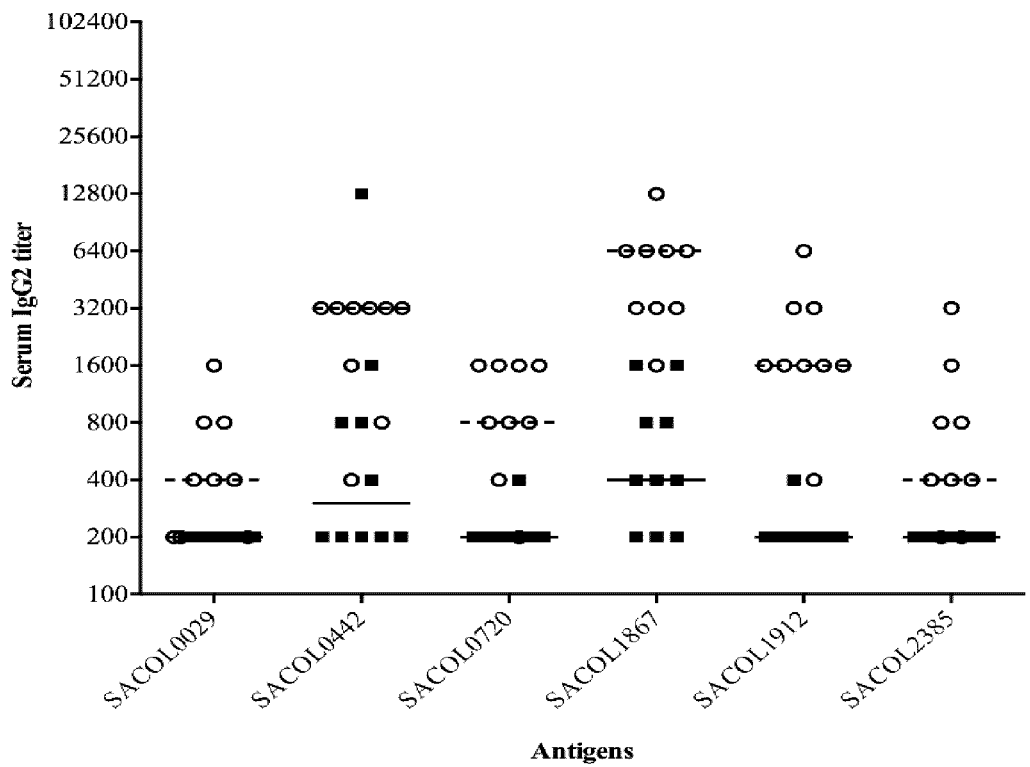
Figure 1D:
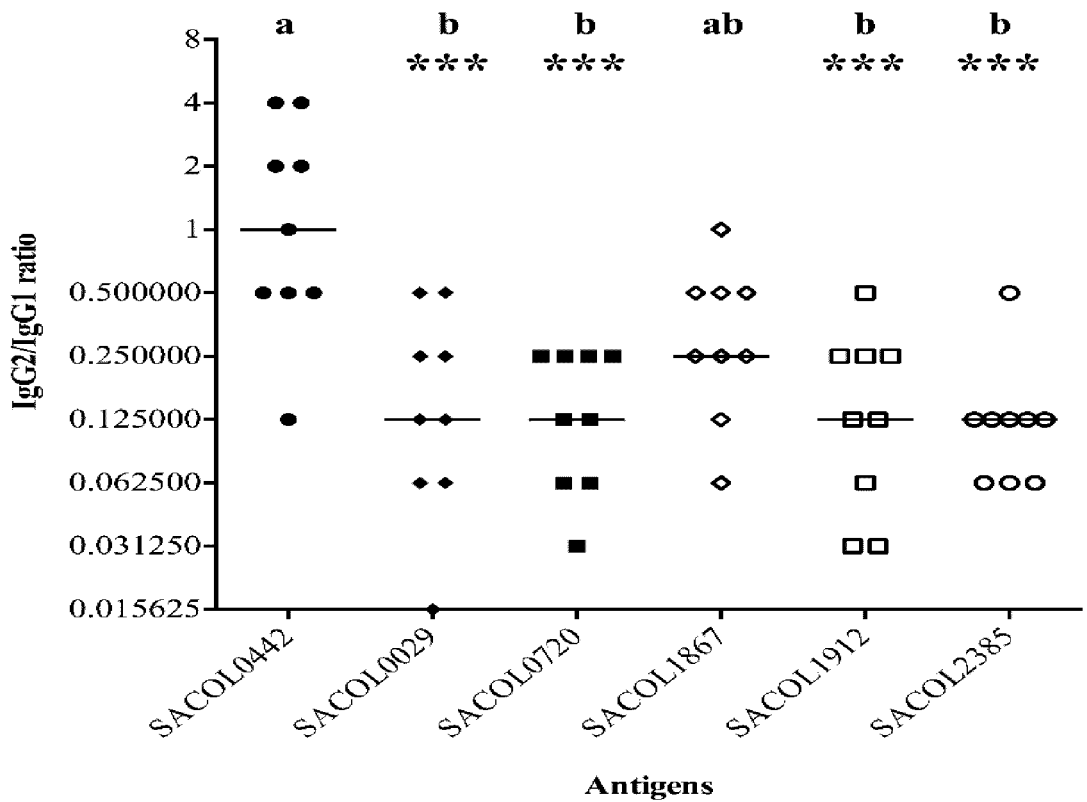

As expected, and as shown in FIGS. 1B-C, immunization induced an increased production of antigen-specific serum IgG1 and IgG2 for the vaccinated group in comparison to the placebo group. Interestingly, the IgG2/IgG1 ratio was 1 for SACOL0442 (see FIG. 1D), which is an indication of a balanced Th1/Th2 immune response to this antigen. For the antigens SACOL0029, SACOL0720, SACOL1912 and SACOL2385, the IgG2/IgG1 ratio is significantly lower than the ratio for SACOL0442 which indicated that these antigens induced mostly an IgG1 antibody response via the Th2 pathway.

Example 3: Antigen Dependent Proliferation of Blood CD4+ and CD8+ Cells Following Vaccination-Vaccine #1

Figure 2:
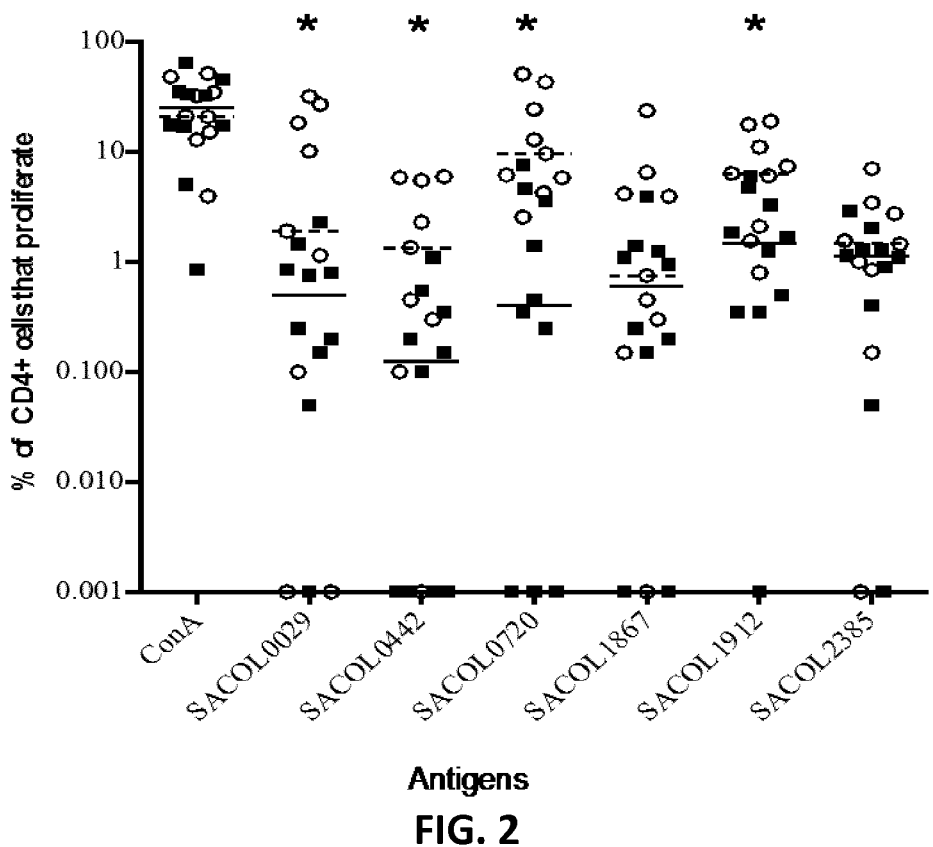
FIG. 2. shows antigen dependent proliferation of blood CD4+ cells from the vaccinated cows (9) and placebo cows (10) four weeks after the second immunization for each antigen. Each symbol represents the percentage of CD4+ cells that have proliferated for each cow after a week of incubation with the positive control (ConA) or each antigen, namely SACOL0029, SACOL0442, SACOL0720, SACOL1867, SACOL1912, and SACOL2385. Open circles (○) represent data for the vaccinated cows, black squares (■) represent data for the placebo cows. Horizontal lines represent the medians: dashed lines represent the medians for the vaccinated cows while continuous lines represent the medians for the placebo cows. Statistical analysis: Mixed procedure of SAS. The symbol * shows the statistical differences between the vaccinated and the placebo groups for antigens SACOL0029, SACOL0442, SACOL0720 and SACOL1912 (*, $P<0.05$). In addition, the proliferation of CD8+ cells was similar for the vaccinated and placebo cows for all antigens with the exception of the antigen SACOL0720 for which higher proliferation of the CD8+ cells was observed for the vaccinated cows (data not shown).
Figure 3:
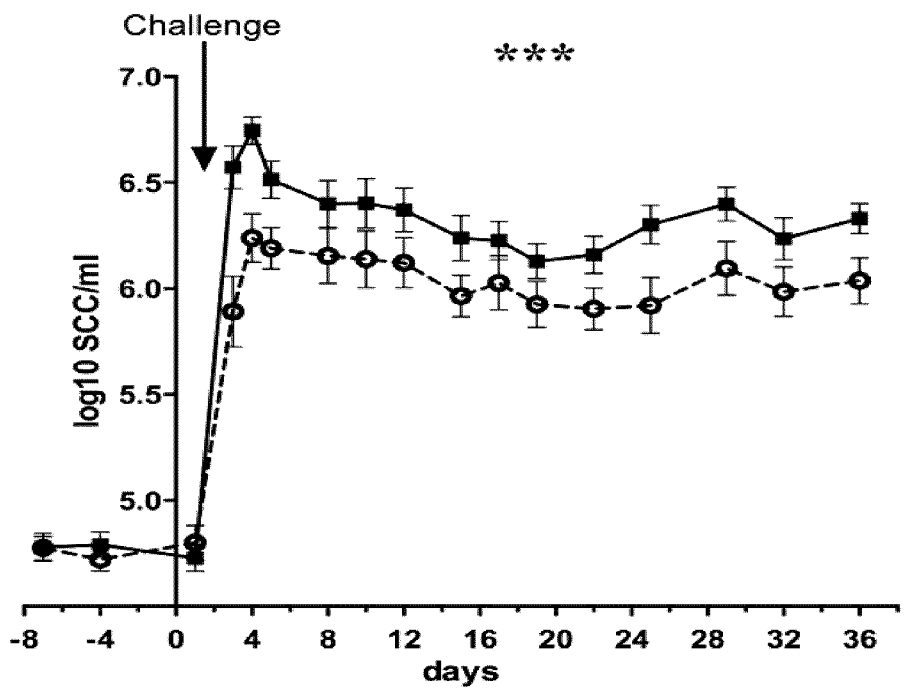
FIG. 3. shows experimental *S. aureus* intramammary infections in dairy cows. Four weeks and 4 days after the second immunization, 63 Colony Forming Unit (CFU) of *S. aureus* were infused into 3 of the 4 quarters of the vaccinated (9) and placebo cows (10) at the evening milking (day 1, arrow in FIG. 3). Aseptic milk samples were taken at morning milking and Somatic Cell Counts (SCC) were determined by Valacta (Ste-Anne-de-Bellevue, QC). Open circles (○) and the dashed line represent data for the vaccinated cows, while the black squares (■) and the continuous line represent data for the placebo cows. Each open circle represents the mean of SCC for all the infected quarters of the vaccinated cows (27) while each square represents the mean of SCC for all the infected quarters of the placebo cows (30 quarters). Over the challenge period, somatic cell counts in milk were found to be significantly lower for the vaccinated cows than for the placebo cows (***; $P<0.001$).

Antigen dependent proliferation of blood CD4+ and CD8+ cells from the vaccinated cows (9) and placebo cows (10) was evaluated as described in Example 1 (Evaluation of the cellular immune response) four weeks after the second immunization (just before the experimental infection) for each antigen. The results for CD4+ cells are shown in FIG. 2, in which each symbol represents the percentage of CD4+ cells that have proliferated for each cow after a week of incubation with the positive control (ConA) or each antigen. Open circles (○) represent data for the vaccinated cows, black squares (■) represent data for the placebo cows. Horizontal lines represent the medians: dashed lines represent the medians for the vaccinated cows while continuous lines represent the medians for the placebo cows.

The symbol * shows the statistical differences between the vaccinated and the placebo groups for antigens SACOL0029, SACOL0442, SACOL0720 and SACOL1912 (*, $P \leq 0.05$).

In addition, the proliferation of CD8+ cells was similar for the vaccinated and placebo cows for all antigens with the exception of the antigen SACOL0720 for with higher proliferation of the CD8+ cells was observed for the vaccinated cows (data not shown). Induction of CD8+ cells also seemed to be important for the resolution of the infection (Riollet et al., 2001; Burton and Erskine, 2003). The vaccine was able to stimulate both cellular (CD8+) and humoral (CD4+) immune response. The vaccine #1 with its different antigens leads to a balanced immune response.

Example 4: Protection Effect of the Vaccine as Evaluated by Following the Evolution of Somatic Cell Counts (SCC)—Vaccine #1

Experimental *S. aureus* IMI infection in dairy cows were carried out and evaluated as described in Example 1 (Experimental *S. aureus* IMI in dairy cows, Evaluation of the *S. aureus* viable counts after experimental infections, Evaluation of the somatic cell counts and Statistical analysis). Four weeks and 4 days after the second immunization, 63 CFU of *S. aureus* were infused into 3 of the 4 quarters of the vaccinated (9) and placebo cows (10) at the evening milking (day 1, arrow in FIG. 3). Aseptic milk samples were taken at morning milking and SCC was determined by Valacta (Ste-Anne-de-Bellevue, QC). The results are shown FIG. 3, in which open circles (○) and the dashed line represent data for the vaccinated cows, while the black squares (■) and the continuous line represent data for the placebo cows. Each open circle represents the mean of SCC for all the infected quarters of the vaccinated cows (27) while each square represents the mean of SCC for all the infected quarters of the placebo cows (30 quarters).

Over the challenge period, SCC in milk were found to be significantly lower for the vaccinated cows than for the placebo cows (***; $P < 0.001$), indicating less inflammation and a better control of the infection in the vaccinated cows.

Example 5: Correlation Between SCC or the Viable Counts of *S. aureus* (CFU) Relative to Serum or Milk IgG Titers Against Specific Antigens—Vaccine #1

Figure 4A:
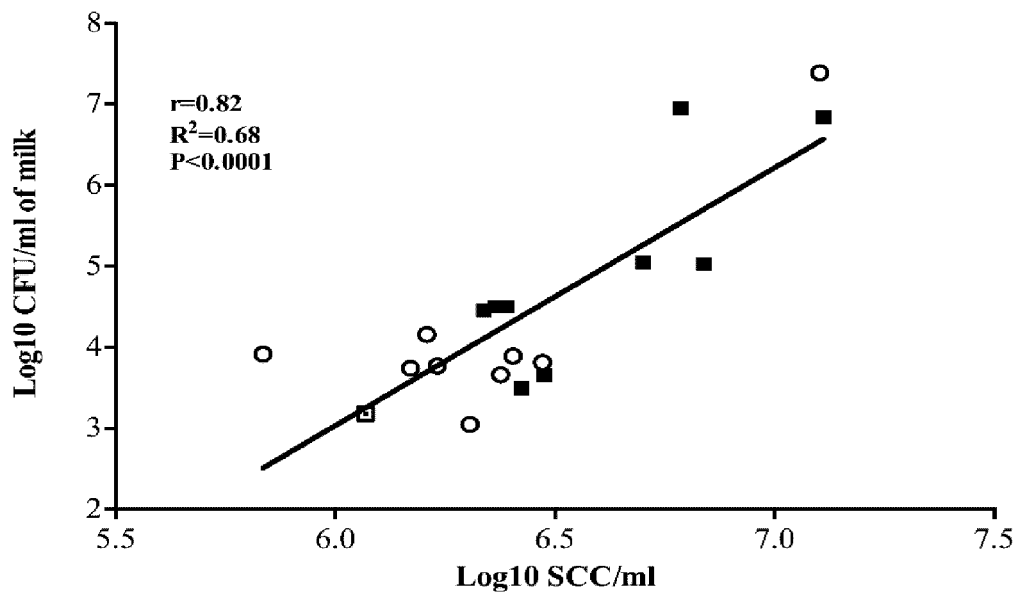
Figure 4B:
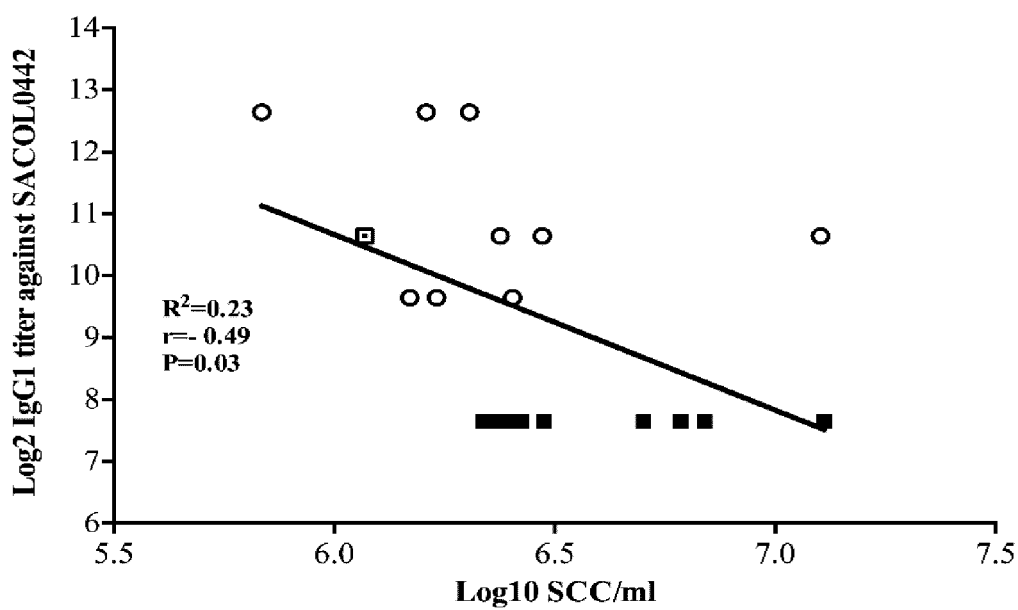

As shown in FIGS. 4A-B, SCC were positively correlated to *S. aureus* CFU of the challenge period (FIG. 4A, $r=0.82$, $P<0.0001$) and negatively correlated to the serum IgG1 titer against SACOL0442 measured prior to the infection (FIG. 4B, $r=-0.49$, $P<0.05$). Vaccination thus had reduced this criterium of inflammation induced by the challenge. A similar analysis was performed with the samples collected at day 10. The same correlations were observed as previously obtained but at this particular time point SCC and *S. aureus* CFU also correlated to the milk IgG2 titer against SACOL0029 (FIG. 4C, $r=-0.48$, $P<0.05$ and $r=-0.58$, $P<0.05$, respectively). These results show that more than one antigen is involved in the immune response against the infection.

Example 6: Materials and Methods for Vaccine Including SACOL0442, SACOL0720, and a Fusion Between SACOL1867 and SACOL0029—Vaccine #2

Production of the Antigens.

Four antigens that are highly expressed during *S. aureus* bovine intramammary infection were selected for inclusion in vaccine #2. The antigens are polypeptides encoded by: SACOL0029 (GenBank™ accession No.: YP_184940.1) (SEQ ID NO: 5), SACOL1867 (GenBank™ accession No.: YP_186695.1) (SEQ ID NO: 38), SACOL0442 (SEQ ID NO: 29), and SACOL0720 (SEQ ID NO: 11). The SACOL0029 and SACOL1867 antigens were included in the form of a fusion. His-tagged recombinant proteins of SACOL0720 and SACOL0029-1867 were engineered and produced by GenScript, Inc. (Piscataway, N.J.). A his-tagged recombinant protein of SACOL0442 was engineered and produced using QIA expression technology (pQE30 plasmid) from Qiagen Inc. (Mississauga, ON, Canada), according to the manufacturers' recommendations. (see FIGS. 21D-E and I, and items II, III and VII for SACOL0720, SACOL0442, and SACOL0029-1867 his-tagged sequences). The surface protein ClfA (SEQ ID NO: 184), was also additionally produced by using the QIA expression vector by cloning the clfA gene from *S. aureus* ATCC 25904. The latter recombinant protein was not part of the vaccine composition but was used in ELISA assays to determine IgG titers of sera against other *S. aureus* proteins such as ClfA.

The vaccine was composed of 300 µg of each of 3 antigens (SACOL0442 and SACOL0720 as defined in Example 1 and the fusion SACOL0029-1867) and with Emulsigen™-D (MVP Technologies, Omaha, Nebr.), CpG ODN 2007 (i.e. TCGTCGTTGTCGTTTTGTCGTT (SEQ ID NO: 194) (IDT, Coralville, Iowa)), and indolicidin (IL-PWKWPWWPWRR (SEQ ID NO: 195, GenScript, Piscataway, N.J., Chemprep Inc., Miami, Fla.) (vaccine #2).

Immunization of Dairy Cows.

Eleven healthy multiparous Holstein cows in mid-lactation were housed in a level II biosafety barn at the Dairy and Swine Research and Development Centre of Agriculture and Agri-Food Canada (Sherbrooke, QC). Cows received the vaccine #2 (vaccinated group). Two immunizations were performed 10 weeks apart, subcutaneously in the neck. No adverse side effects were observed. Blood from the caudal vein and milk samples were taken before the first immunization (preimmune serums) and then every week for the detection of total IgG.

Detection of Total IgG by ELISA.

Detection of total IgG against each of the antigens in serum was performed as previously described with some modifications (Ster et al., *Vet. Immunol. Immunopathol.* (2010), 136: 311-318). Nunc MaxiSorp™ 96-well plates (Thermo Fisher Scientific Inc., Rochester, N.Y.) were coated with the test antigen (5 µg/mL diluted in carbonate/bicarbonate buffer, Sigma Aldrich, Oakville, ON) and incubated overnight at 37° C. The plates were then saturated with the PBS containing 0.5% gelatin (BD, Franklin Lakes, N.J.) for 1 h at 37° C. One hundred microliters of two-fold serial dilutions of the sera in PBS containing 0.5% gelatin and 0.1% Tween™ 20 were loaded into the plates and incubated for 1 h at 37° C. The plates were washed three times with PBS containing 0.1% Tween™ 20. One hundred microliters of horseradish peroxidase (HRP)-conjugated secondary antibody were added to the plate. The secondary antibodies used were a goat anti-bovine IgG (Jackson ImmunoResearch Laboratories Inc., West Grove, Pa.) diluted 1/1000,000 in PBS containing 0.5% gelatin and 0.1% Tween™ 20. After 1 h of incubation at 37° C. followed by 3 washes, peroxidase activity was detected with 3,3',5,5'-tetramethylbenzidine (TMB) reagent (KPL Inc., Gaithersburg, Md.) according to the manufacturer's recommendations.

Example 7: The Fusion of Antigens Induces High Antibody Titers—Vaccine #2

FIG. 5 shows serum total IgG titers for the vaccinated cows for each antigen of the vaccine (including the fused antigens SACOL0029 and SACOL1867 (labeled SACOL0029-1867 on FIG. 5). Each open circle represents the titer four weeks after the second immunization for each cow (just before the experimental infection) whereas each black diamond represents the preimmune titer. Horizontal lines represent the medians: solid line for the preimmune serums, dotted line for the samples taken four weeks after immunization. Titers for the vaccinated cows are higher than the titers of the preimmune serums (, $P<0.01$; *, $P<0.001$ for the other antigens tested).

FIG. 5 thus shows that the vaccine composed of three separate antigens, including a fusion peptide, induces a strong immune response in the cows. Furthermore, FIG. 5 surprisingly shows that the fused antigens SACOL0029 and SACOL1867 (fusion SACOL0029-SACOL1867) raised antibody titers that were above those raised by each of the antigen alone (Compare FIG. 1A vs. FIG. 5) and that such fused antigens provide an additional benefit to the vaccine.

More particularly, when administered individually in a vaccine, the titers of immune cows against SACOL0029 and SACOL1867 reached 3200 and 51200, respectively (FIG. 1A), whereas when these antigens were administered as a fusion, the titers of immune cows reached 12800 and 409600, respectively (FIG. 5), showing that the fusion create an unexpected synergy in the immune response.

Example 8: Materials and Methods for Vaccine Comprising SACOL0029, SACOL1867, and a Fusion Between SACOL1867 and SACOL0029—Vaccine #3

Production of the Antigens.

Three antigens derived from two genes that are highly expressed during *S. aureus* bovine intramammary infection were selected for inclusion in a vaccine. These antigens are: SACOL0029 (GenBank™ accession No.: YP_184940.1) (SEQ ID NO: 5), SACOL1867 (GenBank™ accession No.: YP_186695.1) (SEQ ID NO: 38) and a fusion between SACOL1867 and SACOL0029 (GenBank™ accession No.: YP_184940.1) (SEQ ID NO: 5). His-tagged recombinant proteins of SACOL0029, SACOL1867 and SACOL0029-1867 were engineered and produced by GenScript, Inc. (Piscataway, N.J.). (see FIGS. 21A, F and I, items I, IV and VII for SACOL0029, SACOL1867, and SACOL0029-1867 his-tagged sequences).

Immunization of Mice.

The immunogenic properties of recombinant *S. aureus* proteins encoded by the SACOL0029, SACOL1867 genes and a fusion of SACOL0029 and SACOL1867 were evaluated in mice. Four groups of mice received the exact equimolar quantity of proteins, either in a monovalent form (SACOL0029 or SACOL1867) or in a multivalent form (the fusion SACOL0029-1867 or SACOL0029 together with SACOL1867 in combination), were compared.

In brief, the theoretical molecular weight of each amino acid sequence corresponding to the entire fusion or to the SACOL0029 or SACOL1867 portion of the fusion were calculated using the ExPASy™ Bioinformatic resource portal (http://web.expasy.orglcgi-bin/compute_pi/pi_tool).

Five micrograms of the fusion were administered to one group of mice. The corresponding molar quantity of 5 µg of the SACOL0029-1867 fusion was determined to be 168.55 pmol, in regard to its theoretical molecular weight. An amount of 1.15 µg and 3.69 µg of SACOL0029 and SACOL1867, respectively was administered in two other groups of mice in order to provide 168.55 pmol of each antigen, respectively. The last group of mice received the combination of the two individual antigens (168.55 pmol of each).

For the preparation of the immunization doses, SACOL0029, SACOL1867 and the SACOL0029-1867 fusion polypeptides were individually mixed and suspended in PBS to obtain the final equimolar quantity of each antigenic dose in a volume of 100 µl. Twenty CD-1 female mice were randomly divided into 4 groups: group A (5 mice) received 5 µg of the SACOL0029-1867 fusion protein (Fusion); group B (5 mice) received 1.15 µg of SACOL0029 and 3.69 µg of SACOL1867 (Combination); group C (5 mice) received 1.15 µg of SACOL0029 (0029) and group D received 3.69 µg of SACOL1867 (1867). The CD-1 mice were immunized by two subcutaneous injections in the neck two weeks apart. No adverse side effects were observed during the totality of the experimental immunization period. Blood samples were taken just before the first priming injection (preimmune serums) and ten days after the boost immunization (immune serums). The blood aliquots were allowed to clot at room temperature for an hour, centrifuged at 10,000 g for 10 min at 4° C. The sera were harvested and kept at −20° C. until subsequent analysis.

Detection of Total IgG by ELISA.

Detection of serum total IgG against SACOL0029 and SACOL1867 recombinant proteins was performed as previously described with some modifications (Ster et al., *Vet. Immunol. Immunopathol.* (2010), 136: 311-318). Nunc MaxiSorp™ 96-well plates (Thermo Fisher Scientific Inc., Rochester, N.Y.) were coated with 75 µl of each of the test antigen (6.67 µg/mL diluted in carbonate/bicarbonate buffer, Sigma Aldrich, Oakville, ON) and incubated overnight at room temperature. The plates were then saturated with PBS containing 5% skim milk powder for 1 h at 37° C. One hundred microliters of four-fold serial dilutions of the sera in PBS containing 3% milk and 0.025% Tween™ 20 were loaded into the plates and incubated for 1 h at 37° C. The plates were washed three times with PBS containing 0.05% Tween™ 20. One hundred microliters of horseradish peroxidase (HRP)-conjugated secondary antibody were then added to the plate. The secondary antibody used was a commercial goat anti-mouse IgG (Jackson ImmunoResearch Laboratories Inc., West Grove, Pa.), diluted 1/5000 in PBS containing 3% milk and 0.025% Tween™ 20. After 1 h of incubation at 37° C. followed by 3 washes, peroxidase activity was detected with the addition of one hundred microliters of 3,3',5,5'-tetramethylbenzidine (TMB) reagent (KPL Inc., Gaithersburg, Md., according to the manufacturer's recommendations.

Statistical Analysis

Statistical analysis of the antibody titers and of the correlation was performed using GraphPad Prism™ v6.05.

Example 9: The Fusion of Antigens Induces Significantly Higher Antibody Titers Compared to Monovalent Antigens or a Combination of Antigens—Vaccine #3

Figure 6:
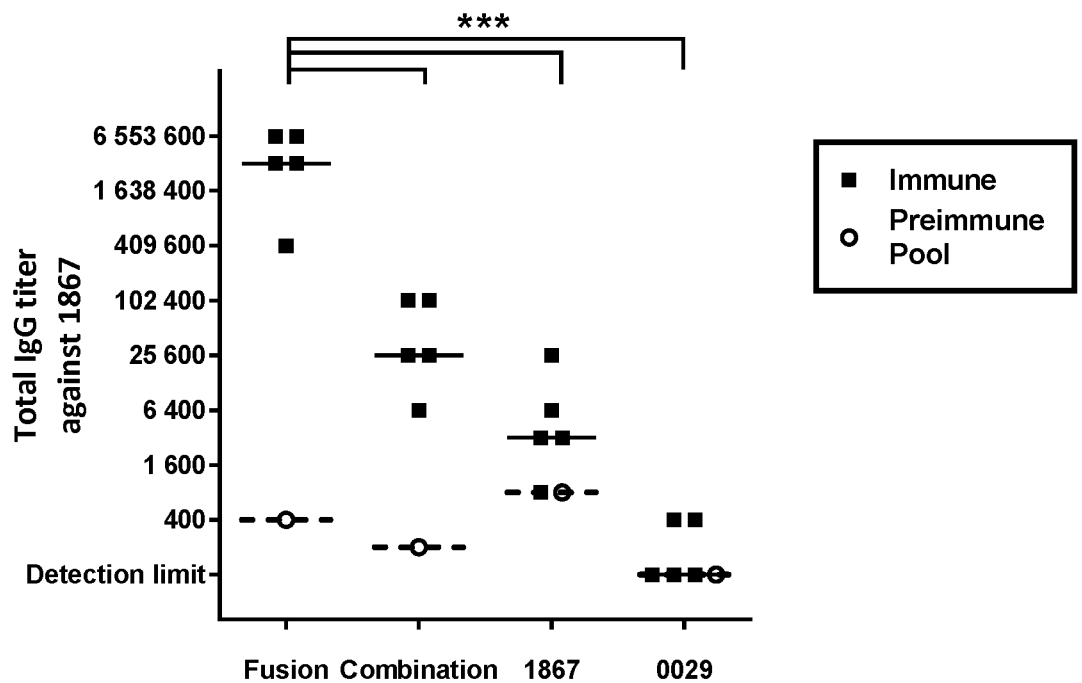
FIG. 6 shows serum total IgG titers against the SACOL1867 antigen of mice immunised with the fusion protein (SACOL0029-1867; fusion), a combination of the separate proteins (SACOL0029+SACOL1867; combination), the SACOL0029 protein only (0029) or SACOL1867 protein only (1867), in equivalent molar quantities. Open circles (○) represent data for preimmune titers, black squares (■) represent data for the immune titers. For the preimmune titers, preimmune sera were mixed equally between the 5 mice of each immunization group to obtain a preimmune pool titer, represented by one open circle per group. For the immune titers, each square symbol represents the titer for one mouse. Horizontal lines represent the medians: black lines represent the medians for the immune serums while dashed lines (and the open circle) represent the medians for the preimmune serums pool. Titers for the vaccinated mice in the fusion, combination and 1867 groups are higher than the titers for the preimmune mice (P<0.001), and the titers of the mice that received SACOL0029 monovalent antigen only were not found to be significantly different from the titers of the preimmune pool against SACOL1867. Statistical significance between immune titers of fusion group versus the combination and the two monovalent vaccines groups is shown (***: P<0.001).

FIG. 6 shows that an antigen (SACOL1867) included in a fusion polypeptide (i.e., the SACOL0029-1867 fusion protein) can induce a strong and specific antibody immune response against that specific antigen (SACOL1867), and, more importantly, that this response can be significantly higher than that obtained with a monovalent form of this antigen (SACOL1867 administered alone) or a multivalent combination of individual polypeptides that are part of the fusion (combination of SACOL1867 plus SACOL0029). Thus, in addition to the advantage of generating an immune response against multiple polypeptidic targets, such fused antigens also provide the additional benefit of greatly improving the antibody titers against those targets.

Example 10: Materials and Methods for Vaccines Including SACOL0720 Fragment(s) and/or SACOL442 Fragment(s)—Vaccines #4-6

Production of the Antigens.

Peptides and amino acid fragments of 15 to 50 amino acids in length and derived from sequences SACOL0442 and/or SACOL0720 were selected based on the presence of B-cell epitopes. Fusions of peptide epitopes were also designed in which an amino acid linker (for example, EAAAKEAAAK (SEQ ID NO: 62), or ERKYK (SEQ ID NO: 61) or KDYERKYKKHIVS (SEQ ID NO: 196)) joined the various epitopes. Peptides and amino acid fragments were synthesized by Biomatik, Inc. (Cambridge, ON). Upon receipt, lyophilised peptides and amino acid fragments were suspended in sterile water at a concentration of 5 mg/mL and stored at −80° C. until day of use.

Immunization of Mice.

Peptides and amino acid fragments were used as antigens for immunization of mice. For the preparation of the immunization doses, each peptide and amino acid fragment or a combination of such were mixed and suspended in PBS containing 20% of the EMULSIGEN®-D oil-in-water emulsion adjuvant to obtain a final dose of 100 μg of polypeptide per dose, unless otherwise specified. CD-1 female mice were randomly divided into different groups of 3 to 4 animals. Mice were immunized by two subcutaneous injections in the neck two weeks apart. No adverse side effects were observed during the totality of the experimental period. Blood samples were taken just before the first priming injection (preimmune serums) and ten days after the boost immunization (immune serums). The blood aliquots were allowed to clot at room temperature for an hour, and then centrifuged at 10,000 g for 10 min at 4° C. The sera were harvested and kept at −20° C. until subsequent analysis.

Detection of Total IgG by ELISA.

Detection of serum total IgG, against specific amino acid sequences found in the antigens used for the immunization of mice, was performed as previously described with some modifications (Ster et al., *Vet. Immunol. Immunopathol.* (2010), 136: 311-318). Nunc MaxiSorp™ 96-well plates (Thermo Fisher Scientific Inc., Rochester, N.Y.) were coated with 100 μl of each of the target amino acid sequences diluted at a final concentration of 5 μg/mL in carbonate/bicarbonate buffer (Sigma Aldrich, Oakville, ON) and incubated overnight at room temperature. The plates were then saturated with PBS containing 5% skim milk powder for 1 h at 37° C. One hundred microliters of four-fold or two-fold serial dilutions of the sera in PBS containing 1% milk and 0.025% Tween™ 20 were loaded into the plates and incubated for 1 h at 37° C. The plates were then washed three times with PBS containing 0.05% Tween™ 20. One hundred microliters of horseradish peroxidase (HRP)-conjugated secondary antibody were then added to the plate. The secondary antibody used was a goat anti-mouse IgG (Jackson ImmunoResearch Laboratories Inc., West Grove, Pa.), diluted 1/5000 in PBS containing 1% milk and 0.025% Tween™ 20. After 1 h of incubation at 37° C. followed by 3 washes with PBS Tween™ 20 and a final wash with PBS, peroxidase activity was detected with 3,3',5,5'-tetramethylbenzidine (TMB) reagent (KPL Inc., Gaithersburg, Md.) according to the manufacturer's recommendations.

Statistical Analysis.

Statistical analysis of the antibody titers and optical densities was performed using GraphPad Prism™ v6.05.

Example 11: Immune Response Against a Fusion of Peptides that Includes Epitopes Encoded from Sequences SACOL0442 and SACOL0720—Vaccine #4

A fusion of peptide epitopes encoded from SACOL0442 and SACOL0720 was used to vaccinate mice (n=4). The sequence of the fusion of peptides was KDGGKYTLESH-KELQEAAAKEAAAKKDIN-KIYFMTDVDLGGPTFVLND (SEQ ID NO: 3) (vaccine #4), where the linker is italicized and the different epitopes are identified in bold characters. The epitopes were KDGGKYTLESHKELQ (SEQ ID NO: 1) encoded from SACOL0442, KDINKIYFMTDVDL (SEQ ID NO: 23) encoded from SACOL0720, and DVDLGGPTFVLND (SEQ ID NO: 24) also encoded from SACOL0720. The IgG antibodies from the sera harvested from the animals were able to bind amino acid fragments comprising B-cell epitopes from either SACOL0442 (i.e. KDGGKYTLESH-KELQ (SEQ ID NO: 1)) and/or SACOL0720 (i.e. QFGFDLKHKKDALA (SEQ ID NO: 21); KDIN-KIYFMTDVDL (SEQ ID NO: 23), DVDLGGPTFVLND (SEQ ID NO: 24)) in ELISA assays with antibody titers of 1/6400 or higher. The fusion of peptides used for immunization and the amino acid fragments or polypeptides used as antibody targets in ELISA assays are shown in Table III below. In this table, the epitopes are in bold and the linker sequence is italicized.

TABLE III

Polypeptide vaccine and antibody response targets

Fusion of peptides used for vaccination

KDGGKYTLESHKELQEAAAKEAAAKKDINKIYFMTDVDLGGPTFVLND (SEQ ID NO: 3)

Peptides and polypeptides targets bound by IgG from vaccinated mice in an ELISA assay

KDGGKYTLESHKELQEAAAKEAAAKKDINKIYFMTDVDLGGPTFVLND (SEQ ID NO: 3) (fusion of peptides);

GEHLPKGNIVINTKDGGKYTLESHKELQKDRENVKINTAD (SEQ ID NO: 2) (fragment encoded by SACOL0442);

KDINKIYFMTDVDLGGPTFVLNDKDYERKYKKHIVSQFGFDLKHKKDALA (SEQ ID NO: 27) (variant comprising fragments encoded by SACOL0720)

SACOL0442 (SEQ ID NO: 55) (i.e. polyhistidine version shown in FIG. 21E, item II);

SACOL0720 (SEQ ID NO: 25) (i.e. polyhistidine version shown in FIG. 21D, item III);

All antibody targets shown above were bound in an ELISA assay by IgG from mice vaccinated with the fusion antigen above.

This demonstrates that a fusion of peptide epitopes encoded by both SACOL0442 and SACOL0720 can be used to immunize and elicit an immune response in a mammal. The obtained immune response includes the production of antibodies that recognize SACOL0442 or SACOL0720, amino acid fragments or variants encoded from either SACOL0442 or SACOL0720.

Example 12: A Fusion of Multiple Epitopes Used as an Antigen in Immunizations Significantly Enhances the Immune Response Against a Single Epitope—Vaccine #4

A fusion of peptide epitopes encoded from SACOL0442 and SACOL0720 was used to vaccinate mice (n=4). The sequence of the fusion of peptides was KDGGKYTLESHKELQEAAAKEAAAKKDINKIYFMTDVDLGGPTFVLND (SEQ ID NO: 3), where the linker is italicized and the different epitopes are identified in bold characters. The epitopes were KDGGKYTLESHKELQ (SEQ ID NO: 1) encoded from SACOL0442, KDINKIYFMTDVDL (SEQ ID NO: 23) encoded from SACOL0720, and DVDLGGPTFVLND (SEQ ID NO: 24) also encoded from SACOL0720. Another group of mice (n=4) was immunized with the single peptide epitope KDGGKYTLESHKELQ (SEQ ID NO: 1), encoded from SACOL0442.

Sera were collected from animals and tested for the presence of IgG antibodies directed toward an amino acid fragment encoded from SACOL0442 (GEHLPKGNIVINTKDGGKYTLESHKELQKDRENVKINTAD) (SEQ ID NO: 2), which contains the peptide epitope KDGGKYTLESHKELQ (SEQ ID NO: 1).

Figure 7:
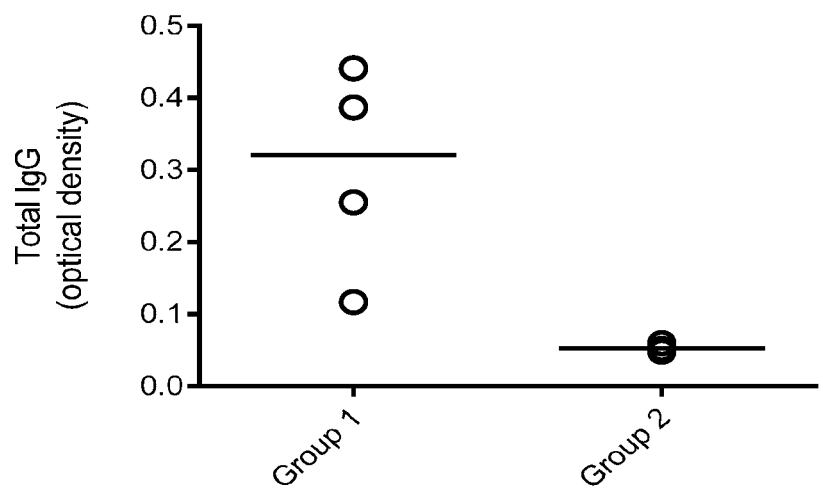
FIG. 7. Serum total IgG (as measured by O.D. 450 nm in the ELISA assay) directed against a B-cell epitope sequence KDGGKYTLESHKELQ (SEQ ID NO: 1) contained in a fragment of the amino acid sequence of SACOL0442 (GEHLPKGNIVINTKDGGKYTLESHKELQK-DRENVKINTAD, SEQ ID NO: 2), and obtained from mice immunized with either a fusion of peptides encoded from SACOL0442 and SACOL0720 KDGGKYTLESH-KELQEAAAKEAAAKKDINKIYFMTDVDLGGPT-FVLND (SEQ ID NO: 3) (Group 1) or the peptide KDGGKYTLESHKELQ (SEQ ID NO: 1) encoded from SACOL0442 (Group 2). Each group was composed of 4 animals (n=4) that were injected two times with equimolar amounts of the sequence KDGGKYTLESHKELQ (SEQ ID NO: 1) (corresponding to 100 μg of KDGGKYTLESH-KELQEAAAKEAAAKKDINKIYFMTDVDLGGPT-FVLND (SEQ ID NO: 3) for Group 1 and 31.25 μg of KDGGKYTLESHKELQ (SEQ ID NO: 1) for Group 2) at a 2-week interval, and sera were prepared from blood harvested one week after the last injection. The ELISA assay was carried out with serum samples diluted 100 000 times and a fragment from SACOL0442 (GEHLPKGNIVINTK-DGGKYTLESHKELQKDRENVKINTAD, (SEQ ID NO: 2)) was used as the target antigen containing the peptide epitope KDGGKYTLESHKELQ (SEQ ID NO: 1). Individual data are expressed as circles on the graph and the medians by bars. The difference between groups was found statistically significant (P<0.0286, Kuskal-Wallis test, GraphPad Prism™ 7.00).

As shown on FIG. 7, immunization with the fusion of three peptide epitopes (one encoded from SACOL0442 and two encoded from SACOL0720) significantly increased the antibody production against an amino acid fragment encoded from SACOL0442 (GEHLPKGNIVINTKDGGKYTLESHKELQKDRENVKINTAD) (SEQ ID NO: 2), which contains the peptide epitope KDGGKYTLESHKELQ (SEQ ID NO: 1), compared to the antibody level obtained when only using the peptide epitope KDGGKYTLESHKELQ (SEQ ID NO: 1) as antigen for immunization.

Example 13: Immune Response Against a Polypeptide Fragment of 50 Amino Acids Encoded a Variant of SACOL0720—Vaccine #5

A group of mice (n=3) was vaccinated with a 50-amino acid peptide fragment (KDINKIYFMTDVDLGGPTFVLNDKDYERKYKKHIVSQFGFDLKHKKDALA (SEQ ID NO: 27)) (vaccine #5) containing B-cell epitopes (bold characters) encoded from the sequence SACOL0720, more specifically epitopes KDINKIYFMTDVDL (SEQ ID NO: 23), DVDLGGPTFVLND (SEQ ID NO: 24) and QFGFDLKHKKDALA (SEQ ID NO: 21). The overall sequence of KDINKIYFMTDVDLGGPTFVLNDKDYERKYKKHIVSQFGFDLKHKKDALA (SEQ ID NO: 27) vary from the native sequence of SACOL0720 by four amino acids in the region linking the epitopes DVDLGGPTFVLND (SEQ ID NO: 24) and QFGFDLKHKKDALA (SEQ ID NO: 21). Vaccine #5 can thus be considered being a variant fragment of SACOL0720 or a fusion of epitopes from SACOL0720, which are spaced by linker ERKYK (SEQ ID NO: 61).

Sera were tested for the presence of IgG antibodies directed toward a fragment of the native protein encoded by SACOL0720 (SEQ ID NO: 25) (i.e. polyhistidine version shown in FIG. 21D, item II). Both mice vaccinated with the peptide fragment corresponding to the variant sequence of amino acids (or fusion SACOL0720-720) produced antibodies that recognized epitopes in the original sequence of amino acids in an ELISA assay with titers of 1/6400 or higher.

This demonstrates that an amino acid fragment that comprises epitopes encoded from sequence SACOL0720 can elicit an immune response in a mammal. This also further demonstrates that a variant of the native sequence has the capacity to stimulate the immune system against the original fragment sequence containing B-cell epitopes.

Example 14: Immune Response Against a Combination of Fusions (Peptide Fusion 0442-0720 and Polypeptide Fusion 0029-1867)—Vaccine #6

A fusion of peptide epitopes encoded from SACOL0442 and SACOL0720 (see sequence in FIG. 21I, Item VII-fusions) was combined to a polypeptide fusion containing sequences of SACOL0029 and SACOL1867 (see sequence in FIG. 21I, Item VII fusions) and was used to vaccinate mice (vaccine #6).

For the preparation of the immunization doses, the peptide fusion 0442-0720 and the polypeptide fusion 1867-0029 were mixed and suspended in PBS containing 20% of the EMULSIGEN®-D oil-in-water emulsion adjuvant to obtain a final dose of 100 µg and 5 µg per dose of the peptide fusion (0442-0720) and the polypeptide fusion (0029-1867), respectively. CD-1 female mice (n=3) were immunized by three subcutaneous injections in the neck. The first two injections were made one week apart and the third injection 3 weeks after the second one. No adverse side effects were observed during the totality of the experimental period. Blood samples were taken just before the first priming injection (preimmune serums) and fourteen days after the last boost immunization (immune serums). The blood aliquots were allowed to clot at room temperature for an hour, and then centrifuged at 10,000 g for 10 min at 4° C. The sera were harvested and kept at −20° C. until subsequent analysis.

The IgG antibodies from the sera harvested from the animals were able to bind amino acid fragments comprising epitopes from either SACOL0442 or SACOL0720 or to polypeptide SACOL0029 or SACOL1867 in ELISA assays with antibody titers of 1/6400 or higher. The fusion of peptides and polypeptides used for immunization and the polypeptides or amino acid fragments used as antibody targets in ELISA assays are shown in the Table IV below.

previously described (Allard et al. 2013). Except otherwise stated, *S. aureus* strains were grown in tryptic soy broth (TSB) and agar (TSA) (BD, ON, Canada), and *Escherichia coli* DH5a were grown in LB and LBA medium (BD). Whenever required, ampicillin (100 µg/ml) (Sigma, Oakville, Ontario, Canada), chloramphenicol (20 µg/ml) (ICN Biomedicals, Irvine, Calif.), and erythromycin (10 µg/ml) (Sigma) were added to agar plates. For the immunological tests, four different bovine mastitis isolates were selected corresponding to some of the predominant *S. aureus* spa types found in Canadian dairy herds and elsewhere in the world (Veh et al., 2015; Mitra et al., 2013). Strain SHY97-3906 (spa t529) was isolated from a case of clinical bovine mastitis that occurred during the lactation period, and CLJ08-3 (spa t359) was originally isolated from a cow with persistent mastitis at dry-off (Allard et al., 2013). Strains Sa3151 (spa t13401) and Sa3181 (spa t267) were obtained from the Canadian Bovine Mastitis and Milk Quality Research Network (CBMMQRN) Mastitis Pathogen Culture Collection (Université de Montreal, Faculté de médecine vétérinaire, St-Hyacinthe, QC, Canada), and were isolated from cases of subclinical intramammary infections.

TABLE IV

Mixed polypeptide fusion vaccine and antibody response targets

A mixture of the fusion of peptides 0442-0720 and polypeptide fusion 0029-1867 was used for vaccination (vaccine #6)
The epitopes are in bold and the linker sequence is italicized 0442-0720: KDGGKYTLESHKELQ*EAAAKEAAAK*KDINKIYFMTDVDLGGPTFVLND (SEQ ID NO: 3)

0029-1867: SACOL0029-*GGGGSGGGGSGGGGS*-SACOL1867 (SEQ ID NO: 55)

Peptides and polypeptides bound by IgG from vaccinated mice in an ELISA assay

GEHLPKGNIVINTKDGGKYTLESHKELQKDRENVKINTAD (fragment encoded by SACOL0442)
(SEQ ID NO: 2)
(see sequence in FIG. 21I, Item VII-fusions);

KDINKIYFMTDVDLGGPTFVLNDKDYERKYKKHIVSQFGFDLKHKKDALA (fragment encoded by SACOL0720)
(SEQ ID NO: 27) (see sequence in FIG. 21I, Item VII-fusions);

SACOL1867 (SEQ ID NO: 40) (see his-tagged sequence in FIG. 21F, Item IV);

SACOL0029 (SEQ ID NO: 8) (see his-tagged sequence in FIG. 21A, Item I);

This demonstrates that a combination of fusions (e.g., peptide fusion 0442-0720 mixed with the polypeptide fusion 0029-1867) can be used to immunize and elicit an immune response in a mammal. The obtained immune response includes the production of antibodies that recognize amino acid sequences encoded from either SACOL0442 or SACOL0720 or SACOL0029 or SACOL1867.

Example 15: Materials and Methods for Attenuated Live Mutant

Bacterial Strains and Growth Conditions.

Strains used in Examples 15-25 are listed in Table V. *S. aureus* ATCC 29213 and its isogenic mutant Δ720 were

TABLE V

Strains and plasmids used in Examples 15-25

| Strain or plasmid | Relevant details | Source or reference |
|---|---|---|
| Strains | | |
| *S. aureus* | | |
| RN4220 | Derivative of 8325-4, acceptor of foreign DNA, r- | Kreiswirth et al. (1983) |
| ATCC29213 | Wild Type, SACOL0720 (vraG) positive, normal phenotype | American Type Culture Collection |
| Δ720 | SACOL0720 (vraG) transposon insertion isogenic mutant of ATCC29213 | Allard et al. (2013) |

TABLE V-continued

Strains and plasmids used in Examples 15-25

| Strain or plasmid | Relevant details | Source or reference |
|---|---|---|
| ΔhemB | hemB::EM$^r$; isogenic mutant of ATCC29213, SCV phenotype | As described herein |
| Δ720ΔhemB | hemB::EM$^r$; isogenic mutant of Δ720, SCV phenotype | As described herein |
| E. coli | | |
| SHY97-3906 (spa t529) | | isolated from a case of clinical bovine mastitis |
| CLJ08-3 (spa t359) | | isolated from a cow with persistent mastitis at dry-off |
| Sa3151 (spa t13401) | | CBMMQRN) Mastitis Pathogen Culture Collection |
| Sa3181 (spa t267) | | CBMMQRN) Mastitis Pathogen Culture Collection |
| DH5α | lacZDM15) hsdR17 recA1 endA1 gyrA96 thi-1 relA1 | Invitrogen (ON, Canada) |
| Plasmids | | |
| pBT2 | Shuttle vector, temperature-sensitive, Apr Cmr | Brückner (1997) |
| PBT-E | pBT2 derivative, inserted ErmA cassette | As described herein |
| pBT-EhemB | pBT2 derivative, for hemB deletion; Ap$^r$Cm$^r$Em$^r$ | As described herein |

Cell Culture Conditions.

An established bovine mammary epithelial cell (BMEC) line, MAC-T (Huynh et al., 1991), was used as a cell culture model of infection. The MAC-T cells were routinely cultured and maintained in Dulbecco's modified Eagle's medium (DMEM) containing 10% heat-inactivated fetal bovine serum (FBS), supplemented with 5 µg/ml insulin (Roche Diagnostics Inc., Laval, Canada) and 1 µg/ml hydrocortisone (Sigma), and incubated at 37° C. in a humidified incubator with 5% $CO_2$. Cell culture reagents were purchased from Wisent (St-Bruno, QC, Canada).

DNA Manipulations.

Recommendations from the manufacturers of kits were followed for genomic DNA isolation (Sigma), plasmid DNA isolation (Qiagen, ON, Canada), extraction of DNA fragments from agarose gels (Qiagen) and purification of PCR products and of digested DNA fragments (Qiagen). An additional treatment of 1 h with lysostaphin (Sigma) at 200 µg/ml was used to achieve efficient lysis of S. aureus cells in genomic and plasmid DNA isolations. Primers (IDT® Integrated DNA Technologies; Coraville, Iowa, USA) were designed to add restriction sites upstream and downstream of the amplified products. PCRs were performed using the Taq DNA Polymerase (NEB, Pickering, ON, Canada) for routine PCR or the Q5 high fidelity DNA Polymerase (NEB) for cloning, and cycling times and temperatures were optimized for each primer pair. Plasmid constructs were generated using E. coli DH5a (Invitrogen, Burlington, ON, Canada), restriction enzymes (NEB), and the T4 DNA ligase (NEB). Plasmid constructs were validated by restriction digestion patterns and DNA sequencing before electroporation in S. aureus RN4220 (Kreiswirth et al., 1983) and in final host strains. Plasmids used in Examples 15-25 are listed in Table V above.

Generation of Live Attenuated S. aureus Strain Δ720 and ΔhemB.

An isogenic hemB mutant of the ATCC 29213 strain was constructed, in which the hemB gene was deleted and replaced by the insertion of an emrA cassette by homologous recombination. S. aureus ATCC 29213 mutant for gene SACOL0720 (Δ720) was generated using the TargeTron™ Gene Knockout System (with the TargeTron™ Vector pNL9164 (Sigma-Aldrich Canada Ltd.) (Chen et al., 2007) for disruption of bacterial genes by insertion of group II introns (fragment size of approx. 2 Kb as previously described (Allard et al., 2013) between nucleotide 803 and 804 in S. aureus ATCC29213. The manufacturer protocols and recommendations were followed.

Generation of ΔhemBΔ720.

Figure 8A:
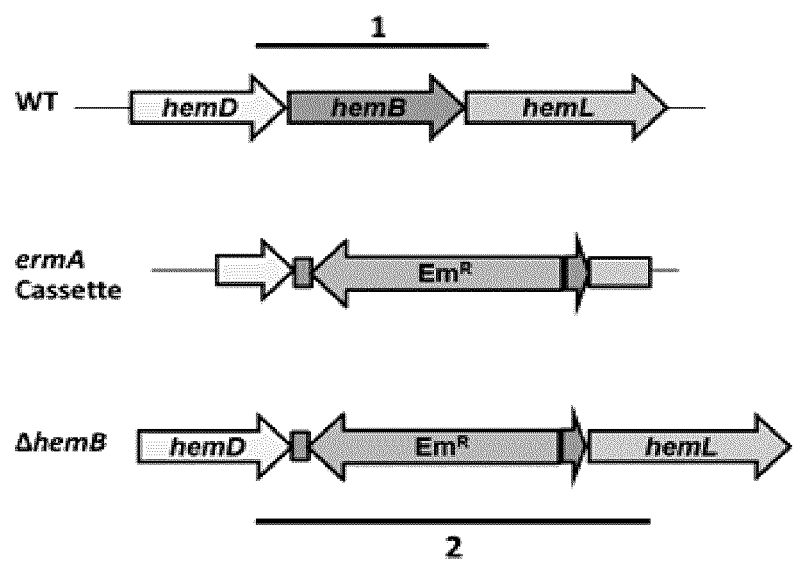
FIGS. 8A-B. Deletion of hemB in ATCC29213 and Δ720 strains of *Staphylococcus aureus*.
Figure 8B:
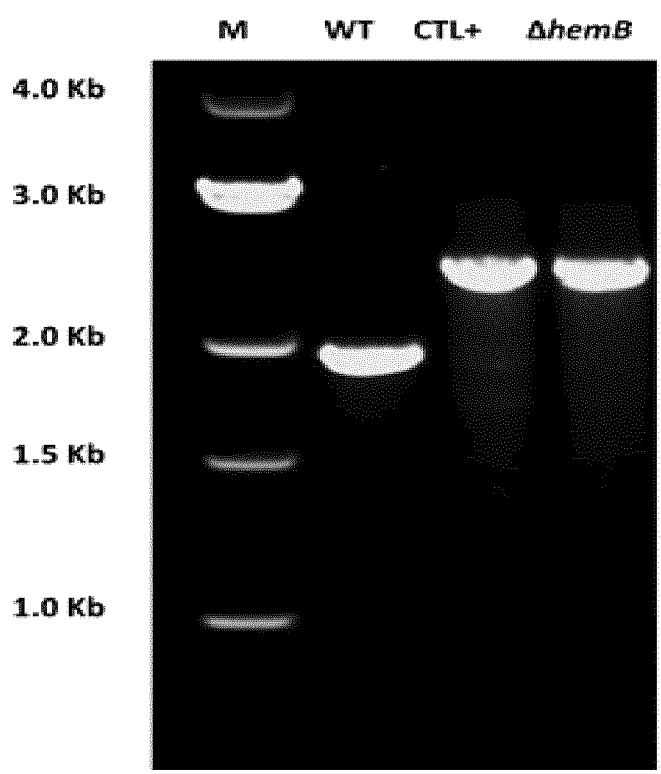

To achieve a second mutation in gene hemB in order to obtain a SCV phenotype in the Δ720 mutant genetic background, another strategy was used: the temperature-sensitive pBT2-hemB:emrA (pBT-E:hemB) was used in a strategy previously described (Mitchell et al., 2008), with some modifications. Briefly, the pBT-E plasmid was constructed by the insertion of an ermA cassette between XbaI and SaiI sites of temperature-sensitive shuttle vector pBT2 (Brückner, 1997). The flanking regions of gene hemB (SA-COL1715) DNA fragments were amplified from S. aureus ATCC 29213 and were cloned on both sides of the ermA cassette into the plasmid pBT-E. The plasmid was then transferred for propagation into S. aureus RN4220 (res-). After bacterial lysis with lysostaphin (200 µg/ml for 1 h at room temperature), plasmid DNA was isolated and used to transform ATCC 29213 and Δ720 by electroporation. For plasmid integration and mutant generation, bacteria were first grown overnight at 30° C. with 10 µg/ml of erythromycin and a 1 µg/ml hemin supplementation (Sigma-Aldrich, ON, Canada). Bacteria were then diluted 1:1000 and grown overnight at 42° C. with 2.5 µg/ml of erythromycin and 1 µg/ml hemin. This step was repeated twice. Finally, bacteria were diluted 1:1000 and grown overnight at 42° C. without antibiotics. Mutants with the inactivated hemB gene were selected as resistant to erythromycin and sensitive to chloramphenicol, together with an SCV phenotype that can be complemented (i.e., reversion to the normal growth phenotype) by a 5 µg/ml hemin supplementation on agar plates. The deletion of hemB in the ATCC 29213 (i.e., ΔhemB) and Δ720 (i.e., ΔhemBΔ720) strains was confirmed by PCR (see FIGS. 8A and B).

Hemin Supplementation in Broth Culture.

To evaluate the capacity of hemin to restore optimal growth kinetics of S. aureus ΔhemB and the double mutant Δ720ΔhemB, overnight bacterial cultures were diluted to an $A_{600\ nm}$ of approximately 0.1 in culture tubes containing fresh BHI supplemented with hemin (Sigma) added at various concentrations. The $A_{600\ nm}$ of cultures was monitored at different points in time during the incubation period at 35° C. (225 rpm).

S. aureus Infection of Bovine Mammary Epithelial Cells (BMECs).

MAC-T BMECs were used for the characterization of intracellular infectivity and persistence of ATCC 29213 (WT) and its isogenic mutants. Forty-eight hours before infection, 1×10$^5$/ml MAC-T cells were seeded on treated 24-well plates (Corning) to obtain 30% confluence. Monolayers were grown to confluence under 10% $CO_2$ at 37° C. Six hours prior to infection, monolayers were washed with DMEM and incubated with invasion medium (IM) (growth medium without antibiotics containing 1% heat-inactivated FBS). Overnight bacterial cultures were diluted 1:20 in fresh TSB and grown to mid-logarithmic growth phase, then washed with PBS and diluted in IM to a multiplicity of infection of 10. Invasion was achieved by incubating monolayers with bacteria for 3 h. Monolayers were then washed with DMEM and incubated with IM containing 20 µg/ml lysostaphin to kill extracellular bacteria. The use of lysostaphin to kill extracellular normal and SCV *S. aureus* was previously validated in cell invasion assays (Moisan et al., 2006 and Tuchscherr et al, 2011). The treatment was allowed for 30 min to determine CFUs at 3 h of infection, or for an additional 12 or 24 h. Then, following extensive washing with Dulbecco's Phosphate-Buffered Saline (DPBS), monolayers were detached with trypsinization and lysed with 0.05% Triton X-100 and PBS was added to obtain a final 1× concentration. The lysate was serially diluted and plated on TSA for CFUs determination.

BMECs Viability and Metabolic Activity Assay.

To determine the cytotoxic damage inflicted by *S. aureus* ATCC 29213 (WT) and its isogenic mutants on MAC-T cells, the MTT cell metabolic activity assay that measures the reduction of 3-[4,5-dimethylthiazol-2-yl]-2,5 diphenyl tetrazolium bromide (MTT) into an insoluble formazan product in viable cells, was performed. The assay followed the method of Kubica et al. (Kubica et al, 2008) with some modifications. Briefly, *S. aureus* infection of cells was achieved as described in the persistence assay, but instead of lysis after 12 h or 24 h, cells were incubated with 100 µl of MTT reagent (5 mg/ml) (Sigma) in DPBS for 2 h at 37° C. Following this, an acidic solvent solution of 16% SDS and 40% PMF, pH 4.7, was added to lyse the cells and solubilize the crystals of formazan overnight. The samples were read using an Epoch microplate reader (Biotek Instruments Inc.) at a wavelength of 570 nm. All assays were performed in triplicate, and control wells with uninfected cells (high viability control) or lysed WT infected cells (bacteria background control; treated with 0.05% triton X-100 for 10 min before MTT addition) were included to each plate. The level of metabolic activity was calculated using the following formula:

(absorbance of the sample−background control)/high control)×100.

Virulence in the Mouse Mastitis Model.

The mouse mastitis model of infection is based on that previously described (Brouillette, 2005; Brouillette, 2004). All the experiments performed with mice were approved by the ethics committee on animal experimentation of the Faculté des sciences of the Université de Sherbrooke and were conducted in accordance with the guidelines of the Canadian Council on Animal Care. Briefly, one hour following removal of 12-14 day-old offspring, lactating CD-1 mice (Charles River Laboratories) were anesthetized with ketamine and xylazine at 87 and 13 mg/kg of body weight, respectively, and mammary glands were inoculated under a binocular. Mammary ducts were exposed by a small cut at the near ends of teats and a 100 µl-bacterial suspension containing $10^2$ CFUs in endotoxin-free phosphate-buffered saline (PBS, Sigma) was injected through the teat canal using a 32-gauge blunt needle. Two glands (fourth on the right [R4] and fourth on the left [L4] from head to tail) were inoculated for each animal. Mammary glands were aseptically harvested at the indicated times, weighed and visually evaluated for inflammation. Bacterial burden was evaluated after mechanical tissue homogenization in PBS, serial dilutions, and plating on agar for CFU determination. In a second experiment, homogenized glands were conserved for protein extraction for myeloperoxidase (MPO) activity enzymatic assays.

Mammary Gland Protein Extraction.

Total protein extraction from mammary glands was performed by an optimized method previously described (Pulli et al., 2013), with some modifications. Mammary tissues were homogenized in a buffer containing a final concentration of potassium phosphate of 50 mM, pH 6.0, and hexadecyltrimethylammonium bromide (CTAB) 50 mM (Sigma). The samples were then sonicated, freeze-thawed in liquid nitrogen, and centrifuged at 2000 g for 15 min at 4° C. Finally, the fat layer was removed by aspiration, and supernatants were saved for a final centrifugation of 15 min at 15 000 g, to discard every cellular debris. Supernatants were distributed in aliquots and kept at −80° C. until use for the enzymatic assays or protein concentration determination as measured by the bicinchoninic acid method (BCA) Protein Assay Kit (Thermo-Scientific).

MPO Activity Assay.

Neutrophil recruitment in mammary tissues was measured by quantification of MPO enzyme activity by the o-dianisidine-$H_2O_2$ method, modified for microplates (Bradley, R D. and Rothstein, GPPC., 1982). In a 96-well microplate, 10 µl of tissue extraction supernatants were incubated with a solution of o-dianisidine hydrochloride (0.167 mg/mL) (Sigma) and 0.0005% $H_2O_2$(Sigma) in 50 mM CTAB phosphate buffer 50 mM, pH 6.0. The MPO activity was measured kinetically with intervals of 15 s over a period of 5 min in an Epoch microplate reader at 460 nm. A Unit of MPO was considered as the amount of enzyme that degrades 1 pmol of $H_2O_2$/min at 25° C., assuming an absorption coefficient of 11.3 $mM^{-1}$ $cm^{-1}$ at 460 nm for o-dianisidine (Zhang et al., 2004). Results were expressed as units of MPO per g of gland.

Mouse Immunizations with the Live Attenuated Mutant Δ720ΔhemB.

The immunogenic properties of the attenuated strain Δ720ΔhemB administered as a live vaccine were evaluated in mice. In preliminary studies, the mice well tolerated intramuscular and subcutaneous (SC) injections of the attenuated strain. The doses of $10^6$, $10^7$ and $10^6$ CFUs and the SC route were selected for subsequent experiments. For the preparation of bacterial inoculum, *S. aureus* Δ720ΔhemB colonies previously grown on BHIA plates were washed twice in ice cold PBS and suspended in PBS containing 15% glycerol, then aliquoted and kept at −80° C. until subsequent use. The viable bacterial counts in the inoculum preparation was validated by serial dilution plating on BHIA. CD-1 mice were randomly divided into 3 groups: group 1 (n=3) received a dose of $10^6$ CFUs; group 2 (n=3), $10^7$ CFUs, and group 3 (n=3), $10^8$ CFUs. Mice were immunized by two subcutaneous injections of bacteria in PBS (100 µl), in the neck, two weeks apart. Blood samples were taken just before the priming injection (preimmune serums) and ten days after the boost immunization (immune serums). Blood aliquots were allowed to clot at room temperature for an hour and then centrifuged at 10,000 g for 10 min at 4° C. The serums were collected and kept at −20° C. until subsequent analysis.

Preparation of *S. aureus* Cell Extracts.

Preparation of *S. aureus* whole cell extracts was done as previously described with some modifications (Asli et al., 2016). Briefly, overnight bacterial cultures were diluted 1/1000 in fresh BHI broth, and then incubated at 35° C. (225 rpm) until an A600 nm of ~0.8 was reached. Bacterial cells were centrifuged and pellets were washed in ice-cold PBS twice and suspended with the addition of 5 ml of PBS per ml of pellet. Bacterial suspensions were first treated with lysostaphin (Sigma) (100 µg/ml of pellet) for 1 h at 37° C., and then 3 µg of protease inhibitor cocktail (Sigma), 8 µg of RNAse A (Sigma) and 8 µg of DNAse (Qiagen) per ml of pellet were added to the suspension. After 30 min at room temperature, cells were mechanically disrupted by 3 to 4 passages in a SLM Aminco™ French Pressure cell disrupter, and then centrifuged at 12,000×g and 4° C. for 10 min to remove unbroken cells. Supernatant was collected and total protein concentration was determined as previously described with the BCA Protein Assay Kit.

Detection of Mouse Total IgG by ELISA.

Detection of serum total IgG against the Δ720ΔhemB vaccination strain and each of the bovine IMI isolates was performed to demonstrate and measure the systemic humoral response generated by the immunization of mice. For target antigens, Nunc MaxiSorp™ 96-well plates (Thermo Fisher Scientific Inc., Rochester, N.Y.) were coated with 100 µl of each of the whole S. aureus cell extracts (10 µg/ml diluted in carbonate/bicarbonate buffer, Sigma), and incubated overnight at room temperature. The plates were then saturated with PBS containing 5% skim milk powder for 1 h at 37° C., followed by a second blocking step with an addition of 5% porcine serum to prevent unspecific S. aureus protein A interactions. One hundred microliters of two-fold serial dilutions of the sera in the dilution buffer (PBS with 2% milk, 5% porcine serum and 0.025% Tween™ 20) were loaded into the plates and incubated for 1 h at 37° C. Plates were then washed three times with PBS containing 0.05% Tween™ 20, and loaded with 100 µl of horseradish peroxidase (HRP)-conjugated goat anti-mouse IgG (Jackson ImmunoResearch Laboratories Inc., West Grove, Pa.) diluted 1/5000 in the dilution buffer. After 1 h of incubation at 37° C. followed by 3 washes, peroxidase activity was detected with 3,3',5,5'-tetramethylbenzidine (TMB) reagent (KPL Inc., Gaithersburg, Md.) according to the manufacturer's recommendations.

Statistical Analysis.

Statistical analyses were carried out with the GraphPad Prism™ software (v.6.02). Intracellular bacterial CFUs and bacterial CFUs/g of gland (IMI in mice) were transformed in base 10 logarithm values before being used for statistical analyses. Statistical tests used for the analysis of each experiment and significance are specified in the figure legends.

Example 16: Construction of Strain S. aureus ATCC 29213 Δ720, ΔhemB and Δ720ΔhemB Live attenuated organisms that mimic natural infection stimulate the immune system in a powerful manner, eliciting broad and robust immune responses that produce both serum and mucosal antibodies, and effector and memory T cells which act synergistically to protect against disease (Detmer, 2006; Kollaritsch, 2000; Pasetti, 2011).

A mutation in gene SACOL0720 was shown to alter the virulence of S. aureus in experimental IMI infections in the cow (Allard et al., 2013).

Further live-attenuated strains were prepared for vaccine purposes based on the phenotypic aspects of S. aureus SCVs. SCVs do not generally generate invasive infections (i.e. additional attenuation) and can be internalized in host cells and therefore will stimulate the cell-mediated immune response in addition to the humoral immune response.

A stable S. aureus SCV was first created through the deletion of the hemB gene (ΔhemB) (see Example 15, Generation of live attenuated S. aureus strain Δ720 and ΔhemB). Further attenuation of this SCV was then achieved by inactivation of gene SACOL0720 (Δ720) (see Example 15, Generation of ΔhemBΔ720).

After infection of MAC-T bovine mammary epithelial cells, the double mutant (Δ720ΔhemB) significantly showed lower internalization and cell destruction compared to that seen with ΔhemB and Δ720, respectively.

Example 17: Strain S. aureus ΔhemBΔ720 is Attenuated in MAC-T Cells

Figure 9A:
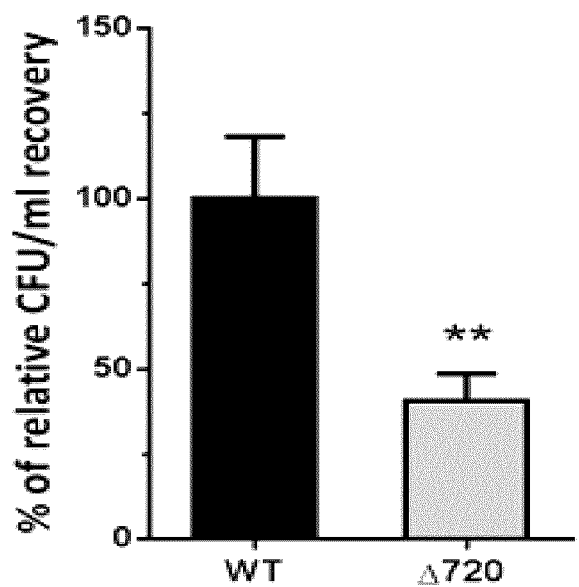
FIGS. 9A-C. show influence of *S. aureus* ΔhemB, Δ720, and ΔhemBΔ720 mutations on MAC-T cell infectivity. MAC-T cells were infected with each of the four strains for 3 h, then were incubated with lysostaphin an additional 30 min (t=3 h), 12 h or 24 h and lysed for measurement of viable intracellular bacteria (CFU).
Figure 9B:
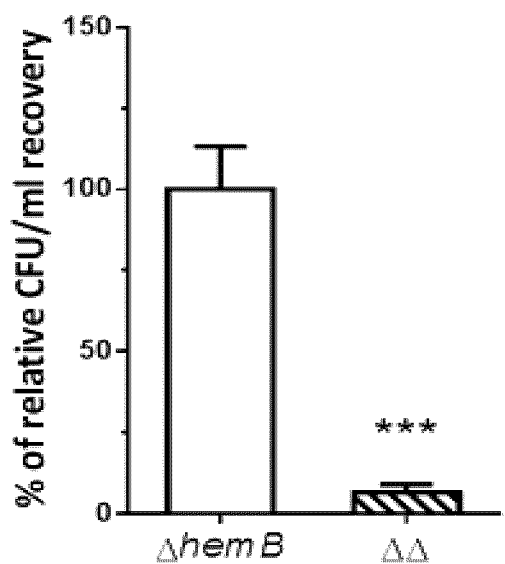
Figure 9C:
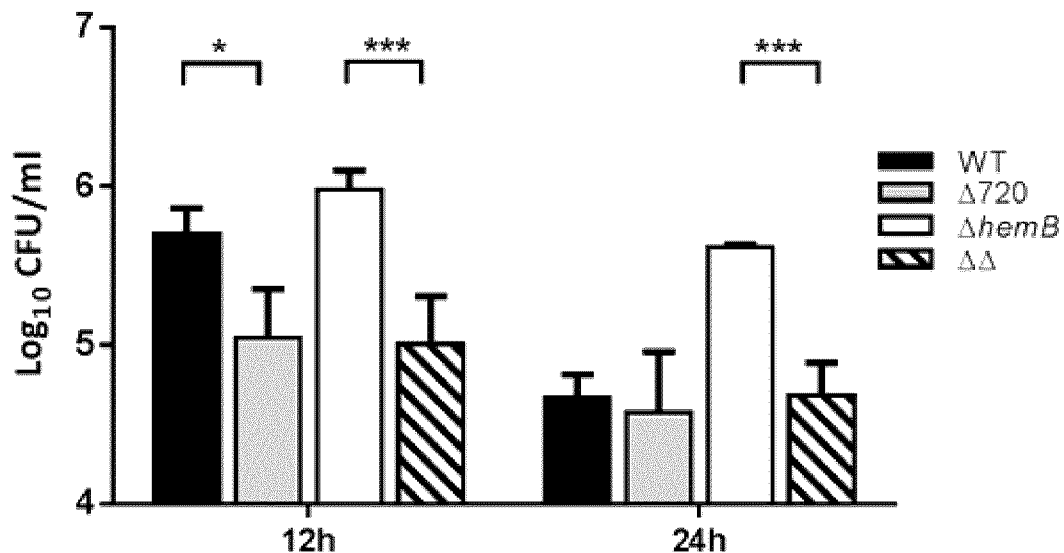
Figure 10:
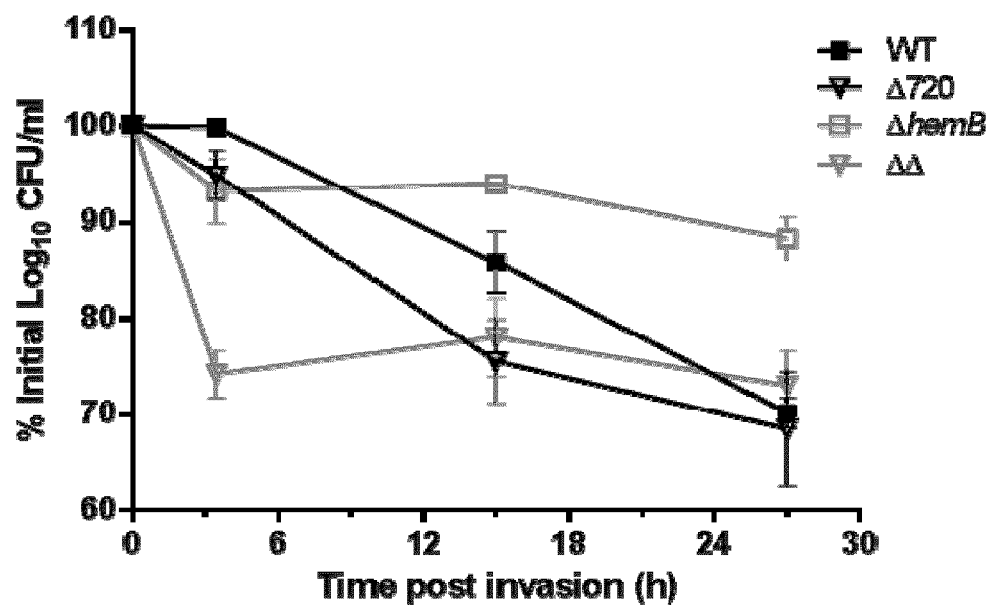
FIG. 10. shows persistence of *S. aureus* ATCC 29213 (WT) and isogenic mutants within MAC-T cells over time. MAC-T cells were infected with each of the four strains for 3 h, then were incubated with lysostaphin an additional 30 min, 12 h or 24 h and lysed for measurement of intracellular bacteria (CFU). Intracellular bacterial CFUs are expressed as the percentage of the initial inoculum after being transformed in base 10 logarithmic values (Log 10 CFU/ml). Values indicate the mean of three independent triplicate experiments with standard deviations.

The infectivity of ATCC 29213 (WT), Δ720, ΔhemB and ΔhemBΔ720 strains were then compared in intracellular persistence assays using MAC-T cells. By comparing the three mutant strains to their isogenic WT parent, distinct effects of mutations in genes hemB and SACOL0720 were observed. A short 3-h incubation of bacteria with cell monolayers followed by the addition of lysostaphin to eliminate extracellular bacteria demonstrated high levels of internalization into MAC-T cells for both WT and ΔhemB strains, based on the recovery of viable intracellular bacteria (CFUs) (FIGS. 9A and B). The single Δ720 mutant however showed significantly less ($P \leq 0.01$) internalization compared to its parental WT strain (FIG. 9A). The reduction in internalization seen in Δ720 was even more pronounced when comparing the double mutant ΔhemBΔ720 to ΔhemB, with a 10-fold reduction of inoculum recovery in this 3-h internalization assay (P 0.001, FIG. 9B). This initial reduction of internalized bacterial load was still apparent 12 and 24 h post invasion (PI) for the double mutant strain ΔhemBΔ720 (FIG. 9C), as illustrated by the 1-$\log^{10}$ reduction of CFU/ml at both time points compared to that observed for ΔhemB ($P \leq 0.001$). The difference in initial intracellular bacterial loads between the single Δ720 mutant and WT strains (FIG. 9A) gradually vanished with longer incubation times (FIG. 9C), as both strains did not well persist in MAC-T cells (FIG. 10). On the opposite, intracellular CFUs recovered for the single ΔhemB strain was significantly higher compared to that recovered for the three other strains at 24 h PI (FIG. 9C, $P \leq 0.001$ against all). Overall and as expected for the SCV phenotype, the ΔhemB strain showed a higher intracellular persistence than any other strain over time (FIG. 10). These results suggest that the Δ720 mutation mainly reduces the internalization process into MAC-T cells. Results further demonstrate that the ΔhemBΔ720 mutant is still capable of internalization and persistence into BMECs but at a much lower degree than that seen with the single ΔhemB mutant.

The ΔhemBΔ720 and ΔhemB SCVs cause low BMEC disruption. As reported above, ΔhemB and ΔhemBΔ720 SCV strains showed a greater persistence over time in MAC-T cells, as illustrated by their sustained viability at 12 and 24 h PI in comparison with WT and Δ720 strains (FIGS. 9C and 10). The percentage of the inoculum recovered from cells stayed nearly the same from 0 to 24 h after lysostaphin addition, both for the double and single hemB mutants, with a slight increase at 12 h, indicating intracellular growth (FIG. 10). Both strains started to decrease at a slow rate after this time of infection. However, the apparent reduction of intracellular CFUs for the WT and Δ720 strains was concomitant with the visual observation of increasing damage to cell monolayers over time, in comparison to that observed with strains of the SCV phenotypes.

MAC-T Cells Viability was Also Evaluated Following Infection by Each of the Four Strains Studied.

Figure 11A:
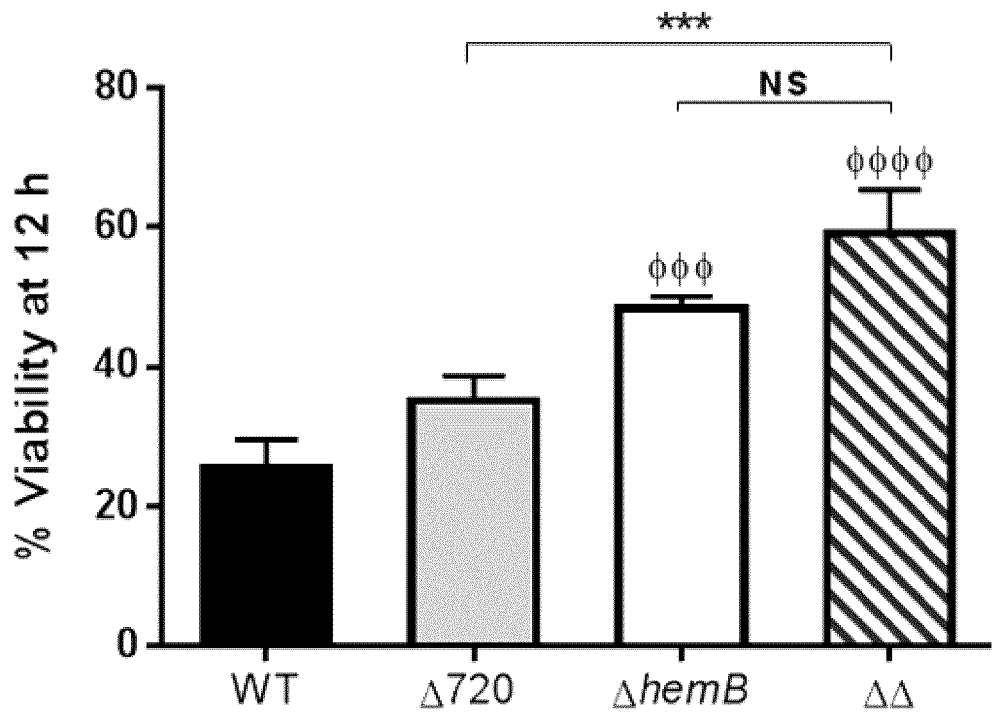
FIGS. 11A-B. shows viability of MAC-T cells infected by *S. aureus* ATCC 29213 (WT) and isogenic mutants. MAC-T cells were infected with each of the four strains for 3 h, then were incubated with lysostaphin for 12 h (FIG. 11A) or 24 h (FIG. 11B). MTT viability assays were then performed with a method described in Kubica et al., 2008. The results are reported as percent viability relative to uninfected cells and are expressed as the mean with SD of three independent experiments done in triplicate. Statistical significance with (ϕ) symbol are compared to the WT (Two-way ANOVA and Tukey's multiple comparisons test: * or ϕ: P≤0.05; : P≤0.01; *: P≤0.001; ϕϕϕϕ: P≤0.0001).
Figure 11B:
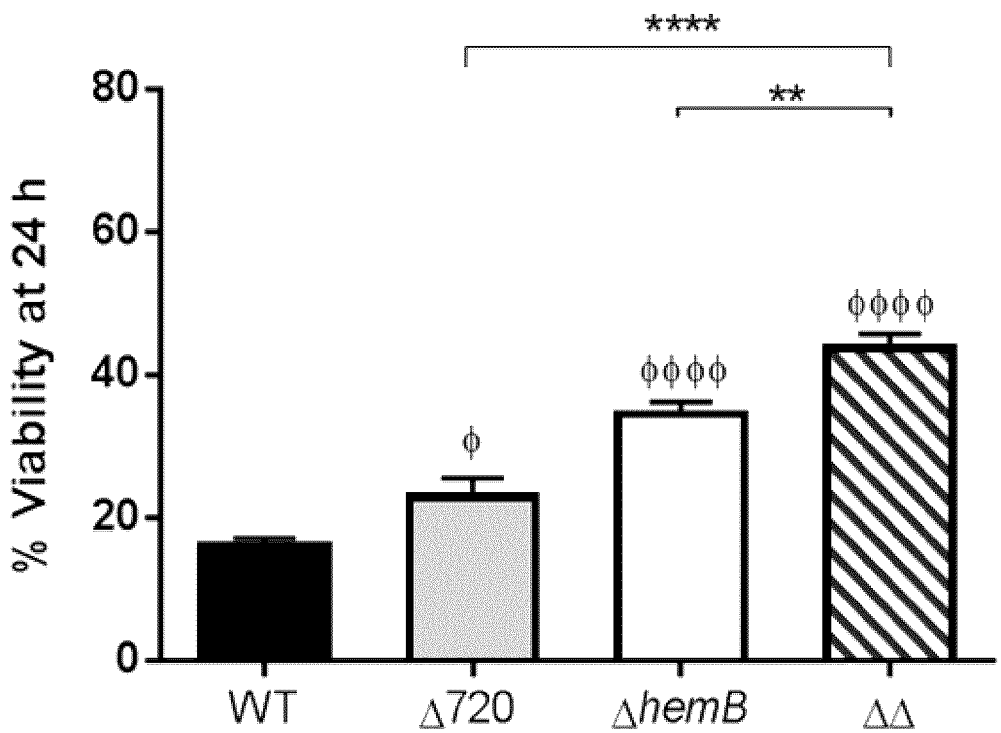

MAC-T cell viability was evaluated by the MTT method (Kubica et al., 2008). Results show that both SCV strains (ΔhemB and ΔhemBΔ720) caused significantly less MAC-T killing in this assay in contrast to the WT and Δ720 strains. When compared to ΔhemB, the WT strain nearly reduced by half the viability of cells at 12 h (FIG. 11A: WT: 25.4%; ΔhemB: 48.4%). This difference was still apparent at 24 h (FIG. 11B: 16.3% vs. 34.5%, respectively), even if the bacterial load was 10 times higher for the ΔhemB mutant (FIG. 9C). The MAC-T cells were more damaged by ΔhemB than by the double mutant Δ720ΔhemB but the difference was only significant at 24 h ($P \leq 0.01$). When compared directly to the WT strain, the double mutant Δ720ΔhemB sustained epithelial cells viability 2.3 times more at 12 h (FIG. 11A) and 2.7 times more at 24 h (FIG. 11B) (12 and 24 h: $P \leq 0.0001$). Therefore, the greater intracellular persistence of both SCVs strains compared to the WT and Δ720 strains over time (FIG. 10) was likely to be attributed to a lower toxicity of the SCVs to MAC-T cells (FIG. 11). Taken together, results from the BMEC infection assays provided evidence of an additive effect of both ΔhemB and Δ720 mutations for the attenuation of the WT strain.

Example 18: Strain *S. aureus* ΔhemBΔ720 is Attenuated in a Mouse IMI Model

Figure 12:
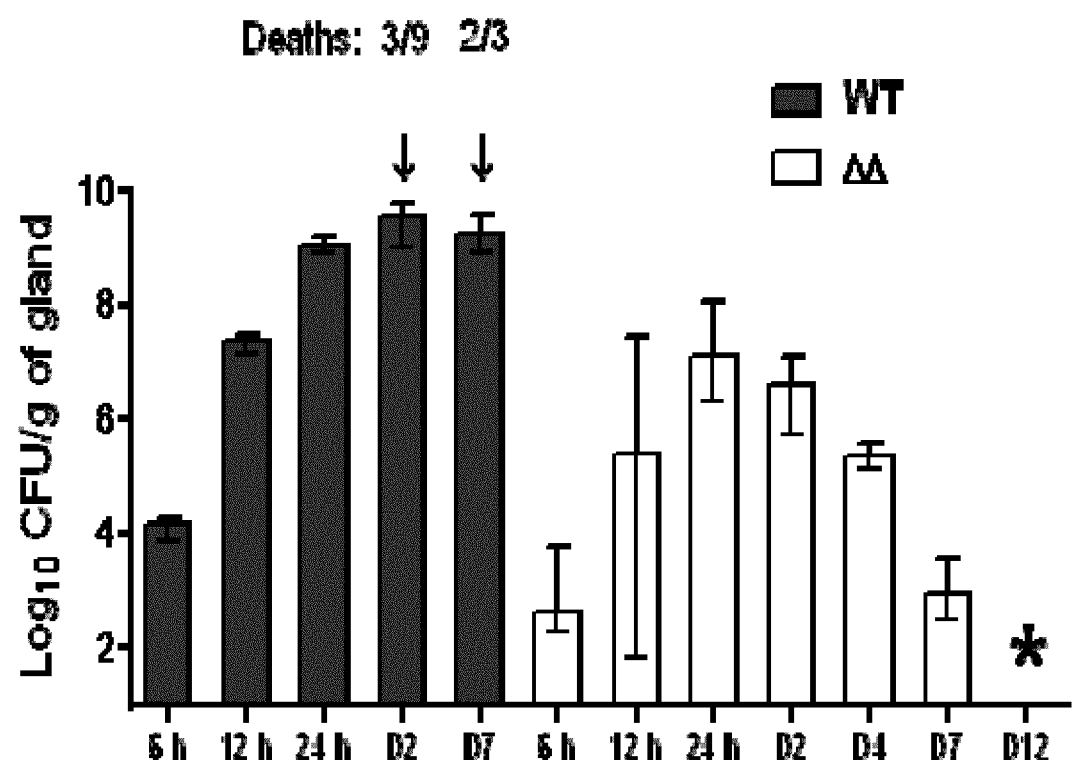
FIG. 12. Shows murine IMIs with the parental (WT) and ΔhemBΔ720 (ΔΔ) strains. Mice were infected as previously described and glands harvested at the indicated hour (h) or day (D) after infection. Each column represents the median value of bacterial CFU counts for a group of glands, and ranges are indicated by bars. A minimum of six glands per group were used excepted for the WT strain at D7 (2 glands: only one mouse survived). Mortality of mice at specific time points is indicated by arrows. The asterisk indicates the clearance of ΔhemBΔ720 from glands (below the detection limit of 10 CFU/gland).

To attest attenuation of ΔhemBΔ720 in an in vivo model of infection, the virulence of the double mutant was evaluated and compared to the WT strain in a murine IMI model (Brouillette and Malouin, 2005). For both strains, the exponential phase of infection took place mainly within the first 12 h post-infection, while the maximal bacterial burden was reached at 24 h for the double mutant and 48 h (day 2 [D2]) for the WT strain (FIG. 12). At 24 h, the double mutant showed a reduction of 1.9 $\log^{10}$ in mean CFU/g of gland compared to WT ($P \leq 0.05$). Also after 24 h, the mutant bacterial burden showed a constant decline until complete bacterial clearance was reached at day 12 (shown by the asterisk on FIG. 12). In contrast, the parental WT strain provoked severe invasive infections compared to the mutant, killing 3 of 9 remaining mice at day 2 and 2 of 3 mice at day 7 (FIG. 12; arrows) before glands could be harvested for those groups. Mice surviving the WT infection maintained high viable counts (9 $\log^{10}$ CFU/g of gland) at day 7, an approximate 5 $\log^{10}$ difference in bacterial burden compared to the double mutant. These results clearly demonstrate a markedly reduced capacity of strain ΔhemBΔ720 to multiply and survive in the mammary gland. The ΔhemBΔ720 double mutant is therefore strongly attenuated in a mouse intramammary infection (IMI) model and is efficiently cleared from mammary glands.

The attenuated strain ΔhemBΔ720 appears ideal for vaccination purposes and for intracellular delivery of antigens. Indeed, the low and temporary internalization of ΔhemBΔ720 should help stimulation of cell-mediated immunity, a component of the immune response that is important for defense against *S. aureus* (Fowler and Proctor, 2014).

Example 19: Inflammatory Response to Δ720ΔhemB and WT Strains Following IMI

Figure 13:
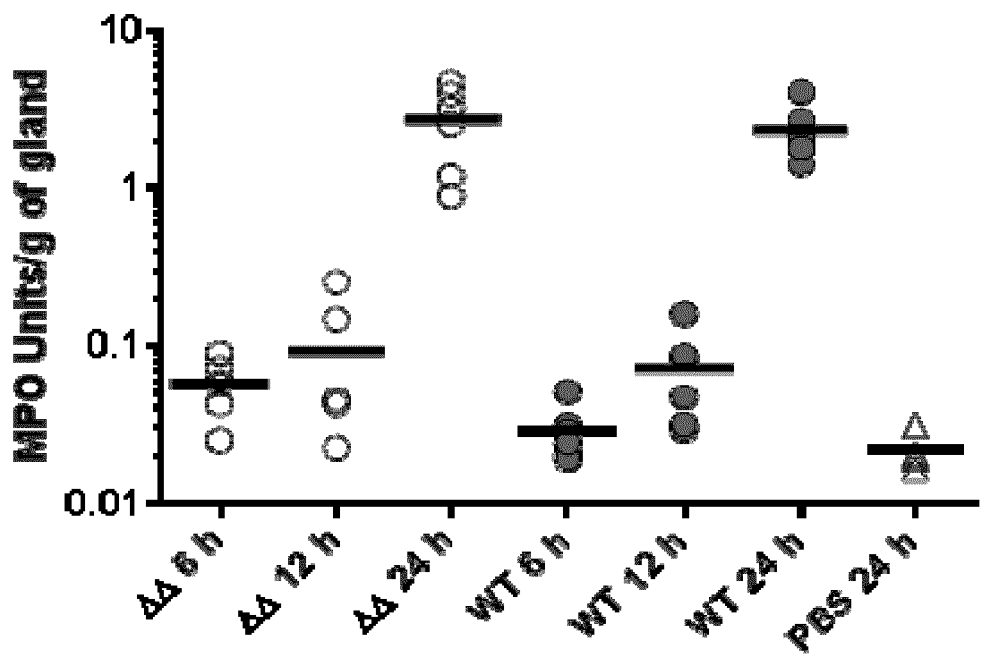
FIG. 13. Double mutant (Δ720ΔhemB) stimulates neutrophil influx in mammary glands to similar levels compared to WT in the first 24 hours following infection. Mice were infected as described in materials and methods, and a control group (PBS) of mice received a sterile PBS injection. Glands were harvested at indicated times, homogenized and kinetically assayed for MPO activity as described in materials and methods. Each dot represents MPO Units for one gland, which is shown as raw values adjusted by gram of gland. Means are represented by thick lines.
Figure 14:
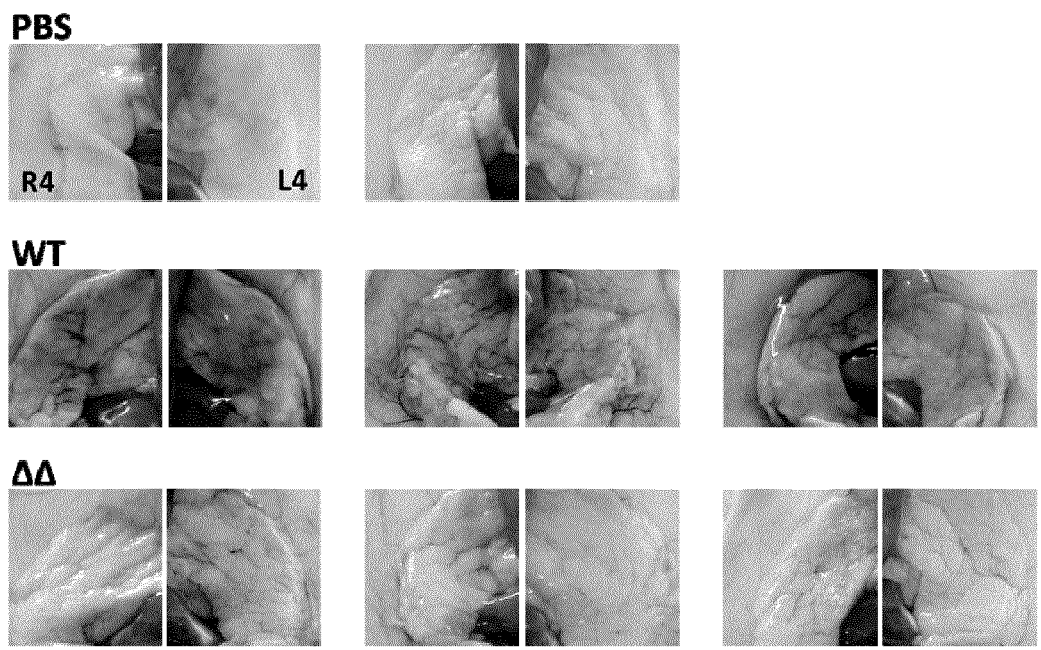
FIG. 14. Visual Inflammation of the large R4 and L4 mammary glands 24 h after mouse IMI with *S. aureus* ATCC 29213 (WT) and the double mutant Δ720ΔhemB (ΔΔ). Mice were infected as described in materials and methods, and control group (PBS) mice received a sterile PBS injection. Pictures show glands that were harvested after 24 h. In each panel, the R4 (left) and L4 (right) glands are shown.

To monitor the inflammatory response (immune response) of the mice to infections with WT and mutant strains, neutrophil infiltration in glands was evaluated by the MPO enzymatic activity of total protein extracts of gland homogenates. MPO activity in biological samples has previously been strongly correlated with absolute number of neutrophils (Xia, 1997), and is hence an adequate marker. During the first hours after infection, neutrophil recruitment followed similar profiles for the double mutant and WT infected glands (FIG. 13), with exponential intensification of apparent neutrophil infiltration from 12 h to 24 h post infection coinciding with bacterial growth albeit with a certain delay. The absolute numbers of polymorphonuclear cells in relation with the bacterial load in mammary glands was previously shown to not always peak at the same time (Brouillette, 2005). No significant difference in MPO activity could be observed at 6, 12 and 24 h between glands infected by mutant and WT strains (FIG. 13). This equivalence in apparent neutrophil infiltration did not however correlate with the visual observation of inflammation at 24 h, at which point the WT infection generated extensive redness of infected glands in comparison to the double mutant (photographs of FIG. 14). On the contrary, mutant infected glands were not visually altered on the macroscopic level compared to PBS controls. The disparity between visual assessment of inflammation and neutrophil infiltration results could be attributed to the differences in bacterial loads (FIGS. 9A-C) and the cytotoxic activity of the WT strain (FIG. 11), and could be coherent with the highly invasive and disseminative capacity of the strain via toxins and enzymes expression. Hence, these results indicate that neutrophil recruitment in the glands infected by the mutant strain was equivalent to that seen with the WT strain and that this was sufficient to allow a subsequent decline and clearance of the mutant bacterial loads.

Figure 15A:
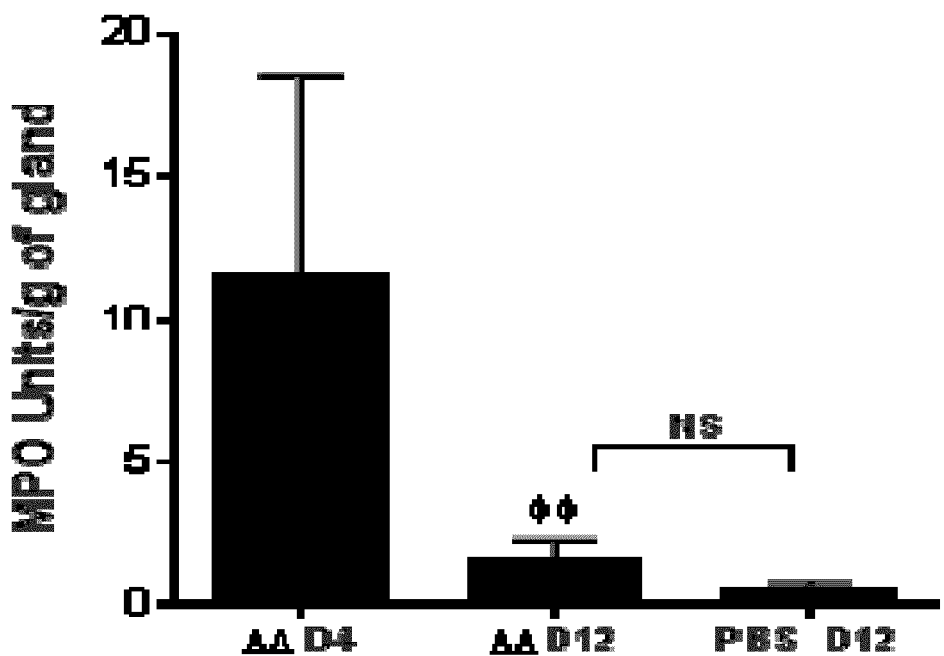
FIG. 15A. Neutrophil infiltration goes back to normal levels after clearance of the double mutant Δ720ΔhemB. Mice were infected as described in materials and methods, and a control group (PBS) of mice received a sterile PBS injection. Glands were harvested at the indicated times, homogenized and kinetically assayed for MPO activity as described in materials and methods. Columns represent means of MPO Units of a group of 6 glands (4 for the PBS control) adjusted by gram of gland, and error bars illustrate standard deviation. Statistical significance between the Day 4 and 12 groups post infection is shown by (D) symbol. One-Way ANOVA and Tukey's multiple comparison tests were used ($\phi\phi$: $P \leq 0.01$; NS: No significant difference between groups).

Lastly, to confirm strain safety, and to assess that this inflammatory response was not consequent to an inadmissible reactogenic strain, MPO activity was monitored in Δ720ΔhemB infected glands 4 and 12 days after infection. The level of activity was then compared to levels obtained with PBS injected mice. As illustrated in FIG. 15, the apparent neutrophil presence in mutant infected glands was still high 4 days after infection, with MPO activity ranging from 8 to 21 Units/g of gland. Besides, gland involution, the process by which the lactating gland returns to a morphologically near pre-pregnant state, is ordinarily associated with neutrophilic recruitment that allows phagocytosis of apoptotic cells during the remodelling of tissue (Stein, 2007). In the days following infection in this model, mice glands are already in that normal state of modification, as indicated by their rapid shrinking. However, the MPO levels in mutant infected glands went through a substantial decline between day 4 and 12, ($P \leq 0.01$). MPO levels were then considered to be back to a normal level at day 12 showing no significant difference from that obtained with the PBS-injected mice. The inflammatory response of Δ720ΔhemB infected glands goes back to normal levels with bacterial clearance (FIG. 15).

Figure 15B:
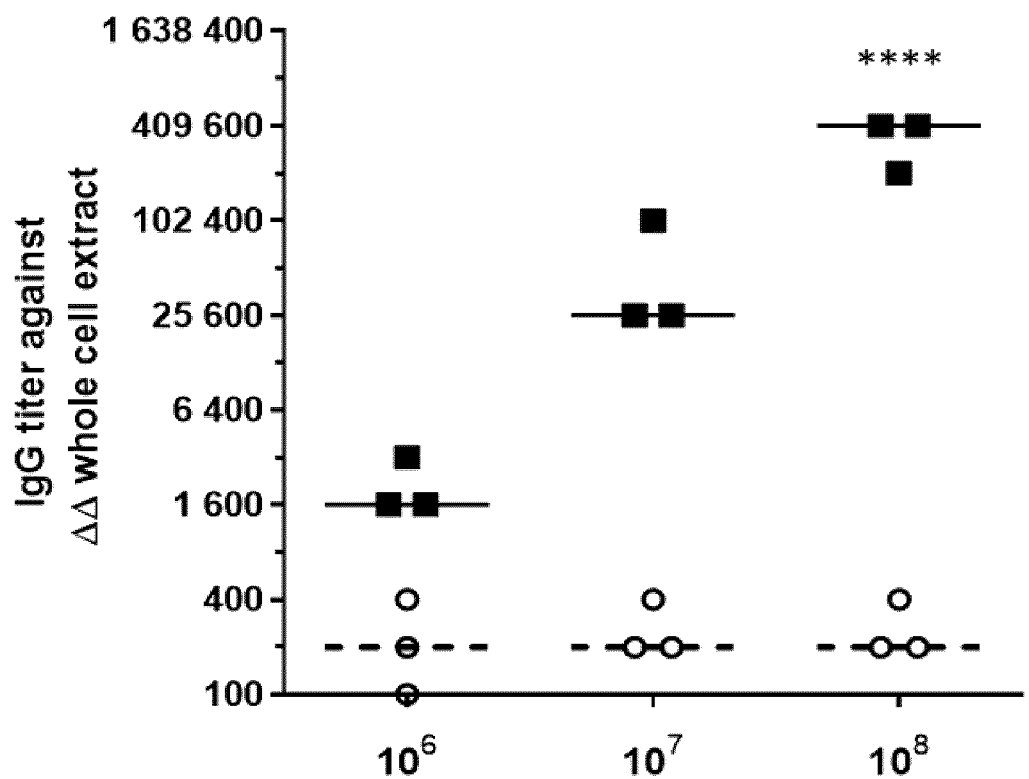
FIGS. 15B-C. Immunization of mice with the live-attenuated double mutant (Δ720ΔhemB) stimulates a strong humoral response against *S. aureus* bovine mastitis isolates of commonly found spa types. Mice were immunized as previously described: serums were collected before priming immunization (Preimmune) and ten days after the boost immunization (Immune).
Figure 15C:
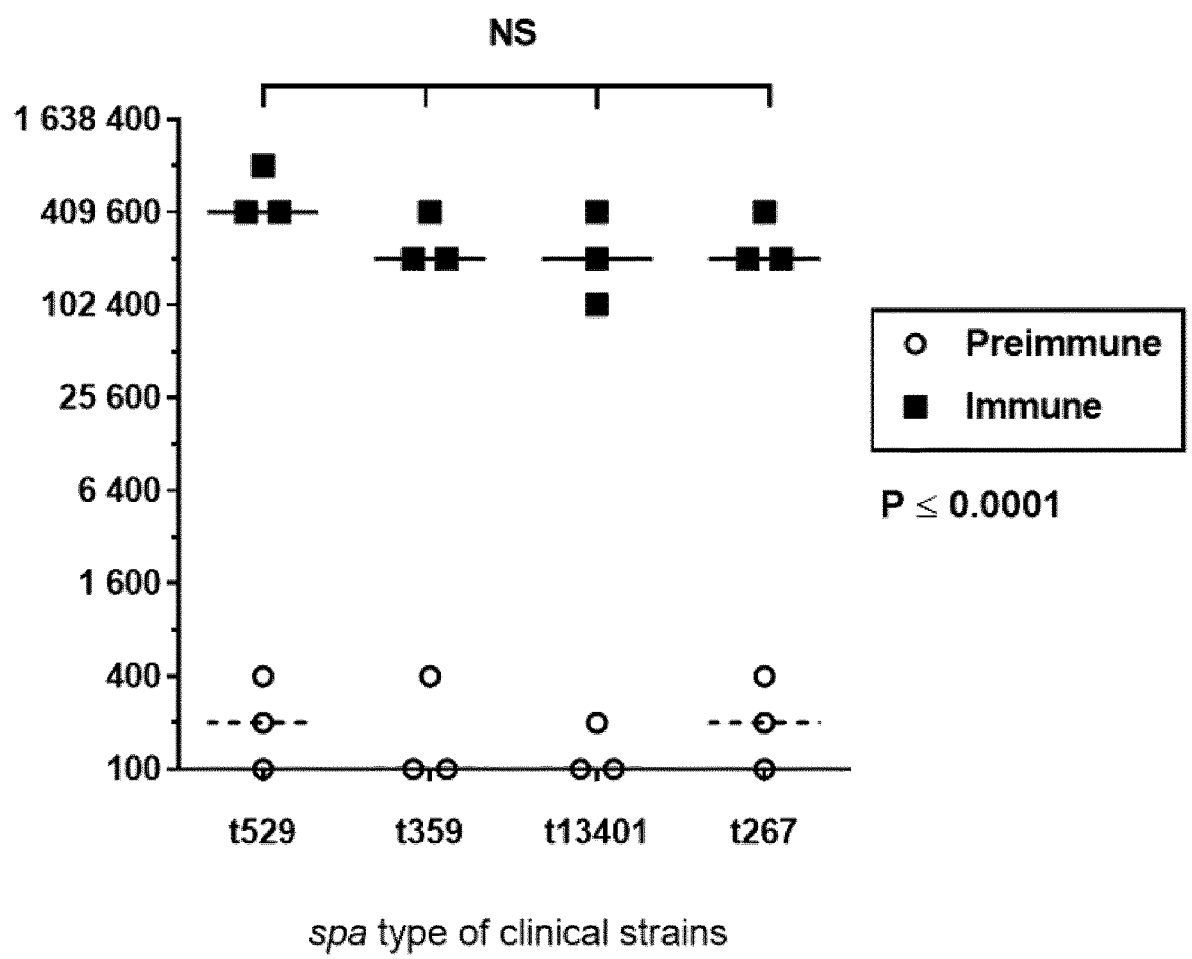

Example 20: Immunization with Δ720GΔhemB Generates a Strong Humoral Response Against Several *S. aureus* Bovine Intramammary Infection Isolates To confirm that immunization with the live Δ720ΔhemB can indeed generate a strong immune response suitable for its use as a putative live vaccine against *S. aureus* intramammary infections, mice were immunized with different doses of the live vaccine and serum total IgGs were assayed for binding to whole cell extracts of a variety of *S. aureus* bovine isolates. First, doses of $10^6$, $10^7$ and $10^8$ CFUs, administered subcutaneously in the neck, triggered no adverse effect such as modification of mice behavior or signs of inflammation or necrosis at the immunization site throughout the immunization period. Furthermore, immunization using increasing amounts of the live double mutant ATCC 29213 Δ720ΔhemB yielded increasing titers of systemic IgG antibodies against a whole cell extract of its own antigens (FIG. 15B). The titers of the immune sera were significantly higher than those of the preimmune sera, demonstrating specificity of antibody production against S. aureus antigens present in the live vaccine. Most importantly, immunization using increasing amounts of Δ720ΔhemB also yielded a consequential rise of antibody titers against a variety S. aureus strains isolated from bovine mastitis, including strains from the major spa types found in Canada and elsewhere in the world (FIG. 15C). These results clearly show that (i) immunization with the double mutant can raise an immune response, and that (ii) the strain background (ATCC 29213) share sufficient common features with bovine mastitis strains so that the antibody response also strongly recognizes strains of major spa types.

Immunization of mice using subcutaneous injections of live Δ720ΔhemB raised a strong humoral response as judged by the high titers of total IgG measured against a whole bacterial cell extract. Also, the vaccine strain Δ720ΔhemB had sufficient common features with bovine mastitis strains so that the antibody response also strongly recognized strains from a variety of common mastitis associated spa types.

Although this demonstrated that the double mutant background (ATCC 29213) share many common features with bovine mastitis strains, such a double mutant can be created in any desired genetic background if one wishes, notably in any strain that was isolated from bovine mastitis, such as but not limited to S. aureus strain RF122.

These results show that a SCV strain having some residual intracellular capabilities can allow immune cells recruitment without establishing a severe infection. Such an SCV strain may act as a live-attenuated vaccine that adequately stimulates the immune response to combat pathogens with intracellular abilities.

Example 21: Material and Methods—SACOL0442, SACOL0720, SACOL0029 and a Fusion Between SACOL1867 and SACOL0029+Attenuated Live Bacteria (Vaccine #7)

Production of the Antigens.

The production of antigens was performed as described in Example 6, in the section production of the antigens except for the additional presence of the antigen SACOL0029. His-tagged recombinant proteins of SACOL0029 were engineered and produced by GenScript, Inc. (Piscataway, N.J.). (see FIG. 21A, item I, his-tagged sequence).

Generation of Live Attenuated S. aureus Strain Δ720 hemB.

The generation of live attenuated S. aureus strain was performed as described in Example 15 (Generation of ΔhemBΔ720).

Immunization of Mice.

The immunogenic properties of recombinant S. aureus proteins encoded by the SACOL0442, SACOL0720, SACOL0029 genes and a fusion of SACOL0029 and SACOL1867 genes in combination, or not, with the live attenuated bacterial strain S. aureus Δ720ΔhemB were evaluated in mice. The mice well tolerated a dose of $10^3$, $10^5$, $10^6$, $10^7$ and $10^8$ CFU by subcutaneous injections in the neck and intramuscular injections in the thigh. The dose of $10^5$ and the subcutaneous route were selected for the following experiments.

For the preparation of bacterial inoculum, S. aureus Δ720ΔhemB colonies previously grown on BHIA plates were washed twice in ice cold PBS and resuspended in PBS containing 15% glycerol, then aliquoted and kept at −80° C. until subsequent use. To obtain the final mice immunization dose, corresponding to $10^5$ CFU of attenuated bacteria, the frozen inoculum bacterial concentration was evaluated by serial dilution plating on BHIA and then was diluted to a final concentration of $10^5$ CFU/ml in PBS on the day of immunization.

For the preparation of protein doses, SACOL0029, SACOL0442, SACOL0720, and the SACOL0029-1867 fusion polypeptide were mixed and suspended in PBS to obtain a final dose of 5 μg each. CD-1 female mice were randomly divided into 3 groups: group 1 (5 mice) received a mixed protein dose (protein Mix); group 2 (5 mice) received an attenuated bacteria (Δ720ΔhemB) dose (Δ720ΔhemB); group 3 (6 mice) received a combination of mixed proteins and attenuated bacteria (combination). CD-1 female mice were immunized by two subcutaneous injections in the neck two weeks apart. The proteins and bacterial strains doses were diluted in PBS as previously described and administered in a final volume of 100 μl for each group of mice. No adverse side effects were observed during the totality of the experimental immunization period. Blood samples were taken just before the first priming injection (preimmune serums) and ten days after the boost immunization (immune serums). The blood aliquots were allowed to clot at room temperature for an hour, centrifuged at 10,000 g for 10 min at 4° C. The sera were harvested and kept at −20° C. until subsequent analysis.

Detection of Total IgG, IgG1 and IgG2 by ELISA.

Detection of serum total IgG, IgG1 and IgG2 against each of the antigens previously used for immunization was performed as previously described with some modifications (Ster et al., *Vet. Immunol. Immunopathol.* (2010), 136: 311-318). In addition, detection of IgG against staphylococcal surface protein ClfA was performed to demonstrate the supplementary advantages of using a live strain to enhance and balance the immune response against S. aureus. Nunc MaxiSorp™ 96-well plates (Thermo Fisher Scientific Inc., Rochester, N.Y.) were coated with 75 μl of each of the test antigen (6.67 μg/mL diluted in carbonate/bicarbonate buffer, Sigma Aldrich, Oakville, ON) and incubated overnight at room temperature. The plates were then saturated with PBS containing 5% skim milk powder for 1 h at 37° C. One hundred microliters of four-fold serial dilutions of the sera in PBS containing 3% milk and 0.025% Tween™ 20 were loaded into the plates and incubated for 1 h at 37° C. The plates were washed three times with PBS containing 0.05% Tween™ 20. One hundred microliters of horseradish peroxidase (HRP)-conjugated secondary antibody were then added to the plate. The secondary antibodies used were a goat anti-mouse IgG, IgG2a and IgG1 (Jackson ImmunoResearch Laboratories Inc., West Grove, Pa.), diluted 1/5000 respectively in PBS containing 3% milk and 0.025% Tween™ 20. After 1 h of incubation at 37° C. followed by 3 washes, peroxidase activity was detected with 3,3',5,5'-tetramethylbenzidine (TMB) reagent (KPL Inc., Gaithersburg, Md.) according to the manufacturer's recommendations.

Statistical Analysis.

Statistical analysis of the antibody titers and of the correlation was performed using GraphPad Prism™ v6.05.

Example 22: The Fusion of Antigens and the Combination with a Live Attenuated *S. aureus* Strain Induces High Antibody Titers in Mice—Vaccine #7

The antigens and live attenuated *S. aureus* strain Δ720ΔhemB are produced as described in Example 21. Mice are immunized and IgGs detected as described in Example 21.

Figure 16:
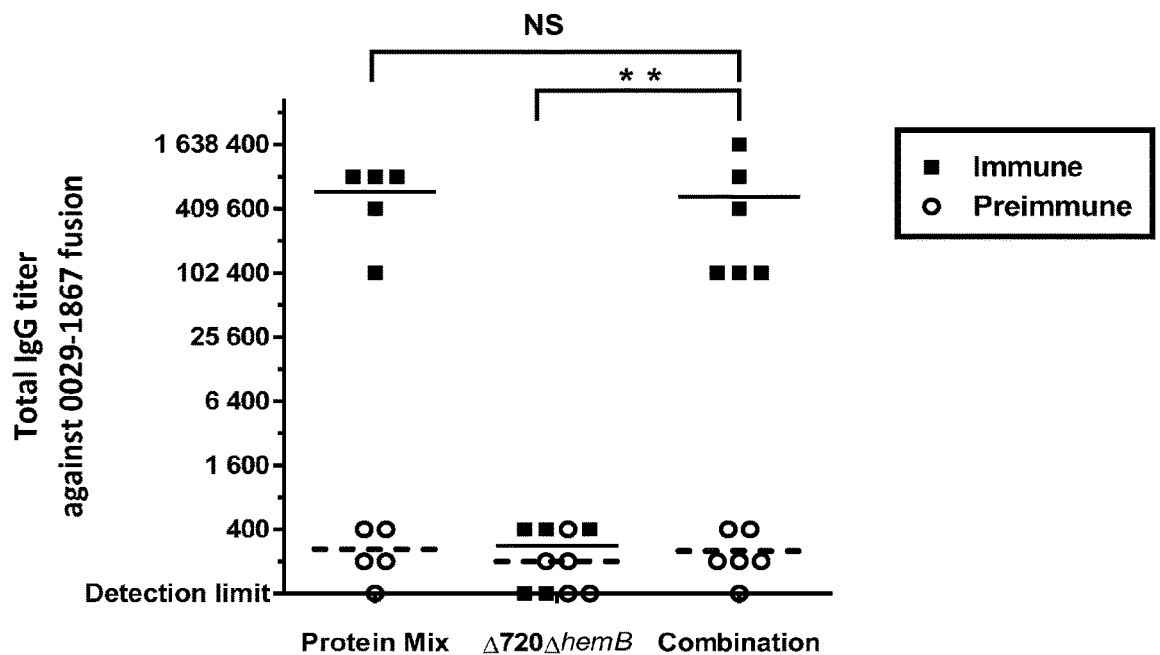
FIG. 16. shows total serum IgG titers against SACOL0029-1867 fusion protein of mice immunised with the protein mix (composed of 5 μg of the antigens SACOL0029, SACOL0442, SACOL0720, and the SACOL0029-1867 fusion), $10^5$ CFU of the attenuated live strain Δ720ΔhemB alone or a combination of the protein mix and the Δ720ΔhemB strain. Open circles (○) represent data for preimmune titers, black squares (■) represent data for the immune titers. Each symbol represents the titer for one mouse. Horizontal lines represent the medians: black lines represent the medians for the immune serums while dashed lines represent the medians for the preimmune serums. Titers for the vaccinated mice in the protein mix group and combination group are higher than the titers for the preimmune mice ($P<0.001$). Statistical significance between immune titers of combination versus the two other vaccinated mice groups is shown (**: $P<0.01$).

The results in FIG. 16 show that immunization with the SACOL0029-1867 fusion either when co-administered with other antigens or with a live attenuated strain) induces high and specific antibody responses in mice.

Example 23: The Live Attenuated *S. aureus* Strain Significantly Improves Antibody Immune Response Against Some Specific Antigens—Vaccine #7

The antigens and live attenuated *S. aureus* strain Δ720ΔhemB are produced as described in Example 21. Mice are immunized and IgGs detected as described in Example 21.

Figure 17:
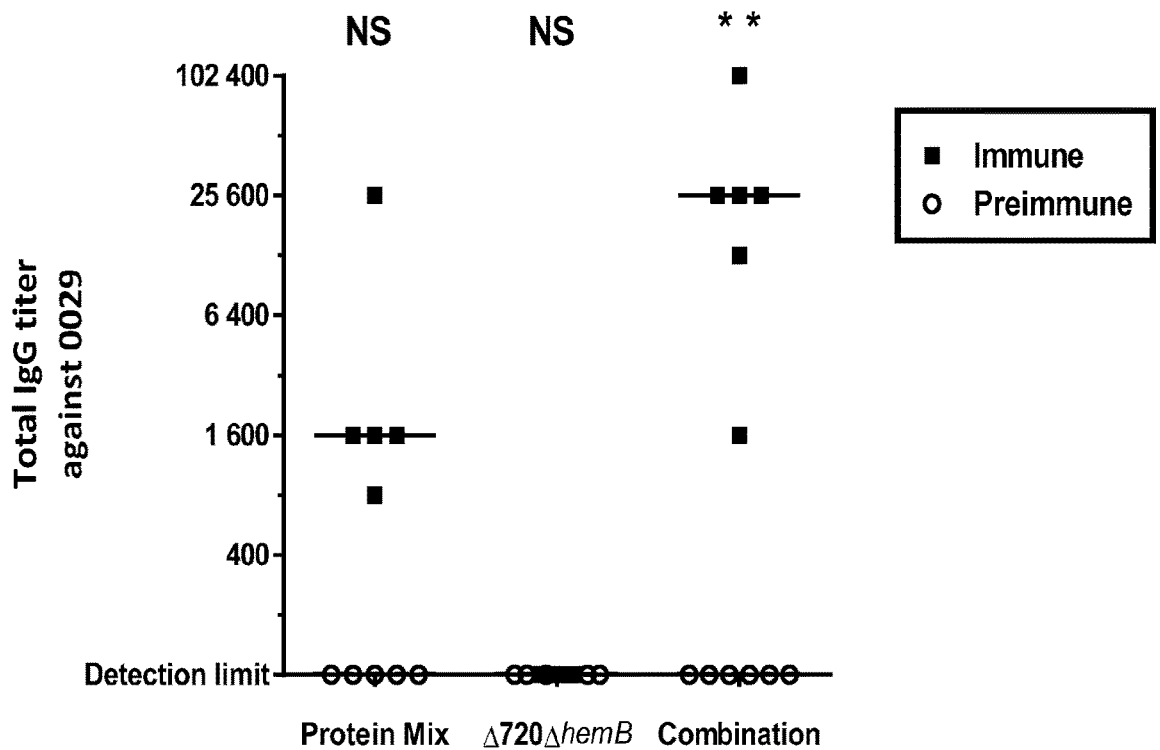
FIG. 17. shows total serum IgG titers against SACOL0029 of mice immunised with the protein mix (composed of 5 μg of the antigens SACOL0029, SACOL0442, SACOL0720, and the SACOL0029-1867 fusion), $10^5$ CFU of the attenuated live strain Δ720ΔhemB alone or a combination of the protein mix and the Δ720ΔhemB strain. Open circles (○) represent data for preimmune titers, black squares (■) represent data for the immune titers. Each symbol represents the total IgG titer for one mouse. Horizontal lines represent the medians: black lines represent the medians for the immune serums while dashed lines represent the medians for the preimmune serums. Statistical significance between immune and preimmune titers of the three mice groups is shown (**: $P<0.01$).

The results in FIG. 17 show that immunization with the attenuated live strain Δ720ΔhemB significantly increases the production of specific IgG antibodies against the SACOL0029 antigen, in comparison to that obtained with IgG antibodies from mice immunized with the protein mix alone.

Example 24: The Live Attenuated *S. aureus* Strain Induces Significant Antibody Titers Against Additional Surface Proteins of *S. aureus*—Vaccine #7

The antigens and live attenuated *S. aureus* strain Δ720ΔhemB are produced as described in Example 21. Mice are immunized and IgGs detected as described in Example 21.

Figure 18:
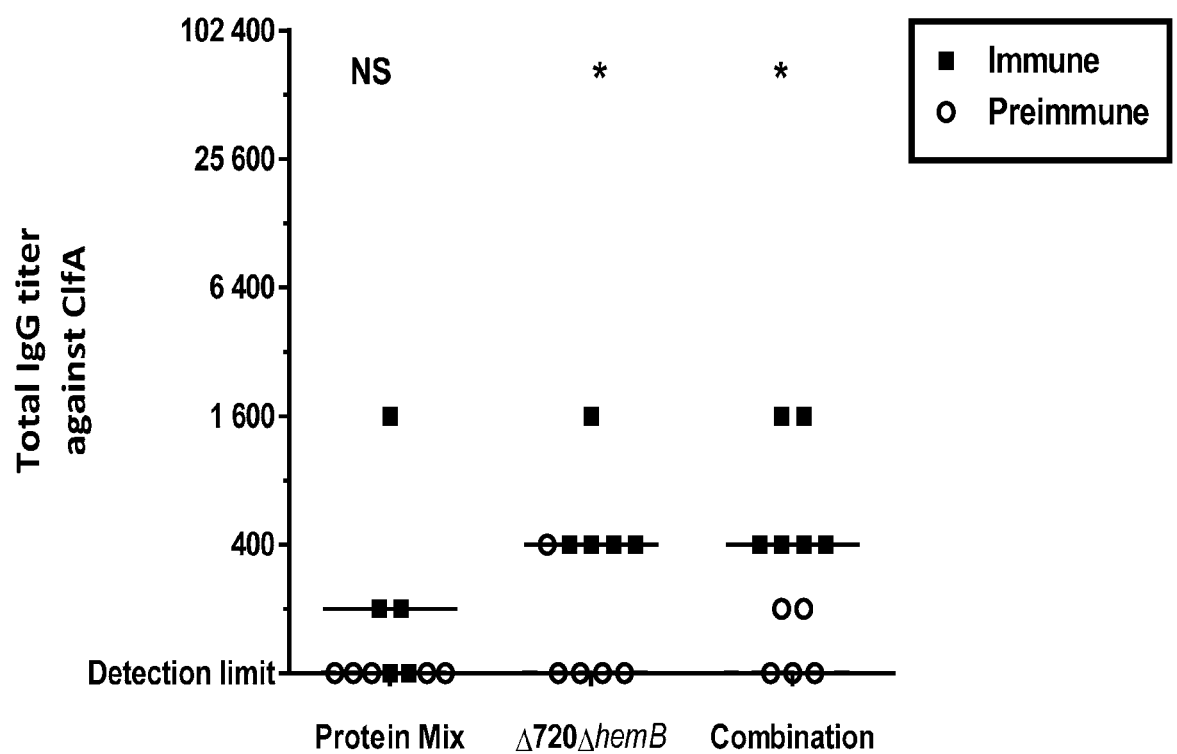
FIG. 18. shows total serum IgG titers against the staphylococcal surface protein ClfA for mice immunised with the SACOL0029, SACOL0442, SACOL0720, and SACOL0029-1867 protein mix, $10^5$ CFU of the attenuated live strain Δ720ΔhemB alone or a combination of the protein mix and Δ720ΔhemB. Open circles (○) represent data for preimmune titers, black squares (■) represent data for the immune titers. Each symbol represents the titer for one mouse. Horizontal lines represent the medians: black lines represent the medians for the immune serums while dashed lines represent the medians for the preimmune serums. Statistical significance between preimmune titers and immune titers is shown (*: $P<0.05$).

The results in FIG. 18 show that immunization with the attenuated live strain Δ720ΔhemB (alone or when co-administered with polypeptide antigens) significantly increases the production of specific antibodies against the staphylococcal surface protein ClfA, compared to that achieved with the protein mix alone composed of SACOL0029, SACOL0442, SACOL0720, and SACOL0029-1867.

Example 25: The Live Attenuated *S. aureus* Strain Significantly Balances the Th1/Th2 Immune Response—Vaccine #7

The antigens and live attenuated *S. aureus* strain Δ720ΔhemB are produced as described in Example 21.

Serum IgG2a and IgG1 isotypes against the SACOL0029-1867 fusion protein were detected in serums of vaccinated mice as previously described and the ratio of IgG2a to IgG1 titers of each mouse was determined. IgG2a isotype is associated with the Th1 immune response in mice, whereas IgG1 is a marker for the Th2 response. As described in Example 5, the induction of IgG2 production in cows and the extent of the IgG2 titers in milk significantly correlates with protection of the cows against a challenge with *S. aureus*, as judged by the levels of the corresponding somatic cells (SCC) or bacterial counts (CFU) in milk of the cows (FIG. 4C).

Figure 19:
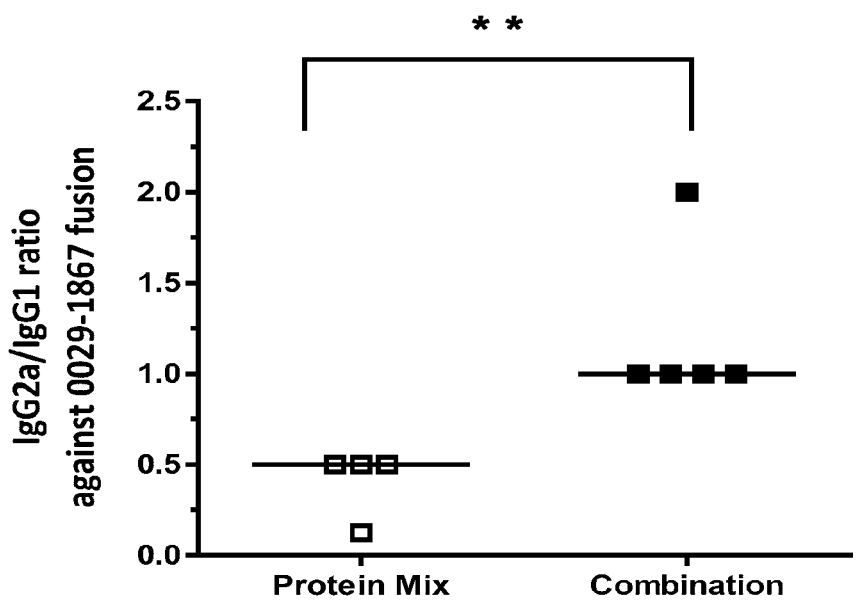
FIG. 19. below shows serum ratio of IgG2a/IgG1 titers against the SACOL0029-1867 fusion polypeptide for mice immunised with the protein mix, or the combination of the protein mix and the attenuated Δ720ΔhemB live strain.
Figure 20:
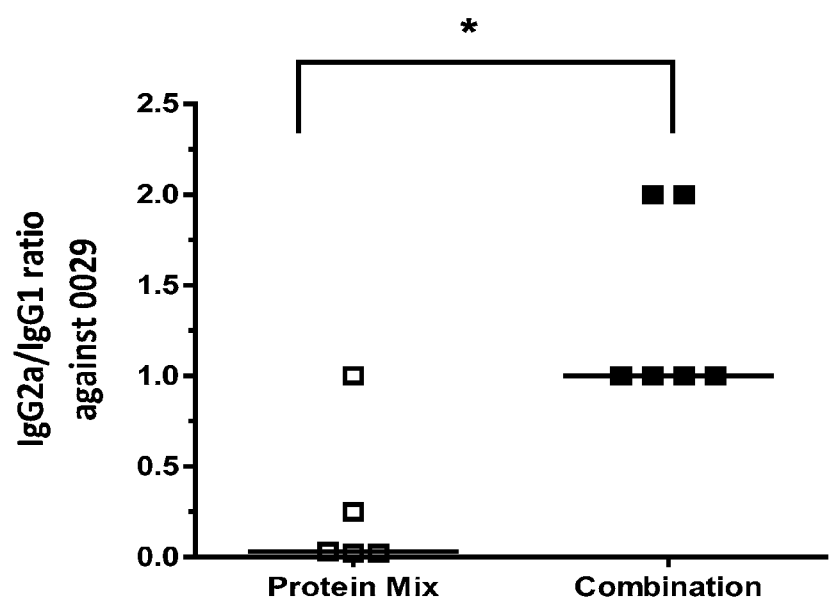
FIG. 20. shows serum ratios against the SACOL0029 antigen. Open squares (D) represent data for preimmune titers, black squares (■) represent data for the immune titers. Each symbol represents the titer ratio for one mouse. Horizontal lines represent the medians. Statistical significance between the protein mix group versus combination group ratios is shown (*: $P<0.05$; **: $P<0.01$).

The results shown in FIGS. 19 and 20 demonstrate that the attenuated live strain Δ720ΔhemB included in the combination immunization vaccine (Δ720ΔhemB *S. aureus* administered with SACOL0029, SACOL0442, SACOL0720, and SACOL0029-1867) induces a significantly higher IgG2a/IgG1 antibody ratio against the SACOL0029-1867 fusion and SACOL0029 proteins than that seen with the protein mix immunization (SACOL0029, SACOL0442, SACOL0720, and SACOL0029-1867), resulting in a significantly more balanced Th1/Th2 response.

Examples 21 to 25 above show that even if a strong antibody response was obtained by the immunization with different antigens (including e.g., SACOL0029-1867 fusion) in a protein mix composition, the immunization of mice with a combination of these antigens with a live attenuated strain significantly improved immune responses against *S. aureus*, by inducing higher antibody titers against some specific antigens (e.g., SACOL0029), by the production of antibodies against other staphylococcal proteins (e.g., ClfA), and by achieving a more balanced IgG2a/IgG1 ratio, a good marker of a stronger Th1 type response, against the antigens co-administered with the live strain.

Example 26: Expression of Recombinant Proteins in Strain *S. aureus* ΔhemBΔ720—Vaccines #8, 9, 10 Etc.

Genes SACOL0442, SACOL0720, SACOL0029, and/or SACOL1867 as well as the fusion (e.g., size of 50 AA or more) of the genes (or of fragments thereof) SACOL0029 and SACOL1867 (SACOL0029-SACOL1867), fusions of fragments (e.g., epitopes) of SACOL720 and/or of SACOL0442 (fusion 720-720) (fusion 442-720) or any other fusion of genes or fragments thereof e.g., SACOL0029-SACOL0442, SACOL0029-SACOL0720, SACOL0029-SACOL0720-SACOL0442, SACOL0029-SACOL0720-SACOL1867, SACOL0029-SACOL1867-SACOL0442 SACOL0442-SACOL0029-SACOL0720, SACOL0442-SACOL0029-SACOL0720, SACOL0442-SACOL1867-SACOL0720, SACOL0720-SACOL0442-SACOL1867, SACOL04029-SACOL1867-SACOL0720-SACOL0442, are cloned in plasmid pCN36 (Charpentier et al., 2004) under a constitutive promoter (PblaZ from plasmid pCN40) (Charpentier et al., 2004) and expressed in the *S. aureus* ΔhemBΔ720 strain. Certain protein antigens proposed herein are predicted to be an exotoxin, enterotoxin or superantigen (e.g., SACOL0442) or proteins useful for protection against host defenses (e.g., SACOL0720) and could potentially interfere with the mammalian immune system and antibody production, and/or show some toxicity in the host. Although such interference was not observed with the vaccine composition and formulations described here, it may be useful to modify the protein or polypeptide expressed in the *S. aureus* ΔhemBΔ720 strain so that the cloned genes do not complement its virulence. For such a purpose, it is possible to use molecular biology techniques to delete or mutate the putative region(s) involved in such protein activity without losing immunogenicity (Chang et al, 2008). This is the approach the applicants used to prepare the antigens of vaccine compositions of the present invention.

Expression of individual recombinant protein products by each of the *S. aureus* ΔhemBΔ720 strains carrying one of the constructed expression vectors is validated by LC-MS/MS analyses. Briefly, strains grown in BHI with 15 μg/ml tetracycline to mid-logarithmic phase were centrifuged and pellets were inactivated with ethanol. Samples were kept at −20° C. until cell lysis and trypsin digestion procedures. Samples are incubated with lysostaphin and trypsin at 37° C., followed by cell disruption by mechanical homogenization using glass beads and a beadbeater. Lysates are then centrifuged for 25 min at 13 000 rpm at 4° C. in order to remove cell debris, before following with protein digestion with trypsin, reduction and alkylation were done by standard procedures before sample injection for protein detection using the MRM method of LC-MS/MS.

Alternatively, recombinant protein expression is also confirmed by Western blots of bacterial lysates.

Example 27: Mouse Immunization with Attenuated Strains Expressing Antigens—Vaccines #8, Etc.

CD-1 female mice are vaccinated by two subcutaneous injections two weeks apart. Each of the *S. aureus* ΔhemBΔ720 strains carrying or not one of the constructed expression vectors, are diluted in saline and administered in a final volume of 100 µl per dose. Group 1 receives a double-mutant strain alone; group 2 receives a double-mutant strain expressing fusion SACOL0029-1867; group 3 receives a double-mutant strain expressing fusion SACOL0029-0442; group 4 receives a double-mutant strain expressing fusion SACOL0029-0720; group 5 receives a mixture of double-mutant strains, one expressing fusion SACOL0029-1867 and the other expressing fusion SACOL0029-0442; group 6 receives a mixture of double-mutant strains, one expressing fusion SACOL0029-1867 and the other expressing fusion SACOL0029-0720; and group 7 receives a mixture of double-mutant strains. Blood samples are taken just before the first injection and twelve days after the second one. The samples are allowed to clot at room temperature for an hour, then centrifuged at 2 000 g for 10 min at 4° C. The supernatants (sera) are harvested and kept at −20° C. until subsequent analysis. Mice are euthanized at day 27 and blood is collected by cardiac puncture. The immune sera are recovered, aliquoted and stored as for the pre-immune sera.

The immune response to vaccination is evaluated by enzyme-linked immunosorbent assay (ELISA) for the presence of serum polyclonal IgG antibodies directed towards *S. aureus* whole cells (Wood strain) or specific recombinant proteins. Anti-mouse IgG-HRP (HRP: horseradish peroxidase) is used as a secondary antibody to detect the colorimetric production of 3,3',5,5'-tetramethylbenzidine (TMB) substrate oxidation by peroxidase activity using a spectrophotometer.

REFERENCES

Allard M, Ster C., Jacob C L, Scholl D, Diarra M S, Lacasse P, and Malouin F, 2013. The expression of a putative exotoxin and an ABC transporter during bovine intramammary infection contributes to the virulence of *Staphylococcus aureus*. Vet. Microbiol. 162:761-70.

Allard, M., C. Ster, L. St-James, P. Lacasse, M. S. Diarra, C. L. Jacob, and F. Malouin. 2008. Transcriptional Analysis of In Vivo-Expressed Genes in *Staphylococcus aureus* During Bovine Mastitis. American Society for Microbiology General Meeting. Boston, USA. Jun. 1-5, 2008 (Poster)

Allard, M., H. Moisan, E. Brouillette, A. L. Gervais, M. Jacques, P. Lacasse, M. S. Diarra, and F. Malouin. 2006. Transcriptional modulation of some *Staphylococcus aureus* iron-regulated genes during growth in vitro and in a tissue cage model in vivo. Microbes Infect. 7:1679-1690.

Asli A, Brouillette E, Krause K M, Nichols W W, Malouin F. Distinctive binding of avibactam to penicillin-binding proteins of gram-negative and gram-positive bacteria. Antimicrob Agents Chemother. 2016; 60: 752-756.

Atalla, H., C. Gyles, and B. Mallard. 2010. Persistence of a *Staphylococcus aureus* small colony variants (*S. aureus* SCV) within bovine mammary epithelial cells. Vet. Microbiol. Elsevier B. V. 143:319-28.

Atalla, H., C. Gyles, and B. Mallard. 2011. *Staphylococcus aureus* small colony variants (SCVs) and their role in disease. Anim. Health Res. Rev. 12:33-45.

Atalla, H., C. Gyles, B. Wilkie, K. Leslie, and B. Mallard. 2009. Somatic cell scores and clinical signs following experimental intramammary infection of dairy cows with a *Staphylococcus aureus* small colony variant (*S. aureus* SCV) in comparison to other bovine strains. Vet. Microbiol. 137:326-34.

Atalla, H., C. Gyles, C. L. Jacob, H. Moisan, F. Malouin, and B. Mallard. 2008. Characterization of a *Staphylococcus aureus* small colony variant (SCV) associated with persistent bovine mastitis. Foodborne Pathog 5:785-799.

Barbagelata, M. S., L. Alvarez, M. Gordiola, L. Tuchscherr, C. von Eiff, K. Becker, D. Sordelli, and F. Buzzola. 2011. Auxotrophic mutant of *Staphylococcus aureus* interferes with nasal colonization by the wild type. Microbes Infect. 13:1081-90.

Barkema, H. W., Y. H. Schukken, and R. N. Zadoks. 2006. Invited Review: The role of cow, pathogen, and treatment regimen in the therapeutic success of bovine *Staphylococcus aureus* mastitis. J Dairy Sci. 89:1877-1895.

Barrio, M. B., P. Rainard, F. B. Gilbert, B. Poutrel. 2003. Assessment of the opsonic activity of purified bovine sIgA following intramammary immunization of cows with *Staphylococcus aureus*. J. Dairy Sci. 86:2884-2894.

Bharathan, M., and I. K. Mullarky. 2011. Targeting mucosal immunity in the battle to develop a mastitis vaccine. J. Mammary Gland Biol. Neoplasia 16:409-19.

Bowdish, D. M. E., Davidson, D. J., Scott, M. G. and Hancock, R. E. W., 2005. Immunomodulatory Activities of Small Host Defense Peptides. Antimicrobial Agents and Chemotherapy, 49(5): 1727-1732.

Bradley R D Rothstein, G, P. P. C. 1982. Cellular and extracellular myeloperoxidase in pyogenic inflammation. Blood 60:618-622.

Bradley, A. 2002. Bovine mastitis: an evolving disease. Vet J. 164:116-128.

Brouillette, E., A. Martinez, B. J. Boyll, N. E. Allen, and F. Malouin. 2004. Persistence of a *Staphylococcus aureus* small-colony variant under antibiotic pressure in vivo. FEMS Immunol. Med. Microbiol. 41:35-41.

Brouillette, E., and F. Malouin. 2005. The pathogenesis and control of *Staphylococcus aureus*-induced mastitis: study models in the mouse. Microbes Infect. 7:560-8.

Brouillette, E., G. Grondin, B. G. Talbot, and F. Malouin. 2005. Inflammatory cell infiltration as an indicator of *Staphylococcus aureus* infection and therapeutic efficacy in experimental mouse mastitis. Vet. Immunol. Immunopathol. 104:163-9.

Brouillette, E., M. Hyodo, Y. Hayakawa, D. K. Karaolis, and F. Malouin. 2005. 3',5'-cyclic diguanylic acid reduces the virulence of biofilm-forming *Staphylococcus aureus* strains in a mouse model of mastitis infection. Antimicrob. Agents Chemother. 49:3109-3113.

Brückner, R. 1997. Gene replacement in *Staphylococcus camosus* and *Staphylococcus xylosus*. FEMS Microbiol. Lett. 151:1-8.

Burlak, C., C. H. Hammer, M. A. Robinson, A. R. Whitney, M. J. McGavin, B. N. Kreiswirth, and F. R. Deleo. 2007. Global analysis of community-associated methicillin-resistant *Staphylococcus aureus* exoproteins reveals molecules produced in vitro and during infection. Cell Microbiol. 9:1172-1190.

Buzzola, F. R., L. P. Alvarez, L. P. N. Tuchscherr, M. S. Barbagelata, S. M. Lattar, L. Calvinho, and D. O. Sordelli. 2007. Differential abilities of capsulated and noncapsulated *Staphylococcus aureus* isolates from diverse agr groups to invade mammary epithelial cells. Infect. Immun. 75:886-91.

Buzzola, F. R., M. S. Barbagelata, R. L. Caccuri, and D. O. Sordelli. 2006. Attenuation and persistence of and ability to induce protective immunity to a *Staphylococcus aureus* aroA mutant in mice. Infect. Immun. 74:3498-506.

Chang, B. S., J. S. Moon, H. M. Kang, Y. I. Kim, H. K. Lee, J. D. Kim, B. S. Lee, H. C. Koo, Y. H. Park. 2008. Protective effects of recombinant staphylococcal enterotoxin type C mutant vaccine against experimental bovine infection by a strain of *Staphylococcus aureus* isolated from subclinical mastitis in dairy cattle. Vaccine. 26:2081-2091.

Charpentier E, Anton A I, Barry P, Alfonso B, Fang Y, Novick R P. 2004. Novel cassette-based shuttle vector system for gram-positive bacteria. Appl Environmental Microbiol 70:6076-6085.

Chen J., H Liu., J. Yang, K. Chou. 2007. Prediction of linear B-cell epitopes using amino acid pair antigenicity scale. Amino Acids 33: 423-428.

Chen et. al, Adv Drug Deliv Rev. (2013), 65(10):1357-69.

Chen Y., L. Caruso, B. McClane, D. Fisher, P. Gupta. 2007. Disruption of a toxin by introduction of a foreign gene into the chromosome of *Clostridium perfringens* using targetron induced mutagenesis. Plasmid. 58:182-189.

Cui, L., J. Lian, and H. Neoh. 2005. DNA microarray-based identification of genes associated with glycopeptide resistance in *Staphylococcus aureus*. Antimicrob. agents . . . 49:3404-3413.

De Groot, A. S., J. McMurry, and L. Moise. 2008. Prediction of immunogenicity: in silico paradigms, ex vivo and in vivo correlates. Curr Opinion in Pharmacol. 8:620-626.

Dehal P S, Joachimiak M P, Price M N, Bates J T, Baumohl J K, Chivian D, Friedland G D, Huang K H, Keller K, Novichkov P S, Dubchak I L, Alm E J, Arkin A P. MicrobesOnline: an integrated portal for comparative and functional genomics. Nucleic Acids Res. 2010 January; 38(Database issue): D396-400. Epub 2009 Nov. 11.

Detmer, A., and J. Glenting. 2006. Live bacterial vaccines—a review and identification of potential hazards. Microb. Cell Fact. 12:1-12.

Diarra, M. S., D. Petitclerc, and P. Lacasse. 2002. Response of *Staphylococcus aureus* isolates from bovine mastitis to exogenous iron sources. J. Dairy Sci. 85:2141-2148.

E L-Manzalawy Y, Dobbs D, Honavar V. 2008a. Predicting linear B-cell epitopes using string kernels. J Mol Recognit 21: 243-255.

E L-Manzalawy Y, Dobbs D, Honavar V. 2008b. Predicting flexible length linear B-cell epitopes. 7th Intentional Conference on Computational Systems Bioinformatics, Stanford, Calif. pp. 121-131

Eng, N. F., S. Garlapati, V. Gerdts, A. Potter, L. A. Babiuk, and G. K. Mutwiri. 2010. The Potential of Polyphosphazenes for Delivery of Vaccine Antigens and Immunotherapeutic Agents. Curr Drug Deliv. 7(1):13-30.

Falla, T. J., D. Karunaratne, N., Hancock, R. E. W. 1996. Mode of Action of the Antimicrobial Peptide Indolicidin. The Journal of Biological Chemistry, 271(32), Issue of August 9, pp. 19298-19303.

Falord, M., G. Karimova, A. Hiron, and T. Msadek. 2012. GraXSR proteins interact with the VraFG ABC transporter to form a five-component system required for cationic antimicrobial peptide sensing and resistance in *Staphylococcus aureus*. Antimicrob. Agents Chemother. 56:1047-58.

Falord, M., U. Mäder, A. Hiron, M. Débarbouillé, and T. Msadek. 2011. Investigation of the *Staphylococcus aureus* GraSR Regulon Reveals Novel Links to Virulence, Stress Response and Cell Wall Signal Transduction Pathways. PLoS One 6:e21323.

Ferens, W. a, and G. a Bohach. 2000. Persistence of *Staphylococcus aureus* on mucosal membranes: superantigens and internalization by host cells. J. Lab. Clin. Med. 135:225-30.

Foster, T. J. 2009. Colonization and infection of the human host by staphylococci: adhesion, survival and immune evasion. Vet. Dermatol. 20:456-70.

Fowler, V., and R. Proctor. 2014. Where does a *Staphylococcus aureus* vaccine stand? Clin. Microbiol. Infect. 20 Suppl 5:66-75.

Garcia, V., M. Gómez, M. Iglesias, N. Sanjuan, M. Gherardi, M. C. Cerquetti, and D. Sordelli. 1996. Intramammary immunization with live-attenuated *Staphylococcus aureus*: microbiological and immunological studies in a mouse mastitis model. FEMS Immunol. Med. Microbiol. 14:45-51.

Gardy, J. L., M. R. Laird, F. Chen, S. Rey, C. J. Walsh, M. Ester and F. S. L. Brinkman. 2005. PSORTb v.2.0: Expanded prediction of bacterial protein subcellular localization and insights gained from comparative proteome analysis. Bioinformatics 21(5):617-623; doi: 10.1093/bioinformatics/bti057

Garzoni, C., P. Francois, A. Huyghe, S. Couzinet, C. Tapparel, Y. Charbonnier, A. Renzoni, S. Lucchini, D. P. Lew, P. Vaudaux, W, L. Kelley, and J. Schrenzel. 2007. A global view of *Staphylococcus aureus* whole genome expression upon internalization in human epithelial cells. BMC Genomics. 8:171.

Gasteiger E., Hoogland C., Gattiker A., Duvaud S., Wilkins M. R., Appel R. D., Bairoch A. Protein Identification and Analysis Tools on the ExPASy Server; (In) John M. Walker (ed): The Proteomics Protocols Handbook, Humana Press (2005), pp. 571-607

Gaupp, R., N. Ledala, and G. a Somerville. 2012. Staphylococcal response to oxidative stress. Front. Cell. Infect. Microbiol. 2:33.

Gläser, R., K. Becker, C. von Eiff, U. Meyer-Hoffert, and J. Harder. 2014. Decreased Susceptibility of *Staphylococcus aureus* Small-Colony Variants Toward Human Antimicrobial Peptides. J. Invest. Dermatol. 134:2347-50.

Goerke, C., S. Campana, M. G. Bayer, G. Döring, K. Botzenhart, and C. Wolz. 2000. Direct quantitative transcript analysis of the agr regulon of *Staphylococcus aureus* during human infection in comparison to the expression profile in vitro. Infect Immun. 68:1304-1311.

Griffiths, K. L., and S. a Khader. 2014. Novel vaccine approaches for protection against intracellular pathogens. Curr. Opin. Immunol. Elsevier Ltd 28:58-63.

Guidry, A. J., L. M. Berning, C. N. Hambleton. 1993. Opsonization of *Staphylococcus aureus* by bovine immunoglobulin isotypes. J. of Dairy Sci. 76:1285-1289.

Hancock, R. E. W., and Diamond, G., 2000. The role of cationic antimicrobial peptides in innate host defences. Trends In Microbiology. 8(9):402.

Haveri, M., A. Roslif, L. Rantala, and S. Pyorala. 2007. Virulence genes of bovine *Staphylococcus aureus* from persistent and nonpersistent intramammary infections with different clinical characteristics. J Appl Microbiol. 103:993-1000.

Hogarth, C. J., J. L. Fitzpatrick, A. M. Nolan, F. J. Young, A. Pitt, and P. D. Eckersall. 2004. Differential protein composition of bovine whey: a comparison of whey from healthy animals and from those with clinical mastitis. Proteomics. 4:2094-2100.

Horsburgh, M. J., J. L. Aish, I. J. White, J. K. Lithgow, S. J. Foster, and L. Shaw. 2002. a B Modulates Virulence Determinant Expression and Stress Resistance: Characterization of a Functional rsbU Strain Derived from *Staphylococcus aureus* 8325-4. J. Bacteriol. 184:5457-5467.

Jayarao, B. M., D. R. Henning. 2001. Prevalence of foodborne pathogens in bulk tank milk. J Dairy Sci. 84:2157-2162.

Kafala, B., and a Sasarman. 1997. Isolation of the *Staphylococcus aureus* hemCDBL gene cluster coding for early steps in heme biosynthesis. Gene 199:231-9.

Kahl B. C., 2014. Small colony variants (SCVs) of *Staphylococcus aureus*—A bacterial survival strategy. Infection, Genetics and Evolution 21: 515-522.

Karaolis, D. K., T. K. Means, D. Yang, M. Takahashi, T. Yoshimura, E. Muraille, D. Philpott, J. T. Schroeder, M. Hyodo, Y. Hayakawa, B. G. Talbot, E. Brouillette, and F. Malouin. 2007. Bacterial c-di-GMP is an immunostimulatory molecule. J Immunol. 178:2171-2181.

Kasturi, S. P. et al. 2011. Programming the magnitude and persistence of antibody responses with innate immunity. Nature 470:543-547.

Kawada-Matsuo, M., and Y. Yoshida. 2011. Role of two-component systems in the resistance of *Staphylococcus aureus* to antibacterial agents. Virulence 2:427-430.

Kawada-Matsuo, M., Y. Yoshida, T. Zendo, J. Nagao, Y. Oogai, Y. Nakamura, K. Sonomoto, N. Nakamura, and H. Komatsuzawa. 2013. Three distinct two-component systems are involved in resistance to the class I bacteriocins, Nukacin ISK-1 and nisin A, in *Staphylococcus aureus*. PLoS One 8: e69455.

Kerro-Dego, O., T. Prysliak, A. a Potter, and J. Perez-Casal. 2006. DNA-protein immunization against the GapB and GapC proteins of a mastitis isolate of *Staphylococcus aureus*. Vet. Immunol. Immunopathol. 113:125-38.

Kollaritsch, H., S. J. Cryz, a B. Lang, C. Herzog, J. U. Que, and G. Wiedermann. 2000. Local and systemic immune responses to combined *Vibrio cholerae* CVD103-HgR and *Salmonella typhi* ty21a live oral vaccines after primary immunization and reimmunization. Vaccine 18:3031-9.

Koo, S. P., A. S. Bayer, H. G. Sahl, R. A. Proctor, M. R. Yeaman, S. Koo, A. S. Bayer, H. Sahl, and R. A. Proctor. 1996. Staphylocidal action of thrombin-induced platelet microbicidal protein is not solely dependent on transmembrane potential. These include: Staphylocidal Action of Thrombin-Induced Platelet Microbicidal Protein Is Not Solely Dependent on Transmembrane Pot 64.

Kraus, D., S. Herbert, S. a Kristian, A. Khosravi, V. Nizet, F. Gotz, and A. Peschel. 2008. The GraRS regulatory system controls *Staphylococcus aureus* susceptibility to antimicrobial host defenses. BMC Microbiol. 8:85.

Kreiswirth, B. N., S. Löfdahl, M. J. Betley, M. O'Reilly, P. M. Schlievert, M. S. Bergdoll, and R. P. Novick. 1983. The toxic shock syndrome exotoxin structural gene is not detectably transmitted by a prophage. Nature 305:709-12.

Kubica, M., K. Guzik, J. Koziel, M. Zarebski, W. Richter, B. Gajkowska, A. Golda, A. Maciag-Gudowska, K. Brix, L. Shaw, T. Foster, and J. Potempa. 2008. A potential new pathway for *Staphylococcus aureus* dissemination: the silent survival of *S. aureus* phagocytosed by human monocyte-derived macrophages. PLoS One 3:e1409.

Kuroda, M., K. Kuwahara-Arai, and K. Hiramatsu. 2000. Identification of the up- and down-regulated genes in vancomycin-resistant *Staphylococcus aureus* strains Mu3 and Mu50 by cDNA differential hybridization method. Biochem. Biophys. Res. Commun. 269:485-90.

Lammers, A., E. Kruijt, K. C. van de, P. J. Nuijten, and H. E. Smith. 2000. Identification of *Staphylococcus aureus* genes expressed during growth in milk: a useful model for selection of genes important in bovine mastitis? Microbiology. 146:981-987.

Larkin M. A., Blackshields G., Brown N. P., Chenna R., McGettigan P. A., McWilliam H.*, Valentin F.*, Wallace I. M., Wilm A., Lopez R., Thompson J. D., Gibson T. J. and Higgins D. G. 2007. ClustalW and ClustalX version 2. Bioinformatics 2007 23(21): 2947-2948.

Leitner, G., O. Krifucks, M. D. Kiran, and N. Balaban. 2011. Vaccine development for the prevention of staphylococcal mastitis in dairy cows. Vet. Immunol. Immunopathol. Elsevier B. V. 142:25-35.

Li, M., D. J. Cha, Y. Lai, A. E. Villaruz, D. E. Sturdevant, and M. Otto. 2007. The antimicrobial peptide-sensing system aps of *Staphylococcus aureus*. Mol. Microbiol. 66:1136-47.

Lin, L., A. S. Ibrahim, X. Xu, J. M. Farber, V. Avanesian, B. Baquir, Y. Fu, S. W. French, J. E. Edwards, and B. Spellberg. 2009. Th1-Th17 cells mediate protective adaptive immunity against *Staphylococcus aureus* and *Candida albicans* infection in mice. PLoS Pathog. 5:e1000703.

Linghua, Z., T. Xingshan, Z. Fengzhen. 2006. The efficacy of CpG oligodinucleotides, in combination with conventional adjuvants, as immunological adjuvants to swine streptococcic septicemia vaccine in piglets in vivo. Int Immunopharmacol. 6:1267-76.

Löffler, B., L. Tuchscherr, S. Niemann, and G. Peters. 2013. *Staphylococcus aureus* persistence in non-professional phagocytes. Int. J. Med. Microbiol. Elsevier GmbH.

Loiselle, M. C., C. Ster, B. G. Talbot, X. Zhao, G. F. Wagner, Y. R. Boisclair, and P. Lacasse. 2009. Impact of postpartum milking frequency on the immune system and the blood metabolite concentration of dairy cows. J Dairy Sci. 92:1900-1912.

Lowe, A. M., D. T. Beattie, and R. L. Deresiewicz. 1998. Identification of novel staphylococcal virulence genes by in vivo expression technology. Mol Microbiol. 27:967-976.

Maresso, A. W., and O. Schneewind. 2006. Iron acquisition and transport in *Staphylococcus aureus*. Biometals. 19:193-203.

Maresso A W, Schneewind O. Sortase as a target of anti-infective therapy. Pharmacol Rev. 2008 March; 60(1): 128-41.

Mayer, S. J., A. E. Waterman, P. M. Keen, N. Craven, and F. J. Bourne. 1988. Oxygen concentration in milk of healthy and mastitic cows and implications of low oxygen tension for the killing of *Staphylococcus aureus* by bovine neutrophils. J Dairy Res 55:513-519.

Meehl, M., S. Herbert, F. Gotz, and A. Cheung. 2007. Interaction of the GraRS two-component system with the VraFG ABC transporter to support vancomycin-intermediate resistance in *Staphylococcus aureus*. Antimicrob. Agents Chemother. 51:2679-89.

Melchior, M. B., M. H. vanOsch, R. M. Graat, E. van Duijkeren, D. J. Mevius, N. Nielen, W. Gaastra, J. Fink-Gremmels. 2009. Biofilm formation and genotyping of *Staphylococcus aureus* bovine mastitis isolates: evidence for lack of penicillin-resistance in Agr-type II strains. Vet. Microbiol. 137:83-89.

Merino, N., A. Toledo-Arana, M. Vergara-Irigaray, J. Valle, C. Solano, E. Calvo, J. A. Lopez, T. J. Foster, J. R. Penadés, and I. Lasa. 2009. Protein A-mediated multicellular behavior in *Staphylococcus aureus*. J. Bacteriol. 191:832-43.

Middleton, J. R., C. D. Luby, and D. S. Adams. 2009. Efficacy of vaccination against staphylococcal mastitis: a review and new data. Vet. Microbiol. 134:192-8.

Middleton, J. R. 2008. *Staphylococcus aureus* antigens and challenges in vaccine development. Expert Rev Vaccines. 7(6):805-815.

Mitchell, G., A. Fugère, K. Pépin Gaudreau, E. Brouillette, E. H. Frost, A. M. Cantin, and F. Malouin. 2013. SigB is a dominant regulator of virulence in *Staphylococcus aureus* small-colony variants. PLoS One 8:e65018.

Mitchell, G., C. A. Lamontagne, E. Brouillette, G. Grondin, B. G. Talbot, M. Grandbois, F. Malouin. 2008. *Staphylococcus aureus* SigB activity promotes a strong fibronectin-bacterium interaction which may sustain host tissue colonization by small-colony variants isolated from cystic fibrosis patients. Mol Microbiol 70:1540-1555.

Mitchell, G., C.-A. Lamontagne, E. Brouillette, G. Grondin, B. G. Talbot, M. Grandbois, and F. Malouin. 2008. *Staphylococcus aureus* SigB activity promotes a strong fibronectin-bacterium interaction which may sustain host tissue colonization by small-colony variants isolated from cystic fibrosis patients. Mol. Microbiol. 70:1540-55.

Mitchell, G., G. Grondin, G. Bilodeau, A. M. Cantin, and F. Malouin. 2011. Infection of Polarized Airway Epithelial Cells by Normal and Small-Colony Variant Strains of *Staphylococcus aureus* Is Increased in Cells with Abnormal Cystic Fibrosis Transmembrane Conductance Regulator Function and Is Influenced by NF-{kappa}B. Infect. Immun. 79:3541-51.

Mitra S D, Velu D, Bhuvana M, Krithiga N, Banerjee A, Shome R, et al. *Staphylococcus aureus* spa type t267, clonal ancestor of bovine subclinical mastitis in India. J Appl Microbiol. 2013; 114: 1604-1615.

Moisan, H., E. Brouillette, C. L. Jacob, P. Langlois-Begin, S. Michaud, and F. Malouin. 2006. Transcription of virulence factors in *Staphylococcus aureus* small-colony variants isolated from cystic fibrosis patients is influenced by SigB. J Bacteriol. 188:64-76.

Myllys, V., J. Ridell, J. Bjorkroth, I. Biese, and S. Pyorala. 1997. Persistence in bovine mastitis of *Staphylococcus aureus* clones as assessed by random amplified polymorphic DNA analysis, ribotyping and biotyping. Vet Microbiol. 57:245-251.

National Mastitis Council. 1996. Current Concept of Bovine Mastitis. 4 ed. National Mastitis Council, Madison, Wis.

Nickerson, S. C., W. E. Owens, L. K. Fox, C. C. Scheifinger, T. R. Shryock, and T. E. Spike. 1999. Comparison of tilmicosin and cephapirin as therapeutics for *Staphylococcus aureus* mastitis at dry-off. J Dairy Sci. 82:696-703.

Novick R P. Autoinduction and signal transduction in the regulation of staphylococcal virulence. Mol Microbiol. 2003 June; 48(6):1429-49.

Novick R P, Geisinger E. Quorum sensing in staphylococci. Annu Rev Genet. 2008; 42: 541-64.

Overton, I. M., S. Graham, K. a Gould, J. Hinds, C. H. Botting, S. Shirran, G. J. Barton, and P. J. Coote. 2011. Global network analysis of drug tolerance, mode of action and virulence in methicillin-resistant *S. aureus*. BMC Syst. Biol. BioMed Central Ltd 5:68.

Owens, W. E., C. H. Ray, J. L. Watts, and R. J. Yancey. 1997. Comparison of success of antibiotic therapy during lactation and results of antimicrobial susceptibility tests for bovine mastitis. J Dairy Sci. 80:313-317.

Park, Y. K., H. C. Koo, S. H. Kim, S. Y. Hwang, W. K. Jung, J. Kim, S. Shin, R. Kim, and Y. Park. 2007. The analysis of milk components and pathogenic bacteria isolated from bovine raw milk in Korea. J Dairy Sci. 90:5405-5414.

Pasetti, M. F., J. K. Simon, M. B. Sztein, and M. M. Levine. 2011. Immunology of gut mucosal vaccines. Immunol. Rev. 239:125-48.

Peles, F., M. Wagner, L. Varga, I. Hein, P. Rieck, K. Gutser, P. Keresztiri, G. Kardos, I. Turcsányi, B. Béri, and A. Szabó. 2007. Characterization of *Staphylococcus aureus* strains isolated from bovine milk in Hungary. Int J Food Microbiol. 118:186-93.

Pellegrino, M., J. Giraudo, C. Raspanti, L. Odierno, and C. Bogni. 2010. Efficacy of immunization against bovine mastitis using a *Staphylococcus aureus* avirulent mutant vaccine. Vaccine 28:4523-8.

Pellegrino, M., J. Giraudo, C. Raspanti, R. Nagel, L. Odierno, V. Primo, and C. Bogni. 2008. Experimental trial in heifers vaccinated with *Staphylococcus aureus* avirulent mutant against bovine mastitis. Vet. Microbiol. 127:186-90.

Peterson, J. D., Umayam, L. A., Dickinson, T., Hickey, E. K., White, O. 2001. The Comprehensive Microbial Resource. Nucleic Acids Res. 29(1): 123-5.

Petitclerc, D., K. Lauzon, A. Cochu, C. Ster, M. S. Diarra, and P. Lacasse. 2007. Efficacy of a lactoferrin-penicillin combination to treat {beta}-lactam-resistant *Staphylococcus aureus* mastitis. J Dairy Sci. 90:2778-2787.

Pragman, A. A., and P. M. Schlievert. 2004. Virulence regulation in *Staphylococcus aureus*: the need for in vivo analysis of virulence factor regulation. FEMS Immunol Med Microbiol. 42:147-154.

Proctor, R. a, C. von Eiff, B. C. Kahl, K. Becker, P. McNamara, M. Herrmann, and G. Peters. 2006. Small colony variants: a pathogenic form of bacteria that facilitates persistent and recurrent infections. Nat. Rev. Microbiol. 4:295-305.

Proctor, R. a. 2012. Challenges for a universal *Staphylococcus aureus* vaccine. Clin. Infect. Dis. 54:1179-86.

Proctor, R. a., A. Kriegeskorte, B. C. Kahl, K. Becker, B. Loffer, and G. Peters. 2014. *Staphylococcus aureus* Small Colony Variants (SCVs): a road map for the metabolic pathways involved in persistent infections. Front. Cell. Infect. Microbiol. 4:1-8.

Pulli, B., M. Ali, R. Forghani, S. Schob, K. L. C. Hsieh, G. Wojtkiewicz, J. J. Linnoila, and J. W. Chen. 2013. Measuring myeloperoxidase activity in biological samples. PLoS One 8: e67976.

Reyher, K. K., S. Dufour, H. W. Barkema, L. Des Coteaux, T. J. Devries, I. R. Dohoo, G. P. Keefe, J.-P. Roy, and D. T. Scholl. 2011. The National Cohort of Dairy Farms—a data collection platform for mastitis research in Canada. J. Dairy Sci. Elsevier 94:1616-26.

Sadowska, B., A. Bonar, C. von Eiff, R. A. Proctor, M. Chmiela, W. Rudnicka, and B. Róialska. 2002. Characteristics of *Staphylococcus aureus*, isolated from airways of cystic fibrosis patients, and their small colony variants. FEMS Immunol. Med. Microbiol. 32:191-7.

Saha, S and Raghava G. P. S., (2006) Prediction of Continuous B-cell Epitopes in an Antigen Using Recurrent Neural Network. Proteins, 65(1), 40-48.

Saha. S and Raghava G. P. S. BcePred: Prediction of Continuous B-Cell Epitopes in Antigenic Sequences Using Physico-chemical Properties. In G. Nicosia, V. Cutello, P. J. Bentley and J. Timis (Eds.) ICARIS 2004, LNCS 3239, 197-204, Springer, 2004.

Sandholm, M., L. Kaartinen, and S. Pyorala. 1990. Bovine mastitis—why does antibiotic therapy not always work? An overview. J Vet Phamacol Therap. 13:248-260.

Schaffer, A. C., and J. C. Lee. 2009. Staphylococcal vaccines and immunotherapies. Infect Dis Clin North Am. 23:153-171.

Sears, P. M. and McCarthy, K. K. 2003. Management and treatment of staphylococcal mastitis. Vet Clin North Am Food Anim Pract 19:171-185.

Sendi, P., and R. a Proctor. 2009. *Staphylococcus aureus* as an intracellular pathogen: the role of small colony variants. Trends Microbiol. 17:54-8.

Senn, M. M., M. Bischoff, C. Von Eiff, B. Berger-bachi, and B. Berger-ba. 2005. a B Activity in a *Staphylococcus aureus* hemB Mutant. J. Bacteriol. 187:7397-7406.

Sibbald, M. J., A. K. Ziebandt, S. Engelmann, M. Hecker, A. de Jong, H. J. Harmsen, G. C. Raangs, I. Stokroos, J. P. Arends, J. Y. Dubois, and J. M. van Dijl. 2006. Mapping the pathways to staphylococcal pathogenesis by comparative secretomics. Microbiol Mol Biol Rev. 70:755-788.

Silanikove, N., F. Shapiro, and G. Leitner. 2007. Posttranslational ruling of xanthine oxidase activity in bovine milk by its substrates. Biochem Biophys Res Commun. 363: 561-565.

Somerville, G. A., and R. A. Proctor. 2009. At the crossroads of bacterial metabolism and virulence factor synthesis in Staphylococci. Microbiol Mol Biol Rev. 73:233-248.

Spellberg, B., and R. Daum. 2012. Development of a vaccine against *Staphylococcus aureus*. Semin. Immunopathol. 34:335-48.

Sprickler A. R. and J. A. Roth. Adjuvants in veterinary vaccines: mode of action and adverse effects. 2003. 17:273-281.

Srinivasan, V., A. A. Sawant, B. E. Gillespie, S. J. Headrick, L. Ceasaris, and S. P. Oliver. 2006. Prevalence of enterotoxin and toxic shock syndrome toxin genes in *Staphylococcus aureus* isolated from milk of cows with mastitis. Foodborne Pathog Dis. 3:274-83.

Srivastava S, Singh V, Kumar V, Verma P C, Srivastava R, Basu V, Gupta V, Rawat A K. Identification of regulatory elements in 16S rRNA gene of *Acinetobacter* species isolated from water sample. Bioinformation. 2008; 3(4): 173-6. Epub 2008 Dec. 6.

Ster, C., M. Allard, S. Boulanger, M. Lamontagne Boulet, J. Mulhbacher, D. a Lafontaine, E. Marsault, P. Lacasse, and F. Malouin. 2013. Experimental treatment of *Staphylococcus aureus* bovine intramammary infection using a guanine riboswitch ligand analog. J. Dairy Sci. Elsevier 96:1000-8.

Sutra, L., and B. Poutrel. 1994. Virulence factors involved in the pathogenesis of bovine intramammary infections due to *Staphylococcus aureus*. J. Med. Microbiol. 40:79-89.

Taverna, F., A. Negri, R. Piccinini, A. Zecconi, S. Nonnis, S. Ronchi, and G. Tedeschi. 2007. Characterization of cell wall associated proteins of a *Staphylococcus aureus* isolated from bovine mastitis case by a proteomic approach. Vet Microbiol. 119:240-247

Tollersrud, T., A. H. Kampen, and K. Kenny. 2006. *Staphylococcus aureus* enterotoxin D is secreted in milk and stimulates specific antibody responses in cows in the course of experimental intramammary infection. Infect Immun. 74:3507-3512.

Tuchscherr, L., E. Medina, M. Hussain, W. Vilker, V. Heitmann, S. Niemann, D. Holzinger, J. Roth, R. a Proctor, K. Becker, G. Peters, and B. Löffler. 2011. *Staphylococcus aureus* phenotype switching: an effective bacterial strategy to escape host immune response and establish a chronic infection. EMBO Mol. Med. 3:129-41.

Tuchscherr, L., V. Heitmann, M. Hussain, D. Viemann, J. Roth, C. von Eiff, G. Peters, K. Becker, and B. Löffler. 2010. *Staphylococcus aureus* small-colony variants are adapted phenotypes for intracellular persistence. J. Infect. Dis. 202:1031-40.

Tuchscherr, L. P., F. R. Buzzola, L. P. Alvarez, J. C. Lee, and D. O. Sordelli. 2008. Antibodies to capsular polysaccharide and clumping factor A prevent mastitis and the emergence of unencapsulated and small-colony variants of *Staphylococcus aureus* in mice. Infect Immun. 76:5738-5744.

Tusnády, G. E. and Simon, I. 2001. The HMMTOP transmembrane topology prediction server" Bioinformatics 17, 849-850.

Veh K A, Klein R C, Ster C, Keefe G, Lacasse P, Scholl D, et al. Genotypic and phenotypic characterization of *Staphylococcus aureus* causing persistent and nonpersistent subclinical bovine intramammary infections during lactation or the dry period. J Dairy Sci. 2015; 98: 155-168

Von Eiff, C., P. McNamara, K. Becker, X. Lei, M. Ziman, B. R. Bochner, G. Peters, and R. A. Proctor. 2006. Phenotype Microarray Profiling of *Staphylococcus aureus* menD and hemB Mutants with the Small-Colony-Variant Phenotype Phenotype Microarray Profiling of *Staphylococcus aureus* menD and hemB Mutants with the Small-Colony-Variant Phenotype t. J. Bacteriol. 188:687-693.

Voyich, J. M., K. R. Braughton, D. E. Sturdevant, A. R. Whitney, B. Said-Salim, S. F. Porcella, R. D. Long, D. W. Dorward, D. J. Gardner, B. N. Kreiswirth, J. M. Musser, and F. R. DeLeo. 2005. Insights into mechanisms used by *Staphylococcus aureus* to avoid destruction by human neutrophils. J Immunol. 175:3907-3919.

Watson, D. L. 1984. Evaluation of attenuated, live staphylococcal mastitis vaccine in lactating heifers. J. Dairy Sci. 67:2608-13.

Whist, A. C., O. Osteràs, and L. Sølverød. 2009. Association between isolation of *Staphylococcus aureus* one week after calving and milk yield, somatic cell count, clinical mastitis, and culling through the remaining lactation. J. Dairy Res. 76:24-35.

WO/2003/091279

WO/2004/043405

WO/2005/007683

WO/2006/059846

WO/2008/152447

Xia, Y., and J. L. Zweier. 1997. Measurement of Myeloperoxidase in Leukocyte-Containing Tissues. Anal. Biochem. 245:93-96.

Yang, S.-J., A. S. Bayer, N. N. Mishra, M. Meehl, N. Ledala, M. R. Yeaman, Y. Q. Xiong, and A. L. Cheung. 2012. The *Staphylococcus aureus* Two-Component Regulatory System, GraRS, Senses and Confers Resistance to Selected Cationic Antimicrobial Peptides. Infect. Immun. 80:74-81.

Zecconi, A., R. Piccinini, and L. K. Fox. 2003. Epidemiologic study of intramammary infections with *Staphylococcus aureus* during a control program in nine commercial dairy herds. J. Am. Vet. Med. Assoc. 223:684-8.

Zhang, C., J. Yang, and L. K. Jennings. 2004. Non—Leukocyte-Derived Reactive Oxygen Species. Diabetes 53:2950-2959.

Ziebandt, A. K., H. Kusch, M. Degner, S. Jaglitz, M. J. Sibbald, J. P. Arends, M. A. Chlebowicz, D. Albrecht, R. Pantucek, J. Doškar, W. Ziebuhr, B. M. Briker, M. Hecker, J. M. van Dijl, and S. Engelmann. 2010. Proteomics uncovers extreme heterogeneity in the *Staphylococcus aureus* exoproteome due to genomic plasticity and variant gene regulation. Proteomics 285(47)36794-36803.

The invention claimed is:

1. A composition comprising a combination of polypeptide constructs comprising SACOL0029 comprising the amino acid sequence of SEQ ID NO: 5, SACOL0442 comprising the amino acid sequence of SEQ ID NO: 29, SACOL0720 comprising the amino acid sequence of SEQ ID NO: 11, SACOL1867 comprising the amino acid sequence of SEQ ID NO: 38, SACOL1912 comprising the amino acid sequence of SEQ ID NO: 43, and SACOL2385 comprising the amino acid sequence of SEQ ID NO: 50 and further comprising an adjuvant.

2. The composition of claim 1, wherein the adjuvant comprises alum, an oil, saponin, cyclic-diguanosine-5'-monophosphate (c-di-GMP), polyphosphasine, indolicidin, pathogen-associated molecular patterns (PAMPS), liposome or a combination of at least two thereof.

3. The composition of claim 1, further comprising a live attenuated form of *Staphylococcus aureus*.

4. The composition of claim 3, wherein the live attenuated form of *Staphylococcus aureus* has a stabilized small colony variant (SCV) phenotype.

5. The composition of claim 4, wherein the live attenuated form of *Staphylococcus aureus* having a stabilized SCV phenotype is a ΔhemBΔ720 *S. aureus*.

6. A composition comprising a mixture of polypeptide constructs comprising SACOL0442 comprising the amino acid sequence of SEQ ID NO: 29, SACOL0720 comprising the amino acid sequence of SEQ ID NO: 11, and a fusion construct comprising SACOL1867 and SACOL0029 comprising the amino acid sequence of SEQ ID NO: 55.

7. The composition of claim 6, wherein the composition further comprises an adjuvant comprises alum, an oil, saponin, cyclic-diguanosine-5'-monophosphate (c-di-GMP), polyphosphasine, indolicidin, pathogen-associated molecular patterns (PAMPS), liposome or a combination of at least two thereof.

8. The composition of claim 6, further comprising a live attenuated form of *Staphylococcus aureus*.

9. The composition of claim 8, wherein the live attenuated form of *Staphylococcus aureus* has a stabilized small colony variant (SCV) phenotype.

10. The composition of claim 9, wherein the live attenuated form of *Staphylococcus aureus* having a stabilized SCV phenotype is a ΔhemBΔ720 *S. aureus*.

11. A composition comprising a mixture of polypeptide constructs comprising SACOL0029 comprising the amino acid sequence of SEQ ID NO: 5, SACOL1867 comprising the amino acid sequence of SEQ ID NO: 38, and a fusion construct comprising SACOL1867 and SACOL0029 comprising the amino acid sequence of SEQ ID NO: 55.

12. The composition of claim 11, wherein the composition further comprises an adjuvant comprises alum, an oil, saponin, cyclic-diguanosine-5'-monophosphate (c-di-GMP), polyphosphasine, indolicidin, pathogen-associated molecular patterns (PAMPS), liposome or a combination of at least two thereof.

13. The composition of claim 11, further comprising a live attenuated form of *Staphylococcus aureus*.

14. The composition of claim 13, wherein the live attenuated form of *Staphylococcus aureus* has a stabilized small colony variant (SCV) phenotype.

15. The composition of claim 14, wherein the live attenuated form of *Staphylococcus aureus* having a stabilized SCV phenotype is a ΔhemBΔ720 *S. aureus*.

16. A polypeptide construct comprising a combination of epitopes from SACOL0442 and SACOL0720 comprising the amino acid sequence of SEQ ID NO: 3.

17. A composition comprising the polypeptide construct of claim 16 and an adjuvant comprises alum, an oil, saponin, cyclic-diguanosine-5'-monophosphate (c-di-GMP), polyphosphasine, indolicidin, pathogen-associated molecular patterns (PAMPS), liposome or a combination of at least two thereof.

18. The composition of claim 17, further comprising a live attenuated form of *Staphylococcus aureus*.

19. The composition of claim 18, wherein the live attenuated form of *Staphylococcus aureus* has a stabilized small colony variant (SCV) phenotype.

20. The composition of claim 19, wherein the live attenuated form of *Staphylococcus aureus* having a stabilized SCV phenotype is a ΔhemBΔ720 *S. aureus*.

21. A polypeptide construct comprising the amino acid sequence of SEQ ID NO: 27.

22. A composition comprising the polypeptide construct of claim 21 and an adjuvant comprises alum, an oil, saponin, cyclic-diguanosine-5'-monophosphate (c-di-GMP), polyphosphasine, indolicidin, pathogen-associated molecular patterns (PAMPS), liposome or a combination of at least two thereof.

23. The composition of claim 22, further comprising a live attenuated form of *Staphylococcus aureus*.

24. The composition of claim 23, wherein the live attenuated form of *Staphylococcus aureus* has a stabilized small colony variant (SCV) phenotype.

25. The composition of claim 24, wherein the live attenuated form of *Staphylococcus aureus* having a stabilized SCV phenotype is a ΔhemBΔ720 *S. aureus*.

26. A composition comprising a mixture of two polypeptide constructs, the first comprising a combination of SACOL0442 and SACOL0720 comprising the amino acid sequence of SEQ ID NO: 3 and the second comprising a polypeptide construct of SACOL0029 and SACOL1867 comprising the amino acid sequence of SEQ ID NO: 55.

27. A composition comprising the polypeptide construct of claim 26 and an adjuvant comprises alum, an oil, saponin, cyclic-diguanosine-5'-monophosphate (c-di-GMP), polyphosphasine, indolicidin, pathogen-associated molecular patterns (PAMPS), liposome or a combination of at least two thereof.

28. The composition of claim 27, further comprising a live attenuated form of *Staphylococcus aureus*.

29. The composition of claim 28, wherein the live attenuated form of *Staphylococcus aureus* has a stabilized small colony variant (SCV) phenotype.

30. The composition of claim 29, wherein the live attenuated form of *Staphylococcus aureus* having a stabilized SCV phenotype is a ΔhemBΔ720 *S. aureus*.

31. A method for treating a Staphylococcal intramammary infection (IMI) in a mammal, said method comprising administrating to said mammal an effective amount of the composition of claim 1.

32. The method of claim 31, wherein said Staphylococcal IMI is caused by one or more *Staphylococcus aureus* strains.

33. The method of claim 31, wherein said mammal is a cow.

* * * * *